US012240833B2

(12) United States Patent
Hunt et al.

(10) Patent No.: US 12,240,833 B2
(45) Date of Patent: Mar. 4, 2025

(54) PYRIDAZINONE COMPOUNDS AND USES THEREOF

(71) Applicant: Edgewise Therapeutics, Inc., Boulder, CO (US)

(72) Inventors: Kevin Hunt, Boulder, CO (US); Kevin Koch, Boulder, CO (US); Alan Russell, Boulder, CO (US); Stephen Schlachter, Boulder, CO (US); Paul Winship, Cambridge (GB); Grace Uzoho, Cambridge (GB); Chris Steele, Cambridge (GB)

(73) Assignee: EDGEWISE THERAPEUTICS, INC., Boulder, CO (US)

( * ) Notice: Subject to any disclaimer, the term of this patent is extended or adjusted under 35 U.S.C. 154(b) by 175 days.

(21) Appl. No.: 17/827,547

(22) Filed: May 27, 2022

(65) Prior Publication Data

US 2023/0048816 A1  Feb. 16, 2023

Related U.S. Application Data

(63) Continuation of application No. 17/088,468, filed on Nov. 3, 2020, now Pat. No. 11,390,606, which is a continuation of application No. PCT/US2019/060148, filed on Nov. 6, 2019.

(60) Provisional application No. 62/756,552, filed on Nov. 6, 2018.

(51) Int. Cl.
| | |
|---|---|
| *C07D 403/04* | (2006.01) |
| *A61P 21/00* | (2006.01) |
| *C07D 237/04* | (2006.01) |
| *C07D 401/04* | (2006.01) |
| *C07D 401/14* | (2006.01) |
| *C07D 403/10* | (2006.01) |
| *C07D 403/14* | (2006.01) |
| *C07D 405/10* | (2006.01) |
| *C07D 405/14* | (2006.01) |
| *C07D 417/10* | (2006.01) |

(52) U.S. Cl.
CPC ............ *C07D 403/04* (2013.01); *A61P 21/00* (2018.01); *C07D 237/04* (2013.01); *C07D 401/04* (2013.01); *C07D 401/14* (2013.01); *C07D 403/10* (2013.01); *C07D 403/14* (2013.01); *C07D 405/10* (2013.01); *C07D 405/14* (2013.01); *C07D 417/10* (2013.01)

(58) Field of Classification Search
CPC .. C07D 403/04; C07D 237/04; C07D 401/04; C07D 401/14; C07D 403/10; C07D 403/14; C07D 405/10; C07D 405/14; C07D 417/10; A61P 21/00
See application file for complete search history.

(56) References Cited

U.S. PATENT DOCUMENTS

| | | | |
|---|---|---|---|
| 5,698,554 A | 12/1997 | Ishida et al. | |
| 5,753,642 A | 5/1998 | Michelotti et al. | |
| 5,846,514 A | 12/1998 | Foster et al. | |
| 6,005,117 A | 12/1999 | Wehner et al. | |
| 6,334,997 B1 | 1/2002 | Foster et al. | |
| 7,763,617 B2 | 7/2010 | Kohno et al. | |
| 8,445,489 B2 | 5/2013 | Stieber et al. | |
| 8,580,781 B2 | 11/2013 | Dorsch et al. | |
| 8,604,036 B2 | 12/2013 | Dorsch et al. | |
| 8,673,916 B2 | 3/2014 | Bacon et al. | |
| 9,566,310 B2 | 2/2017 | Burkin et al. | |
| 10,556,914 B2 * | 2/2020 | Dinges | A61P 25/30 |
| 11,091,464 B2 | 8/2021 | Hunt et al. | |
| 11,236,065 B2 | 2/2022 | Hunt et al. | |
| 11,390,606 B2 | 7/2022 | Hunt et al. | |
| 2004/0067955 A1 | 4/2004 | Tabuchi et al. | |
| 2006/0189621 A1 | 8/2006 | Sato et al. | |
| 2008/0207902 A1 | 8/2008 | Kohno et al. | |
| 2008/0293719 A1 | 11/2008 | Dorsch et al. | |
| 2010/0168072 A1 | 7/2010 | Wynne et al. | |
| 2010/0179148 A1 | 7/2010 | Stieber et al. | |
| 2011/0098269 A1 | 4/2011 | Becknell et al. | |
| 2012/0289698 A1 | 11/2012 | Ashcraft et al. | |
| 2014/0072536 A1 | 3/2014 | Burkin et al. | |
| 2014/0094457 A1 | 4/2014 | Gardner et al. | |
| 2015/0376167 A1 | 12/2015 | Jorand-Lebrun et al. | |
| 2016/0074464 A1 | 3/2016 | Sabharwal et al. | |
| 2018/0147228 A1 | 5/2018 | Baiazitov | |
| 2018/0169130 A1 | 6/2018 | Lorain et al. | |

(Continued)

FOREIGN PATENT DOCUMENTS

| | | |
|---|---|---|
| CA | 3105681 A1 | 1/2020 |
| CN | 101326167 A | 12/2008 |

(Continued)

OTHER PUBLICATIONS

CAS registry No. 1103508-75-3; Date entered STN: Feb. 10, 2009; Chemical name: 4-(1-(3-carbamimidoylbenzyl)-6-oxo-1,6-dihydropyridazin-3-yl)-N-(3-(piperidin-1-yl)propyl)benzamide.

CAS registry No. 922866-23-7; Date entered STN: Feb. 23, 2007; 2-[(4-fluorophenyl)methyl]-6-[4-(1-piperidinyl)phenyl]-3(2H)-pyridazinone.

CAS registry No. 922866-82-8; Date entered STN: Feb. 23, 2007; Chemical name: 2-[(2,5-dimethylphenyl)methyl]-6-[4-(1-piperidinyl)phenyl]-3(2H)-pyridazinone.

CAS registry No. 922867-00-3: Date entered STN: Feb. 23, 2007; Chemical name: 2-[(2,4-dichlorophenyl) methyl]-6-[4-(1-piperidinyl)phenyl]-3(2H)-pyridazinone.

(Continued)

*Primary Examiner* — Erich A Leeser

(74) *Attorney, Agent, or Firm* — Wilson Sonsini Goodrich & Rosati

(57) ABSTRACT

Substituted pyridazinone compounds, conjugates, and pharmaceutical compositions for use in the treatment of neuromuscular diseases, such as Duchenne Muscular Dystrophy (DMD), are disclosed herein. The disclosed compounds are useful, among other things, in the treating of DMD and modulating inflammatory inhibitors IL-1, IL-6 or TNF-α.

28 Claims, 6 Drawing Sheets

(56) References Cited

U.S. PATENT DOCUMENTS

| | | |
|---|---|---|
| 2018/0280385 A1 | 10/2018 | Wollin et al. |
| 2018/0303821 A1 | 10/2018 | Sonner et al. |
| 2019/0248779 A1 | 8/2019 | Parks et al. |
| 2019/0256474 A1 | 8/2019 | Parks et al. |
| 2021/0130327 A1 | 5/2021 | Hunt et al. |
| 2022/0081410 A1 | 3/2022 | Hunt et al. |
| 2022/0106291 A1 | 4/2022 | Hunt et al. |
| 2023/0150977 A1 | 5/2023 | Koch et al. |
| 2023/0159513 A1 | 5/2023 | Koch et al. |
| 2023/0293518 A1 | 9/2023 | Russell |
| 2023/0321091 A1 | 10/2023 | Russell |
| 2023/0338375 A1 | 10/2023 | Russell |
| 2024/0025879 A1 | 1/2024 | Hunt et al. |

FOREIGN PATENT DOCUMENTS

| | | |
|---|---|---|
| CN | 101678214 A | 3/2010 |
| CN | 103002897 A | 3/2013 |
| CN | 103570730 A | 2/2014 |
| CN | 104968658 A | 10/2015 |
| CN | 106467495 A | 3/2017 |
| CN | 108947912 A | 12/2018 |
| DE | 286354 A5 | 1/1991 |
| DE | 102005057924 A1 | 6/2007 |
| EP | 2611798 B1 | 4/2015 |
| EP | 3877052 A1 | 9/2021 |
| EP | 3877367 A1 | 9/2021 |
| EP | 3877376 A1 | 9/2021 |
| EP | 4149465 A1 | 3/2023 |
| EP | 4149466 A1 | 3/2023 |
| EP | 4149467 A1 | 3/2023 |
| EP | 4149620 A1 | 3/2023 |
| EP | 4149621 A1 | 3/2023 |
| JP | S6140270 A | 2/1986 |
| JP | 2009518323 A | 5/2009 |
| JP | 2010528994 A | 8/2010 |
| JP | 2010528995 A | 8/2010 |
| JP | 2013525376 A | 6/2013 |
| JP | 2015527409 A | 9/2015 |
| JP | 2016508505 A | 3/2016 |
| JP | WO2020017587 A1 | 8/2021 |
| JP | 2022506685 A | 1/2022 |
| JP | 2022506686 A | 1/2022 |
| JP | 2022506687 A | 1/2022 |
| JP | 7162132 B2 | 10/2022 |
| JP | 7170133 B2 | 11/2022 |
| JP | 2022174578 A | 11/2022 |
| JP | 2022189961 A | 12/2022 |
| KR | 20150123937 A | 11/2015 |
| WO | WO-0194319 A1 | 12/2001 |
| WO | WO-2006095666 A1 | 9/2006 |
| WO | WO-2007044796 A2 | 4/2007 |
| WO | WO-2008103277 A2 | 8/2008 |
| WO | WO-2008145242 A1 | 12/2008 |
| WO | WO-2009006959 A1 | 1/2009 |
| WO | WO-2009024221 A1 | 2/2009 |
| WO | WO-2010048149 A2 | 4/2010 |
| WO | WO-2011133882 A1 | 10/2011 |
| WO | WO-2011133888 A1 | 10/2011 |
| WO | WO-2012021707 A2 | 2/2012 |
| WO | WO-2013057101 A1 | 4/2013 |
| WO | WO-2014031928 A2 | 2/2014 |
| WO | WO-2014096965 A2 | 6/2014 |
| WO | WO-2014121931 A1 | 8/2014 |
| WO | WO-2017028798 A1 | 2/2017 |
| WO | WO-2018081377 A1 | 5/2018 |
| WO | WO-2018081378 A1 | 5/2018 |
| WO | WO-2018081381 A1 | 5/2018 |
| WO | WO-2018187553 A1 | 10/2018 |
| WO | WO-2019043123 A1 | 3/2019 |
| WO | WO-2019084499 A1 | 5/2019 |
| WO | WO-2019222633 A1 | 11/2019 |
| WO | WO-2019236625 A1 | 12/2019 |
| WO | WO-2020097258 A1 | 5/2020 |
| WO | WO-2020097265 A1 | 5/2020 |
| WO | WO-2020097266 A1 | 5/2020 |
| WO | WO-2021231546 A1 | 11/2021 |
| WO | WO-2021231565 A1 | 11/2021 |
| WO | WO-2021231572 A1 | 11/2021 |
| WO | WO-2021231615 A1 | 11/2021 |
| WO | WO-2021231630 A1 | 11/2021 |
| WO | WO-2023091606 | 5/2023 |
| WO | WO2023220180 | 11/2023 |
| WO | WO-2024055007 A1 | 3/2024 |

OTHER PUBLICATIONS

CAS registry No. 922867-06-9; Date entered STN: Feb. 23, 2007; Chemical name: 2-[(3,4-dichlorophenyl) methyl]-6-[4-(1-piperidinyl)phenyl]-3(2H)-pyridazinone.

CAS registry No. 922935-15-7; Date entered STN: Feb. 23, 2007; Chemical name: 2-[(3-fluorophenyl)methyl]-6-[4-(1-piperidinyl)phenyl]-3(2H)-pyridazinone.

CAS registry No. 922935-69-1; Date entered STN: Feb. 23, 2007; Chemical name: 2-[(2-methylphenyl)methyl]-6-[4-(1-piperidinyl)phenyl]-3(2H)-pyridazinone.

CAS registry No. 922935-77-1; Date entered STN: Feb. 23, 2007; Chemical name: 6-[4-(1-piperidinyl) phenyl]-2-[[3-(trifluoromethyl)phenyl]methyl]-3(2H)-pyridazinone.

CAS registry No. 922935-98-6; Date entered STN: Feb. 23, 2007; Chemical name: 2-[(4-chlorophenyl)methyl]-6-[4-(1-piperidinyl)phenyl]-3(2H)-pyridazinone.

CAS registry No. 922980-68-5; Date entered STN: Feb. 23, 2007; Chemical name: 2-[(2-fluorophenyl)methyl]-6-[4-(1-piperidinyl)phenyl]-3(2H)-pyridazinone.

CAS registry No. 922981-23-5; Date entered STN: Feb. 23, 2007; Chemical name: 2-[(3-nitrophenyl)methyl]-6-[4-(1-piperidinyl)phenyl]-3(2H)-pyridazinone.

CAS registry No. 922981-25-7; Date entered STN: Feb. 23, 2007; Chemical name: 6-[4-(1-piperidinyl) phenyl]-2-[[4-(trifluoromethyl)phenyl]methyl]-3(2H)-pyridazinone.

CAS registry No. 922981-41-7; Date entered STN: Feb. 23, 2007; Chemical name: 2-[(2-chlorophenyl)methyl]-6-[4-(1-piperidinyl)phenyl]-3(2H)-pyridazinone.

CAS registry No. 922981-44-0; Date entered STN: Feb. 23, 2007; Chemical name: 2-[(3-chlorophenyl) methyl]-6-[4-(1-piperidinyl)phenyl]-3(2H)-pyridazinone.

CAS registry No. 923063-37-0; Date entered STN: Feb. 26, 2007; Chemical name: 2-[(3-methylphenyl)methyl]-6-[4-(1-piperidinyl)phenyl]-3(2H)-pyridazinone.

CAS registry No. 923063-76-7; Date entered STN: Feb. 26, 2007; Chemical name: 2-[(4-methylphenyl)methyl]-6-[4-(1-piperidinyl)phenyl]-3(2H)-pyridazinone.

CAS registry No. 923063-82-5; Date entered STN: Feb. 26, 2007; Chemical name: 2-[(4-bromophenyl)methyl]-6-[4-(1-piperidinyl)phenyl]-3(2H)-pyridazinone.

CAS registry No. 923063-90-5; Date entered STN: Feb. 26, 2007; Chemical name: 2-[(4-nitrophenyl)methyl]-6-[4-(1-piperidinyl)phenyl]-3(2H)-pyridazinone.

CAS registry No. 923063-98-3; Date entered STN: Feb. 26, 2007; Chemical name: 2-[(2-chloro-6-fluorophenyl)methyl]-6-[4-(1-piperidinyl)phenyl]-3(2H)-pyridazinone.

U.S. Appl. No. 17/345,909 Notice of Allowance dated May 1, 2024.

Donovan et al., EDG-5506 targets fast skeletal myosin and reduces muscle damage biomarkers in a phase 1 trial in Becker muscular dystrophy (BMD). Neuromuscular Disorders, Elsevier Ltd., GB, vol. 32, Oct. 1, 2022, abstract p. 124.

PCT/US2023/073790 International Search Report and Written Opinion dated Dec. 13, 2023.

Co-pending PCT Application No. PCT/US2023/021739, inventor Koch, Kevin, filed on May 10, 2023.

Co-pending U.S. Appl. No. 18/053,332, inventor Russell; Alan, filed Nov. 7, 2022.

Co-pending U.S. Appl. No. 18/053,343, inventor RussellAlan, filed Nov. 7, 2022.

Co-pending U.S. Appl. No. 18/053,350, inventor RussellAlan, filed Nov. 7, 2022.

(56) References Cited

OTHER PUBLICATIONS

Dean. Recent Advances in the Synthesis and Applications of Radiolabeled Compounds for Drug Discovery and Development. In: Curr. Pharm. Des., 6(10):110 (2000) (Preface only).
English machine translation for WO 2017/02798 (Feb. 23, 2017). 49 pages.
Evans. Synthesis of radiolabeled compounds. J Radioanal Chem 64(1-2):9-32 (1981).
Fedorak et al. A novel colon-specific steroid prodrug enhances sodium chloride absorption in rat colitis. Am. J. Physiol. 269:G210-218 (1995).
Fieser, et al. Fieser and Fieser's Reagents for Organic Synthesis. John Wiley and Sons. 1994.
George W.; Varma, Rajender S., The Synthesis of Radiolabeled Compounds via Organometallic Intermediates, Tetrahedron, 1989, 45(21), 6601-21.
Greene, et al. Protective Groups in Organic Synthesis. John Wiley & Sons, 1991.
Higuchi et al. Pro-drugs as Novel Delivery Systems, vol. 14 of the A.C.S. Symposium Series; and in Bioreversible Carriers in Drug Design, ed. Edward B. Roche, American Pharmaceutical Association and Pergamon Press (1987).
Hochhaus et al. A selective HPLC/RIA for dexamethasone and its prodrug dexamethasone-21-sulphobenzoate sodium in biological fluids. Biomed. Chrom. 6:283-286 (1992).
Hudkins, Robert L. et al., Discovery and characterization of 6-{4-[3-(R)-2-Methylpyrrolidin-1-yl)propoxy]phenyl}-2 H-pyridazin-3-one(CEP-26401, Irdabisant): A potent, selective histamine H 3 Receptor inverse agonist, Journal of Medicinal Chemistry, vol. 54, No. 13, Jul. 14, 2011, pp. 4781-4792, XP055829893.
Larock, A. Comprehensive Organic Transformations. VCH Publishers, (1989).
Larsen et al. Prodrug forms for the sulfonamide group. I. Evaluation of N-acyl derivatives, N-sulfonylaminides, N-sulfonylsulfilimines and sulfonylureas as possible prodrug derivatives. Int. J. Pharmaceutics 37:87-95 (1987).
Larsen, et al. Prodrug forms for the sulfonamide group. Part 2. Water-soluble amino acid derivatives of N-Methyl-sulfonamides as possible prodrugs. Int. J. Pharm. 1988; 47:103-110.
Lu et al. Optimization and Synthesis of Pyridazinone Derivatives as Novel Inhibitors of Hepatitis B Virus by Inducing Genome-free Capsid Formation. ACS Infect. Dis. 2017, 3, 199-205. Published Dec. 18, 2016.
Lu et al. Optimization and Synthesis of pyridazinone derivatives as novel inhibitors of Hepatitis B virus by inducing genome-free capsid formation. Supporting information for infect. Dis. (3, 199-205), p. S1-S68. (2016).
McKinstry-Wu, et al., Discovery of a Novel General Anesthetic Chemotype Using High-throughput Screening. Anesthesiology, 2015; 122:325-33.
McLoed et al. A Glucocorticoid Prodrug Facilitates Normal Mucosal Function in Rat Colitis Without Adrenal Suppression. Gastroenterol 106:405-413 (1994).
National Center for Biotechnology Information (2022). PubChem Compound Summary for CID 7660155. Retrieved Mar. 10, 2022 from https://pubchem.ncbi.nlm.nih.gov/compound/7660155.
National Center for Biotechnology Information (2022). PubChem Compound Summary for CID 7662323. Retrieved Mar. 10, 2022 from https://pubchem.ncbi.nlm.nih.gov/compound/7662323.
National Center for Biotechnology Information (2022). PubChem Compound Summary for CID 8698959. Retrieved Mar. 10, 2022 from https://pubchem.ncbi.nlm.nih.gov/compound/8698959.
National Center for Biotechnology Information (2022). PubChem Compound Summary for CID 8698960. Retrieved Mar. 10, 2022 from https://pubchem.ncbi.nlm.nih.gov/compound/8698960.
Paquette, et al. Encyclopedia of Reagents for Organic Synthesis. John Wiley and Sons (1995).
PCT/US2019/060148 International Search Report and Written Opinion date Apr. 2, 2020.
PCT/US2019/060155 International Search Report and Written Opinion dated Mar. 5, 2020.
PCT/US2019/060157 International Search Report and Written Opinion dated Mar. 5, 2020.
PCT/US2021/031952 International Search Report and Written Opinion dated Nov. 18, 2021.
PCT/US2021/031979 International Search Report and Written Opinion dated Aug. 13, 2021.
PCT/US2021/031989 International Search Report and Written Opinion dated Aug. 13, 2021.
PCT/US2021/032048 International Search Report and Written Opinion dated Aug. 25, 2021.
PCT/US2021/032064 International Search Report and Written Opinion dated Aug. 25, 2021.
PCT/US2022/050313 International Search Report and Written Opinion dated Feb. 8, 2023.
Pitarch et al., Etude chhimque et pharmacologique d'une serie de pyridazones substituees. European Journal of Medicinal Chemistry 9(6): 644-650 (1974).
SG11202104713R Written Opinion Report dated Jan. 4, 2023.
Sinkula et al. Rationale for design of biologically reversible drug derivatives: prodrugs. J. Pharm. Sci. 64:181-210 (1975).
U.S. Appl. No. 17/088,466 Notice of Allowance dated Aug. 26, 2021.
U.S. Appl. No. 17/088,466 Office Action dated May 7, 2021.
U.S. Appl. No. 17/088,468 Notice of Allowance dated Apr. 12, 2022.
U.S. Appl. No. 17/088,468 Office Action dated Aug. 20, 2021.
U.S. Appl. No. 17/088,468 Office Action dated May 5, 2021.
U.S. Appl. No. 17/088,469 Notice of Allowance dated May 6, 2021.
U.S. Appl. No. 17/345,909 Notice of Allowance dated May 15, 2023.
U.S. Appl. No. 17/345,909 Office Action dated Jan. 27, 2023.
Yukawa, et al., Design, Synthesis, and biological evaluation of a novel series of peripheral-selective noradrenaline reuptake inhibitors—PArt 3, Bioorganic & Medicinal Chemistry 2016; 24: 3716-3726.
Cepeda et al., Functional Properties of Faba Bean (*Vicia faba*) Protein Flour Dried by Spray Drying and Freeze Drying. Journal of Food Engineering, 36(3):303-310(1998).
Co-pending U.S. Appl. No. 18/460,464, inventors Hunt; Kevin et al., filed Sep. 1, 2023.
Co-pending PCT Application No. PCT/US2023/073790, inventors Donovan; Joanne et al., filed on Sep. 8, 2023.
Liu et al., Pyridazinone Derivatives Displaying Highly Potent and Selective Inhibitory Activities Against C-met Tyrosine Kinase. European journal of medicinal chemistry, 108:322-333(2016).
Miyaura, et al. Palladium-Catalyzed Cross-Coupling Reactions of Organoboron Compounds. Chem. Rev.. 1995; 95(7):2457-2483.
PCT/US2023/021739 International Search Report and Written Opinion dated Nov. 26, 2023.
PubChem CID 56643059 https://pubchem.ncbi.nlm.nih.gov/compound/56643059 Date create: Feb. 29, 2012.
PubChem CID 56643068 https://pubchem.ncbi.nlm.nih.gov/compound/56643068 Date create: Feb. 29, 2012.
PubChem SID 371083532 https://pubchem.ncbi.nlm.nih.gov/substance/371083532 Source: Ambinter, Deposit Date: May 25, 2018, Available, Modify Date: May 25, 2018; CID: 51044092.
PubChem SID 371425619 https://pubchem.ncbi.nlm.nih.gov/substance/371425619 Source: Ambinter, Deposit Date: May 25, 2018, Available, Modify Date: May 25, 2018; CID: 51048704.
Registry(STN)[online], date of retrieval: Nov. 13, 2023: Dec. 7, 2011 RN:1350041-75-6, 2010. 7.16 RN: 1232768-39-6, 2007. 2.26 RN:923076-66-8, 2007. 2.23 RN:922973-89-5.
Salives et al., Solid-Phase Syntheses of 6-Arylpyridazin-3(2H)-Ones. J. Comb. Chem, 3:414-420 (2005).
U.S. Appl. No. 17/345,909 Notice of Allowance dated Aug. 9, 2023.
Pitarch et al., Chemical and pharmacological study of a series of substituted pyridazones, (English Google translation of relevant sections), European Journal of Medicinal Chemistry, 9(5): 644-650 (1974).

(56) References Cited

OTHER PUBLICATIONS

Ubogu, Inflammorty Neuropathies: Pathology, molecular markers and targets for specific thereapeutic intervention, Acta Neuropathol., 130(4): 445-468 (2015).

* cited by examiner

PYRIDAZINONE COMPOUNDS AND USES THEREOF

CROSS-REFERENCE

This application is a continuation No. U.S. patent application Ser. No. 17/088,468, filed Nov. 3, 2020, which is a continuation of International Patent Application No. PCT/US2019/060148, filed Nov. 6, 2019, which claims the benefit of U.S. Provisional Application Ser. No. 62/756,552 filed Nov. 6, 2018, each of which is hereby incorporated herein by reference in its entirety.

BACKGROUND OF THE INVENTION

Skeletal muscle is the largest organ system in the human body, serving two primary purposes. The first is force production to enable muscle contraction, locomotion, and postural maintenance; the second is glucose, fatty acid and amino acid metabolism. The contraction of skeletal muscle during every-day activity and exercise is naturally connected to muscle stress, breakdown and remodeling which is important for muscle adaptation. In individuals with neuromuscular conditions, such as Duchenne Muscular Dystrophy (DMD), muscle contractions lead to continued rounds of amplified muscle breakdown that the body struggles to repair. Eventually, as patients age, a pathophysiological process emerges that leads to excess inflammation, fibrosis, and fatty deposit accumulation in the muscle, portending a steep decline in physical function and contribution to mortality.

DMD is a genetic disorder affecting skeletal muscle and is characterized by progressive muscle degeneration and weakness. There remains a need for treatments that reduce muscle breakdown in patients with neuromuscular conditions such as DMD.

SUMMARY OF THE INVENTION

The present disclosure generally relates to substituted pyridazinone compounds or salts of Formula (I), (Ia), (Ib), (Ic), (Id), (Ie), (II), (II') or (IIa) and pharmaceutical compositions thereof. The substituted pyridazinone compounds or salts of Formula (I), (Ia), (Ib), (Ic), (Id), (Ie), (II), (II') or (IIa) disclosed herein may be used to treat or prevent neuromuscular diseases. In some embodiments, a compound or salt of Formula (I), (Ia), (Ib), (Ic), (Id), (Ie), (II), (II') or (IIa) is an inhibitor of skeletal muscle contraction. In some embodiments, a compound or salt of Formula (I), (Ia), (Ib), (Ic), (Id), (Ie), (II), (II') or (IIa) is an inhibitor of myosin. In some embodiments, a compound or salt of Formula (I), (Ia), (Ib), (Ic), (Id), (Ie), (II), (II') or (IIa) is an inhibitor of skeletal muscle myosin II.

In certain embodiments, the disclosure provides a method of treating activity-induced muscle damage, comprising administering to a subject in need thereof a compound or salt of any one of Formula (I), (Ia), (Ib), (Ic), (Id), (Ie), (II), (II'), (IIa), (III) or (III'). In certain embodiments, the subject in need of treatment has a neuromuscular condition or movement disorder. Examples of neuromuscular conditions include Duchenne Muscular Dystrophy, Becker muscular dystrophy, myotonic dystrophy 1, myotonic dystrophy 2, facioscapulohumeral muscular dystrophy, oculopharyngeal muscular dystrophy, limb girdle muscular dystrophy, tendinitis, and carpal tunnel syndrome. In some embodiments, said movement disorder comprises muscle spasticity. In some embodiments, said muscle spasticity may be selected from spasticity associated with multiple sclerosis, Parkinson's disease, Alzheimer's disease, or cerebral palsy, or injury, or a traumatic event such as stroke, traumatic brain injury, spinal cord injury, hypoxia, meningitis, encephalitis, phenylketonuria, or amyotrophic lateral sclerosis.

The disclosure provides compound and salts thereof for use in treating disease. In certain aspects, the disclosure provides a compound of Formula (I), (Ia), (Ib), (Ic), (Id), (II), (II') or (IIa), pharmaceutical compositions thereof as well as methods of use in the treatment of disease.

In certain aspects, the disclosure provides a compound, represented by the structure of Formula (I):

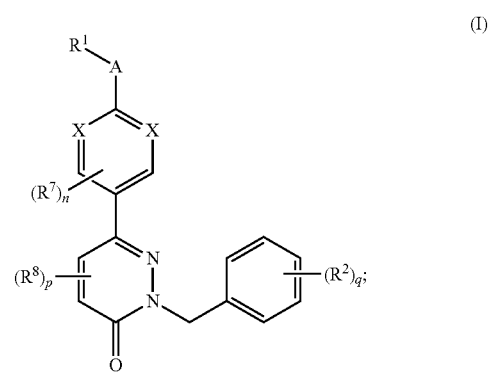

or a salt thereof, wherein:
each X is independently selected from $C(R^3)$, N, and $N^+(-O^-)$ wherein at least one X is N or $N^+(-O^-)$;
A is selected from $-O-$, $-NR^4-$, $-CR^5R^6-$, $-C(O)-$, $-S-$, $-S(O)-$, and $-S(O)_2-$;
$R^1$ is selected from:
$C_{1-6}$ alkyl, $C_{2-6}$ alkenyl, and $C_{2-6}$ alkynyl, each of which is optionally substituted with one or more substituents independently selected from halogen, $-OR^{10}$, $-SR^{10}$, $-N(R^{10})_2$, $-C(O)R^{10}$, $-C(O)N(R^{10})_2$, $-N(R^{10})C(O)R^{10}$, $-N(R^{10})C(O)N(R^{10})_2$, $-OC(O)N(R^{10})_2$, $-N(R^{10})C(O)OR^{10}$, $-C(O)OR^{10}$, $-OC(O)R^{10}$, $-S(O)R^{10}$, $-S(O)_2R^{10}$, $-NO_2$, $=O$, $=S$, $=N(R^{10})$, $-CN$, $C_{3-10}$ carbocycle, and 3- to 10-membered heterocycle, wherein the $C_{3-10}$ carbocycle and 3- to 10-membered heterocycle are each optionally substituted with one or more $R^9$; and
$C_{3-10}$ carbocycle and 3- to 10-membered heterocycle, each of which is optionally substituted with one or more substituents independently selected from halogen, $-OR^{10}$, $-SR^{10}$, $-N(R^{10})_2$, $-C(O)R^{10}$, $-C(O)N(R^{10})_2$, $-N(R^{10})C(O)R^{10}$, $-N(R^{10})C(O)N(R^{10})_2$, $-OC(O)N(R^{10})_2$, $-N(R^{10})C(O)OR^{10}$, $-C(O)OR^{10}$, $-OC(O)R^{10}$, $-S(O)R^{10}$, $-S(O)_2R^{10}$, $-NO_2$, $=O$, $=S$, $=N(R^{10})$, and $-CN$; or
$R^1$ together with $R^3$ form a 5- to 10-membered heterocycle or $C_{5-10}$ carbocycle, wherein the 5- to 10-membered heterocycle or $C_{5-10}$ carbocycle is optionally substituted with one or more $R^9$; or $R^1$ together with $R^5$ form a 3- to 10-membered heterocycle or saturated $C_{3-10}$ carbocycle, wherein the 3- to 10-membered heterocycle or saturated $C_{3-10}$ carbocycle is optionally substituted with one or more $R^9$; or $R^1$ together with $R^4$ form a 3- to 10-membered heterocycle, wherein the 3- to 10-membered heterocycle is optionally substituted with one or more $R^9$; and when A is —NR⁴—, R¹ is additionally selected from hydrogen, and when A is —C(O)—, R¹ is additionally selected from —N(R¹⁰)₂ and —OR¹⁰;

each R² is independently selected from:
halogen, —OR¹⁰, —SR¹⁰, —N(R¹⁰)₂, —C(O)R¹⁰, —C(O)N(R¹⁰)₂, —N(R¹⁰)C(O)R¹⁰, —N(R¹⁰)C(O)N(R¹⁰)₂, —OC(O)N(R¹⁰)₂, —N(R¹⁰)C(O)OR¹⁰, —C(O)OR¹⁰, —OC(O)R¹⁰, —S(O)R¹⁰, —S(O)₂R¹⁰, —NO₂, and —CN;

$C_{1-3}$ alkyl, $C_{2-3}$ alkenyl, and $C_{2-3}$ alkynyl, each of which is optionally substituted with one or more substituents independently selected from halogen, —OR¹⁰, —SR¹⁰, —N(R¹⁰)₂, —C(O)R¹⁰, —C(O)N(R¹⁰)₂, —N(R¹⁰)C(O)R¹⁰, —N(R¹⁰)C(O)N(R¹⁰)₂, —OC(O)N(R¹⁰)₂, —N(R¹⁰)C(O)OR¹⁰, —C(O)OR¹⁰, —OC(O)R¹⁰, —S(O)R¹⁰, —S(O)₂R¹⁰, —NO₂, =O, =S, =N(R¹⁰), and —CN; and $C_{3-10}$ carbocycle optionally substituted with one or more substituents independently selected from: halogen, —OR¹⁰, —SR¹⁰, —N(R¹⁰)₂, —C(O)R¹⁰, —C(O)N(R¹⁰)₂, —N(R¹⁰)C(O)R¹⁰, —N(R¹⁰)C(O)N(R¹⁰)₂, —OC(O)N(R¹⁰)₂, —N(R¹⁰)C(O)OR¹⁰, —C(O)OR¹⁰, —OC(O)R¹⁰, —S(O)R¹⁰, —S(O)₂R¹⁰, —NO₂, =O, =S, =N(R¹⁰), and —CN;

R³, R⁵, and R⁶ are each independently selected from:
hydrogen, halogen, —OR¹⁰, —SR¹⁰, —N(R¹⁰)₂, —NO₂, and —CN; and $C_{1-6}$ alkyl optionally substituted with one or more substituents independently selected from halogen, —OR¹⁰, —SR¹⁰, —N(R¹⁰)₂, —NO₂, and —CN; or R³ together with R¹ form a 5- to 10-membered heterocycle or $C_{5-10}$ carbocycle, wherein the 5- to 10-membered heterocycle or $C_{5-10}$ carbocycle is optionally substituted with one or more R⁹; or R⁵ together with R¹ form a 3- to 10-membered heterocycle or saturated $C_{3-10}$ carbocycle, wherein the 3- to 10-membered heterocycle or saturated $C_{3-10}$ carbocycle is optionally substituted with one or more R⁹.

R⁴ is independently selected from:
hydrogen; and $C_{1-6}$ alkyl optionally substituted with one or more substituents independently selected from halogen, —OR¹⁰, —SR¹⁰, —N(R¹⁰)₂, —NO₂, and —CN; or R⁴ together with R¹ form a 3- to 10-membered heterocycle, which is optionally substituted with one or more R⁹.

R⁷ and R⁸ are independently selected from:
halogen, —OR¹⁰, —SR¹⁰, —N(R¹⁰)₂, —NO₂, —CN, —CHF₂, —CF₃, —CH₂F, and $C_{2-6}$ alkyl optionally substituted with one or more substituents independently selected from halogen, —OR¹⁰, —SR¹⁰, —N(R¹⁰)₂, —NO₂, and —CN;

each R⁹ is independently selected from:
halogen, —OR¹⁰, —SR¹⁰, —N(R¹⁰)₂, —C(O)R¹⁰, —C(O)N(R¹⁰)₂, —N(R¹⁰)C(O)R¹⁰, —N(R¹⁰)C(O)N(R¹⁰)₂, —OC(O)N(R¹⁰)₂, —N(R¹⁰)C(O)OR¹⁰, —C(O)OR¹⁰, —OC(O)R¹⁰, —S(O)R¹⁰, —S(O)₂R¹⁰, —NO₂, =O, =S, =N(R¹⁰), and —CN; and $C_{1-3}$ alkyl, $C_{2-3}$ alkenyl, and $C_{2-3}$ alkynyl, each of which is optionally substituted with one or more substituents independently selected from halogen, —OR¹⁰, —SR¹⁰, —N(R¹⁰)₂, —C(O)R¹⁰, —C(O)N(R¹⁰)₂, —N(R¹⁰)C(O)R¹⁰, —N(R¹⁰)C(O)N(R¹⁰)₂, —OC(O)N(R¹⁰)₂, —N(R¹⁰)C(O)OR¹⁰, —C(O)OR¹⁰, —OC(O)R¹⁰, —S(O)R¹⁰, —S(O)₂R¹⁰, —NO₂, =O, =S, =N(R¹⁰), and —CN;

each R¹⁰ is independently selected from:
hydrogen;

$C_{1-6}$ alkyl, $C_{2-6}$ alkenyl, and $C_{2-6}$ alkynyl, each of which is optionally substituted with one or more substituents independently selected from halogen, —CN, —OH, —SH, —NO₂, —NH₂, =O, =S, —O—$C_{1-6}$ alkyl, —S—$C_{1-6}$ alkyl, —N($C_{1-6}$ alkyl)₂, —NH($C_{1-6}$ alkyl), $C_{3-10}$ carbocycle, and 3- to 10-membered heterocycle; and $C_{3-10}$ carbocycle, and 3- to 10-membered heterocycle, each of which is optionally substituted with one or more substituents independently selected from halogen, —CN, —OH, —SH, —NO₂, —NH₂, =O, =S, —O—$C_{1-6}$ alkyl, —S—$C_{1-6}$ alkyl, —N($C_{1-6}$ alkyl)₂, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and haloalkyl;

n is 0, 1, or 2;
p is 0, 1, or 2; and
q is 1, 2, 3, 4, or 5, and when R¹ is other than —CH₃, q is further selected from 0.

In certain aspects, the disclosure provides a compound represented by the structure of Formula (II):

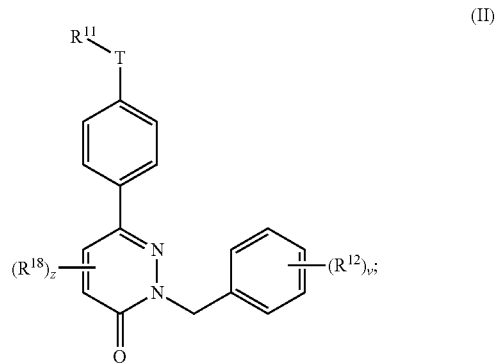

(II)

or a salt thereof, wherein:
T is selected from —O—, —NR¹⁴—, —CR¹⁵R¹⁶—, —C(O)—, —S—, —S(O)—, and —S(O)₂;

R¹¹ is selected from:
$C_{1-6}$ alkyl, $C_{2-6}$ alkenyl, and $C_{2-6}$ alkynyl, each of which is substituted with one or more substituents independently selected from halogen, —OR²⁰, —SR²⁰, —N(R²⁰)₂, —C(O)R²⁰, —C(O)N(R²⁰)₂, —N(R²⁰)C(O)R²⁰, —N(R²⁰)C(O)N(R²⁰)₂, —OC(O)N(R²⁰)₂, —N(R²⁰)C(O)OR²⁰, —C(O)OR²⁰, —OC(O)R²⁰, —S(O)R²⁰, —S(O)₂R²⁰, —NO₂, =O, =S, =N(R²⁰), —CN, $C_{3-5}$ carbocycle, and 3- to 10-membered heterocycle, wherein the $C_{3-10}$ carbocycle and 3- to 10-membered heterocycle are each optionally substituted with one or more R⁹;

and $C_{3-10}$ carbocycle and 3- to 10-membered heterocycle, each of which is optionally substituted with one or more substituents independently selected from halogen, —OR²⁰, —SR²⁰, —N(R²⁰)₂, —C(O)R²⁰, —C(O)N(R²⁰)₂, —N(R²⁰)C(O)R²⁰, —N(R²⁰)C(O)N(R²⁰)₂, —OC(O)N(R²⁰)₂, —N(R²⁰)C(O)OR²⁰, —C(O)OR²⁰, —OC(O)R²⁰, —S(O)R²⁰, —S(O)₂R²⁰, —NO₂, =O, =S, =N(R²⁰), and —CN; or R¹¹ together with R¹⁵ form a 3- to 10-membered heterocycle or $C_{3-10}$ carbocycle, wherein the 3- to 10-membered heterocycle or saturated $C_{3-10}$ carbocycle is optionally substituted with one or more R¹⁹;

or $R^{11}$ together with $R^{14}$ form a 3- to 10-membered heterocycle, wherein the 3- to 10-membered heterocycle is optionally substituted with one or more $R^{19}$;

when T is —$NR^{14}$—, $R^{11}$ is additionally selected from hydrogen, and when T is —C(O)—, $R^{11}$ is additionally selected from —$N(R^{20})_2$ and —$OR^{20}$;

each $R^{12}$ is independently selected from:
  halogen, —$OR^{20}$, —$SR^{20}$, —$N(R^{20})_2$, —$C(O)R^{20}$, —$C(O)N(R^{20})_2$, —$N(R^{20})C(O)N(R^{20})_2$, —$OC(O)N(R^{20})_2$, $C(O)OR^{20}$, —$OC(O)R^{20}$, —$S(O)R^{20}$, —$S(O)_2R^{20}$, —$NO_2$, and —CN;
  $C_{1-3}$ alkyl optionally substituted with one or more substituents independently selected from halogen, —$OR^{20}$, —$SR^{20}$, —$N(R^{20})_2$, —$C(O)R^{20}$, —$C(O)N(R^{20})_2$, —$N(R^{20})C(O)R^{20}$, —$C(O)OR^{20}$, —$N(R^{20})C(O)N(R^{20})_2$, —$OC(O)N(R^{20})_2$, —$N(R^{20})C(O)OR^{20}$, —$OC(O)R^{20}$, —$S(O)R^{20}$, —$S(O)_2R^{20}$, —$NO_2$, =O, =S, =$N(R^{20})$, and —CN; and
  $C_{3-10}$ carbocycle optionally substituted with one or more substituents independently selected from halogen, —$OR^{20}$, —$SR^{20}$, —$N(R^{20})_2$, —$C(O)R^{20}$, —$C(O)N(R^{20})_2$, —$N(R^{20})C(O)R^{20}$, —$N(R^{20})C(O)N(R^{20})_2$, —$OC(O)N(R^{20})_2$, —$N(R^{20})C(O)OR^{20}$, —$C(O)OR^{20}$, —$OC(O)R^{20}$, —$S(O)R^{20}$, —$S(O)_2R^{20}$, —$NO_2$, =O, =S, =$N(R^{20})$, and —CN;

$R^{14}$ is independently selected from:
  hydrogen; and
  $C_{1-6}$ alkyl optionally substituted with one or more substituents independently selected from halogen, —$OR^{20}$, —$SR^{20}$, —$N(R^{20})_2$, —$NO_2$, and —CN; or
  $R^{14}$ together with $R^{11}$ form a 3- to 5-membered heterocycle, which is optionally substituted with one or more $R^{19}$;

$R^{15}$ together with $R^{11}$ form a saturated $C_{3-10}$ carbocycle or 3- to 10-membered heterocycle, which is optionally substituted with one or more $R^{19}$.

$R^{16}$ is independently selected from:
  hydrogen, halogen, —$OR^{20}$, —$SR^{20}$, —$N(R^{20})_2$, —$NO_2$, —CN, and $C_{1-6}$ alkyl optionally substituted with one or more substituents independently selected from halogen, —$OR^{20}$, —$SR^{20}$, —$N(R^{20})_2$, —$NO_2$, and —CN;

$R^{18}$ is independently selected from:
  halogen, —$SR^{20}$, —$N(R^{20})_2$, —$NO_2$, and $C_{2-6}$ alkyl optionally substituted with one or more substituents independently selected from halogen, —$OR^{20}$, —$SR^{20}$, —$N(R^{20})_2$, —$NO_2$, and —CN $R^{19}$ is independently selected from:
  halogen, —$OR^{20}$, —$SR^{20}$, —$N(R^{20})_2$, —$C(O)R^{20}$, —$C(O)N(R^{20})_2$, —$N(R^{20})C(O)R^{20}$, —$N(R^{20})C(O)N(R^{20})_2$, —$OC(O)N(R^{20})_2$, —$N(R^{20})C(O)OR^{20}$, —$C(O)OR^{20}$, —$OC(O)R^{20}$, —$S(O)R^{20}$, —$S(O)_2R^{20}$, —$NO_2$, =O, =S, =$N(R^{10})$, and —CN; and
  $C_{1-3}$ alkyl, $C_{2-3}$ alkenyl, and $C_{2-3}$ alkynyl, each of which is optionally substituted with one or more substituents independently selected from halogen, —$OR^{20}$, —$SR^{20}$, —$N(R^{20})_2$, —$C(O)R^{20}$, —$C(O)N(R^{20})_2$, —$N(R^{20})C(O)R^{20}$, —$N(R^{20})C(O)N(R^{20})_2$, —$OC(O)N(R^{20})_2$, —$N(R^{20})C(O)OR^{20}$, —$C(O)OR^{20}$, —$OC(O)R^{20}$, —$S(O)R^{20}$, —$S(O)_2R^{20}$, —$NO_2$, =O, =S, =$N(R^{20})$, and —CN;

each $R^{20}$ is independently selected from:
  hydrogen;
  $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —$N(C_{1-6}$ alkyl$)_2$, —NH($C_{1-6}$ alkyl), $C_{3-10}$ carbocycle, and 3- to 10-membered heterocycle; and
  $C_{3-10}$ carbocycle, and 3- to 10-membered heterocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —$N(C_{1-6}$ alkyl$)_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and haloalkyl;

z is 0, 1, or 2; and
v is 1, 2, 3, 4, or 5.

In certain aspects, the disclosure provides a method of treating activity-induced muscle damage, comprising administering to a subject in need thereof a compound or salt of Formula (III):

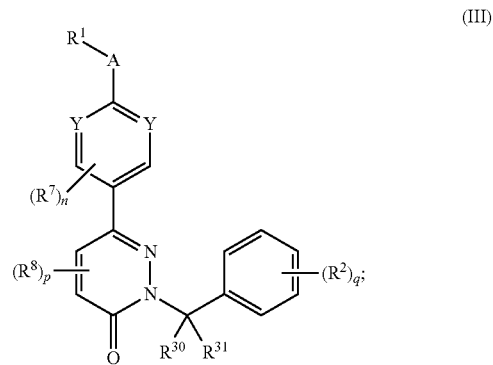

(III)

or a salt thereof, wherein:
  each Y is independently selected from $C(R^3)$, N, and $N^+(-O^-)$;
  A is absent or selected from —O—, —$NR^4$—, —$CR^5R^6$—, —C(O)—, —S—, —S(O)—, and —$S(O)_2$—;
  $R^1$ is selected from:
    $C_{1-6}$ alkyl, $C_{2-6}$ alkenyl, and $C_{2-6}$ alkynyl, each of which is optionally substituted with one or more substituents independently selected from halogen, —$OR^{10}$, —$SR^{10}$, —$N(R^{10})_2$, —$C(O)R^{10}$, —$C(O)N(R^{10})_2$, —$N(R^{10})C(O)R^{10}$, —$N(R^{10})C(O)N(R^{10})_2$, —$OC(O)N(R^{10})_2$, —$N(R^{10})C(O)OR^{10}$, —$C(O)OR^{10}$, —$OC(O)R^{10}$, —$S(O)R^{10}$, —$S(O)_2R^{10}$, —$NO_2$, =O, =S, =$N(R^{10})$, —CN, $C_{3-10}$ carbocycle, and 3- to 10-membered heterocycle, wherein the $C_{3-10}$ carbocycle and 3- to 10-membered heterocycle are each optionally substituted with one or more $R^9$; and
    $C_{3-10}$ carbocycle and 3- to 10-membered heterocycle, each of which is optionally substituted with one or more substituents independently selected from halogen, —$OR^{10}$, —$SR^{10}$, —$N(R^{10})_2$, —$C(O)R^{10}$, —$C(O)N(R^{10})_2$, —$N(R^{10})C(O)R^{10}$, —$N(R^{10})C(O)N(R^{10})_2$, —$OC(O)N(R^{10})_2$, —$N(R^{10})C(O)OR^{10}$, —$C(O)OR^{10}$, —$OC(O)R^{10}$, —$S(O)R^{10}$, —$S(O)_2R^{10}$, —$NO_2$, =O, =S, =$N(R^{10})$, and —CN; or
    $R^1$ together with $R^3$ form a 5- to 10-membered heterocycle or $C_{5-10}$ carbocycle, wherein the 5- to 10-membered heterocycle or $C_{5-10}$ carbocycle is optionally substituted with one or more $R^9$; or $R^1$ together with $R^5$ form a 3- to 10-membered heterocycle or saturated $C_{3-10}$ carbocycle, wherein the 3- to 10-membered heterocycle or saturated $C_{3-10}$ carbocycle is optionally substituted with one or more $R^9$; or $R^1$ together with $R^4$ form a 3- to 10-membered heterocycle, wherein the 3- to 10-membered heterocycle is optionally substituted with one or more $R^9$; and when A is —$NR^4$—, $R^1$ is additionally selected from hydrogen, and when A is —C(O)—, $R^1$ is additionally selected from —$N(R^{10})_2$ and —$OR^{10}$;

when A is absent, $R^1$ is further selected from halogen, —$OR^{10}$, —$SR^{10}$, —$N(R^{10})_2$, —$C(O)R^{10}$, —$C(O)N(R^{10})_2$, —$N(R^{10})C(O)R^{10}$, —$N(R^{10})C(O)N(R^{10})_2$, —$OC(O)N(R^{10})_2$, —$N(R^{10})C(O)OR^{10}$, —$C(O)OR^{10}$, —$OC(O)R^{10}$, —$S(O)R^{10}$, —$S(O)_2R^{10}$, —$NO_2$, and —CN;

each $R^2$ is independently selected from:
  halogen, —$OR^{10}$, —$SR^{10}$, —$N(R^{10})_2$, —$C(O)R^{10}$, —$C(O)N(R^{10})_2$, —$N(R^{10})C(O)R^{10}$, —$N(R^{10})C(O)N(R^{10})_2$, —$OC(O)N(R^{10})_2$, —$N(R^{10})C(O)OR^{10}$, —$C(O)OR^{10}$, —$OC(O)R^{10}$, —$S(O)R^{10}$, —$S(O)_2R^{10}$, —$NO_2$, and —CN;
  $C_{1-3}$ alkyl, $C_{2-3}$ alkenyl, and $C_{2-3}$ alkynyl, each of which is optionally substituted with one or more substituents independently selected from halogen, —$OR^{10}$, —$SR^{10}$, —$N(R^{10})_2$, —$C(O)R^{10}$, —$C(O)N(R^{10})_2$, —$N(R^{10})C(O)R^{10}$, —$N(R^{10})C(O)N(R^{10})_2$, —$OC(O)N(R^{10})_2$, —$N(R^{10})C(O)OR^{10}$, —$C(O)OR^{10}$, —$OC(O)R^{10}$, —$S(O)R^{10}$, —$S(O)_2R^{10}$, —$NO_2$, =O, =S, =$N(R^{10})$, and —CN; and
  $C_{3-10}$ carbocycle optionally substituted with one or more substituents independently selected from: halogen, —$OR^{10}$, —$SR^{10}$, —$N(R^{10})_2$, —$C(O)R^{10}$, —$C(O)N(R^{10})_2$, —$N(R^{10})C(O)R^{10}$, —$N(R^{10})C(O)N(R^{10})_2$, —$OC(O)N(R^{10})_2$, —$N(R^{10})C(O)OR^{10}$, —$C(O)OR^{10}$, —$OC(O)R^{10}$, —$S(O)R^{10}$, —$S(O)_2R^{10}$, —$NO_2$, =O, =S, =$N(R^{10})$, and —CN each $R^3$, $R^5$, and $R^6$ is independently selected from:
  hydrogen, halogen, —$OR^{10}$, —$SR^{10}$, —$N(R^{10})_2$, —$NO_2$, and —CN; and
  $C_{1-6}$ alkyl optionally substituted with one or more substituents independently selected from halogen, —$OR^{10}$, —$SR^{10}$, —$N(R^{10})_2$, —$NO_2$, and —CN; or
  $R^3$ together with $R^1$ form a 5- to 10-membered heterocycle or $C_{5-10}$ carbocycle, wherein the 5- to 10-membered heterocycle or $C_{5-10}$ carbocycle is optionally substituted with one or more $R^9$; or $R^5$ together with $R^1$ form a 3- to 10-membered heterocycle or saturated $C_{3-10}$ carbocycle, wherein the 3- to 10-membered heterocycle or saturated $C_{3-10}$ carbocycle is optionally substituted with one or more $R^9$;

$R^4$ is independently selected from:
  hydrogen; and
  $C_{1-6}$ alkyl optionally substituted with one or more substituents independently selected from halogen, —$OR^{10}$, —$SR^{10}$, —$N(R^{10})_2$, —$NO_2$, and —CN; or
  $R^4$ together with $R^1$ form a 3- to 10-membered heterocycle, which is optionally substituted with one or more $R^9$;

each $R^7$ and $R^8$ is independently selected from:
  halogen, —$OR^{10}$, —$SR^{10}$, —$N(R^{10})_2$, —$NO_2$, —CN, —$CHF_2$, —$CF_3$, —$CH_2F$, and $C_{2-6}$ alkyl optionally substituted with one or more substituents independently selected from halogen, —$OR^{10}$, —$SR^{10}$, —$N(R^{10})_2$, —$NO_2$, and —CN;

each $R^9$ is independently selected from:
  halogen, —$OR^{10}$, —$SR^{10}$, —$N(R^{10})_2$, —$C(O)R^{10}$, —$C(O)N(R^{10})_2$, —$N(R^{10})C(O)R^{10}$, —$N(R^{10})C(O)N(R^{10})_2$, —$OC(O)N(R^{10})_2$, —$N(R^{10})C(O)OR^{10}$, —$C(O)OR^{10}$, —$OC(O)R^{10}$, —$S(O)R^{10}$, —$S(O)_2R^{10}$, —$NO_2$, =O, =S, =$N(R^{10})$, and —CN; and
  $C_{1-3}$ alkyl, $C_{2-3}$ alkenyl, and $C_{2-3}$ alkynyl, each of which is optionally substituted with one or more substituents independently selected from halogen, —$OR^{10}$, —$SR^{10}$, —$N(R^{10})_2$, —$C(O)R^{10}$, —$C(O)N(R^{10})_2$, —$N(R^{10})C(O)R^{10}$, —$N(R^{10})C(O)N(R^{10})_2$, —$OC(O)N(R^{10})_2$, —$N(R^{10})C(O)OR^{10}$, —$C(O)OR^{10}$, —$OC(O)R^{10}$, —$S(O)R^{10}$, —$S(O)_2R^{10}$, —$NO_2$, =O, =S, =$N(R^{10})$, and —CN;

each $R^{10}$ is independently selected from:
  hydrogen;
  $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, and 3- to 10-membered heterocycle; and
  $C_{3-10}$ carbocycle, and 3- to 10-membered heterocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl;

$R^{30}$ and $R^{31}$ are independently selected from $R^{10}$ or $R^{30}$ and $R^{31}$ come together to form a $C_{3-7}$ carbocycle, or 3- to 7-membered heterocycle, wherein $C_{3-7}$ carbocycle and 3- to 7-membered heterocycle are optionally substituted with one or more substituents independently selected from $R^9$;

n is 0, 1, or 2;
p is 0, 1, or 2; and
q is 0, 1, 2, 3, 4, or 5.

In certain aspects, the disclosure provides a method of treating a neuromuscular condition or treating activity-induced muscle damage or of inhibiting muscle myosin II, comprising administering to a subject in need thereof a compound or salt of any one of Formula (I), (Ia), (Ib), (Ic), (Id), (Ie), (II), (II') or (IIa).

In certain aspects, the disclosure provides a method of treating a movement disorder, comprising administering to a subject in need thereof a compound or salt of any one of Formula (I), (Ia), (Ib), (Ic), (Id), (Ie), (II), (II') or (IIa).

In certain aspects, the disclosure provides a pharmaceutical composition comprising a compound or salt of any one of Formula (I), (Ia), (Ib), (Ic), (Id), (Ie), (II), (II') or (IIa) and a pharmaceutically acceptable excipient.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

DETAILED DESCRIPTION OF THE INVENTION

Figure 1:
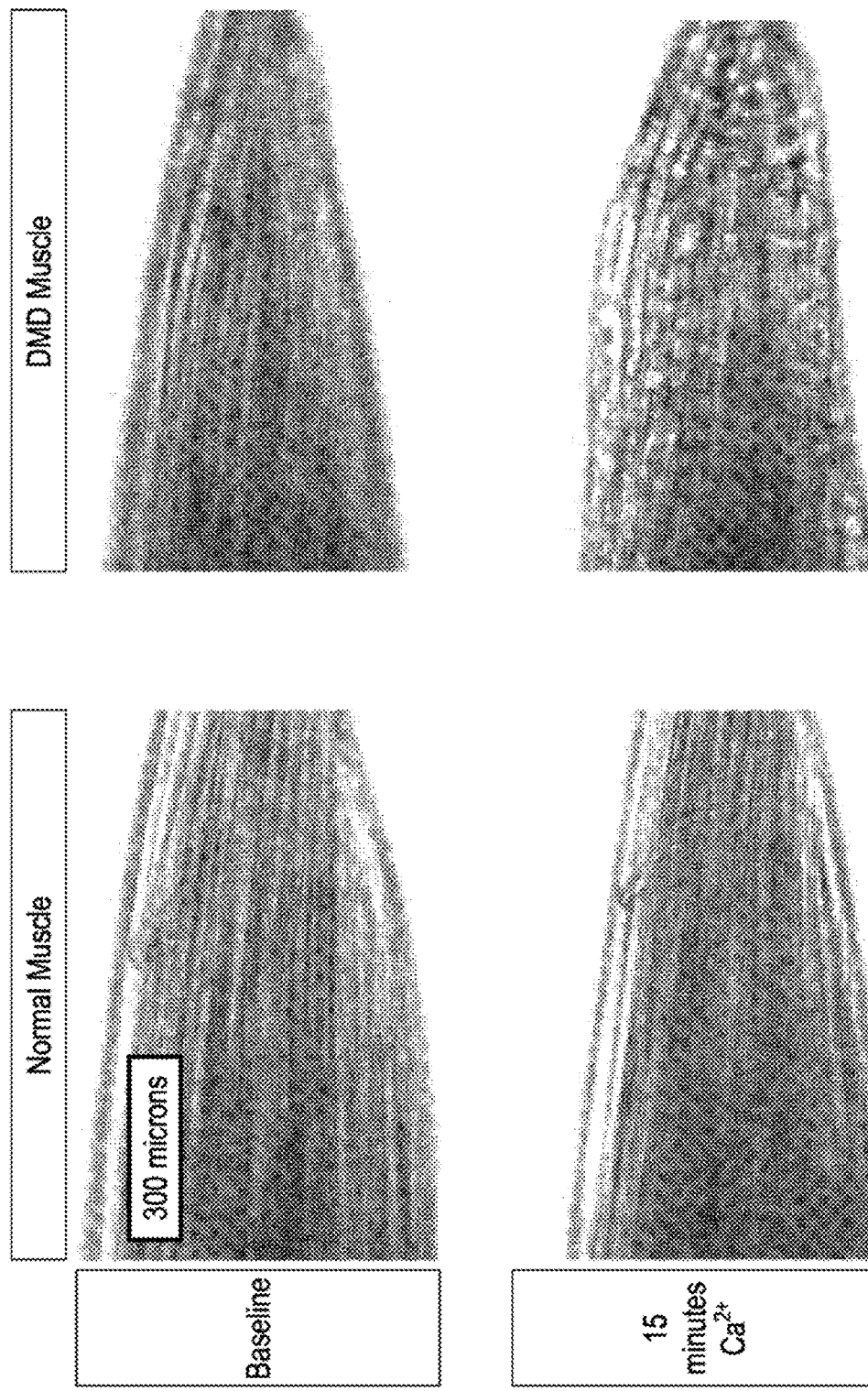
FIG. 1 depicts excessive contraction-induced injuries, which precede the inflammation and irreversible fibrosis that characterizes late-stage DMD pathology.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

In certain aspects, the disclosure provides methods for treating neuromuscular conditions through selective inhibition of fast-fiber skeletal muscle myosin. In particular, methods of the disclosure may be used in the treatment of DMD and other neuromuscular conditions.

Skeletal muscle is mainly composed of two types of fibers, slow-twitch muscle fiber (i.e., type I) and fast-twitch muscle fiber (i.e., type II). In each muscle, the two types of fibers are configured in a mosaic-like arrangement, with differences in fiber type composition in different muscles and at different points in growth and development. Slow-twitch muscle fibers have excellent aerobic energy production ability. Contraction rate of the slow-twitch muscle fiber is low but tolerance to fatigue is high. Slow-twitch muscle fibers typically have a higher concentration of mitochondria and myoglobin than do fast-twitch fibers and are surrounded by more capillaries than are fast-twitch fibers. Slow-twitch fibers contract at a slower rate due to lower myosin ATPase activity and produce less power compared to fast-twitch fibers, but they are able to maintain contractile function over longer-terms, such as in stabilization, postural control, and endurance exercises.

Fast twitch muscle fibers in humans are further divided into two main fiber types depending on the specific fast skeletal myosin they express (Type IIa, IIx/d). A third type of fast fiber (Type IIb) exists in other mammals but is rarely identified in human muscle. Fast-twitch muscle fibers have excellent anaerobic energy production ability and are able to generate high amounts of tension over a short period of time. Typically, fast-twitch muscle fibers have lower concentrations of mitochondria, myoglobin, and capillaries compared to slow-twitch fibers, and thus can fatigue more quickly. Fast-twitch muscles produce quicker force required for power and resistance activities.

The proportion of the type I and type II can vary in different individuals. For example, non-athletic individuals can have close to 50% of each muscle fiber types. Power athletes can have a higher ratio of fast-twitch fibers, e.g., 70-75% type II in sprinters. Endurance athletes can have a higher ratio of slow-twitch fibers, e.g., 70-80% in distance runners. The proportion of the type I and type II fibers can also vary depending on the age of an individual. The proportion of type II fibers, especially the type IIx, can decline as an individual ages, resulting in a loss in lean muscle mass.

Figure 2:
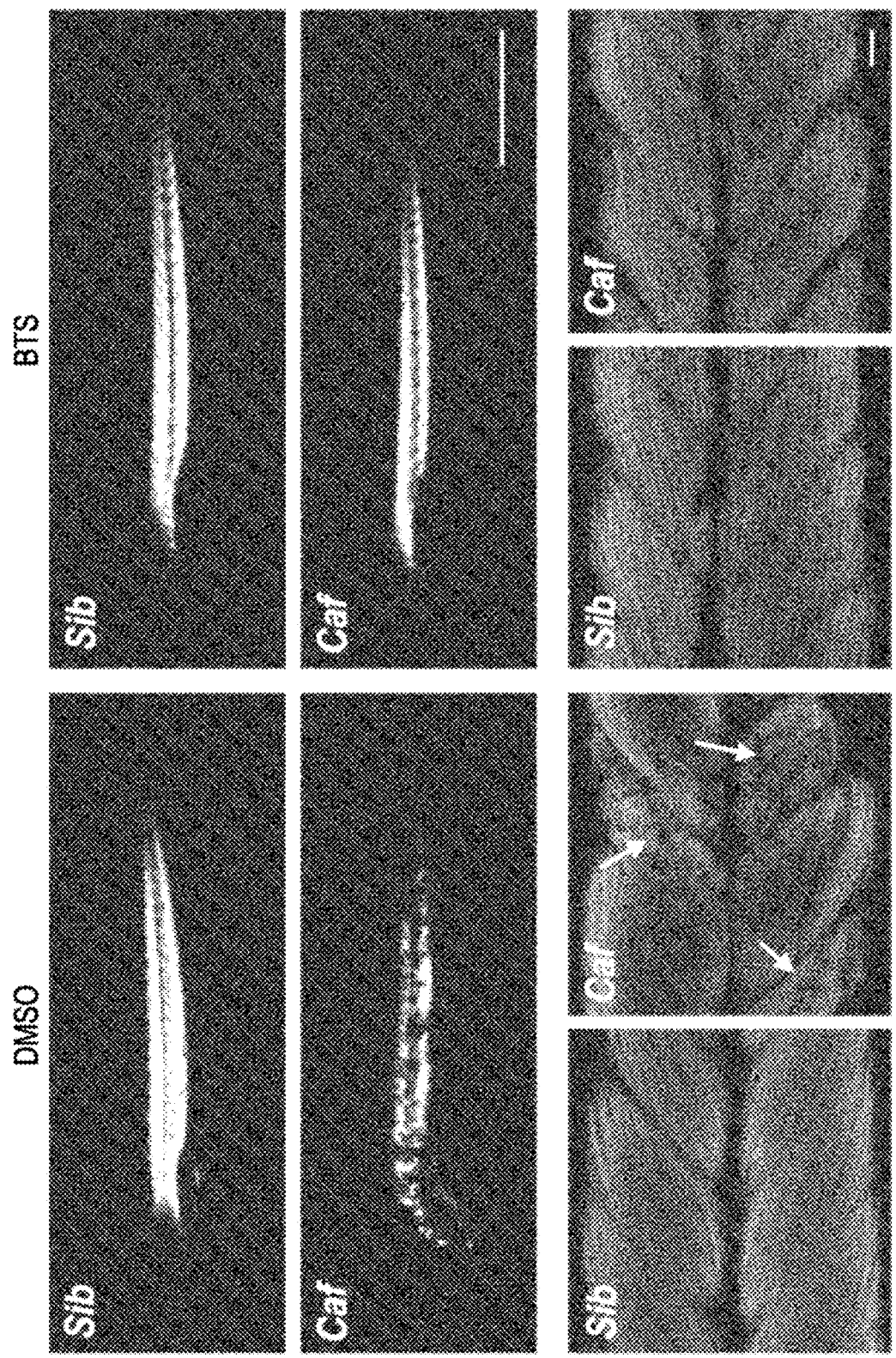
FIG. 2 N-benzyl-p-tolyl-sulfonamide (BTS), an inhibitor of fast-fiber skeletal muscle myosin, has been shown to protect muscles from pathological muscle derangement in embryos from zebrafish model of DMD.

The contractile action of skeletal muscle leads to muscle damage in subjects with neuromuscular disease, e.g., DMD, and this damage appears to be more prevalent in fast fibers. It has been observed that acute force drop after lengthening injury is greater in predominantly fast type II fiber muscles compared to predominantly slow type I fiber muscles in dystrophy mouse models. It has also been demonstrated that the degree of acute force drop and histological damage in dystrophy mouse models is proportional to peak force development during lengthening injury. Excessive contraction-induced injuries, which precede the inflammation and irreversible fibrosis that characterizes late-stage DMD pathology are shown in FIG. 1 [Figure adapted: Claflin and Brooks, Am J Brooks, Physiol Cell, 2008,]. Contraction-induced muscle damage in these patients may be reduced by limiting peak force generation in type II fibers and possibly increasing reliance on healthier type I fibers. N-benzyl-p-tolyl-sulfonamide (BTS), an inhibitor of fast-fiber skeletal muscle myosin, has been shown to protect muscles from pathological muscle derangement in embryos from zebrafish model of DMD as shown in FIG. 2. [Source: Li and Arner, PLoSONE, 2015].

Inhibitors of skeletal muscle myosin that are not selective for the type II fibers may lead to unwanted inhibition of skeletal muscle contraction including respiratory function and unwanted inhibition of cardiac activity as the heart shares several structural components (such as type I myosin) with type I skeletal muscle fibers. While not wishing to be bound by a particular mechanistic theory, this disclosure provides selective inhibitors of fast-fiber skeletal muscle myosin as a treatment option for DMD and other neuromuscular conditions. The targeted inhibition of type II skeletal muscle myosin may reduce skeletal muscle contractions while minimizing the impact on a subject's daily activities.

Definitions

Unless defined otherwise, all technical and scientific terms used herein have the same meaning as is commonly understood by one of skill in the art to which this invention belongs.

As used in the specification and claims, the singular form "a", "an" and "the" includes plural references unless the context clearly dictates otherwise.

The term "$C_{x-y}$" or "$C_x$-$C_y$" when used in conjunction with a chemical moiety, such as alkyl, alkenyl, or alkynyl is meant to include groups that contain from x to y carbons in the chain. For example, the term "$C_{1-6}$alkyl" refers to substituted or unsubstituted saturated hydrocarbon groups, including straight-chain alkyl and branched-chain alkyl groups that contain from 1 to 6 carbons.

The terms "$C_{x-y}$alkenyl" and "$C_{x-y}$alkynyl" refer to substituted or unsubstituted unsaturated aliphatic groups analogous in length and possible substitution to the alkyls described above, but that contain at least one double or triple bond, respectively.

The term "carbocycle" as used herein refers to a saturated, unsaturated or aromatic ring in which each atom of the ring is carbon. Carbocycle includes 3- to 10-membered monocyclic rings, 5- to 12-membered bicyclic rings, 5- to 12-membered spiro bicycles, and 5- to 12-membered bridged rings. Each ring of a bicyclic carbocycle may be selected from saturated, unsaturated, and aromatic rings. In an exemplary embodiment, an aromatic ring, e.g., phenyl, may be fused to a saturated or unsaturated ring, e.g., cyclohexane, cyclopentane, or cyclohexene. A bicyclic carbocycle includes any combination of saturated, unsaturated and aromatic bicyclic rings, as valence permits. A bicyclic carbocycle further includes spiro bicyclic rings such as spiropentane. A bicyclic carbocycle includes any combination of ring sizes such as 3-3 spiro ring systems, 4-4 spiro ring systems, 4-5 fused ring systems, 5-5 fused ring systems, 5-6 fused ring systems, 6-6 fused ring systems, 5-7 fused ring systems, 6-7 fused ring systems, 5-8 fused ring systems, and 6-8 fused ring systems. Exemplary carbocycles include cyclopentyl, cyclohexyl, cyclohexenyl, adamantyl, phenyl, indanyl, naphthyl, and bicyclo[1.1.1]pentanyl.

The term "aryl" refers to an aromatic monocyclic or aromatic multicyclic hydrocarbon ring system. The aromatic monocyclic or aromatic multicyclic hydrocarbon ring system contains only hydrogen and carbon and from five to eighteen carbon atoms, where at least one of the rings in the ring system is aromatic, i.e., it contains a cyclic, delocalized (4n+2) π-electron system in accordance with the Hückel theory. The ring system from which aryl groups are derived include, but are not limited to, groups such as benzene, fluorene, indane, indene, tetralin and naphthalene.

The term "cycloalkyl" refers to a saturated ring in which each atom of the ring is carbon. Cycloalkyl may include monocyclic and polycyclic rings such as 3- to 10-membered monocyclic rings, 5- to 12-membered bicyclic rings, 5- to 12-membered spiro bicycles, and 5- to 12-membered bridged rings. In certain embodiments, a cycloalkyl comprises three to ten carbon atoms. In other embodiments, a cycloalkyl comprises five to seven carbon atoms. The cycloalkyl may be attached to the rest of the molecule by a single bond. Examples of monocyclic cycloalkyls include, e.g., cyclopropyl, cyclobutyl, cyclopentyl, cyclohexyl, cycloheptyl, and cyclooctyl. Polycyclic cycloalkyl radicals include, for example, adamantyl, spiropentane, norbornyl (i.e., bicyclo[2.2.1]heptanyl), decalinyl, 7.7 dimethyl bicyclo[2.2.1]heptanyl, bicyclo[1.1.1]pentanyl, and the like.

The term "cycloalkenyl" refers to a saturated ring in which each atom of the ring is carbon and there is at least one double bond between two ring carbons. Cycloalkenyl may include monocyclic and polycyclic rings such as 3- to 10-membered monocyclic rings, 6- to 12-membered bicyclic rings, and 5- to 12-membered bridged rings. In other embodiments, a cycloalkenyl comprises five to seven carbon atoms. The cycloalkenyl may be attached to the rest of the molecule by a single bond. Examples of monocyclic cycloalkenyls include, e.g., cyclopentenyl, cyclohexenyl, cycloheptenyl, and cyclooctenyl.

The term "halo" or, alternatively, "halogen" or "halide," means fluoro, chloro, bromo or iodo. In some embodiments, halo is fluoro, chloro, or bromo.

The term "haloalkyl" refers to an alkyl radical, as defined above, that is substituted by one or more halo radicals, for example, trifluoromethyl, dichloromethyl, bromomethyl, 2,2,2-trifluoroethyl, 1-chloromethyl-2-fluoroethyl, and the like. In some embodiments, the alkyl part of the haloalkyl radical is optionally further substituted as described herein.

The term "heterocycle" as used herein refers to a saturated, unsaturated or aromatic ring comprising one or more heteroatoms. Exemplary heteroatoms include N, O, Si, P, B, and S atoms. Heterocycles include 3- to 10-membered monocyclic rings, 6- to 12-membered bicyclic rings, 5- to 12-membered spiro cycles, and 5- to 12-membered bridged rings. A bicyclic heterocycle includes any combination of saturated, unsaturated and aromatic bicyclic rings, as valence permits. In an exemplary embodiment, an aromatic ring, e.g., pyridyl, may be fused to a saturated or unsaturated ring, e.g., cyclohexane, cyclopentane, morpholine, piperidine or cyclohexene. A bicyclic heterocycle includes any combination of ring sizes such as 4-5 fused ring systems, 5-5 fused ring systems, 5-6 fused ring systems, 6-6 fused ring systems, 5-7 fused ring systems, 6-7 fused ring systems, 5-8 fused ring systems, and 6-8 fused ring systems. A bicyclic heterocycle further includes spiro bicyclic rings, e.g., 5 to 12-membered spiro rings such as 2-oxa-6-azaspiro[3.3]heptane.

The term "heteroaryl" refers to a radical derived from a 5 to 18 membered aromatic ring radical that comprises two to seventeen carbon atoms and from one to six heteroatoms selected from nitrogen, oxygen and sulfur. As used herein, the heteroaryl radical is a monocyclic, bicyclic, tricyclic or tetracyclic ring system, wherein at least one of the rings in the ring system is aromatic, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzoxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pyridinyl, and thiophenyl (i.e. thienyl).

The term "heterocycloalkyl" refers to a saturated ring with carbon atoms and at least one heteroatom. Exemplary heteroatoms include N, O, Si, P, B, and S atoms. Heterocycloalkyl may include monocyclic and polycyclic rings such as 3- to 10-membered monocyclic rings, 6- to 12-membered bicyclic rings, 5- to 12-membered spiro bicycles, and 5- to 12-membered bridged rings. The heteroatoms in the heterocycloalkyl radical are optionally oxidized. One or more nitrogen atoms, if present, are optionally quaternized. The heterocycloalkyl is attached to the rest of the molecule through any atom of the heterocycloalkyl, valence permitting, such as any carbon or nitrogen atoms of the heterocycloalkyl. Examples of heterocycloalkyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 2-oxa-6-azaspiro[3.3]heptane, and 1,1-dioxo-thiomorpholinyl.

The term "heterocycloalkenyl" refers to an unsaturated ring with carbon atoms and at least one heteroatom and there is at least one double bond between two ring carbons. Heterocycloalkenyl does not include heteroaryl rings. Exemplary heteroatoms include N, O, Si, P, B, and S atoms. Heterocycloalkenyl may include monocyclic and polycyclic rings such as 3- to 10-membered monocyclic rings, 6- to 12-membered bicyclic rings, and 5- to 12-membered bridged rings. In other embodiments, a heterocycloalkenyl comprises five to seven ring atoms. The heterocycloalkenyl may be attached to the rest of the molecule by a single bond. Examples of monocyclic cycloalkenyls include, e.g., pyrroline (dihydropyrrole), pyrazoline (dihydropyrazole), imidazoline (dihydroimidazole), triazoline (dihydrotriazole), dihydrofuran, dihydrothiophene, oxazoline (dihydrooxazole), isoxazoline (dihydroisoxazole), thiazoline (dihydrothiazole), isothiazoline (dihydroisothiazole), oxadiazoline (dihydrooxadiazole), thiadiazoline (dihydrothiadiazole), dihydropyridine, tetrahydropyridine, dihydropyridazine, tetrahydropyridazine, dihydropyrimidine, tetrahydropyrimidine, dihydropyrazine, tetrahydropyrazine, pyran, dihydropyran, thiopyran, dihydrothiopyran, dioxine, dihydrodioxine, oxazine, dihydrooxazine, thiazine, and dihydrothiazine.

The term "substituted" refers to moieties having substituents replacing a hydrogen on one or more carbons or substitutable heteroatoms, e.g., an NH or NH$_2$ of a compound. It will be understood that "substitution" or "substituted with" includes the implicit proviso that such substitution is in accordance with permitted valence of the substituted atom and the substituent, and that the substitution results in a stable compound, i.e., a compound which does not spontaneously undergo transformation such as by rearrangement, cyclization, elimination, etc. In certain embodiments, substituted refers to moieties having substituents replacing two hydrogen atoms on the same carbon atom, such as substituting the two hydrogen atoms on a single carbon with an oxo, imino or thioxo group. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds.

In some embodiments, substituents may include any substituents described herein, for example: halogen, hydroxy, oxo (=O), thioxo (=S), cyano (—CN), nitro (—NO$_2$), imino (=N—H), oximo (=N—OH), hydrazino (=N—NH$_2$), —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2), and —R$^b$—S(O)$_t$N(R$^a$)$_2$ (where t is 1 or 2); and alkyl, alkenyl, alkynyl, aryl, aralkyl, aralkenyl, aralkynyl, cycloalkyl, cycloalkylalkyl, heterocycloalkyl, heterocycloalkylalkyl, heteroaryl, and heteroarylalkyl, any of which may be optionally substituted by alkyl, alkenyl, alkynyl, halogen, haloalkyl, haloalkenyl, haloalkynyl, oxo (=O), thioxo (=S), cyano (—CN), nitro (—NO$_2$), imino (=N—H), oximo (=N—OH), hydrazine (=N—NH$_2$), —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2) and —R$^b$—S(O)$_t$N(R$^a$)$_2$ (where t is 1 or 2); wherein each R$^a$ is independently selected from hydrogen, alkyl, cycloalkyl, cycloalkylalkyl, aryl, aralkyl, heterocycloalkyl, heterocycloalkylalkyl, heteroaryl, or heteroarylalkyl, wherein each R$^a$, valence permitting, may be optionally substituted with alkyl, alkenyl, alkynyl, halogen, haloalkyl, haloalkenyl, haloalkynyl, oxo (=O), thioxo (=S), cyano (—CN), nitro (—NO$_2$), imino (=N—H), oximo (=N—OH), hydrazine (=N—NH$_2$), —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2) and —R$^b$—S(O)$_t$N(R$^a$)$_2$ (where t is 1 or 2); and wherein each R$^b$ is independently selected from a direct bond or a straight or branched alkylene, alkenylene, or alkynylene chain, and each R$^c$ is a straight or branched alkylene, alkenylene or alkynylene chain.

Double bonds to oxygen atoms, such as oxo groups, are represented herein as both "=O" and "(O)". Double bonds to nitrogen atoms are represented as both "=NR" and "(NR)". Double bonds to sulfur atoms are represented as both "=S" and "(S)".

The phrases "parenteral administration" and "administered parenterally" as used herein means modes of administration other than enteral and topical administration, usually by injection, and includes, without limitation, intravenous, intramuscular, intra-arterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable excipient" or "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "salt" or "pharmaceutically acceptable salt" refers to salts derived from a variety of organic and inorganic counter ions well known in the art. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts.

As used herein, "treatment" or "treating" refers to an approach for obtaining beneficial or desired results with respect to a disease, disorder, or medical condition including but not limited to a therapeutic benefit and/or a prophylactic benefit. A therapeutic benefit can include, for example, the eradication or amelioration of the underlying disorder being treated. Also, a therapeutic benefit can include, for example, the eradication or amelioration of one or more of the physiological symptoms associated with the underlying disorder such that an improvement is observed in the subject, notwithstanding that the subject may still be afflicted with the underlying disorder. In certain embodiments, for prophylactic benefit, the compositions are administered to a subject at risk of developing a particular disease, or to a subject reporting one or more of the physiological symptoms of a disease, even though a diagnosis of this disease may not have been made. Treatment via administration of a compound described herein does not require the involvement of a medical professional.

Compounds

The following is a discussion of compounds and salts thereof that may be used in the methods of the disclosure. The compounds and salts are described in Formulas (I), (Ia), (Ib), (Ic), (Id), (Ie), (II), (IIa), and (III).

In certain aspects, disclosed herein is a compound or a pharmaceutically acceptable salt thereof, represented by Formula (I):

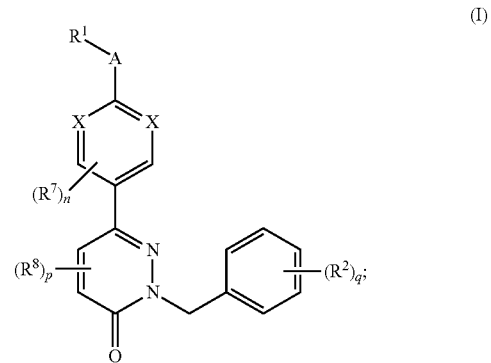

(I)

or a salt thereof, wherein:

each X is independently selected from $C(R^3)$, N, and $N^+(\text{—O}^-)$ wherein at least one X is N or $N^+(\text{—O}^-)$;

A is selected from —O—, —$NR^4$—, —$CR^5R^6$—, —C(O)—, —S—, —S(O)—, and —$S(O)_2$—;

$R^1$ is selected from:

$C_{1-6}$ alkyl, $C_{2-6}$ alkenyl, and $C_{2-6}$ alkynyl, each of which is optionally substituted with one or more substituents independently selected from halogen, —$OR^{10}$, —$SR^{10}$, —$N(R^{10})_2$, —$C(O)R^{10}$, —$C(O)N(R^{10})_2$, —$N(R^{10})C(O)R^{10}$, —$N(R^{10})C(O)N(R^{10})_2$, —$OC(O)N(R^{10})_2$, —$N(R^{10})C(O)OR^{10}$, —$C(O)OR^{10}$, —$OC(O)R^{10}$, —$S(O)R^{10}$, —$S(O)_2R^{10}$, —$NO_2$, =O, =S, =$N(R^{10})$, —CN, $C_{3-10}$ carbocycle, and 3- to 10-membered heterocycle, wherein the $C_{3-10}$ carbocycle and 3- to 10-membered heterocycle are each optionally substituted with one or more $R^9$; and $C_{3-10}$ carbocycle and 3- to 10-membered heterocycle, each of which is optionally substituted with one or more substituents independently selected from halogen, —$OR^{10}$, —$SR^{10}$, —$N(R^{10})_2$, —$C(O)R^{10}$, —$C(O)N(R^{10})_2$, —$N(R^{10})C(O)R^{10}$, —$N(R^{10})C(O)N(R^{10})_2$, —$OC(O)N(R^{10})_2$, —$N(R^{10})C(O)OR^{10}$, —$C(O)OR^{10}$, —$OC(O)R^{10}$, —$S(O)R^{10}$, —$S(O)_2R^{10}$, —$NO_2$, =O, =S, =$N(R^{10})$, —CN, $C_{1-6}$ alkyl, $C_{2-6}$ alkenyl, $C_{2-6}$ alkynyl, $C_{3-10}$ carbocycle, and 3- to 10-membered heterocycle; wherein $C_{1-6}$ alkyl, $C_{2-6}$ alkenyl, $C_{2-6}$ alkynyl, $C_{3-10}$ carbocycle, and 3- to 10-membered heterocycle are each optionally substituted with one or more $R^9$; or $R^1$ together with $R^3$ form a 5- to 10-membered heterocycle or $C_{5-10}$ carbocycle, wherein the 5- to 10-membered heterocycle or $C_{5-10}$ carbocycle is optionally substituted with one or more $R^9$; or $R^1$ together with $R^5$ form a 3- to 10-membered heterocycle or saturated $C_{3-10}$ carbocycle, wherein the 3- to 10-membered heterocycle or saturated $C_{3-10}$ carbocycle is optionally substituted with one or more $R^9$; or $R^1$ together with $R^4$ form a 3- to 10-membered heterocycle, wherein the 3- to 10-membered heterocycle is optionally substituted with one or more $R^9$; and when A is —$NR^4$—, $R^1$ is additionally selected from hydrogen, and when A is —C(O)—, $R^1$ is additionally selected from —$N(R^{10})_2$ and —$OR^{10}$;

each $R^2$ is independently selected from halogen, —$OR^{10}$, —$SR^{10}$, —$N(R^{10})_2$, —$C(O)R^{10}$, —$C(O)N(R^{10})_2$, —$N(R^{10})C(O)R^{10}$, —$N(R^{10})C(O)N(R^{10})_2$, —$OC(O)N(R^{10})_2$, —$N(R^{10})C(O)OR^{10}$, —$C(O)OR^{10}$, —$OC(O)R^{10}$, —$S(O)R^{10}$, —$S(O)_2R^{10}$, —$NO_2$, and —CN;

$C_{1-3}$ alkyl, $C_{2-3}$ alkenyl, and $C_{2-3}$ alkynyl, each of which is optionally substituted with one or more substituents independently selected from halogen, —$OR^{10}$, —$SR^{10}$, —$N(R^{10})_2$, —$C(O)R^{10}$, —$C(O)N(R^{10})_2$, —$N(R^{10})C(O)R^{10}$, —$N(R^{10})C(O)N(R^{10})_2$, —$OC(O)N(R^{10})_2$, —$N(R^{10})C(O)OR^{10}$, —$C(O)OR^{10}$, —$OC(O)R^{10}$, —$S(O)R^{10}$, —$S(O)_2R^{10}$, —$NO_2$, =O, =S, =$N(R^{10})$, and —CN; and $C_{3-10}$ carbocycle optionally substituted with one or more substituents independently selected from: halogen, —$OR^{10}$, —$SR^{10}$, —$N(R^{10})_2$, —$C(O)R^{10}$, —$C(O)N(R^{10})_2$, —$N(R^{10})C(O)R^{10}$, —$N(R^{10})C(O)N(R^{10})_2$, —$OC(O)N(R^{10})_2$, —$N(R^{10})C(O)OR^{10}$, —$C(O)OR^{10}$, —$OC(O)R^{10}$, —$S(O)R^{10}$, —$S(O)_2R^{10}$, —$NO_2$, =O, =S, =$N(R^{10})$, —CN, $C_{1-6}$ alkyl, $C_{2-6}$ alkenyl, $C_{2-6}$ alkynyl, $C_{3-10}$ carbocycle, and 3- to 10-membered heterocycle; wherein $C_{1-6}$ alkyl, $C_{2-6}$ alkenyl, $C_{2-6}$ alkynyl, $C_{3-10}$ carbocycle, and 3- to 10-membered heterocycle are each optionally substituted with one or more $R^9$;

$R^3$, $R^5$, and $R^6$ are each independently selected from:

hydrogen, halogen, —$OR^{10}$, —$SR^{10}$, —$N(R^{10})_2$, —$NO_2$, and —CN; and $C_{1-6}$ alkyl optionally substituted with one or more substituents independently selected from halogen, —$OR^{10}$, —$SR^{10}$, —$N(R^{10})_2$, —$NO_2$, and —CN; or $R^3$ together with $R^1$ form a 5- to 10-membered heterocycle or $C_{5-10}$ carbocycle, wherein the 5- to 10-membered heterocycle or $C_{5-10}$ carbocycle is optionally substituted with one or more $R^9$; or $R^5$ together with $R^1$ form a 3- to 10-membered heterocycle or saturated $C_{3-10}$ carbocycle, wherein the 3- to 10-membered heterocycle or saturated $C_{3-10}$ carbocycle is optionally substituted with one or more $R^9$.

$R^4$ is independently selected from:

hydrogen; and $C_{1-6}$ alkyl optionally substituted with one or more substituents independently selected from halogen, —$OR^{10}$, —$SR^{10}$, —$N(R^{10})_2$, —$NO_2$, and —CN; or $R^4$ together with $R^1$ form a 3- to 10-membered heterocycle, which is optionally substituted with one or more $R^9$.

$R^7$ and $R^8$ are each independently selected from:

halogen, —$OR^{10}$, —$SR^{10}$, —$N(R^{10})_2$, —$NO_2$, —CN, —$CHF_2$, —$CF_3$, —$CH_2F$, and $C_{2-6}$ alkyl optionally substituted with one or more substituents independently selected from halogen, —$OR^{10}$, —$SR^{10}$, —$N(R^{10})_2$, —$NO_2$, and —CN;

each $R^9$ is independently selected from:

halogen, —$OR^{10}$, —$SR^{10}$, —$N(R^{10})_2$, —$C(O)R^{10}$, —$C(O)N(R^{10})_2$, —$N(R^{10})C(O)R^{10}$, —$N(R^{10})C(O)N(R^{10})_2$, —$OC(O)N(R^{10})_2$, —$N(R^{10})C(O)OR^{10}$, —$C(O)OR^{10}$, —$OC(O)R^{10}$, —$S(O)R^{10}$, —$S(O)_2R^{10}$, —$NO_2$, =O, =S, =$N(R^{10})$, and —CN; and $C_{1-3}$ alkyl, $C_{2-3}$ alkenyl, and $C_{2-3}$ alkynyl, each of which is optionally substituted with one or more substituents independently selected from halogen, —$OR^{10}$, —$SR^{10}$, —$N(R^{10})_2$, —$C(O)R^{10}$, —$C(O)N(R^{10})_2$, —$N(R^{10})C(O)R^{10}$, —$N(R^{10})C(O)N(R^{10})_2$, —$OC(O)N(R^{10})_2$, —$N(R^{10})C(O)OR^{10}$, —$C(O)OR^{10}$, —$OC(O)R^{10}$, —$S(O)R^{10}$, —$S(O)_2R^{10}$, —$NO_2$, =O, =S, =$N(R^{10})$, and —CN;

each $R^{10}$ is independently selected from:

hydrogen;

$C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —$N(C_{1-6}$ alkyl$)_2$, —$NH(C_{1-6}$ alkyl), $C_{3-10}$ carbocycle, and 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —$N(C_{1-6}$ alkyl$)_2$, —$NH(C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and haloalkyl (e.g., $C_{1-6}$haloalkyl);

n is 0, 1, or 2;

p is 0, 1, or 2; and q is 1, 2, 3, 4, or 5, and when $R^1$ is other than —$CH_3$, q is further selected from 0.

In certain aspects, for a compound or salt of Formula (I):

$R^1$ is selected from:

$C_{1-6}$ alkyl, $C_{2-6}$ alkenyl, and $C_{2-6}$ alkynyl, each of which is optionally substituted with one or more substituents independently selected from halogen, —$OR^{10}$, —$SR^{10}$, —$N(R^{10})_2$, —$C(O)R^{10}$, —$C(O)N(R^{10})_2$, —$N(R^{10})C(O)R^{10}$, —$N(R^{10})C(O)N(R^{10})_2$, —$OC(O)N(R^{10})_2$, —$N(R^{10})C(O)OR^{10}$, —$C(O)OR^{10}$, —$OC(O)R^{10}$, —$S(O)R^{10}$, —$S(O)_2R^{10}$, —$NO_2$, =O, =S, =$N(R^{10})$, —CN, $C_{3-10}$ carbocycle, and 3- to 10-membered heterocycle, wherein the $C_{3-10}$ carbocycle and 3- to 10-membered heterocycle are each optionally substituted with one or more $R^9$; and $C_{3-10}$ carbocycle and 3- to 10-membered heterocycle, each of which is optionally substituted with one or more substituents independently selected from halogen, —$OR^{10}$, —$SR^{10}$, —$N(R^{10})_2$, —$C(O)R^{10}$, —$C(O)N(R^{10})_2$, —$N(R^{10})C(O)R^{10}$, —$N(R^{10})C(O)N(R^{10})_2$, —$OC(O)N(R^{10})_2$, —$N(R^{10})C(O)OR^{10}$, —$C(O)OR^{10}$, —$OC(O)R^{10}$, —$S(O)R^{10}$, —$S(O)_2R^{10}$, —$NO_2$, =O, =S, =$N(R^{10})$, and —CN; or $R^1$ together with $R^3$ form a 5- to 10-membered heterocycle or $C_{5-10}$ carbocycle, wherein the 5- to 10-membered heterocycle or $C_{5-10}$ carbocycle is optionally substituted with one or more $R^9$; or $R^1$ together with $R^5$ form a 3- to 10-membered heterocycle or saturated $C_{3-10}$ carbocycle, wherein the 3- to 10-membered heterocycle or saturated $C_{3-10}$ carbocycle is optionally substituted with one or more $R^9$; or $R^1$ together with $R^4$ form a 3- to 10-membered heterocycle, wherein the 3- to 10-membered heterocycle is optionally substituted with one or more $R^9$; and when A is —$NR^4$—, $R^1$ is additionally selected from hydrogen, and when A is —C(O)—, $R^1$ is additionally selected from —$N(R^{10})_2$ and —$OR^{10}$;

each $R^2$ is independently selected from:

halogen, —$OR^{10}$, —$SR^{10}$, —$N(R^{10})_2$, —$C(O)R^{10}$, —$C(O)N(R^{10})_2$, —$N(R^{10})C(O)R^{10}$, —$N(R^{10})C(O)N $(R^{10})_2$, —OC(O)N$(R^{10})_2$, —N$(R^{10})$C(O)OR$^{10}$, —C(O)OR$^{10}$, —OC(O)R$^{10}$, —S(O)R$^{10}$, —S(O)$_2$R$^{10}$, —NO$_2$, and —CN;

$C_{1-3}$ alkyl, $C_{2-3}$ alkenyl, and $C_{2-3}$ alkynyl, each of which is optionally substituted with one or more substituents independently selected from halogen, —OR$^{10}$, —SR$^{10}$, —N$(R^{10})_2$, —C(O)R$^{10}$, —C(O)N$(R^{10})_2$, —N$(R^{10})$C(O)R$^{10}$, —N$(R^{10})$C(O)N$(R^{10})_2$, —OC(O)N$(R^{10})_2$, —N$(R^{10})$C(O)OR$^{10}$, —C(O)OR$^{10}$, —OC(O)R$^{10}$, —S(O)R$^{10}$, —S(O)$_2$R$^{10}$, —NO$_2$, =O, =S, =N$(R^{10})$, and —CN; and $C_{3-10}$ carbocycle optionally substituted with one or more substituents independently selected from: halogen, —OR$^{10}$, —SR$^{10}$, —N$(R^{10})_2$, —C(O)R$^{10}$, —C(O)N$(R^{10})_2$, —N$(R^{10})$C(O)R$^{10}$, —N$(R^{10})$C(O)N$(R^{10})_2$, —OC(O)N$(R^{10})_2$, —N$(R^{10})$C(O)OR$^{10}$, —C(O)OR$^{10}$, —OC(O)R$^{10}$, —S(O)R$^{10}$, —S(O)$_2$R$^{10}$, —NO$_2$, =O, =S, =N$(R^{10})$, and —CN;

each $R^{10}$ is independently selected from:
hydrogen;

$C_{1-6}$ alkyl, $C_{2-6}$ alkenyl, and $C_{2-6}$ alkynyl, each of which is optionally substituted with one or more substituents independently selected from halogen, —CN, —OH, —SH, —NO$_2$, —NH$_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, and 3- to 10-membered heterocycle; and $C_{3-10}$ carbocycle, and 3- to 10-membered heterocycle, each of which is optionally substituted with one or more substituents independently selected from halogen, —CN, —OH, —SH, —NO$_2$, —NH$_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and haloalkyl.

In certain embodiments, for a compound or salt of Formula (I), each X is independently selected from C(R$^3$) and N wherein at least one X is N. In some embodiments, one X is N and one X is C(R$^3$). In some embodiments, one X is N$^+$(—O$^-$) and one X is C(R$^3$). In some embodiments, each X is N. In some embodiments, one X is N, and one X is N$^+$(—O$^-$).

In certain embodiments, for a compound or salt of Formula (I), each X is further selected from C(R$^3$).

In some embodiments, a compound or salt thereof of Formula (I) is represented by Formula (Ia):

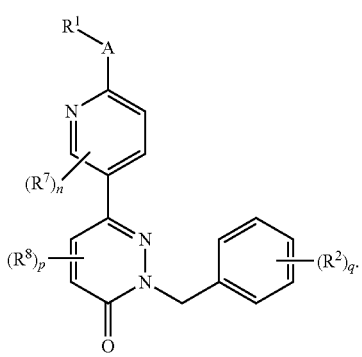

(Ia)

In some embodiments, a compound or salt thereof of Formula (I) is represented by Formula (Ib):

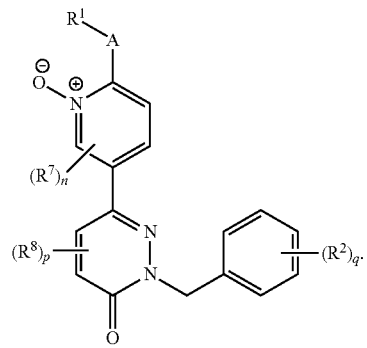

(Ib)

In some embodiments, a compound or salt thereof of Formula (I) is represented by Formula (Ic):

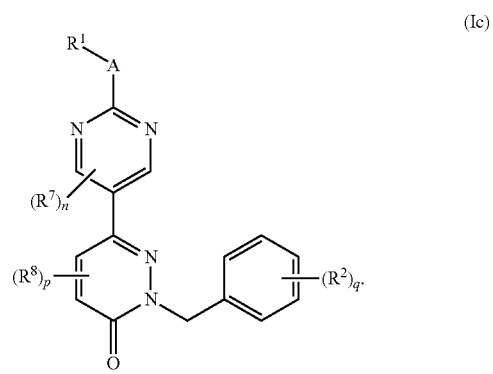

(Ic)

In some embodiments, a compound or salt thereof of Formula (I) is represented by Formula (Id):

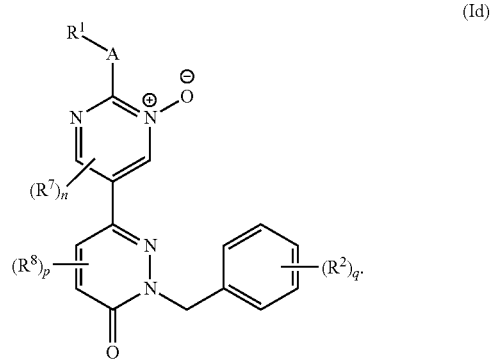

(Id)

In some embodiments, a compound or salt thereof of Formula (I) is represented by Formula (Ia) or (Ib):

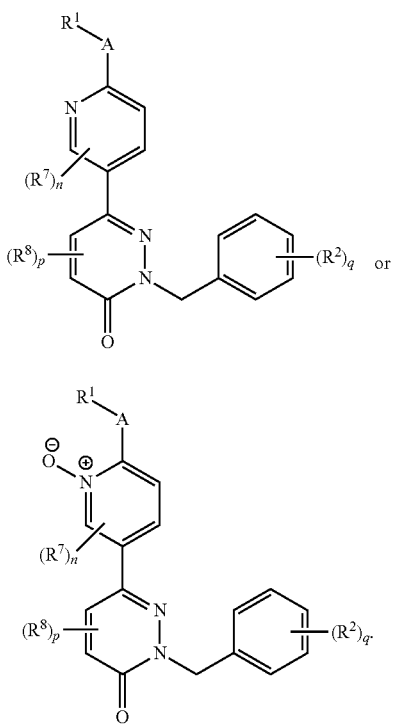

(Ia)

(Ib)

In some embodiments, a compound or salt thereof of Formula (I) is represented by Formula (Ic) or (Id):

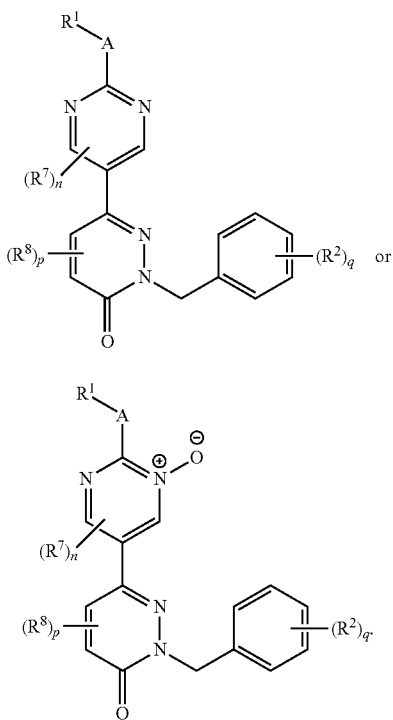

(Ic)

(Id)

In some embodiments, a compound or salt thereof of Formula (I) is represented by Formula (Ia) or (Ic):

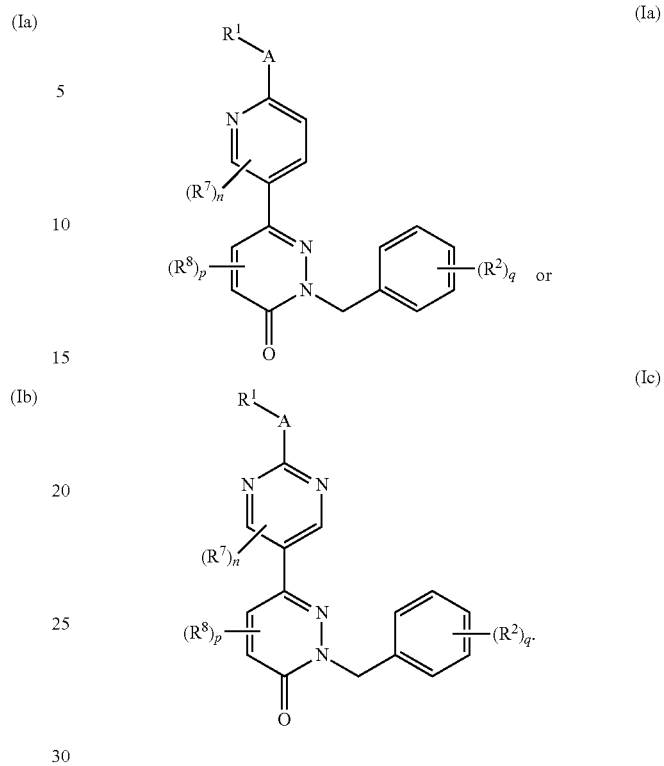

(Ia)

(Ic)

In certain embodiments, for a compound or salt of any one of Formula (I), (Ia), (Ib), (Ic), or (Id), A is selected from —O—, —NR$^4$—, —CR$^5$R$^6$—, and —C(O)—. In some embodiments, A is selected from —O— and —NR$^4$. In some embodiments, A is —O—. In some embodiments, A is —C(O)—. In some embodiments, A is —NR$^4$—, such as —NH—.

In certain embodiments, for a compound or salt of any one of Formula (I), (Ia), (Ib), (Ic), or (Id), R$^1$ is C$_{1-6}$ alkyl optionally substituted with one or more substituents independently selected from halogen, —OR$^{10}$, —SR$^{10}$, —N(R$^{10}$)$_2$, —C(O)R$^{10}$, —C(O)N(R$^{10}$)$_2$, —N(R$^{10}$)C(O)R$^{10}$, —C(O)OR$^{10}$, —OC(O)R$^{10}$, —N(R$^{10}$)C(O)N(R$^{10}$)$_2$, —OC(O)N(R$^{10}$)$_2$, —N(R$^{10}$)C(O)OR$^{10}$, —S(O)R$^{10}$, —S(O)$_2$R$^{10}$, —NO$_2$, =O, =S, =N(R$^{10}$), —CN, C$_{3-10}$ carbocycle and 3- to 10-membered heterocycle, wherein the C$_{3-10}$ carbocycle and 3- to 10-membered heterocycle are each optionally substituted with one or more R$^9$. In some embodiments, R$^1$ is C$_{1-6}$ alkyl substituted with one or more substituents independently selected from halogen, —OR$^{10}$, —SR$^{10}$, —N(R$^{10}$)$_2$, —C(O)R$^{10}$, —C(O)N(R$^{10}$)$_2$, —N(R$^{10}$)C(O)R$^{10}$, —C(O)OR$^{10}$, —OC(O)R$^{10}$, —N(R$^{10}$)C(O)N(R$^{10}$)$_2$, —OC(O)N(R$^{10}$)$_2$, —N(R$^{10}$)C(O)OR$^{10}$, —S(O)R$^{10}$, —S(O)$_2$R$^{10}$, —NO$_2$, =O, =S, =N(R$^{10}$), —CN, C$_{3-10}$ carbocycle and 3- to 10-membered heterocycle, wherein the C$_{3-10}$ carbocycle and 3- to 10-membered heterocycle are each optionally substituted with one or more R$^9$. In some embodiments, R$^1$ is C$_{1-6}$ alkyl substituted with one or more substituents independently selected from halogen, —OR$^{10}$, —N(R$^{10}$)$_2$, —C(O)R$^{10}$, —C(O)N(R$^{10}$)$_2$, —N(R$^{10}$)C(O)R$^{10}$, —C(O)OR$^{10}$, —OC(O)R$^{10}$, —NO$_2$, =O, =N(R$^{10}$), —CN, C$_{3-10}$ carbocycle and 3- to 10-membered heterocycle, wherein the C$_{3-10}$ carbocycle and 3- to 10-membered heterocycle are each optionally substituted with one or more R$^9$. In some embodiments, R$^1$ is selected from C$_{1-3}$ alkyl optionally substituted with one or more substituents independently selected from halogen, —OR$^{10}$, —SR$^{10}$, —N(R$^{10}$)$_2$, —NO$_2$, =O, =S, =N(R$^{10}$), —CN, C$_{3-10}$ carbocycle and 3- to 10-membered heterocycle, wherein the C$_{3-10}$ carbocycle and 3- to 10-membered heterocycle are each optionally substituted with one or more R$^9$. In some embodiments, R$^1$ is C$_{1-3}$ alkyl substituted with one or more substituents independently selected from halogen, —OR$^{10}$, —N(R$^{10}$)$_2$, —NO$_2$, =O, —CN, C$_{3-10}$ carbocycle and 3- to 10-membered heterocycle, wherein the C$_{3-10}$ carbocycle and 3- to 10-membered heterocycle are each optionally substituted with one or more R$^9$. In some embodiments, R$^1$ is C$_{1-3}$ alkyl substituted with one or more halogen substituents. In some embodiments, R$^1$ is a C$_{1-3}$ fluoroalkyl. In some embodiments, R$^1$ is selected from —CHF$_2$, —CH$_2$F, —CF$_3$, —CH$_2$CHF$_2$, CH$_2$CH$_2$F, or —CH$_2$CF$_3$. In some embodiments, R$^1$ is CH$_2$CN. In some embodiments, R$^1$ is not unsubstituted methyl. In some embodiments, R$^1$ is —NH$_2$. In some embodiments, when A is —C(O)—, R$^1$ is —NH$_2$. In some embodiments, R$^1$ is C$_{1-3}$ alkyl substituted with —OR$^{10}$, wherein R$^{10}$ is C$_{1-3}$ alkyl substituted with one or more halogens. In some embodiments, R$^1$ is —CH$_2$CH$_2$—OR$^{10}$, wherein R$^{10}$ is —CHF$_2$ or —CH$_3$. In some embodiments, R$^1$ is C$_{1-3}$ alkyl substituted with =O. In some embodiments, R$^1$ is —C(O)—CH$_3$. In some embodiments, R$^1$ is —CH$_3$. In some embodiments, R$^1$ is selected from C$_{3-10}$ carbocycle and 3- to 10-membered heterocycle, wherein the C$_{3-10}$ carbocycle and 3- to 10-membered heterocycle are each optionally substituted with one or more R$^9$. In some embodiments, R$^1$ is C$_{3-10}$ carbocycle. In some embodiments, R$^1$ is C$_{3-5}$ carbocycle. In some embodiments, R$^1$ is cyclopropyl. In some embodiments, R$^1$ is a C$_{1-3}$ alkyl substituted with a 4- to 6-membered heterocycle, wherein the 4- to 6-membered heterocycle is substituted with one or more R$^9$. In some embodiments, R$^1$ is methyl substituted with a 4- to 6-membered heterocycle selected from:

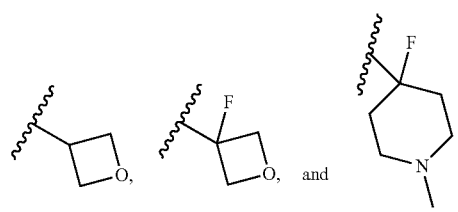

In certain embodiments, for a compound or salt of Formula (I), (Ia), (Ib), (Ic), or (Id), R$^1$ is selected from C$_{1-3}$ alkyl optionally substituted with one or more substituents independently selected from halogen, —OR$^{10}$, and 3- to 6-membered heterocycle optionally substituted with one or more R$^9$, and C$_{3-5}$ carbocycle optionally substituted with one or more R$^9$.

In certain embodiments, for a compound or salt of Formula (I), (Ia), (Ib), (Ic), or (Id), R$^1$ is selected from C$_{1-3}$ alkyl optionally substituted with one or more substituents independently selected from halogen, —OR$^{10}$, and 3- to 6-membered heterocycle optionally substituted with one or more R$^9$, and C$_{3-5}$ carbocycle optionally substituted with one or more R$^9$, wherein each R$^9$ is selected from C$_{1-3}$ alkyl, C$_{1-3}$ haloalkyl and halogen.

In certain embodiments, for a compound or salt of Formula (I), (Ia), (Ib), (Ic), or (Id), R$^1$ is selected from —CH$_3$, —CF$_3$, —CH$_2$F, —CHF$_2$, —CH$_2$CHF$_2$, —CH$_2$CF$_3$, —C(=O)CH$_3$,

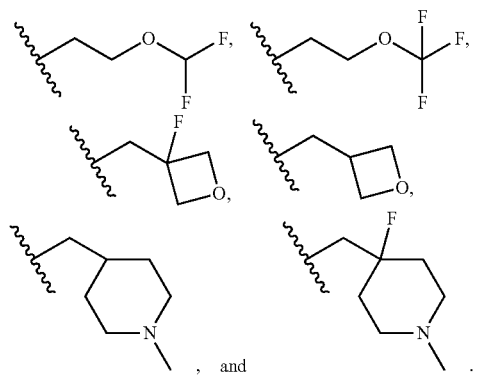

In certain embodiments, for a compound or salt of any one of Formula (I), (Ia), (Ib), (Ic), or (Id), R$^1$ is selected from optionally substituted C$_3$-C$_6$ cycloalkyl, such as cyclopropyl, cyclobutyl, cyclopentyl, bicyclopentyl, and spiropentyl, any of which is optionally substituted. In certain embodiments, R$^1$ is selected from alkyl, e.g., methyl, ethyl, propyl, iso-propyl, t-butyl, iso-butyl, sec-butyl, any of which may be optionally substituted. In certain embodiments, R$^1$ is selected from:

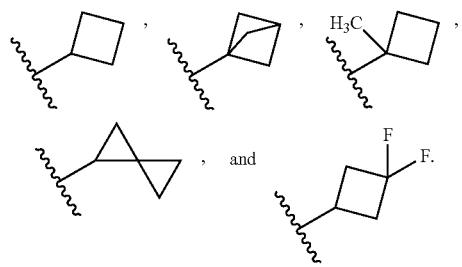

In certain embodiments, R$^1$ is selected from:

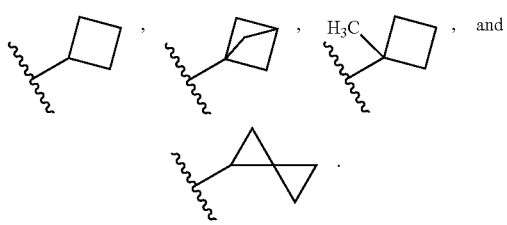

In certain embodiments, R$^1$ is selected from optionally substituted

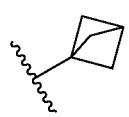

In some embodiments, for a compound or salt of any one of Formula (I), (Ia), (Ib), (Ic), or (Id), R$^1$ is selected from optionally substituted C$_3$ cycloalkyl.

In certain embodiments, for a compound or salt of Formula (I), R$^1$ together with R$^3$ form a 5- to 10-membered heterocycle or $C_{5-10}$ carbocycle, wherein the 5- to 10-membered heterocycle or $C_{5-10}$ carbocycle is optionally substituted with one or more $R^9$. In some embodiments, $R^1$ together with $R^3$ form a $C_{5-10}$ carbocycle or 5- to 10-membered heterocycle, such as a $C_{5-6}$ carbocycle or 5- to 6-membered heterocycle, for example:

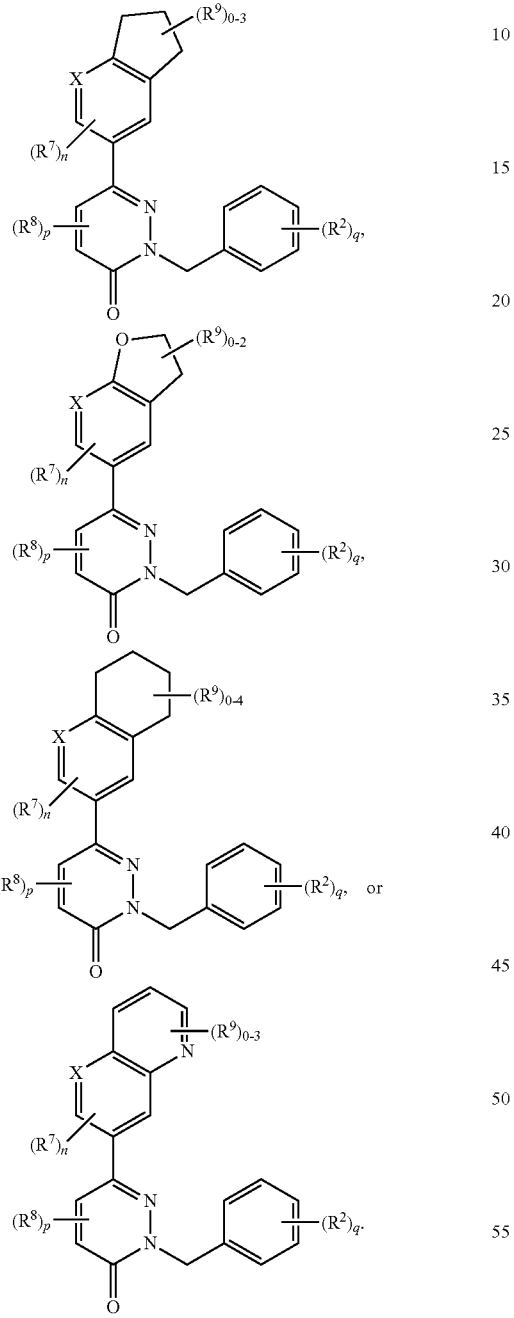

In certain embodiments, for a compound or salt of Formula (I), $R^1$ together with $R^5$ form a 3- to 10-membered heterocycle or saturated $C_{3-10}$ carbocycle, wherein the 3- to 10-membered heterocycle or saturated $C_{3-10}$ carbocycle is optionally substituted with one or more $R^9$. In some embodiments, $R^1$ together with $R^5$ form a 3- to 10-membered heterocycle or saturated $C_{3-10}$ carbocycle, for example:

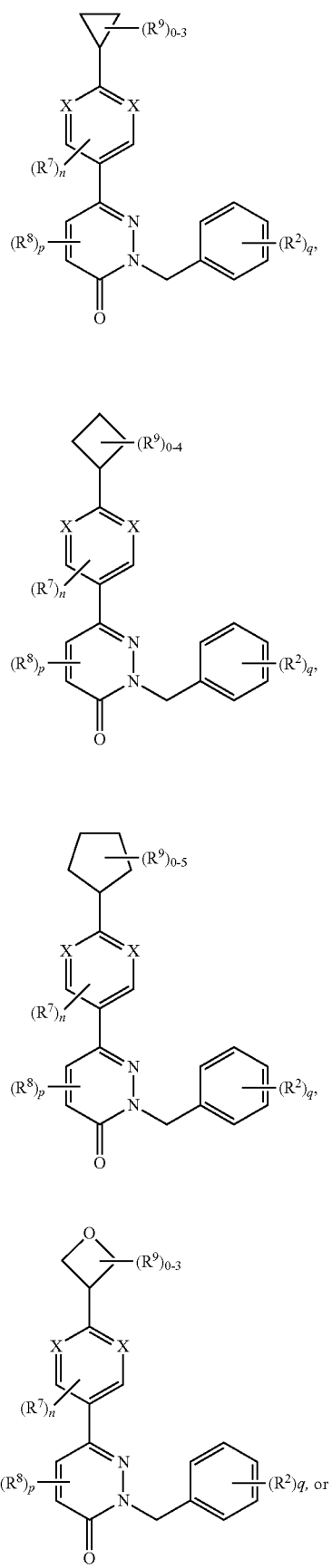

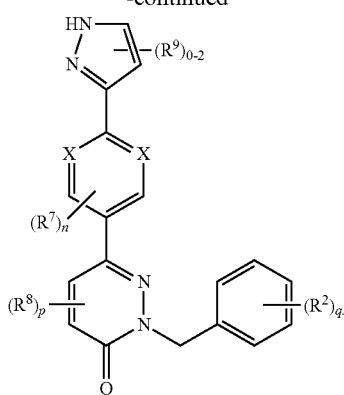

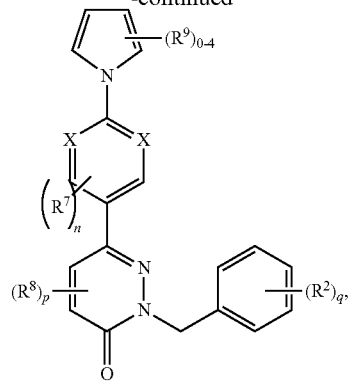

In certain embodiments, for a compound or salt of Formula (I), $R^1$ together with $R^4$ form a 3- to 10-membered heterocycle, wherein the 3- to 10-membered heterocycle is optionally substituted with one or more $R^9$. In some embodiments, $R^1$ together with $R^4$ form a 3- to 10-membered heterocycle, for example:

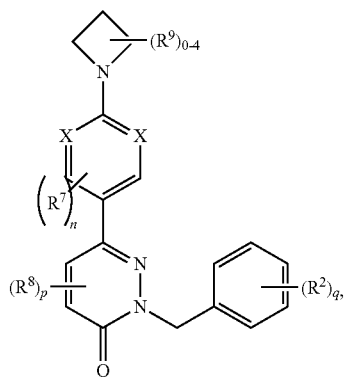

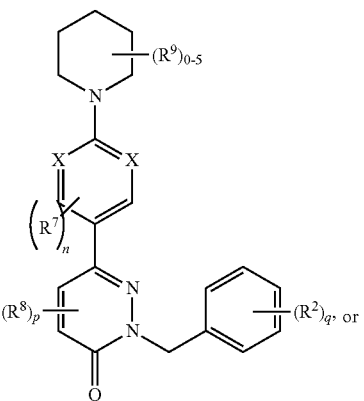

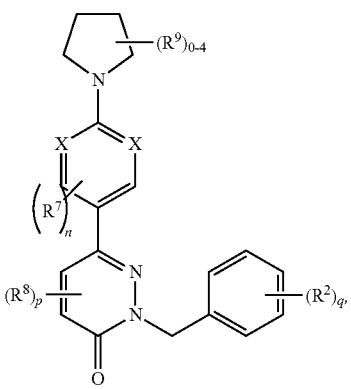

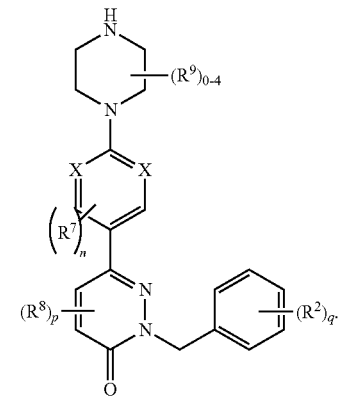

In some embodiments, for a compound or salt of any one of Formula (I), (Ia), (Ib), (Ic), or (Id), $R^1$ together with $R^4$ form a 3- to 10-membered heterocycle, wherein the 3- to 10-membered heterocycle is optionally substituted with one or more $R^9$.

In some embodiments, for a compound or salt of any one of Formula (I), (Ia), (Ib), (Ic), or (Id), the 3- to 10-membered heterocycle formed from $R^1$ together with $R^4$ is selected from a 4-, 5-, 6- or 7-membered ring any of which is optionally substituted with one or more $R^9$.

In some embodiments, for a compound or salt of any one of Formula (I), (Ia), (Ib), (Ic), or (Id), the 3- to 10-membered heterocycle formed from $R^1$ together with $R^4$ is selected from:

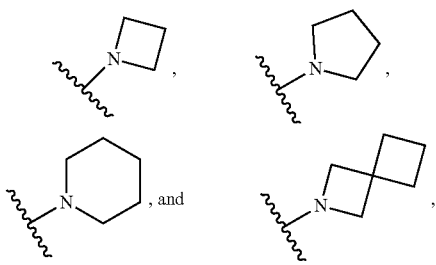

any of which is optionally substituted with one or more $R^9$.

In some embodiments, for a compound or salt of any one of Formula (I), (Ia), (Ib), (Ic), or (Id), the 3- to 10-membered heterocycle formed from $R^1$ together with $R^4$ is selected from:

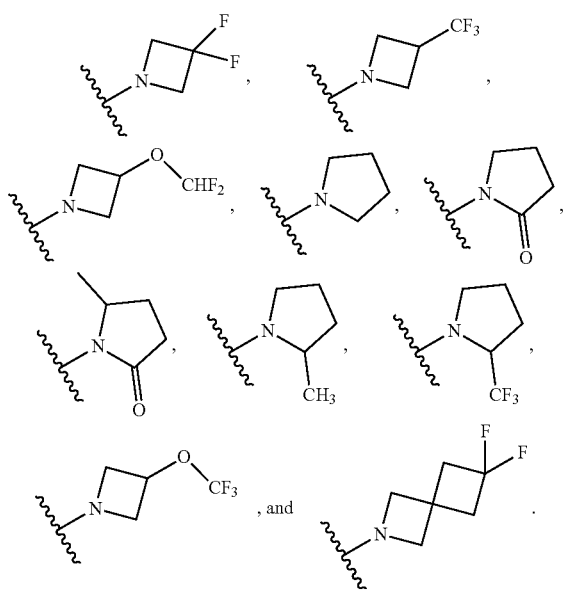

In some embodiments, for a compound or salt of any one of Formula (I), (Ia), (Ib), (Ic), (Id), when there is an $R^2$ at either or both ortho positions of the phenyl ring relative to the point of connectivity to the rest of the molecule, each ortho $R^2$ is independently selected from halogen, —$OR^{10}$, —$SR^{10}$, —$N(R^{10})_2$, —$NO_2$, —CN, and $C_{1-3}$ alkyl optionally substituted with one or more substituents independently selected from halogen, —$OR^{10}$, —$SR^{10}$, —$N(R^{10})_2$, —$NO_2$, and —CN. In some embodiments, for a compound or salt of any one of Formula (I), (Ia), (Ib), (Ic), (Id), when there is an $R^2$ at either or both ortho positions of the phenyl ring relative to the point of connectivity to the rest of the molecule, each $R^2$ is independently selected from halogen, —OH, —$OCH_3$, —$OCF_3$, and $C_{1-3}$ alkyl optionally substituted with one or more substituents independently selected from halogen.

In some embodiments, for a compound or salt of any one of Formula (I), (Ia), (Ib), (Ic), (Id), if there is an $R^2$ at either ortho positions of the phenyl ring relative to the point of connectivity to the rest of the molecule, the $R^2$ is not selected from carbocycle or heterocycle. In some embodiments, for a compound or salt of any one of Formula (I), (Ia), (Ib), (Ic), (Id), there is not an $R^2$ at either ortho positions of the phenyl ring relative to the point of connectivity to the rest of the molecule.

In some embodiments, for a compound or salt of any one of Formula (I), (Ia), (Ib), (Ic), (Id), each $R^2$ is independently selected from halogen, —$OR^{10}$, —$SR^{10}$, —$N(R^{10})_2$, —$NO_2$, —CN, and $C_{1-3}$ alkyl optionally substituted with one or more substituents independently selected from halogen, —$OR^{10}$, —$SR^{10}$, —$N(R^{10})_2$, —$NO_2$, and —CN. In some embodiments, for a compound or salt of any one of Formula (I), (Ia), (Ib), (Ic), (Id), each $R^2$ is selected from —Cl, —F, and —OH.

In certain embodiments, for a compound or salt of one of Formula (I), (Ia), (Ib), (Ic), or (Id), $R^2$ is selected from $C_{3-6}$ cycloalkyl, such as cyclopropyl, cyclobutyl, cyclopentyl, bicyclopentyl, and spiropentyl, any of which is optionally substituted. In certain embodiments, $R^2$ is

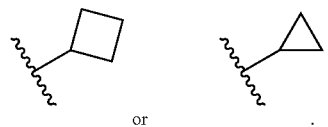

In certain embodiments, for a compound or salt of any one of Formula (I), (Ia), (Ib), (Ic), or (Id), q is 0, 1, or 2. In certain embodiments, q is 0.

In certain embodiments, for a compound or salt of any one of Formula (I), (Ia), (Ib), (Ic), or (Id), each $R^3$ is selected from hydrogen, halogen, —$OR^{10}$, —$SR^{10}$, —$N(R^{10})_2$, —$NO_2$, —CN, and $C_{1-6}$ alkyl optionally substituted with one or more substituents independently selected from halogen, —$OR^{10}$, —$SR^{10}$, —$N(R^{10})_2$, —$NO_2$, and —CN. In some embodiments, $R^3$ is hydrogen. In some embodiments, $R^3$ together with $R^1$ form a 5- to 6-membered heterocycle or $C_{5-6}$ carbocycle, wherein the 5- to 6-membered heterocycle or $C_{5-6}$ carbocycle is optionally substituted with one or more $R^9$. In some embodiments, $R^3$ together with $R^1$ form a 5 membered heterocycle substituted with zero, one, or two methyl groups, for example:

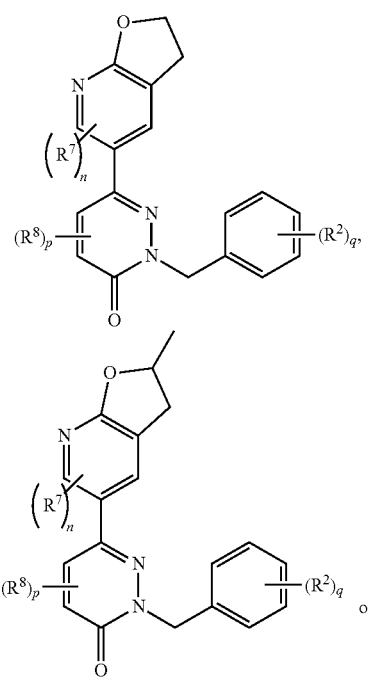

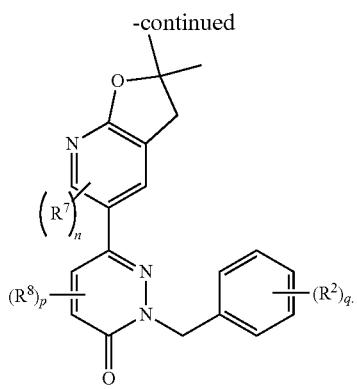

In certain embodiments, for a compound or salt of any one of Formula (I), (Ia), (Ib), (Ic), (Id), $R^4$ is independently selected from hydrogen; and $C_{1-6}$ alkyl optionally substituted with one or more substituents independently selected from halogen, —$OR^{10}$, —$SR^{10}$, —$N(R^{10})_2$, —$NO_2$, and —CN; or $R^4$ together with $R^1$ form a 3- to 10-membered heterocycle, which is optionally substituted with one or more $R^9$. In some embodiments, $R^4$ is hydrogen. In some embodiments, $R^4$ is methyl. In some embodiments, $R^4$ together with $R^1$ form a 4- to 5-membered heterocycle, which is optionally substituted with one or more $R^9$, wherein $R^9$ is selected from methyl, —$CH_2F$, —$CHF_2$, —$CF_3$, —F, —$OCF_3$, and —$OCHF_2$.

In certain embodiments, for a compound or salt of any one of Formula (I), (Ia), (Ib), (Ic), (Id), each $R^5$ and $R^6$ is independently selected from hydrogen, halogen, —$OR^{10}$, —$SR^{10}$, —$N(R^{10})_2$, —$NO_2$, —CN, and $C_{1-6}$ alkyl optionally substituted with one or more substituents independently selected from halogen, —$OR^{10}$, —$SR^{10}$, —$N(R^{10})_2$, —$NO_2$, and —CN. In some embodiments, $R^1$ together with $R^5$ form a 3- to 10-membered heterocycle or saturated $C_{3-10}$ carbocycle. In some embodiments, $R^1$ together with $R^5$ form a cyclopropyl ring.

In certain embodiments, for a compound or salt of any one of Formula (I), (Ia), (Ib), (Ic), (Id), each $R^7$ and $R^8$ is independently selected from halogen, —$OR^{10}$, —$SR^{10}$, —$N(R^{10})_2$, —$NO_2$, —CN, —$CHF_2$, —$CF_3$, —$CH_2F$, and $C_{2-6}$ alkyl optionally substituted with one or more substituents independently selected from halogen, —$OR^{10}$, —$SR^{10}$, —$N(R^{10})_2$, —$NO_2$, and —CN.

In certain embodiments, for a compound or salt of any one of Formula (I), (Ia), (Ib), (Ic), or (Id), each $R^9$ is independently selected from halogen, —$OR^{10}$, —$SR^{10}$, —$N(R^{10})_2$, —$NO_2$, =O, =S, —CN; and $C_{1-3}$ alkyl, $C_{2-3}$ alkenyl, $C_{2-3}$ alkynyl, each of which is optionally substituted with one or more substituents independently selected from halogen, —$OR^{10}$, —$SR^{10}$, —$N(R^{10})_2$, —$NO_2$, —CN. In some embodiments, $R^9$ is a halogen. In some embodiments, $R^9$ is a —F. In some embodiments, $R^9$ is a $C_{1-3}$ haloalkyl. In some embodiments, $R^9$ is a $C_{1-3}$ alkyl substituted with one or more fluorine substituents. In some embodiments, $R^9$ is —$CH_2F$, —$CHF_2$ or —$CF_3$. In some embodiments, $R^9$ is an unsubstituted $C_{1-3}$ alkyl. In some embodiments, $R^9$ is methyl. In some embodiments, $R^9$ is —$OR^{10}$. In some embodiments, $R^9$ is —$OR^{10}$, and $R^{10}$ is $C_{1-3}$ haloalkyl. In some embodiments, $R^9$ is —$OR^{10}$, and $R^{10}$ is —$CH_2F$, —$CHF_2$ or —$CF_3$. In some embodiments, two $R^9$ groups come together to form a 3- to 10-membered heterocycle or $C_{3-10}$ carbocycle optionally substituted with one or more $R^{10}$. In some embodiments, two $R^9$ groups come together to form a spirocyclic $C_{3-5}$ carbocycle substituted with one of more fluorine substituents. In some embodiments, two $R^9$ groups come together to form spirocyclic cyclcobutane substituted with two fluorine substituents.

In certain embodiments, for a compound or salt of any one of Formula (I), (Ia), (Ib), (Ic), or (Id), each $R^{10}$ is independently selected from hydrogen; and $C_{1-6}$ alkyl optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —$N(C_{1-6}$ alkyl$)_2$, —$NH(C_{1-6}$ alkyl$)$, $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =0, =S, —O—$C_{1-6}$ alkyl, —S—$C_{1-6}$ alkyl, —$N(C_{1-6}$ alkyl$)_2$, —$NH(C_{1-6}$ alkyl$)$, $C_{1-6}$ alkyl, $C_{3-10}$ carbocycle, 3- to 10-membered heterocycle, and haloalkyl. In some embodiments, $R^{10}$ is —F.

In certain embodiments, for a compound or salt of any one of Formula (I), (Ia), (Ib), (Ic), (Id), n is 0.

In certain embodiments, for a compound or salt of any one of Formula (I), (Ia), (Ib), (Ic), (Id), p is 0.

In certain embodiments, a compound of Formula (I) is represented by Formula (Ie):

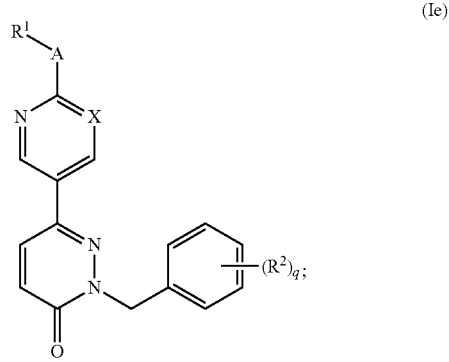

or a salt thereof, wherein:

A is selected from —O—, —$NR^4$—, —$CR^5R^6$—, and —C(O)—;

X is independently selected from $C(R^3)$ and N;

$R^1$ is selected from:
  $C_{1-6}$ alkyl optionally substituted with one or more substituents independently selected from halogen, —$OR^{10}$, —$N(R^{10})_2$, —$C(O)R^{10}$, —CN, $C_{3-6}$ carbocycle, and 4- to 6-membered heterocycle, wherein the $C_{3-6}$ carbocycle and 4- to 6-membered heterocycle are each optionally substituted with one or more $R^9$; and
  $C_{3-6}$ carbocycle; or
  $R^1$ together with $R^3$ form a 5- to 10-membered heterocycle, wherein the 5- to 10-membered heterocycle is optionally substituted with one or more $R^9$; or $R^1$ together with $R^5$ form a saturated $C_{3-5}$ carbocycle; or
  $R^1$ together with $R^4$ form a 4- to 6-membered heterocycle, wherein the 4- to 6-membered heterocycle is optionally substituted with one or more $R^9$; and
  when A is —C(O)—, $R^1$ is additionally selected from —$N(R^{10})_2$ and —$OR^{10}$;

each $R^2$ is independently selected from halogen and halogen, —$OR^{10}$, —$SR^{10}$, —$N(R^{10})_2$, —$NO_2$, —CN;

each $R^9$ is independently selected from:
  halogen, —$OR^{10}$, —$SR^{10}$, —$N(R^{10})_2$, —$NO_2$, —CN; and $C_{1-3}$ alkyl optionally substituted with one or more substituents independently selected from halogen, —OR$^{10}$, —SR$^{10}$, —N(R$^{10}$)$_2$, —NO$_2$, and —CN;

two R$^9$ groups come together to form a 4- to 6-membered heterocycle or $C_{3-6}$ carbocycle optionally substituted with one or more R$^{10}$, wherein the 4- to 6-membered heterocycle or $C_{3-6}$ carbocycle is optionally spirocyclic;

each R$^{10}$ is independently selected from
hydrogen; and
$C_{1-6}$ alkyl optionally substituted with one or more substituents independently selected from halogen, —CN, —OH, —SH, —NO$_2$, —NH$_2$, —O—$C_{1-6}$ alkyl, —N($C_{1-6}$ alkyl)$_2$, and —NH($C_{1-6}$ alkyl).

In certain embodiments, for a compound or salt of Formula (Ie): each R$^9$ is independently selected from:
halogen, —OR$^{10}$, —SR$^{10}$, —N(R$^{10}$)$_2$, —NO$_2$, —CN; and
$C_{1-3}$ alkyl optionally substituted with one or more substituents independently selected from halogen, —OR$^{10}$, —SR$^{10}$, —N(R$^{10}$)$_2$, —NO$_2$, and —CN.

In certain embodiments, for a compound or salt of any one of Formula (I), (Ia), (Ib), (Ic), or (Id), R$^1$-A is further selected from hydrogen. For example, a compound of the disclosure may be represented by:

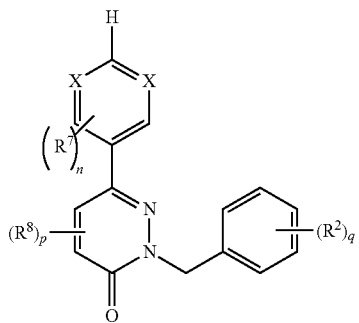

or a salt thereof, wherein R$^7$, R$^2$, X, p, q and n are as previously described for Formula (I). In certain embodiments, for a compound or salt of any one of Formula (I), (Ia), (Ib), (Ic), or (Id), R$^1$-A is further selected from halogen and $C_1$-$C_3$ alkyl, e.g., $C_2$-$C_3$ alkyl. In certain embodiments, for a compound or salt of any one of Formula (I), (Ia), (Ib), (Ic), or (Id), R$^1$-A is further selected from halogen.

In certain embodiments, a compound of the disclosure is selected from a compound of Table 1 or a salt thereof.

In certain aspects, disclosed herein is a compound represented by Formula (II'):

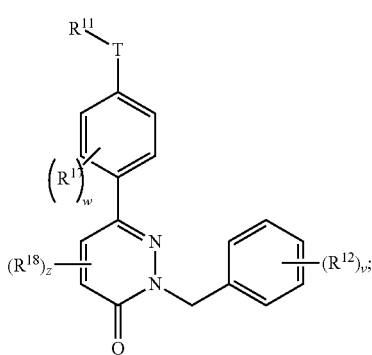

or a salt thereof, wherein:
T is selected from —O—, —NR$^{14}$—, —CR$^{15}$R$^{16}$—, —C(O)—, —S—, —S(O)—, and —S(O)$_2$;
R$^{11}$ is selected from;
$C_{1-6}$ alkyl, $C_{2-6}$ alkenyl, and $C_{2-6}$ alkynyl, each of which is substituted with one or more substituents independently selected from halogen, —OR$^{20}$, —SR$^{20}$, —N(R$^{20}$)$_2$, —C(O)R$^{20}$, —C(O)N(R$^{20}$)$_2$, —N(R$^{20}$)C(O)R$^{20}$, —N(R$^{20}$)C(O)N(R$^{20}$)$_2$, —OC(O)N(R$^{20}$)$_2$, —N(R$^{20}$)C(O)OR$^{20}$, —C(O)OR$^{20}$, —OC(O)R$^{20}$, —S(O)R$^{20}$, —S(O)$_2$R$^{20}$, —NO$_2$, =O, =S, =N(R$^{20}$), —CN, $C_{3-10}$ carbocycle, and 3- to 10-membered heterocycle, wherein the $C_{3-10}$ carbocycle and 3- to 10-membered heterocycle are each optionally substituted with one or more R$^{19}$.
and $C_{3-10}$ carbocycle and 3- to 10-membered heterocycle, each of which is optionally substituted with one or more substituents independently selected from halogen, —OR$^{20}$, —SR$^{20}$, —N(R$^{20}$)$_2$, —C(O)R$^{20}$, —C(O)N(R$^{20}$)$_2$, —N(R$^{20}$)C(O)R$^{20}$, —N(R$^{20}$)C(O)N(R$^{20}$)$_2$, —OC(O)N(R$^{20}$)$_2$, —N(R$^{20}$)C(O)OR$^{20}$, —C(O)OR$^{20}$, —OC(O)R$^{20}$, —S(O)R$^{20}$, —S(O)$_2$R$^{20}$, —NO$_2$, =O, =S, =N(R$^{20}$), and —CN; or
R$^{11}$ together with R$^{17}$ form a 5- to 10-membered heterocycle or $C_{5-10}$ carbocycle, wherein the 5- to 10-membered heterocycle or $C_{5-10}$ carbocycle is optionally substituted with one or more R$^{19}$; or R$^{11}$ together with R$^{15}$ form a 3- to 10-membered heterocycle or $C_{3-10}$ carbocycle, wherein the 3- to 10-membered heterocycle or saturated $C_{3-10}$ carbocycle is optionally substituted with one or more R$^{19}$; or R$^{11}$ together with R$^{14}$ form a 3- to 10-membered heterocycle, wherein the 3- to 10-membered heterocycle is optionally substituted with one or more R$^{19}$.
when T is —NR$^{14}$—, R$^{11}$ is additionally selected from hydrogen, and when T is —C(O)—, R$^{11}$ is additionally selected from —N(R$^{20}$)$_2$ and —OR$^{20}$;
each R$^{12}$ is independently selected from:
halogen, —OR$^{20}$, —SR$^{20}$, —N(R$^{20}$)$_2$, —C(O)R$^{20}$, —C(O)N(R$^{20}$)$_2$, —N(R$^{20}$)C(O)R$^{20}$, —N(R$^{20}$)C(O)N(R$^{20}$)$_2$, —OC(O)N(R$^{20}$)$_2$, —N(R$^{20}$)C(O)OR$^{20}$, —C(O)OR$^{20}$, —OC(O)R$^{20}$, —S(O)R$^{20}$, —S(O)$_2$R$^{20}$, —NO$_2$, —CN;
$C_{1-3}$ alkyl, $C_{2-3}$ alkenyl, $C_{2-3}$ alkynyl, each of which is optionally substituted with one or more substituents independently selected from halogen, —OR$^{20}$, —SR$^{20}$, —N(R$^{20}$)$_2$, —C(O)R$^{20}$, —C(O)N(R$^{20}$)$_2$, —N(R$^{20}$)C(O)R$^{20}$, —C(O)OR$^{20}$, —N(R$^{20}$)C(O)N(R$^{20}$)$_2$, —OC(O)N(R$^{20}$)$_2$, —N(R$^{20}$)C(O)OR$^{20}$, —OC(O)R$^{20}$, —S(O)R$^{20}$, —S(O)$_2$R$^{20}$, —NO$_2$, =O, =S, =N(R$^{20}$), and —CN; and
$C_{3-10}$ carbocycle optionally substituted with one or more substituents independently selected from halogen, —OR$^{20}$, —SR$^{20}$, —N(R$^{20}$)$_2$, —C(O)R$^{20}$, —C(O)N(R$^{20}$)$_2$, —N(R$^{20}$)C(O)R$^{20}$, —N(R$^{20}$)C(O)N(R$^{20}$)$_2$, —OC(O)N(R$^{20}$)$_2$, —N(R$^{20}$)C(O)OR$^{20}$, —C(O)OR$^{20}$, —OC(O)R$^{20}$, —S(O)R$^{20}$, —S(O)$_2$R$^{20}$, —NO$_2$, =O, =S, =N(R$^{20}$), and —CN;
R$^{14}$ is independently selected from:
hydrogen; and
$C_{1-6}$ alkyl optionally substituted with one or more substituents independently selected from halogen, —OR$^{20}$, —SR$^{20}$, —N(R$^{20}$)$_2$, —NO$_2$, and —CN; or
R$^{14}$ together with R$^{11}$ form a 3- to 10-membered heterocycle, which is optionally substituted with one or more R$^{19}$.

$R^{15}$ and $R^{16}$ are independently selected from:
  hydrogen, halogen, —$OR^{20}$, —$SR^{20}$, —$N(R^{20})_2$, —$NO_2$, —CN, and $C_{1-6}$ alkyl optionally substituted with one or more substituents independently selected from halogen, —$OR^{20}$, —$SR^{20}$, —$N(R^{20})_2$, —$NO_2$, and —CN;
  or $R^{15}$ together with $R^{11}$ form a saturated $C_{3-10}$ carbocycle or 3- to 10-membered heterocycle, which is optionally substituted with one or more $R^{19}$.
each $R^{17}$ and $R^{18}$ is independently selected from:
  halogen, —$SR^{20}$, —$N(R^{20})_2$, —$NO_2$, —CN, and $C_{1-6}$ alkyl optionally substituted with one or more substituents independently selected from halogen, —$OR^{20}$, —$SR^{20}$, —$N(R^{20})_2$, —$NO_2$, and —CN; or
  $R^{17}$ together with $R^{11}$ form a $C_{5-10}$ carbocycle or 5- to 10-membered heterocycle, which is optionally substituted with one or more $R^{19}$;
$R^{19}$ is independently selected from:
  halogen, —$OR^{20}$, —$SR^{20}$, —$N(R^{20})_2$, —$C(O)R^{20}$, —$C(O)N(R^{20})_2$, —$N(R^{20})C(O)R^{20}$, —$N(R^{20})C(O)N(R^{20})_2$, —$OC(O)N(R^{20})_2$, —$N(R^{20})C(O)OR^{20}$, —$C(O)OR^{20}$, —$OC(O)R^{20}$, —$S(O)R^{20}$, —$S(O)_2R^{20}$, —$NO_2$, =O, =S, =$N(R^{10})$, and —CN; and
  $C_{1-3}$ alkyl, $C_{2-3}$ alkenyl, and $C_{2-3}$ alkynyl, each of which is optionally substituted with one or more substituents independently selected from halogen, —$OR^{20}$, —$SR^{20}$, —$N(R^{20})_2$, —$C(O)R^{20}$, —$C(O)N(R^{20})_2$, —$N(R^{20})C(O)R^{20}$, —$N(R^{20})C(O)N(R^{20})_2$, —$OC(O)N(R^{20})_2$, —$N(R^{20})C(O)OR^{20}$, —$C(O)OR^{20}$, —$OC(O)R^{20}$, —$S(O)R^{20}$, —$S(O)_2R^{20}$, —$NO_2$, =O, =S, =$N(R^{20})$, and —CN;
each $R^{20}$ is independently selected from:
  hydrogen;
  $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —$N(C_{1-6}$ alkyl$)_2$, —$NH(C_{1-6}$ alkyl), $C_{3-10}$ carbocycle, and 3- to 10-membered heterocycle; and
  $C_{3-10}$ carbocycle, and 3- to 10-membered heterocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —$N(C_{1-6}$ alkyl$)_2$, —$NH(C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and haloalkyl;
w is 0, 1, or 2
z is 0, 1, or 2; and
v is 1, 2, 3, 4, or 5, and when $R^{11}$ is other than —$CH_3$, v is further selected from 0.

In certain aspects, disclosed herein is a compound represented by Formula (II):

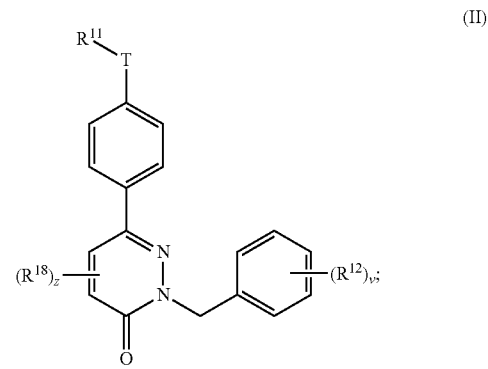

(II)

or a salt thereof, wherein:
T is selected from —O—, —$NR^{14}$—, —$CR^{15}R^{16}$—, —C(O)—, —S—, —S(O)—, and —$S(O)_2$;
$R^{11}$ is selected from:
  $C_{1-6}$ alkyl, $C_{2-6}$ alkenyl, and $C_{2-6}$ alkynyl, each of which is substituted with one or more substituents independently selected from halogen, —$OR^{20}$, —$SR^{20}$, —$N(R^{20})_2$, —$C(O)R^{20}$, —$C(O)N(R^{20})_2$, —$N(R^{20})C(O)R^{20}$, —$N(R^{20})C(O)N(R^{20})_2$, —$OC(O)N(R^{20})_2$, —$N(R^{20})C(O)OR^{20}$, —$C(O)OR^{20}$, —$OC(O)R^{20}$, —$S(O)R^{20}$, —$S(O)_2R^{20}$, —$NO_2$, =O, =S, =$N(R^{20})$, —CN, $C_{3-5}$ carbocycle, and 3- to 10-membered heterocycle, wherein the $C_{3-5}$ carbocycle and 3- to 10-membered heterocycle are each optionally substituted with one or more $R^{19}$;
  and $C_{3-10}$ carbocycle and 3- to 10-membered heterocycle, each of which is optionally substituted with one or more substituents independently selected from halogen, —$OR^{20}$, —$SR^{20}$, —$N(R^{20})_2$, —$C(O)R^{20}$, —$C(O)N(R^{20})_2$, —$N(R^{20})C(O)R^{20}$, —$N(R^{20})C(O)N(R^{20})_2$, —$OC(O)N(R^{20})_2$, —$N(R^{20})C(O)OR^{20}$, —$C(O)OR^{20}$, —$OC(O)R^{20}$, —$S(O)R^{20}$, —$S(O)_2R^{20}$, —$NO_2$, =O, =S, =$N(R^{20})$, and —CN; or
  $R^{11}$ together with $R^{15}$ form a 3- to 10-membered heterocycle or $C_{3-10}$ carbocycle, wherein the 3- to 10-membered heterocycle or saturated $C_{3-10}$ carbocycle is optionally substituted with one or more $R^{19}$; or $R^{11}$ together with $R^{14}$ form a 3- to 10-membered heterocycle, wherein the 3- to 10-membered heterocycle is optionally substituted with one or more $R^{19}$.
when T is —$NR^{14}$—, $R^{11}$ is additionally selected from hydrogen, and when T is —C(O)—, $R^{11}$ is additionally selected from —$N(R^{20})_2$ and —$OR^{20}$;
each $R^{12}$ is independently selected from:
  halogen, —$OR^{20}$, —$SR^{20}$, —$N(R^{20})_2$, —$C(O)R^{20}$, —$C(O)N(R^{20})_2$, —$N(R^{20})C(O)N(R^{20})_2$, —$OC(O)N(R^{20})_2$, —$C(O)OR^{20}$, —$OC(O)R^{20}$, —$S(O)R^{20}$, —$S(O)_2R^{20}$, —$NO_2$, —CN;
  $C_{1-3}$ alkyl optionally substituted with one or more substituents independently selected from halogen, —$OR^{20}$, —$SR^{20}$, —$N(R^{20})_2$, —$C(O)R^{20}$, —$C(O)N(R^{20})_2$, —$N(R^{20})C(O)R^{20}$, —$C(O)OR^{20}$, —$N(R^{20})C(O)N(R^{20})_2$, —$OC(O)N(R^{20})_2$, —$N(R^{20})C(O)OR^{20}$, —$OC(O)R^{20}$, —$S(O)R^{20}$, —$S(O)_2R^{20}$, —$NO_2$, =O, =S, =$N(R^{20})$, and —CN; and
  $C_{3-10}$ carbocycle optionally substituted with one or more substituents independently selected from halogen, —$OR^{20}$, —$SR^{20}$, —$N(R^{20})_2$, —$C(O)R^{20}$, —$C(O)N(R^{20})_2$, —$N(R^{20})C(O)R^{20}$, —$N(R^{20})C(O)N(R^{20})_2$, —$OC(O)N(R^{20})_2$, —$N(R^{20})C(O)OR^{20}$, —$C(O)OR^{20}$, —OC(O)R$^{20}$, —S(O)R$^{20}$, —S(O)$_2$R$^{20}$, —NO$_2$, =O, =S, =N(R$^{20}$), and —CN;

R$^{14}$ is independently selected from
  hydrogen; and
  C$_{1-6}$ alkyl optionally substituted with one or more substituents independently selected from halogen, —OR$^{20}$, —SR$^{20}$, —N(R$^{20}$)$_2$, —NO$_2$, and —CN; or
  R$^{14}$ together with R$^{11}$ form a 3- to 10-membered heterocycle, which is optionally substituted with one or more R$^{19}$;

R$^{15}$ together with R$^{11}$ form a saturated C$_{3-10}$ carbocycle or 3- to 10-membered heterocycle, which is optionally substituted with one or more R$^{19}$.

R$^{16}$ is independently selected from:
  hydrogen, halogen, —OR$^{20}$, —SR$^{20}$, —N(R$^{20}$)$_2$, —NO$_2$, —CN, and C$_{1-6}$ alkyl optionally substituted with one or more substituents independently selected from halogen, —OR$^{20}$, —SR$^{20}$, —N(R$^{20}$)$_2$, —NO$_2$, and —CN;

R$^{18}$ is independently selected from:
  halogen, —SR$^{20}$, —N(R$^{20}$)$_2$, —NO$_2$, and C$_{2-6}$ alkyl optionally substituted with one or more substituents independently selected from halogen, —OR$^{20}$, —SR$^{20}$, —N(R$^{20}$)$_2$, —NO$_2$, and —CN;

R$^{19}$ is independently selected from
  halogen, —OR$^{20}$, —SR$^{20}$, —N(R$^{20}$)$_2$, —C(O)R$^{20}$, —C(O)N(R$^{20}$)$_2$, —N(R$^{20}$)C(O)R$^{20}$, —N(R$^{20}$)C(O)N(R$^{20}$)$_2$, —OC(O)N(R$^{20}$)$_2$, —N(R$^{20}$)C(O)OR$^{20}$, —C(O)OR$^{20}$, —OC(O)R$^{20}$, —S(O)R$^{20}$, —S(O)$_2$R$^{20}$, —NO$_2$, =O, =S, =N(R$^{10}$), and —CN; and
  C$_{1-3}$ alkyl, C$_{2-3}$ alkenyl, and C$_{2-3}$ alkynyl, each of which is optionally substituted with one or more substituents independently selected from halogen, —OR$^{20}$, —SR$^{20}$, —N(R$^{20}$)$_2$, —C(O)R$^{20}$, —C(O)N(R$^{20}$)$_2$, —N(R$^{20}$)C(O)R$^{20}$, —N(R$^{20}$)C(O)N(R$^{20}$)$_2$, —OC(O)N(R$^{20}$)$_2$, —N(R$^{20}$)C(O)OR$^{20}$, —C(O)OR$^{20}$, —OC(O)R$^{20}$, —S(O)R$^{20}$, —S(O)$_2$R$^{20}$, —NO$_2$, =O, =S, =N(R$^{20}$), and —CN;

each R$^{20}$ is independently selected from
  hydrogen;
  C$_{1-6}$ alkyl, C$_{2-6}$ alkenyl, and C$_{2-6}$ alkynyl, each of which is optionally substituted with one or more substituents independently selected from halogen, —CN, —OH, —SH, —NO$_2$, —NH$_2$, =O, =S, —O—C$_{1-6}$ alkyl, —S—C$_{1-6}$ alkyl, —N(C$_{1-6}$ alkyl)$_2$, —NH(C$_{1-6}$ alkyl), C$_{3-10}$ carbocycle, and 3- to 10-membered heterocycle; and
  C$_{3-10}$ carbocycle, and 3- to 10-membered heterocycle, each of which is optionally substituted with one or more substituents independently selected from halogen, —CN, —OH, —SH, —NO$_2$, —NH$_2$, =O, =S, —O—C$_{1-6}$ alkyl, —S—C$_{1-6}$ alkyl, —N(C$_{1-6}$ alkyl)$_2$, —NH(C$_{1-6}$ alkyl), C$_{1-6}$ alkyl, C$_{2-6}$ alkenyl, C$_{2-6}$ alkynyl, C$_{3-10}$ carbocycle, 3- to 10-membered heterocycle, and haloalkyl;

z is 0, 1, or 2; and
v is 1, 2, 3, 4, or 5.

In certain embodiments, for a compound or salt of Formula (II) or (II'), T is selected from —O—, —NR$^{14}$—, —CR$^{15}$R$^{16}$—, and —C(O)—. In some embodiments, T is selected from —O— and —NR$^{14}$—. In some embodiments, T is —O—. In some embodiments, T is —C(O)—. In some embodiments, T is —NR$^{14}$—, such as —NH—.

In certain embodiments, for a compound or salt of any one of Formula (II) or (II'), R$^{11}$ is C$_{1-6}$ alkyl optionally substituted with one or more substituents independently selected from halogen, —OR$^{20}$, —SR$^{20}$, —N(R$^{20}$)$_2$, —C(O)R$^{20}$, —C(O)N(R$^{20}$)$_2$, —N(R$^{20}$)C(O)R$^{20}$, —C(O)OR$^{20}$, —OC(O)R$^{20}$, —N(R$^{20}$)C(O)N(R$^{20}$)$_2$, —OC(O)N(R$^{20}$)$_2$, —N(R$^{20}$)C(O)OR$^{20}$, —S(O)R$^{20}$, —S(O)$_2$R$^{20}$, —NO$_2$, =O, =S, =N(R$^{20}$), —S(O)R$^{20}$, C$_{3-5}$ carbocycle and 3- to 10-membered heterocycle, wherein the C$_{3-5}$ carbocycle and 3- to 10-membered heterocycle are each optionally substituted with one or more R$^{19}$. In some embodiments, R$^{11}$ is C$_{1-6}$ alkyl substituted with one or more substituents independently selected from halogen, —OR$^{20}$, —SR$^{20}$, —N(R$^{20}$)$_2$, —C(O)R$^{20}$, —C(O)N(R$^{20}$)$_2$, —N(R$^{20}$)C(O)R$^{20}$, —C(O)OR$^{20}$, —OC(O)R$^{20}$, —N(R$^{20}$)C(O)N(R$^{20}$)$_2$, —OC(O)N(R$^{20}$)$_2$, —N(R$^{20}$)C(O)OR$^{20}$, —S(O)R$^{20}$, —S(O)$_2$R$^{20}$, —NO$_2$, =O, =S, =N(R$^{20}$), —CN, C$_{3-5}$ carbocycle and 3- to 10-membered heterocycle, wherein the C$_{3-5}$ carbocycle and 3- to 10-membered heterocycle are each optionally substituted with one or more R$^{19}$. In some embodiments, R$^{11}$ is C$_{1-6}$ alkyl substituted with one or more substituents independently selected from halogen, —OR$^{20}$, —N(R$^{20}$)$_2$, —C(O)R$^{20}$, —C(O)N(R$^{20}$)$_2$, —N(R$^{20}$)C(O)R$^{20}$, —C(O)OR$^{20}$, —OC(O)R$^{20}$, —NO$_2$, =O, =N(R$^{20}$), —CN, C$_{3-5}$ carbocycle and 3- to 10-membered heterocycle, wherein the C$_{3-5}$ carbocycle and 3- to 10-membered heterocycle are each optionally substituted with one or more R$^{19}$. In some embodiments, R$^{11}$ is selected from C$_{1-3}$ alkyl optionally substituted with one or more substituents independently selected from halogen, —OR$^{20}$, —SR$^{20}$, —N(R$^{20}$)$_2$, —NO$_2$, =O, =S, =N(R$^{20}$), —CN, C$_{3-5}$ carbocycle and 3- to 10-membered heterocycle, wherein the C$_3$-s carbocycle and 3- to 10-membered heterocycle are each optionally substituted with one or more R$^{19}$. In some embodiments, R$^{11}$ is C$_{1-3}$ alkyl substituted with one or more substituents independently selected from halogen, —OR$^{20}$, —N(R$^{20}$)$_2$, —NO$_2$, =O, —CN, C$_{3-5}$ carbocycle and 3- to 10-membered heterocycle, wherein the C$_{3-5}$ carbocycle and 3- to 10-membered heterocycle are each optionally substituted with one or more R$^{19}$. In some embodiments, R$^{11}$ is C$_{1-3}$ alkyl substituted with one or more halogen substituents. In some embodiments, R$^{11}$ is a C$_{1-3}$ fluoroalkyl. In some embodiments, R$^{11}$ is selected from —CHF$_2$, —CH$_2$F, —CF$_3$, —CH$_2$CHF$_2$, CH$_2$CH$_2$F, or —CH$_2$CF$_3$. In some embodiments, R$^{11}$ is CH$_2$CN. In some embodiments, R$^{11}$ is not unsubstituted methyl. In some embodiments, R$^{11}$ is —NH$_2$. In some embodiments, when A is —C(O)—, R$^{11}$ is —NH$_2$. In some embodiments, R$^{11}$ is C$_{1-3}$ alkyl substituted with —OR$^{20}$, wherein R$^{20}$ is C$_{1-3}$ alkyl substituted with one or more halogens. In some embodiments, R$^{11}$ is —CH$_2$CH$_2$—OR$^{20}$, wherein R$^{20}$ is —CHF$_2$ or —CH$_3$. In some embodiments, R$^{11}$ is C$_{1-3}$ alkyl substituted with =O. In some embodiments, R$^{11}$ is —C(O)—CH$_3$. In some embodiments, R$^{11}$ is —CH$_3$. In some embodiments, R$^{11}$ is selected from C$_{3-5}$ carbocycle and 3- to 10-membered heterocycle, wherein the C$_{3-5}$ carbocycle and 3- to 10-membered heterocycle are each optionally substituted with one or more R$^{19}$. In some embodiments, R$^{11}$ is C$_{3-5}$ carbocycle. In some embodiments, R$^{11}$ is cyclopropyl. In some embodiments, R$^{11}$ is a C$_{1-3}$ alkyl substituted with a 4- to 6-membered heterocycle, wherein the 4- to 6-membered heterocycle is substituted with one or more R$^{19}$. In some embodiments, R$^{11}$ is methyl substituted with a 4- to 6-membered heterocycle selected from

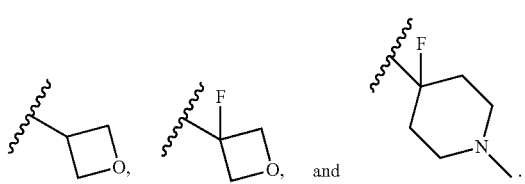

In certain embodiments, for a compound or salt of any one of Formula (II) or (II'), $R^{11}$ is selected from optionally substituted $C_3$-$C_6$ cycloalkyl, such as cyclopropyl, cyclobutyl, cyclopentyl, bicyclopentyl, and spiropentyl, any of which is optionally substituted. In certain embodiments, $R^{11}$ is selected from alkyl, e.g., methyl, ethyl, propyl, isopropyl, t-butyl, iso-butyl, sec-butyl, any of which may be optionally substituted. In certain embodiments, $R^{11}$ is selected from:

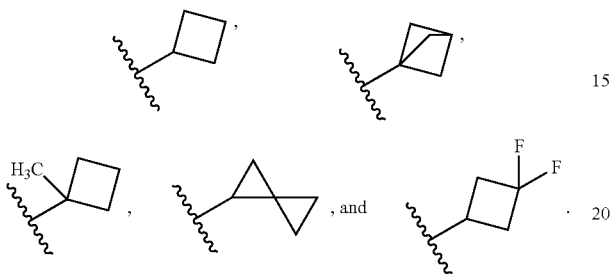

In certain embodiments, $R^{11}$ is selected from:

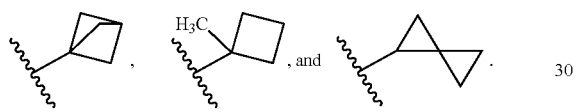

In certain embodiments, $R^{11}$ is selected from optionally substituted

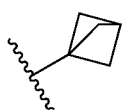

In certain embodiments, for a compound or salt of Formula (II) or (II'), $R^{11}$ together with $R^{17}$ form a 5- to 10-membered heterocycle or $C_{5-10}$ carbocycle, wherein the 5- to 10-membered heterocycle or $C_{5-10}$ carbocycle is optionally substituted with one or more $R^{19}$. In some embodiments, $R^{11}$ together with $R^{17}$ form a $C_{5-10}$ carbocycle or 5- to 10-membered heterocycle, such as a $C_{5-6}$ carbocycle or 5- to 6-membered heterocycle, for example:

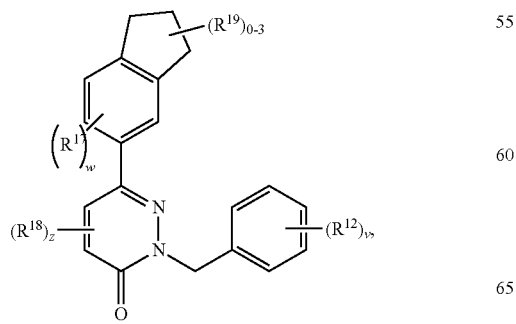

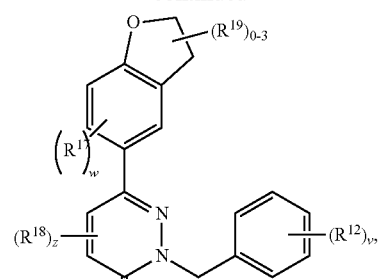

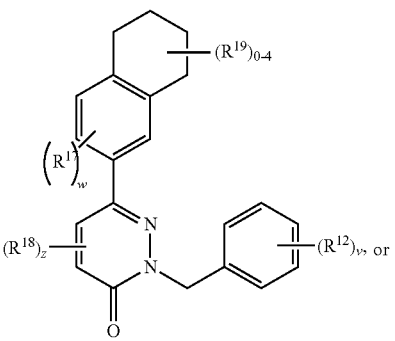

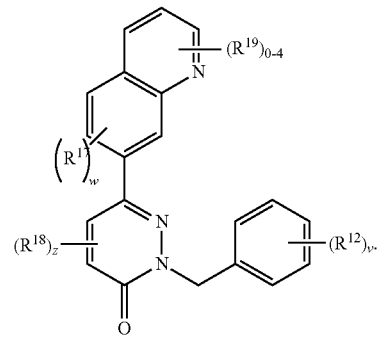

In certain embodiments, for a compound or salt of Formula (II) or (II'), $R^{11}$ together with $R^{15}$ form a 3- to 10-membered heterocycle or saturated $C_{3-10}$ carbocycle, wherein the 3- to 10-membered heterocycle or saturated $C_{3-10}$ carbocycle is optionally substituted with one or more $R^{19}$. In some embodiments, $R^{11}$ together with $R^{15}$ form a 3- to 10-membered heterocycle or saturated $C_{3-10}$ carbocycle, for example:

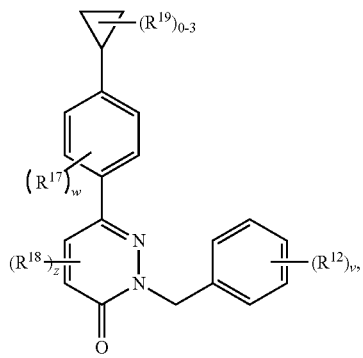

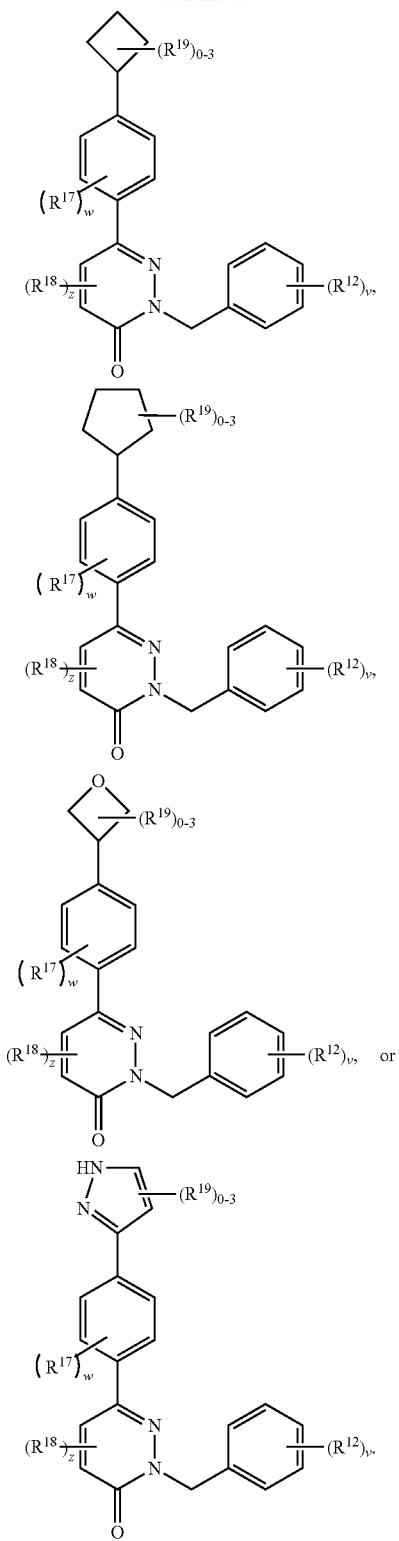

In certain embodiments, for a compound or salt of Formula (II) or (II'), $R^{11}$ together with $R^{14}$ form a 3- to 10-membered heterocycle, wherein the 3- to 10-membered heterocycle is optionally substituted with one or more $R^{19}$. In some embodiments, $R^{11}$ together with $R^{14}$ form a 3- to 10-membered heterocycle, for example:

In some embodiments, for a compound or salt of any one of Formula (II) or (II'), each $R^{12}$ is independently selected from halogen, —OR$^{20}$, —SR$^{20}$, —N(R$^{20}$)$_2$, —NO$_2$, —CN, and $C_{1-3}$ alkyl optionally substituted with one or more substituents independently selected from halogen, —OR$^{20}$, —SR$^{20}$, —N(R$^{20}$)$_2$, —NO$_2$, and —CN. In some embodiments, each $R^{12}$ is selected from —Cl, —F, and —OH.

In certain embodiments, for a compound or salt of Formula (II) or (II'), $R^{12}$ is selected from $C_{3-6}$ cycloalkyl, such as cyclopropyl, cyclobutyl, cyclopentyl, bicyclopentyl, and spiropentyl, any of which is optionally substituted. In certain embodiments, $R^{12}$ is

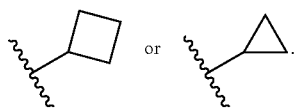

In certain embodiments, v is 0, 1, or 2. In certain embodiments, v is 0.

In some embodiments, for a compound or salt of any one of Formula (II) or (II'), when there is an $R^{12}$ at either or both ortho positions of the phenyl ring relative to the point of connectivity to the rest of the molecule, each ortho $R^{12}$ is independently selected from halogen, —$OR^{20}$, —$SR^{20}$, —$N(R^{20})_2$, —$NO_2$, —CN, and $C_{1-3}$ alkyl optionally substituted with one or more substituents independently selected from halogen, —$OR^{20}$, —$SR^{20}$, —$N(R^{20})_2$, —$NO_2$, and —CN. In some embodiments, for a compound or salt of any one of Formula (II) or (II'), when there is an $R^{12}$ at either or both ortho positions of the phenyl ring relative to the point of connectivity to the rest of the molecule, each $R^{12}$ is independently selected from halogen, —OH, —$OCH_3$, —$OCF_3$, and $C_{1-3}$ alkyl optionally substituted with one or more substituents independently selected from halogen.

In some embodiments, for a compound or salt of any of Formula (II) or (II'), if there is an $R^{12}$ at either ortho positions of the phenyl ring relative to the point of connectivity to the rest of the molecule, the $R^{12}$ is not selected from carbocycle or heterocycle. In some embodiments, for a compound or salt of any one of Formula (II) or (II'), there is not an $R^{12}$ at either ortho positions of the phenyl ring relative to the point of connectivity to the rest of the molecule.

In certain embodiments, for a compound or salt of any one of Formula (II) or (II'), $R^{14}$ is selected from hydrogen; and $C_{1-6}$ alkyl optionally substituted with one or more substituents independently selected from halogen, —$OR^{20}$, —$SR^{20}$, —$N(R^{20})_2$, —$NO_2$, and —CN; or $R^{14}$ together with $R^{11}$ form a 3- to 10-membered heterocycle, which is optionally substituted with one or more $R^{19}$. In some embodiments, $R^{14}$ is hydrogen. In some embodiments, $R^{14}$ is methyl. In some embodiments, $R^{14}$ together with $R^{11}$ form a 4- to 5-membered heterocycle, which is optionally substituted with one or more $R^{19}$, wherein $R^{19}$ is selected from methyl, —$CH_2F$, —$CHF_2$, —$CF_3$, —F, —$OCF_3$, and —$OCHF_2$.

In certain embodiments, for a compound or salt of any one of Formula (II) or (II'), each $R^{15}$ and $R^{16}$ is independently selected from hydrogen, halogen, —$OR^{20}$, —$SR^{20}$, —$N(R^{20})_2$, —$NO_2$, —CN, and $C_{1-6}$ alkyl optionally substituted with one or more substituents independently selected from halogen, —$OR^{20}$, —$SR^{20}$, —$N(R^{20})_2$, —$NO_2$, and —CN. In some embodiments, $R^{11}$ together with $R^{15}$ form a 3- to 10-membered heterocycle or saturated $C_{3-10}$ carbocycle. In some embodiments, $R^{11}$ together with $R^{15}$ form a cyclopropyl ring.

In certain embodiments, for a compound or salt of any one of Formula (II) or (II'), each $R^{17}$ is independently selected from halogen, —$OR^{20}$, —$SR^{20}$, —$N(R^{20})_2$, —$NO_2$, —CN, —$CHF_2$, —$CF_3$, —$CH_2F$, and $C_{2-6}$ alkyl optionally substituted with one or more substituents independently selected from halogen, —$OR^{20}$, —$SR^{20}$, —$N(R^{20})_2$, —$NO_2$, and —CN.

In certain embodiments, for a compound or salt of any one of Formula (II) or (II'), each $R^{18}$ is independently selected from halogen, —$OR^{20}$, —$SR^{20}$, —$N(R^{20})_2$, —$NO_2$, —$CHF_2$, —$CF_3$, —$CH_2F$, and $C_{2-6}$ alkyl optionally substituted with one or more substituents independently selected from halogen, —$OR^{20}$, —$SR^{20}$, —$N(R^{20})_2$, —$NO_2$, and —CN.

In some embodiments, for a compound or salt of any one of Formula (II) or (II'), $R^{17}$ together with $R^{11}$ form a 5- to 6-membered heterocycle or $C_{5-6}$ carbocycle, wherein the 5- to 6-membered heterocycle or $C_{5-6}$ carbocycle is optionally substituted with one or more $R^{19}$. In some embodiments, $R^{17}$ together with $R^{11}$ form a 5 membered heterocycle substituted with zero, one, or two methyl groups, for example:

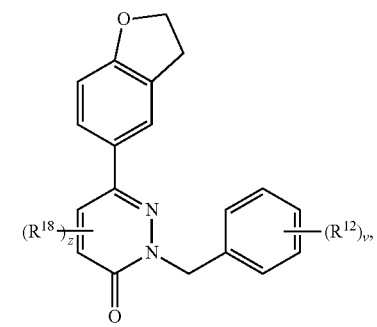

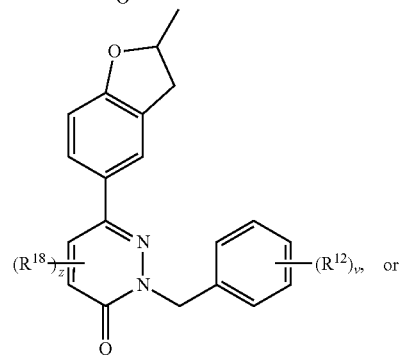

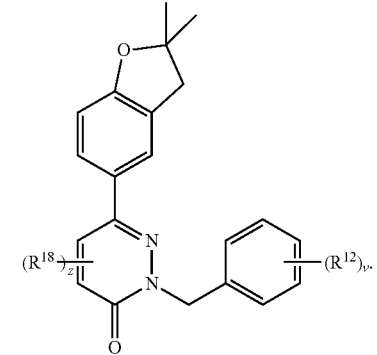

In certain embodiments, for a compound or salt of any one of Formula (II) or (II'), each $R^{19}$ is independently selected from halogen, —$OR^{20}$, —$SR^{20}$, —$N(R^{20})_2$, —$NO_2$, =O, =S, —CN; and $C_{1-3}$ alkyl, $C_{2-3}$ alkenyl, $C_{2-3}$ alkynyl, each of which is optionally substituted with one or more substituents independently selected from halogen, —$OR^{20}$, —$SR^{20}$, —$N(R^{20})_2$, —$NO_2$, —CN. In some embodiments, $R^{19}$ is a halogen. In some embodiments, $R^{19}$ is a —F. In some embodiments, $R^{19}$ is a $C_{1-3}$ haloalkyl. In some embodiments, $R^{19}$ is a $C_{1-3}$ alkyl substituted with one or more fluorine substituents. In some embodiments, $R^{19}$ is —$CH_2F$, —$CHF_2$ or —$CF_3$. In some embodiments, $R^{19}$ is an unsubstituted $C_{1-3}$ alkyl. In some embodiments, $R^{19}$ is methyl. In some embodiments, $R^{19}$ is —$OR^{20}$. In some embodiments, $R^{19}$ is —$OR^{20}$, and $R^{20}$ is haloalkyl. In some embodiments, $R^{19}$ is —$OR^{20}$, and $R^{20}$ is —$CH_2F$, —$CHF_2$ or —$CF_3$. In some embodiments, two $R^{19}$ groups come together to form a 3- to 10-membered heterocycle or $C_{3-10}$ carbocycle optionally substituted with one or more $R^{20}$. In some embodiments, two $R^{19}$ groups come together to form a spirocyclic $C_{3-5}$ carbocycle substituted with one of more fluorine substituents. In some embodiments, two $R^{19}$ groups come together to form spirocyclic cyclcobutane substituted with two fluorine substituents.

In certain embodiments, for a compound or salt of any one of Formula (II) or (II'), each $R^{20}$ is independently selected from hydrogen; and $C_{1-6}$ alkyl optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{3-10}$ carbocycle, 3- to 10-membered heterocycle, and haloalkyl. In some embodiments, $R^{20}$ is —F.

In certain embodiments, for a compound of Formula (II), w is 0.

In certain embodiments, for a compound of Formula (II) or (II'), z is 0.

In certain embodiments, for a compound of Formula (II) or (II'), v is 1 or 2.

In certain embodiments, a compound of Formula (II) is represented by Formula (IIa):

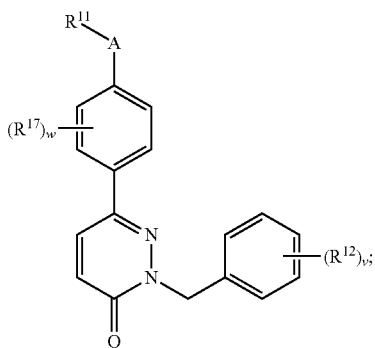

(IIa)

or a salt thereof, wherein:
A is selected from —O—, —$NR^{14}$—, —$CR^{15}R^{16}$—, and —C(O)—;
$R^{11}$ is selected from:
  $C_{1-6}$ alkyl optionally substituted with one or more substituents independently selected from halogen, —$OR^{20}$, —$N(R^{20})_2$, —$C(O)R^{20}$, —CN, $C_{3-6}$ carbocycle, and 4- to 6-membered heterocycle, wherein the $C_{3-6}$ carbocycle and 4- to 6-membered heterocycle are each optionally substituted with one or more $R^9$; and
  $C_{3-6}$ carbocycle; or
  $R^{11}$ together with $R^{13}$ form a 5- to 10-membered heterocycle, wherein the 5- to 10-membered heterocycle is optionally substituted with one or more $R^{19}$; or $R^{11}$ together with $R^{15}$ form a saturated $C_{3-5}$ carbocycle or; or $R^{11}$ together with $R^{14}$ form a 4- to 6-membered heterocycle, wherein the 4- to 6-membered heterocycle is optionally substituted with one or more $R^{19}$; and
  when A is —C(O)—, $R^{11}$ is additionally selected from —$N(R^{20})_2$ and —$OR^{20}$;
each $R^{12}$ is independently selected from halogen, —$OR^{20}$, —$SR^{20}$, —$N(R^{20})_2$, —$NO_2$, —CN;
$R^{17}$ together with $R^{11}$ form a 5- to 10-membered heterocycle optionally substituted with one or more $R^{19}$
each $R^{19}$ is independently selected from:
  halogen, —$OR^{20}$, —$SR^{20}$, —$N(R^{20})_2$, —$NO_2$, —CN; and
  $C_{1-3}$ alkyl optionally substituted with one or more substituents independently selected from halogen, —$OR^{20}$, —$SR^{20}$, —$N(R^{20})_2$, —$NO_2$, and —CN; and
  two $R^{19}$ groups come together to form a 4- to 6-membered heterocycle or $C_{3-6}$ carbocycle optionally substituted with one or more $R^{20}$, wherein the 4- to 6-membered heterocycle or $C_{3-6}$ carbocycle is optionally spirocyclic;
each $R^{20}$ is independently selected from:
  hydrogen; and
  $C_{1-6}$ alkyl optionally substituted with one or more substituents independently selected from halogen, —CN, —OH, —SH, —$NO_2$, —$NH_2$, —O—$C_{1-6}$ alkyl, —N($C_{1-6}$ alkyl)$_2$, and —NH($C_{1-6}$ alkyl);
w is 0 or 1; and
v is 1 or 2.

In certain embodiments, for a compound or salt of Formula (II') or (IIa), w is 0.

In certain embodiments, for a compound or salt of any one of Formula (II), (II') or (IIa), $R^{11}$-T is further selected from hydrogen. For example, a compound of Formula (II') may be further selected from:

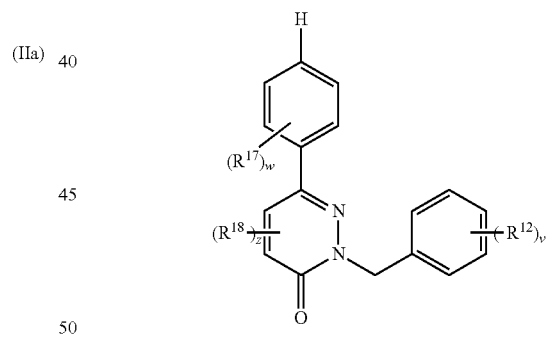

or a salt thereof wherein $R^{17}$, $R^{18}$, $R^{12}$, w, z, and v are as described for Formula (II').

In certain embodiments, a compound of the disclosure is selected from a compound of Table 2 or a salt thereof.

Chemical entities having carbon-carbon double bonds or carbon-nitrogen double bonds may exist in Z- or E-form (or cis- or trans-form). Furthermore, some chemical entities may exist in various tautomeric forms. Unless otherwise specified, compounds described herein are intended to include all Z-, E- and tautomeric forms as well.

A "tautomer" refers to a molecule wherein a proton shift from one atom of a molecule to another atom of the same molecule is possible. The compounds presented herein, in certain embodiments, exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

hedron, 1989, 45(21), 6601-21; and Evans, E. Anthony. Synthesis of radiolabeled compounds, J. Radioanal. Chem., 1981, 64(1-2), 9-32.

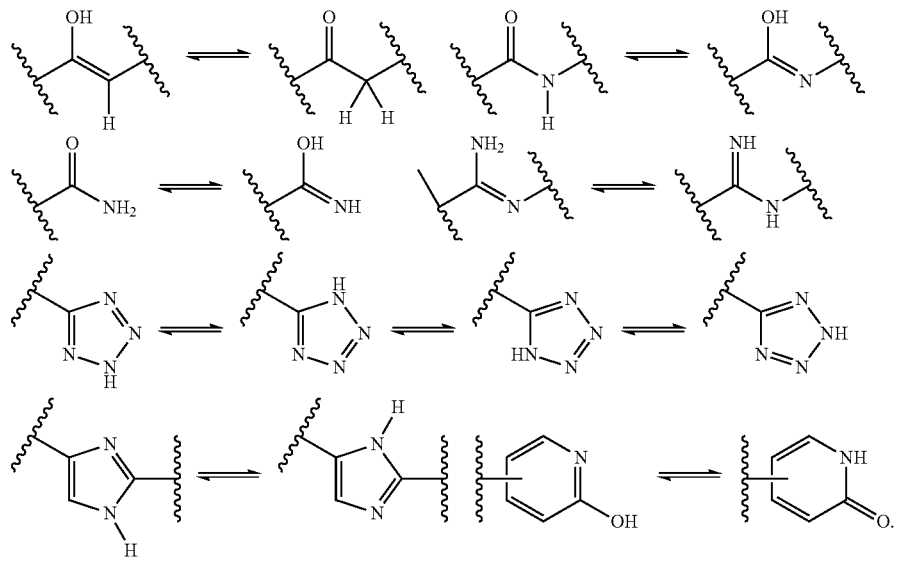

The compounds disclosed herein, in some embodiments, are used in different enriched isotopic forms, e.g., enriched in the content of $^2$H, $^3$H, $^{11}$C, $^{13}$C and/or $^{14}$C. In one particular embodiment, the compound is deuterated in at least one position. Such deuterated forms can be made by the procedure described in U.S. Pat. Nos. 5,846,514 and 6,334,997. As described in U.S. Pat. Nos. 5,846,514 and 6,334,997, deuteration can improve the metabolic stability and or efficacy, thus increasing the duration of action of drugs.

Unless otherwise stated, compounds described herein are intended to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of the present disclosure.

The compounds of the present disclosure optionally contain unnatural proportions of atomic isotopes at one or more atoms that constitute such compounds. For example, the compounds may be labeled with isotopes, such as for example, deuterium ($^2$H), tritium ($^3$H), iodine-125 ($^{125}$I) or carbon-14 ($^{14}$C). Isotopic substitution with $^2$H, $^{11}$C, $^{13}$C, $^{14}$C, $^{15}$C, $^{12}$N, $^{13}$N, $^{15}$N, $^{16}$N, $^{16}$O, $^{17}$O, $^{14}$F, $^{15}$F, $^{16}$F, $^{17}$F, $^{18}$F, $^{33}$S, $^{34}$S, $^{35}$S, $^{36}$S, $^{35}$Cl, $^{37}$Cl, $^{79}$Br, $^{81}$Br, and $^{125}$I are all contemplated. All isotopic variations of the compounds of the present invention, whether radioactive or not, are encompassed within the scope of the present invention.

In certain embodiments, the compounds disclosed herein have some or all of the $^1$H atoms replaced with $^2$H atoms. The methods of synthesis for deuterium-containing compounds are known in the art and include, by way of non-limiting example only, the following synthetic methods.

Deuterium substituted compounds are synthesized using various methods such as described in: Dean, Dennis C.; Editor. Recent Advances in the Synthesis and Applications of Radiolabeled Compounds for Drug Discovery and Development. [In: Curr., Pharm. Des., 2000; 6(10)] 2000, 110 pp; George W.; Varma, Rajender S. The Synthesis of Radiolabeled Compounds via Organometallic Intermediates, Tetra- Deuterated starting materials are readily available and are subjected to the synthetic methods described herein to provide for the synthesis of deuterium-containing compounds. Large numbers of deuterium-containing reagents and building blocks are available commercially from chemical vendors, such as Aldrich Chemical Co.

Compounds of the present invention also include crystalline and amorphous forms of those compounds, pharmaceutically acceptable salts, and active metabolites of these compounds having the same type of activity, including, for example, polymorphs, pseudopolymorphs, solvates, hydrates, unsolvated polymorphs (including anhydrates), conformational polymorphs, and amorphous forms of the compounds, as well as mixtures thereof.

Included in the present disclosure are salts, particularly pharmaceutically acceptable salts, of the compounds described herein. The compounds of the present disclosure that possess a sufficiently acidic, a sufficiently basic, or both functional groups, can react with any of a number of inorganic bases, and inorganic and organic acids, to form a salt. Alternatively, compounds that are inherently charged, such as those with a quaternary nitrogen, can form a salt with an appropriate counterion, e.g., a halide such as bromide, chloride, or fluoride, particularly bromide.

The compounds described herein may in some cases exist as diastereomers, enantiomers, or other stereoisomeric forms. The compounds presented herein include all diastereomeric, enantiomeric, and epimeric forms as well as the appropriate mixtures thereof. Separation of stereoisomers may be performed by chromatography or by forming diastereomers and separating by recrystallization, or chromatography, or any combination thereof. (Jean Jacques, Andre Collet, Samuel H. Wilen, "Enantiomers, Racemates and Resolutions", John Wiley And Sons, Inc., 1981, herein incorporated by reference for this disclosure). Stereoisomers may also be obtained by stereoselective synthesis.

The methods and compositions described herein include the use of amorphous forms as well as crystalline forms (also known as polymorphs). The compounds described herein may be in the form of pharmaceutically acceptable salts. As well, in some embodiments, active metabolites of these compounds having the same type of activity are included in the scope of the present disclosure. In addition, the compounds described herein can exist in unsolvated as well as solvated forms with pharmaceutically acceptable solvents such as water, ethanol, and the like. The solvated forms of the compounds presented herein are also considered to be disclosed herein.

In certain embodiments, compounds or salts of the compounds may be prodrugs, e.g., wherein a hydroxyl in the parent compound is presented as an ester or a carbonate, or carboxylic acid present in the parent compound is presented as an ester. The term "prodrug" is intended to encompass compounds which, under physiologic conditions, are converted into pharmaceutical agents of the present disclosure. One method for making a prodrug is to include one or more selected moieties which are hydrolyzed under physiologic conditions to reveal the desired molecule. In other embodiments, the prodrug is converted by an enzymatic activity of the host animal such as specific target cells in the host animal. For example, esters or carbonates (e.g., esters or carbonates of alcohols or carboxylic acids and esters of phosphonic acids) are preferred prodrugs of the present disclosure.

Prodrug forms of the herein described compounds, wherein the prodrug is metabolized in vivo to produce a compound as set forth herein are included within the scope of the claims. In some cases, some of the herein-described compounds may be a prodrug for another derivative or active compound.

Prodrugs are often useful because, in some situations, they may be easier to administer than the parent drug. They may, for instance, be bioavailable by oral administration whereas the parent is not. Prodrugs may help enhance the cell permeability of a compound relative to the parent drug. The prodrug may also have improved solubility in pharmaceutical compositions over the parent drug. Prodrugs may be designed as reversible drug derivatives, for use as modifiers to enhance drug transport to site-specific tissues or to increase drug residence inside of a cell.

In some embodiments, the design of a prodrug increases the lipophilicity of the pharmaceutical agent. In some embodiments, the design of a prodrug increases the effective water solubility. See, e.g., Fedorak et al., *Am. J. Physiol.*, 269: G210-218 (1995); McLoed et al., *Gastroenterol*, 106: 405-413 (1994); Hochhaus et al., *Biomed. Chrom.*, 6:283-286 (1992); J. Larsen and H. Bundgaard, *Int. J Pharmaceutics*, 37, 87 (1987); J. Larsen et al., *Int. J. Pharmaceutics*, 47, 103 (1988); Sinkula et al., *J. Pharm. Sci.*, 64:181-210 (1975); T. Higuchi and V. Stella, *Pro-drugs as Novel Delivery Systems*, Vol. 14 of the *A.C.S. Symposium Series*; and Edward B. Roche, Bioreversible Carriers in Drug Design, American Pharmaceutical Association and Pergamon Press, 1987, all incorporated herein for such disclosure). According to another embodiment, the present disclosure provides methods of producing the above-defined compounds. The compounds may be synthesized using conventional techniques. Advantageously, these compounds are conveniently synthesized from readily available starting materials.

Synthetic chemistry transformations and methodologies useful in synthesizing the compounds described herein are known in the art and include, for example, those described in R. Larock, *Comprehensive Organic Transformations* (1989); T. W. Greene and P. G. M. Wuts, *Protective Groups in Organic Synthesis*, 2d. Ed (1991); L. Fieser and M. Fieser, *Fieser and Fieser's Reagents for Organic Synthesis* (1994); and L. Paquette, ed., *Encyclopedia of Reagents for Organic Synthesis* (1995).

Therapeutic Applications

Methods of administration of a compound or salt of Formula (I), (Ia), (Ib), (Ic), (Id), (Ie), (II), (II'), or (IIa) discussed herein may be used for the treatment of neuromuscular conditions and movement disorders. Examples of neuromuscular conditions include but are not limited to Duchenne Muscular Dystrophy, Becker muscular dystrophy, myotonic dystrophy 1, myotonic dystrophy 2, facioscapulohumeral muscular dystrophy, oculopharyngeal muscular dystrophy, limb girdle muscular dystrophies, tendinitis and carpal tunnel syndrome. Examples of movement disorders include but are not limited to muscle spasticity disorders, spasticity associated with multiple sclerosis, Parkinson's disease, Alzheimer's disease, or cerebral palsy, or injury or a traumatic event such as stroke, traumatic brain injury, spinal cord injury, hypoxia, meningitis, encephalitis, phenylketonuria, or amyotrophic lateral sclerosis. Also included are other conditions that may respond to the inhibition of skeletal myosin II, skeletal troponin C, skeletal troponin I, skeletal tropomyosin, skeletal troponin T, skeletal regulatory light chains, skeletal myosin binding protein C or skeletal actin.

In some embodiments, disclosed herein are methods to treat neuromuscular and movement disorders by the administration of a compound or salt of Formula (I), (Ia), (Ib), (Ic), (Id), (Ie), (II), (II') or (IIa). In some embodiments, disclosed herein are methods to treat neuromuscular and movement disorders by the administration of a compound or salt of Formula (III):

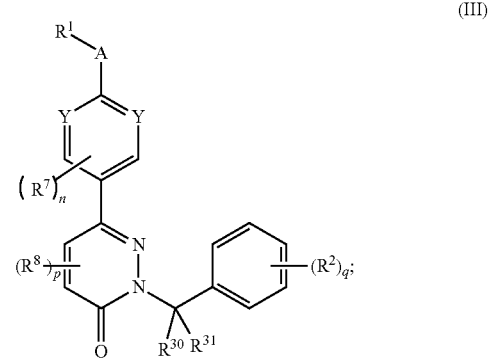

or a salt thereof, wherein:
each Y is independently selected from C($R^3$), N, and $N^+$(—$O^-$);
A is absent or selected from —O—, —$NR^4$—, —$CR^5R^6$—, —C(O)—, —S—, —S(O)—, and —S($O)_2$—;
$R^1$ is selected from:
$C_{1-6}$ alkyl, $C_{2-6}$ alkenyl, and $C_{2-6}$ alkynyl, each of which is optionally substituted with one or more substituents independently selected from halogen, —$OR^{10}$, —$SR^{10}$, —N($R^{10})_2$, —C(O)$R^{10}$, —C(O)N($R^{10})_2$, —N($R^{10}$)C(O)$R^{10}$, —N($R^{10}$)C(O)N($R^{10})_2$, —OC(O)N($R^{10})_2$, —N($R^{10}$)C(O)O$R^{10}$, —C(O)O$R^{10}$, —OC(O)$R^{10}$, —S(O)$R^{10}$, —S($O)_2R^{10}$, —$NO_2$, =O, =S, =N($R^{10}$), —CN, $C_{3-10}$ carbocycle, and 3- to 10-membered heterocycle, wherein the $C_{3-10}$ carbocycle and 3- to 10-membered heterocycle are each optionally substituted with one or more $R^9$; and $C_{3-10}$ carbocycle and 3- to 10-membered heterocycle, each of which is optionally substituted with one or more substituents independently selected from halogen, —OR$^{10}$, —SR$^{10}$, —N(R$^{10}$)$_2$, —C(O)R$^{10}$, —C(O)N(R$^{10}$)$_2$, —N(R$^{10}$)C(O)R$^{10}$, —N(R$^{10}$)C(O)N(R$^{10}$)$_2$, —OC(O)N(R$^{10}$)$_2$, —N(R$^{10}$)C(O)OR$^{10}$, —C(O)OR$^{10}$, —OC(O)R$^{10}$, —S(O)R$^{10}$, —S(O)$_2$R$^{10}$, —NO$_2$, =O, =S, =N(R$^{10}$), and —CN; or $R^1$ together with $R^3$ form a 5- to 10-membered heterocycle or $C_{5-10}$ carbocycle, wherein the 5- to 10-membered heterocycle or $C_{5-10}$ carbocycle is optionally substituted with one or more $R^9$; or $R^1$ together with $R^5$ form a 3- to 10-membered heterocycle or saturated $C_{3-10}$ carbocycle, wherein the 3- to 10-membered heterocycle or saturated $C_{3-10}$ carbocycle is optionally substituted with one or more $R^9$; or $R^1$ together with $R^4$ form a 3- to 10-membered heterocycle, wherein the 3- to 10-membered heterocycle is optionally substituted with one or more $R^9$; and when A is —NR$^4$—, $R^1$ is additionally selected from hydrogen, and when A is —C(O)—, $R^1$ is additionally selected from —N(R$^{10}$)$_2$ and —OR$^{10}$;

when A is absent $R^1$ is further selected from halogen, —OR$^{10}$, —SR$^{10}$, —N(R$^{10}$)$_2$, —C(O)R$^{10}$, —C(O)N(R$^{10}$)$_2$, —N(R$^{10}$)C(O)R$^{10}$, —N(R$^{10}$)C(O)N(R$^{10}$)$_2$, —OC(O)N(R$^{10}$)$_2$, —N(R$^{10}$)C(O)OR$^{10}$, —C(O)OR$^{10}$, —OC(O)R$^{10}$, —S(O)R$^{10}$, —S(O)$_2$R$^{10}$, —NO$_2$, and —CN;

each $R^2$ is independently selected from:

halogen, —OR$^{10}$, —SR$^{10}$, —N(R$^{10}$)$_2$, —C(O)R$^{10}$, —C(O)N(R$^{10}$)$_2$, —N(R$^{10}$)C(O)R$^{10}$, —N(R$^{10}$)C(O)N(R$^{10}$)$_2$, —OC(O)N(R$^{10}$)$_2$, —N(R$^{10}$)C(O)OR$^{10}$, —C(O)OR$^{10}$, —OC(O)R$^{10}$, —S(O)R$^{10}$, —S(O)$_2$R$^{10}$, —NO$_2$, and —CN;

$C_{1-3}$ alkyl, $C_{2-3}$ alkenyl, and $C_{2-3}$ alkynyl, each of which is optionally substituted with one or more substituents independently selected from halogen, —OR$^{10}$, —SR$^{10}$, —N(R$^{10}$)$_2$, —C(O)R$^{10}$, —C(O)N(R$^{10}$)$_2$, —N(R$^{10}$)C(O)R$^{10}$, —N(R$^{10}$)C(O)N(R$^{10}$)$_2$, —OC(O)N(R$^{10}$)$_2$, —N(R$^{10}$)C(O)OR$^{10}$, —C(O)OR$^{10}$, —OC(O)R$^{10}$, —S(O)R$^{10}$, —S(O)$_2$R$^{10}$, —NO$_2$, =O, =S, =N(R$^{10}$), and —CN; and $C_{3-10}$ carbocycle optionally substituted with one or more substituents independently selected from: halogen, —OR$^{10}$, —SR$^{10}$, —N(R$^{10}$)$_2$, —C(O)R$^{10}$, —C(O)N(R$^{10}$)$_2$, —N(R$^{10}$)C(O)R$^{10}$, —N(R$^{10}$)C(O)N(R$^{10}$)$_2$, —OC(O)N(R$^{10}$)$_2$, —N(R$^{10}$)C(O)OR$^{10}$, —C(O)OR$^{10}$, —OC(O)R$^{10}$, —S(O)R$^{10}$, —S(O)$_2$R$^{10}$, —NO$_2$, =O, =S, =N(R$^{10}$), and —CN each $R^3$, $R^5$, and $R^6$ is independently selected from:

hydrogen, halogen, —OR$^{10}$, —SR$^{10}$, —N(R$^{10}$)$_2$, —NO$_2$, and —CN; and $C_{1-6}$ alkyl optionally substituted with one or more substituents independently selected from halogen, —OR$^{10}$, —SR$^{10}$, —N(R$^{10}$)$_2$, —NO$_2$, and —CN; or $R^3$ together with $R^1$ form a 5- to 10-membered heterocycle or $C_{5-10}$ carbocycle, wherein the 5- to 10-membered heterocycle or $C_{5-10}$ carbocycle is optionally substituted with one or more $R^9$; or $R^5$ together with $R^1$ form a 3- to 10-membered heterocycle or saturated $C_{3-10}$ carbocycle, wherein the 3- to 10-membered heterocycle or saturated $C_{3-10}$ carbocycle is optionally substituted with one or more $R^9$;

$R^4$ is independently selected from:

hydrogen; and $C_{1-6}$ alkyl optionally substituted with one or more substituents independently selected from halogen, —OR$^{10}$, —SR$^{10}$, —N(R$^{10}$)$_2$, —NO$_2$, and —CN; or $R^4$ together with $R^1$ form a 3- to 10-membered heterocycle, which is optionally substituted with one or more $R^9$;

each $R^7$ and $R^8$ is independently selected from:

halogen, —OR$^{10}$, —SR$^{10}$, —N(R$^{10}$)$_2$, —NO$_2$, —CN, —CHF$_2$, —CF$_3$, —CH$_2$F, and $C_{2-6}$ alkyl optionally substituted with one or more substituents independently selected from halogen, —OR$^{10}$, —SR$^{10}$, —N(R$^{10}$)$_2$, —NO$_2$, and —CN;

each $R^9$ is independently selected from:

halogen, —OR$^{10}$, —SR$^{10}$, —N(R$^{10}$)$_2$, —C(O)R$^{10}$, —C(O)N(R$^{10}$)$_2$, —N(R$^{10}$)C(O)R$^{10}$, —N(R$^{10}$)C(O)N(R$^{10}$)$_2$, —OC(O)N(R$^{10}$)$_2$, —N(R$^{10}$)C(O)OR$^{10}$, —C(O)OR$^{10}$, —OC(O)R$^{10}$, —S(O)R$^{10}$, —S(O)$_2$R$^{10}$, —NO$_2$, =O, =S, =N(R$^{10}$), and —CN; and $C_{1-3}$ alkyl, $C_{2-3}$ alkenyl, and $C_{2-3}$ alkynyl, each of which is optionally substituted with one or more substituents independently selected from halogen, —OR$^{10}$, —SR$^{10}$, —N(R$^{10}$)$_2$, —C(O)R$^{10}$, —C(O)N(R$^{10}$)$_2$, —N(R$^{10}$)C(O)R$^{10}$, —N(R$^{10}$)C(O)N(R$^{10}$)$_2$, —OC(O)N(R$^{10}$)$_2$, —N(R$^{10}$)C(O)OR$^{10}$, —C(O)OR$^{10}$, —OC(O)R$^{10}$, —S(O)R$^{10}$, —S(O)$_2$R$^{10}$, —NO$_2$, =O, =S, =N(R$^{10}$), and —CN;

each $R^{10}$ is independently selected from:

hydrogen;

$C_{1-6}$ alkyl, $C_{2-6}$ alkenyl, and $C_{2-6}$ alkynyl, each of which is optionally substituted with one or more substituents independently selected from halogen, —CN, —OH, —SH, —NO$_2$, —NH$_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, and 3- to 10-membered heterocycle; and $C_{3-10}$ carbocycle, and 3- to 10-membered heterocycle, each of which is optionally substituted with one or more substituents independently selected from halogen, —CN, —OH, —SH, —NO$_2$, —NH$_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and haloalkyl;

$R^{30}$ and $R^{31}$ are independently selected from $R^{10}$ or $R^{30}$ and $R^{31}$ come together to form a $C_{3-7}$ carbocycle, or 3- to 7-membered heterocycle, wherein $C_{3-7}$ carbocycle and 3- to 7-membered heterocycle are optionally substituted with one or more substituents independently selected from $R^9$;

n is 0, 1, or 2;

p is 0, 1, or 2; and q is 0, 1, 2, 3, 4, or 5.

In some embodiments, disclosed herein are methods to treat neuromuscular and movement disorders by the administration of a compound or salt of Formula (III'):

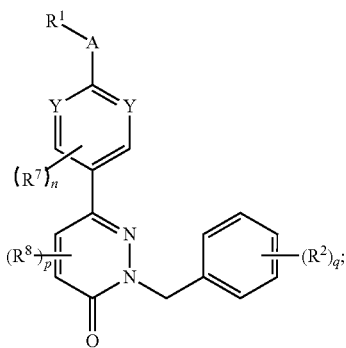

(III')

or a salt thereof, wherein:

each Y is independently selected from $C(R^3)$, N, and $N^+(—O^-)$;

A is selected from —O—, —$NR^4$—, —$CR^5R^6$—, —C(O)—, —S—, —S(O)—, and —$S(O)_2$—;

$R^1$ is selected from:

$C_{1-6}$ alkyl, $C_{2-6}$ alkenyl, and $C_{2-6}$ alkynyl, each of which is optionally substituted with one or more substituents independently selected from halogen, —$OR^{10}$, —$SR^{10}$, —$N(R^{10})_2$, —$C(O)R^{10}$, —$C(O)N(R^{10})_2$, —$N(R^{10})C(O)R^{10}$, —$N(R^{10})C(O)N(R^{10})_2$, —$OC(O)N(R^{10})_2$, —$N(R^{10})C(O)OR^{10}$, —$C(O)OR^{10}$, —$OC(O)R^{10}$, —$S(O)R^{10}$, —$S(O)_2R^{10}$, —$NO_2$, =O, =S, =$N(R^{10})$, —CN, $C_{3-10}$ carbocycle, and 3- to 10-membered heterocycle, wherein the $C_{3-10}$ carbocycle and 3- to 10-membered heterocycle are each optionally substituted with one or more $R^9$; and $C_{3-10}$ carbocycle and 3- to 10-membered heterocycle, each of which is optionally substituted with one or more substituents independently selected from halogen, —$OR^{10}$, —$SR^{10}$, —$N(R^{10})_2$, —$C(O)R^{10}$, —$C(O)N(R^{10})_2$, —$N(R^{10})C(O)R^{10}$, —$N(R^{10})C(O)N(R^{10})_2$, —$OC(O)N(R^{10})_2$, —$N(R^{10})C(O)OR^{10}$, —$C(O)OR^{10}$, —$OC(O)R^{10}$, —$S(O)R^{10}$, —$S(O)_2R^{10}$, —$NO_2$, =O, =S, =$N(R^{10})$, and —CN; or $R^1$ together with $R^3$ form a 5- to 10-membered heterocycle or $C_{5-10}$ carbocycle, wherein the 5- to 10-membered heterocycle or $C_{5-10}$ carbocycle is optionally substituted with one or more $R^9$; or $R^1$ together with $R^5$ form a 3- to 10-membered heterocycle or saturated $C_{3-10}$ carbocycle, wherein the 3- to 10-membered heterocycle or saturated $C_{3-10}$ carbocycle is optionally substituted with one or more $R^9$; or $R^1$ together with $R^4$ form a 3- to 10-membered heterocycle, wherein the 3- to 10-membered heterocycle is optionally substituted with one or more $R^9$; and when A is —$NR^4$—, $R^1$ is additionally selected from hydrogen, and when A is —C(O)—, $R^1$ is additionally selected from —$N(R^{10})_2$ and —$OR^{10}$;

each $R^2$ is independently selected from:

halogen, —$OR^{10}$, —$SR^{10}$, —$N(R^{10})_2$, —$C(O)R^{10}$, —$C(O)N(R^{10})_2$, —$N(R^{10})C(O)R^{10}$, —$N(R^{10})C(O)N(R^{10})_2$, —$OC(O)N(R^{10})_2$, —$N(R^{10})C(O)OR^{10}$, —$C(O)OR^{10}$, —$OC(O)R^{10}$, —$S(O)R^{10}$, —$S(O)_2R^{10}$, —$NO_2$, and —CN; and $C_{1-3}$ alkyl, $C_{2-3}$ alkenyl, and $C_{2-3}$ alkynyl, each of which is optionally substituted with one or more substituents independently selected from halogen, —$OR^{10}$, —$SR^{10}$, —$N(R^{10})_2$, —$C(O)R^{10}$, —$C(O)N(R^{10})_2$, —$N(R^{10})C(O)R^{10}$, —$N(R^{10})C(O)N(R^{10})_2$, —$OC(O)N(R^{10})_2$, —$N(R^{10})C(O)OR^{10}$, —$C(O)OR^{10}$, —$OC(O)R^{10}$, —$S(O)R^{10}$, —$S(O)_2R^{10}$, —$NO_2$, =O, =S, =$N(R^{10})$, and —CN;

each $R^3$, $R^5$, and $R^6$ is independently selected from:

hydrogen, halogen, —$OR^{10}$, —$SR^{10}$, —$N(R^{10})_2$, —$NO_2$, and —CN; and $C_{1-6}$ alkyl optionally substituted with one or more substituents independently selected from halogen, —$OR^{10}$, —$SR^{10}$, —$N(R^{10})_2$, —$NO_2$, and —CN; or $R^3$ together with $R^1$ form a 5- to 10-membered heterocycle or $C_{5-10}$ carbocycle, wherein the 5- to 10-membered heterocycle or $C_{5-10}$ carbocycle is optionally substituted with one or more $R^9$; $R^5$ together with $R^1$ form a 3- to 10-membered heterocycle or saturated $C_{3-10}$ carbocycle, wherein the 3- to 10-membered heterocycle or saturated $C_{3-10}$ carbocycle is optionally substituted with one or more $R^9$;

$R^4$ is independently selected from:

hydrogen; and $C_{1-6}$ alkyl optionally substituted with one or more substituents independently selected from halogen, —$OR^{10}$, —$SR^{10}$, —$N(R^{10})_2$, —$NO_2$, and —CN; or $R^4$ together with $R^1$ form a 3- to 10-membered heterocycle, which is optionally substituted with one or more $R^9$;

each $R^7$ and $R^8$ is independently selected from:

halogen, —$OR^{10}$, —$SR^{10}$, —$N(R^{10})_2$, —$NO_2$, —CN, —$CHF_2$, —$CF_3$, —$CH_2F$, and $C_{2-6}$ alkyl optionally substituted with one or more substituents independently selected from halogen, —$OR^{10}$, —$SR^{10}$, —$N(R^{10})_2$, —$NO_2$, and —CN;

each $R^9$ is independently selected from:

halogen, —$OR^{10}$, —$SR^{10}$, —$N(R^{10})_2$, —$C(O)R^{10}$, —$C(O)N(R^{10})_2$, —$N(R^{10})C(O)R^{10}$, —$N(R^{10})C(O)N(R^{10})_2$, —$OC(O)N(R^{10})_2$, —$N(R^{10})C(O)OR^{10}$, —$C(O)OR^{10}$, —$OC(O)R^{10}$, —$S(O)R^{10}$, —$S(O)_2R^{10}$, —$NO_2$, =O, =S, =$N(R^{10})$, and —CN; and $C_{1-3}$ alkyl, $C_{2-3}$ alkenyl, and $C_{2-3}$ alkynyl, each of which is optionally substituted with one or more substituents independently selected from halogen, —$OR^{10}$, —$SR^{10}$, —$N(R^{10})_2$, —$C(O)R^{10}$, —$C(O)N(R^{10})_2$, —$N(R^{10})C(O)R^{10}$, —$N(R^{10})C(O)N(R^{10})_2$, —$OC(O)N(R^{10})_2$, —$N(R^{10})C(O)OR^{10}$, —$C(O)OR^{10}$, —$OC(O)R^{10}$, —$S(O)R^{10}$, —$S(O)_2R^{10}$, —$NO_2$, =O, =S, =$N(R^{10})$, and —CN;

each $R^{10}$ is independently selected from:

hydrogen;

$C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —$N(C_{1-6}$ alkyl$)_2$, —$NH(C_{1-6}$ alkyl), $C_{3-10}$ carbocycle, and 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —$N(C_{1-6}$ alkyl$)_2$, —$NH(C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and haloalkyl;

n is 0, 1, or 2;

p is 0, 1, or 2; and q is 0, 1, 2, 3, 4, or 5.

In certain embodiments, for a compound or salt of Formula (III) or (III'), at least one Y is N, and $N^+(—O^-)$. In certain embodiments, for a compound or salt of Formula (III) or (III'), one Y is N and the other is C(R³) or each Y is N.

In certain embodiments, for a compound or salt of Formula (III) or (III'), each Y is independently selected from C(R³) and N wherein at least one Y is N. In some embodiments, one Y is N and one Y is C(R³). In some embodiments, one Y is N⁺(—O⁻) and one Y is C(R³). In some embodiments, each Y is N. In some embodiments, one Y is N, and one Y is N⁺(—O⁻). In certain embodiments, for a compound or salt of Formula (III) or (III'), each Y is C(R³).

In certain embodiments, for a compound or salt of any one of Formula (III) or (III'), A is selected from —O—, —NR⁴—, —CR⁵R⁶—, and —C(O)—. In some embodiments, A is selected from —O— and —NR⁴. In some embodiments, A is —O—. In some embodiments, A is —C(O)—. In some embodiments, A is —NR⁴—, such as —NH—.

In certain embodiments, for a compound or salt of any one of Formula (III) or (III'), $R^1$ is $C_{1-6}$ alkyl optionally substituted with one or more substituents independently selected from halogen, —OR¹⁰, —SR¹⁰, —N(R¹⁰)₂, —C(O)R¹⁰, —C(O)N(R¹⁰)₂, —N(R¹⁰)C(O)R¹⁰, —C(O)OR¹⁰, —OC(O)R¹⁰, —N(R¹⁰)C(O)N(R¹⁰)₂, —OC(O)N(R¹⁰)₂, —N(R¹⁰)C(O)OR¹⁰, —S(O)R¹⁰, —S(O)₂R¹⁰, —NO₂, =O, =S, =N(R¹⁰), —CN, $C_{3-10}$ carbocycle and 3- to 10-membered heterocycle, wherein the $C_{3-10}$ carbocycle and 3- to 10-membered heterocycle are each optionally substituted with one or more $R^9$. In some embodiments, $R^1$ is $C_{1-6}$ alkyl substituted with one or more substituents independently selected from halogen, —OR¹⁰, —SR¹⁰, —N(R¹⁰)₂, —C(O)R¹⁰, —C(O)N(R¹⁰)₂, —N(R¹⁰)C(O)R¹⁰, —C(O)OR¹⁰, —OC(O)R¹⁰, —N(R¹⁰)C(O)N(R¹⁰)₂, —OC(O)N(R¹⁰)₂, —N(R¹⁰)C(O)OR¹⁰, —S(O)R¹⁰, —S(O)₂R¹⁰, —NO₂, =O, =S, =N(R¹⁰), —CN, $C_{3-10}$ carbocycle and 3- to 10-membered heterocycle, wherein the $C_{3-10}$ carbocycle and 3- to 10-membered heterocycle are each optionally substituted with one or more $R^9$.

In certain embodiments, for a compound or salt of any one of Formula (III) or (III'), $R^1$ is $C_{1-6}$ alkyl substituted with one or more substituents independently selected from halogen, —OR¹⁰, —N(R¹⁰)₂, —C(O)R¹⁰, —C(O)N(R¹⁰)₂, —N(R¹⁰)C(O)R¹⁰, —C(O)OR¹⁰, —OC(O)R¹⁰, —NO₂, =O, =N(R¹⁰), —CN, $C_{3-10}$ carbocycle and 3- to 10-membered heterocycle, wherein the $C_{3-10}$ carbocycle and 3- to 10-membered heterocycle are each optionally substituted with one or more $R^9$. In some embodiments, $R^1$ is selected from $C_{1-3}$ alkyl optionally substituted with one or more substituents independently selected from halogen, —OR¹⁰, —SR¹⁰, —N(R¹⁰)₂, —NO₂, =O, =S, =N(R¹⁰), —CN, $C_{3-10}$ carbocycle and 3- to 10-membered heterocycle, wherein the $C_{3-10}$ carbocycle and 3- to 10-membered heterocycle are each optionally substituted with one or more $R^9$. In some embodiments, $R^1$ is $C_{1-3}$ alkyl substituted with one or more substituents independently selected from halogen, —OR¹⁰, —N(R¹⁰)₂, —NO₂, =O, —CN, $C_{3-10}$ carbocycle and 3- to 10-membered heterocycle, wherein the $C_{3-10}$ carbocycle and 3- to 10-membered heterocycle are each optionally substituted with one or more $R^9$. In some embodiments, $R^1$ is $C_{1-3}$ alkyl substituted with one or more halogen substituents. In some embodiments, $R^1$ is a $C_{1-3}$ fluoroalkyl. In some embodiments, $R^1$ is selected from —CHF₂, —CH₂F, —CF₃, —CH₂CHF₂, CH₂CH₂F, or —CH₂CF₃. In some embodiments, $R^1$ is not unsubstituted methyl. In some embodiments, $R^1$ is —NH₂. In some embodiments, when A is —C(O)—, $R^1$ is —NH₂. In some embodiments, $R^1$ is $C_{1-3}$ alkyl substituted with —OR¹⁰, wherein R¹⁰ is $C_{1-3}$ alkyl substituted with one or more halogens. In some embodiments, $R^1$ is —CH₂CH₂—OR¹⁰, wherein R¹⁰ is —CHF₂ or —CH₃. In some embodiments, $R^1$ is $C_{1-3}$ alkyl substituted with =O. In some embodiments, $R^1$ is —C(O)—CH₃. In some embodiments, $R^1$ is —CH₃. In some embodiments, $R^1$ is selected from $C_{3-10}$ carbocycle and 3- to 10-membered heterocycle, wherein the $C_{3-10}$ carbocycle and 3- to 10-membered heterocycle are each optionally substituted with one or more $R^9$. In some embodiments, $R^1$ is $C_{3-10}$ carbocycle. In some embodiments, $R^1$ is $C_{3-5}$ carbocycle. In some embodiments, $R^1$ is cyclopropyl. In some embodiments, $R^1$ is a $C_{1-3}$ alkyl substituted with a 4- to 6-membered heterocycle, wherein the 4- to 6-membered heterocycle is substituted with one or more $R^9$. In some embodiments, $R^1$ is-methyl substituted with a 4- to 6-membered heterocycle selected from

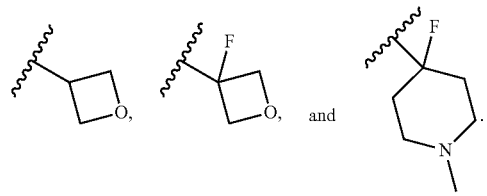

In certain embodiments, for a compound or salt of any one of Formula (III) or (III'), $R^1$ is selected from optionally substituted $C_3$-$C_6$ cycloalkyl, such as cyclopropyl, cyclobutyl, cyclopentyl, bicyclopentyl, and spiropentyl, any of which is optionally substituted. In certain embodiments, $R^1$ is selected from alkyl, e.g., methyl, ethyl, propyl, iso-propyl, t-butyl, iso-butyl, sec-butyl, any of which may be optionally substituted. In certain embodiments, $R^1$ is selected from:

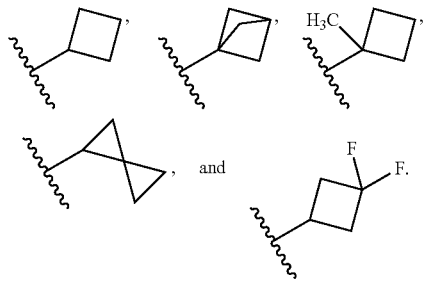

In certain embodiments, $R^1$ is selected from optionally substituted.

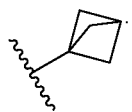

In certain embodiments, for a compound or salt of Formula (III) or (III'), $R^1$ together with $R^3$ form a 5- to 10-membered heterocycle or $C_{5-10}$ carbocycle, wherein the 5- to 10-membered heterocycle or $C_{5-10}$ carbocycle is optionally substituted with one or more $R^9$. In some embodiments, $R^1$ together with $R^3$ form a $C_{5-10}$ carbocycle or 5- to 10-membered heterocycle, such as a $C_{5-6}$ carbocycle or 5- to 6-membered heterocycle, for example:

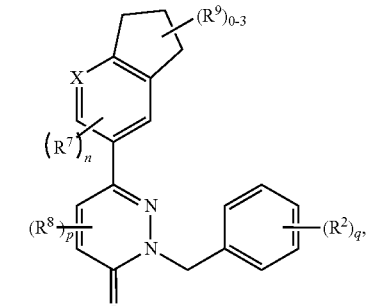

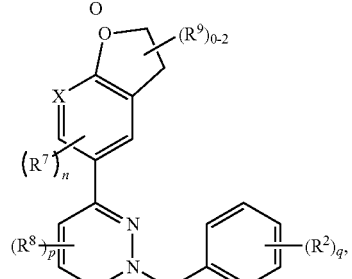

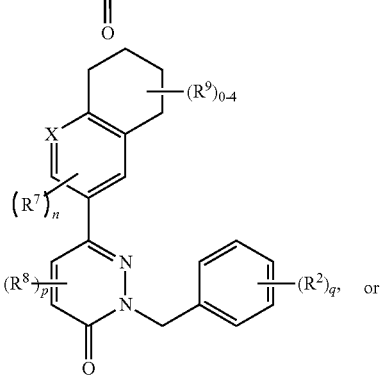

In certain embodiments, for a compound or salt of Formula (III) or (III'), $R^1$ together with $R^5$ form a 3- to 10-membered heterocycle or saturated $C_{3-10}$ carbocycle, wherein the 3- to 10-membered heterocycle or saturated $C_{3-10}$ carbocycle is optionally substituted with one or more $R^9$. In some embodiments, $R^1$ together with $R^5$ form a 3- to 10-membered heterocycle or saturated $C_{3-10}$ carbocycle, for example:

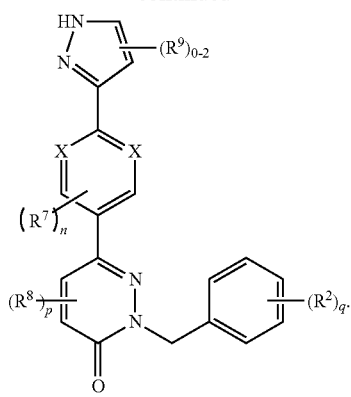

In certain embodiments, for a compound or salt of Formula (III) or (III'), $R^1$ together with $R^4$ form a 3- to 10-membered heterocycle, wherein the 3- to 10-membered heterocycle is optionally substituted with one or more $R^9$. In some embodiments, $R^1$ together with $R^4$ form a 3- to 10-membered heterocycle, for example:

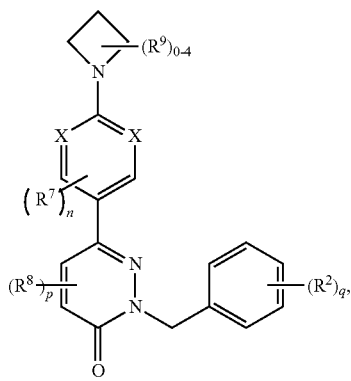

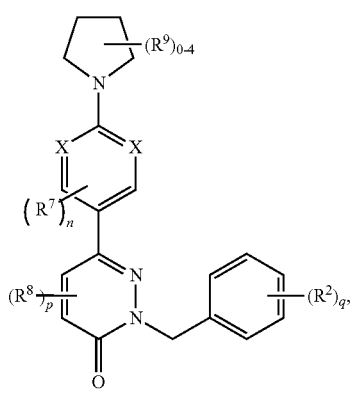

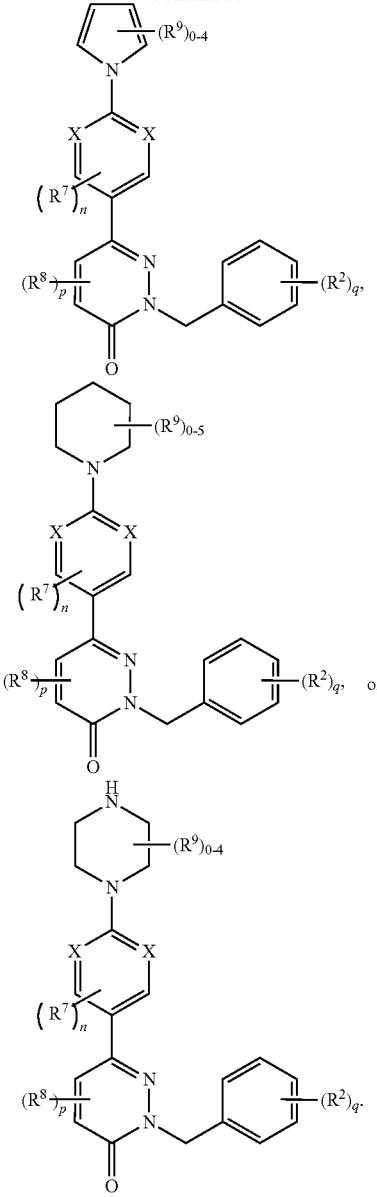

In some embodiments, for a compound or salt of any one of Formula (III) or (III'), each $R^2$ is independently selected from halogen, $-OR^{10}$, $-SR^{10}$, $-N(R^{10})_2$, $-NO_2$, $-CN$, and $C_{1-3}$ alkyl optionally substituted with one or more substituents independently selected from halogen, $-OR^{10}$, $-SR^{10}$, $-N(R^{10})_2$, $-NO_2$, and $-CN$. In some embodiments, for a compound or salt of any one of Formula (III) or (III'), $R^2$ is selected from $-Cl$, $-F$, and $-OH$. In certain embodiments, q is 0, 1, or 2. In certain embodiments, q is 0.

In some embodiments, for a compound or salt of any one of Formula (III) or (III'), when there is an $R^2$ at either or both ortho positions of the phenyl ring relative to the point of connectivity to the rest of the molecule, each ortho $R^2$ is independently selected from halogen, $-OR^{10}$, $-SR^{10}$, $-N(R^{10})_2$, $-NO_2$, $-CN$, and $C_{1-3}$ alkyl optionally substituted with one or more substituents independently selected from halogen, $-OR^{10}$, $-SR^{10}$, $-N(R^{10})_2$, $-NO_2$, and $-CN$. In some embodiments, for a compound or salt of any one of Formula (III) or (III'), when there is an $R^2$ at either or both ortho positions of the phenyl ring relative to the point of connectivity to the rest of the molecule, each $R^2$ is independently selected from halogen, —OH, —OCH$_3$, —OCF$_3$, and C$_{1-3}$ alkyl optionally substituted with one or more substituents independently selected from halogen.

In some embodiments, for a compound or salt of any of Formula (III) or (III'), if there is an $R^2$ at either ortho positions of the phenyl ring relative to the point of connectivity to the rest of the molecule, the $R^2$ is not selected from carbocycle or heterocycle. In some embodiments, for a compound or salt of any one of Formula (III) or (III'), there is not an $R^2$ at either ortho positions of the phenyl ring relative to the point of connectivity to the rest of the molecule.

In certain embodiments, for a compound or salt of Formula (III) or (III'), each $R^3$ is selected from hydrogen, halogen, —OR$^{10}$, —SR$^{10}$, —N(R$^{10}$)$_2$, —NO$_2$, —CN, and C$_{1-6}$ alkyl optionally substituted with one or more substituents independently selected from halogen, —OR$^{10}$, —SR$^{10}$, —N(R$^{10}$)$_2$, —NO$_2$, and —CN. In some embodiments, $R^3$ is hydrogen. In some embodiments, $R^3$ together with $R^1$ form a 5- to 6-membered heterocycle or C$_{5-6}$ carbocycle, wherein the 5- to 6-membered heterocycle or C$_{5-6}$ carbocycle is optionally substituted with one or more $R^9$. In some embodiments, $R^3$ together with $R^1$ form a 5 membered heterocycle substituted with zero, one, or two methyl groups, for example:

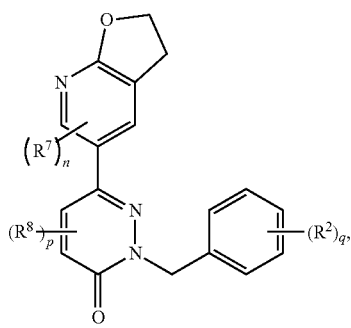

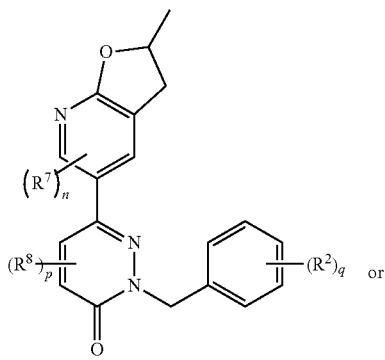 or

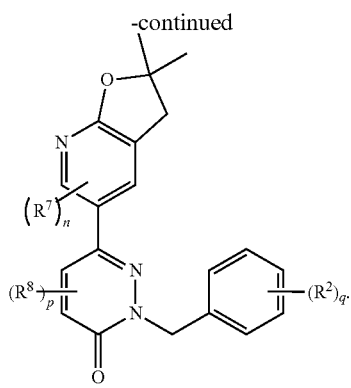

In certain embodiments, for a compound or salt of any one of Formula (III) or (III'), $R^4$ is independently selected from hydrogen; and C$_{1-6}$ alkyl optionally substituted with one or more substituents independently selected from halogen, —OR$^{10}$, —SR$^{10}$, —N(R$^{10}$)$_2$, —NO$_2$, and —CN; or $R^4$ together with $R^1$ form a 3- to 10-membered heterocycle, which is optionally substituted with one or more $R^9$. In some embodiments, $R^4$ is hydrogen. In some embodiments, $R^4$ is methyl. In some embodiments, $R^4$ together with $R^1$ form a 4- to 5-membered heterocycle, which is optionally substituted with one or more $R^9$, wherein $R^9$ is selected from methyl, —CH$_2$F, —CHF$_2$, —CF$_3$, —F, —OCF$_3$, and —OCHF$_2$.

In certain embodiments, for a compound or salt of any one of Formula (III) or (III'), each $R^5$ and $R^6$ is independently selected from hydrogen, halogen, —OR$^{10}$, —SR$^{10}$, —N(R$^{10}$)$_2$, —NO$_2$, —CN, and C$_{1-6}$ alkyl optionally substituted with one or more substituents independently selected from halogen, —OR$^{10}$, —SR$^{10}$, —N(R$^{10}$)$_2$, —NO$_2$, and —CN. In some embodiments, $R^1$ together with $R^5$ form a 3- to 10-membered heterocycle or saturated C$_{3-10}$ carbocycle. In some embodiments, $R^1$ together with $R^5$ form a cyclopropyl ring.

In certain embodiments, for a compound or salt of any one of Formula (III) or (III'), each $R^7$ and $R^8$ is independently selected from halogen, —OR$^{10}$, —SR$^{10}$, —N(R$^{10}$)$_2$, —NO$_2$, —CN, —CHF$_2$, —CF$_3$, —CH$_2$F, and C$_{2-6}$ alkyl optionally substituted with one or more substituents independently selected from halogen, —OR$^{10}$, —SR$^{10}$, —N(R$^{10}$)$_2$, —NO$_2$, and —CN.

In certain embodiments, for a compound or salt of any one of Formula (III) or (III'), each $R^9$ is independently selected from halogen, —OR$^{10}$, —SR$^{10}$, —N(R$^{10}$)$_2$, —NO$_2$, =O, =S, —CN; and C$_{1-3}$ alkyl, C$_{2-3}$ alkenyl, C$_{2-3}$ alkynyl, each of which is optionally substituted with one or more substituents independently selected from halogen, —OR$^{10}$, —SR$^{10}$, —N(R$^{10}$)$_2$, —NO$_2$, —CN. In some embodiments, $R^9$ is a halogen. In some embodiments, $R^9$ is a —F. In some embodiments, $R^9$ is a C$_{1-3}$ haloalkyl. In some embodiments, $R^9$ is a C$_{1-3}$ alkyl substituted with one or more fluorine substituents. In some embodiments, $R^9$ is —CH$_2$F, —CHF$_2$ or —CF$_3$. In some embodiments, $R^9$ is an unsubstituted C$_{1-3}$ alkyl. In some embodiments, $R^9$ is methyl. In some embodiments, $R^9$ is —OR$^{10}$. In some embodiments, $R^9$ is —OR$^{10}$, and $R^{10}$ is C$_{1-3}$ haloalkyl. In some embodiments, $R^9$ is —OR$^{10}$, and $R^{10}$ is —CH$_2$F, —CHF$_2$ or —CF$_3$. In some embodiments, two $R^9$ groups come together to form a 3- to 10-membered heterocycle or C$_{3-10}$ carbocycle optionally substituted with one or more $R^{10}$. In some embodiments, two $R^9$ groups come together to form a spirocyclic C$_{3-5}$ carbocycle substituted with one of more fluorine substituents. In some embodiments, two R⁹ groups come together to form spirocyclic cyclcobutane substituted with two fluorine substituents.

In certain embodiments, for a compound or salt of any one of Formula (III) or (III'), each $R^{10}$ is independently selected from hydrogen; and $C_{1-6}$ alkyl optionally substituted with one or more substituents independently selected from halogen, —CN, —OH, —SH, —NO₂, —NH₂, =O, =S, —O—$C_{1-6}$ alkyl, —S—$C_{1-6}$ alkyl, —N($C_{1-6}$ alkyl)₂, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —NO₂, —NH₂, =O, =S, —O—$C_{1-6}$ alkyl, —S—$C_{1-6}$ alkyl, —N($C_{1-6}$ alkyl)₂, —NH($C_{1-6}$ alkyl), $C_{1-6}$ alkyl, $C_{3-10}$ carbocycle, 3- to 10-membered heterocycle, and haloalkyl. In some embodiments, $R^{10}$ is —F.

In certain embodiments, for a compound or salt of any one of Formula (III) or (III'), n is 0.

In certain embodiments, for a compound or salt of any one of Formula (III) or (III'), p is 0.

In certain embodiments, for a compound or salt of any one of Formula (III) or (III'), $R^1$-A is further selected from hydrogen. For example, a compound of Formula (III) or (III') may be further selected from:

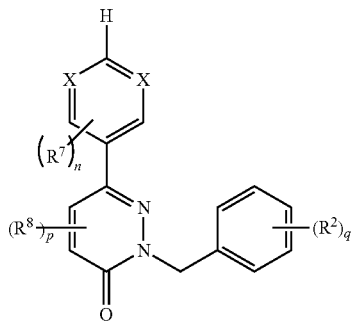

or a salt thereof.

Presented herein are methods to treat neuromuscular and movement disorders by reduction of skeletal muscle contraction. Treatment of subjects with neuromuscular and movement disorders with a selective fast skeletal muscle (type II) myosin inhibitor of a compound or salt of Formula (I), (Ia), (Ib), (Ic), (Id), (Ie), (II), (II'), (IIa), (III) or (III') may reduce muscle breakdown by preventing excessive uncoordinated muscle contractures resulting in less muscle damage. Furthermore, methods of the disclosure may reduce muscle damage while minimizing the impact on physical function in subjects. Preservation of function may occur both by limiting damaging levels of force generation in type II fibers and by increasing reliance on healthier type I fibers. Reduction of skeletal muscle contraction or uncoordinated muscle contractures can be reduced by the inhibition of skeletal myosin II. In certain embodiments, the inhibitor of skeletal myosin II is a compound or salt of Formula (I), (Ia), (Ib), (Ic), (Id), (Ie), (II), (II'), (IIa), (III) or (III') as disclosed herein.

In some embodiments, disclosed herein is a method of inhibiting muscle myosin II, comprising administering a compound of Formula (I), (Ia), (Ib), (Ic), (Id), (Ie), (II), (II'), (IIa), (III) or (III') to a subject in need thereof. In some embodiments, the compound or salt does not appreciably inhibit cardiac muscle contraction. In some embodiments, the compound or salt reduces cardiac muscle force by less than 10%.

In some aspects, methods of treating neuromuscular conditions or movement disorders may comprise administering a compound or salt of Formula (I), (Ia), (Ib), (Ic), (Id), (Ie), (II), (II'), (IIa), (III) or (III') to inhibit skeletal muscle contraction. In some embodiments, the compound or salt of Formula (I), (Ia), (Ib), (Ic), (Id), (Ie), (II), (II'), (IIa), (III) or (III') does not significantly inhibit cardiac muscle contraction. In some embodiments, cardiac muscle contraction is inhibited by 20% or less. In some embodiments, cardiac muscle contraction is inhibited by 15% or less. In some embodiments, cardiac muscle contraction is inhibited by 10% or less. In some embodiments, cardiac muscle contraction is inhibited by 9% or less. In some embodiments, cardiac muscle contraction is inhibited by 8% or less. In some embodiments, cardiac muscle contraction is inhibited by 7% or less. In some embodiments, cardiac muscle contraction is inhibited by 6% or less. In some embodiments, cardiac muscle contraction is inhibited by 5% or less. In some embodiments, cardiac muscle contraction is inhibited by 4% or less. In some embodiments, cardiac muscle contraction is inhibited by 3% or less. In some embodiments, cardiac muscle contraction is inhibited by 2% or less. In some embodiments, cardiac muscle contraction is inhibited by 1% or less.

A subject's activities of daily life (ADL) or habitual physical activity may be monitored prior to and following the treatment with a compound or salt of Formula (I), (Ia), (Ib), (Ic), (Id), (Ie), (II), (II'), (IIa), (III) or (III'). ADL or habitual physical activity is subject-dependent and may range from simple walking to extensive exercise depending on the subject's ability and routine. Treatment options and dosages of the skeletal muscle contraction inhibitors discussed herein may be personalized to a subject such that the ADL and habitual physical activity remains unchanged.

In some aspects, methods of treating neuromuscular conditions or movement disorders may comprise administering a compound or salt of Formula (I), (Ia), (Ib), (Ic), (Id), (Ie), (II), (II'), (IIa), (III) or (III') to inhibit skeletal muscle contraction. a compound or salt of Formula (I), (Ia), (Ib), (Ic), (Id), (Ie), (II), (II'), (IIa), (III) or (III') may be given in an amount relative to the amount needed to reduce skeletal muscle contraction by 50%. The compound or salt of Formula (I), (Ia), (Ib), (Ic), (Id), (Ie), (II), (II'), (IIa), (III) or (III') may be administered in an amount less than the amount needed to reduce skeletal muscle contraction by 50% relative to pre-treatment skeletal muscle contraction capacity of the subject. The compound or salt of Formula (I), (Ia), (Ib), (Ic), (Id), (Ie), (II), (II'), (IIa), (III) or (III') may be administered in an amount that reduces skeletal muscle contraction by 5% to 45% relative to pre-treatment skeletal muscle contraction capacity of said subject. In some cases, the compound or salt of Formula (I), (Ia), (Ib), (Ic), (Id), (Ie), (II), (II'), (IIa), (III) or (III') may be administered in an amount that reduces skeletal muscle contraction by less than 10%, less than 15%, less than 20%, less than 25%, less than 30%, less than 35%, less than 40%, less than 45% or even less than 50% relative to pre-treatment skeletal muscle contraction capacity of said subject. In certain embodiments, the compound or salt of Formula (I), (Ia), (Ib), (Ic), (Id), (Ie), (II), (II'), (IIa), (III) or (III') may be administered in an amount that reduces skeletal muscle contraction from 1% to 50% relative to pre-treatment skeletal muscle contraction capacity of said subject.

In some aspects, methods of treating neuromuscular conditions or movement disorders may comprise administering a compound or salt of Formula (I), (Ia), (Ib), (Ic), (Id), (Ie), (II), (II'), (IIa), (III) or (III') to inhibit type I skeletal muscle contraction. The inhibitor of type I skeletal muscle contraction may be given in an amount relative to the amount needed to reduce type I skeletal muscle contraction by 20%. The inhibitor of type I skeletal muscle contraction may be administered in an amount less than the amount needed to reduce type I skeletal muscle contraction by 20% relative to pre-treatment type I skeletal muscle contraction capacity of the subject. The inhibitor of type I skeletal muscle contraction may be administered in an amount that reduces type I skeletal muscle contraction by 0.01% to 20% relative to pre-treatment type I skeletal muscle contraction capacity of said subject. In some cases, the inhibitor may be administered in an amount that reduces type I skeletal muscle contraction by less than 0.01%, less than 0.1%, less than 0.5%, less than 1%, less than 5%, less than 10%, less than 15% or less than 20% relative to pre-treatment type I skeletal muscle contraction capacity of said subject. In certain embodiments, the inhibitor may be administered in an amount that reduces type I skeletal muscle contraction from 0.010% to 20% relative to pre-treatment type I skeletal muscle contraction capacity of said subject.

In some aspects, methods of treating neuromuscular conditions or movement disorders may comprise administering a compound or salt of Formula (I), (Ia), (Ib), (Ic), (Id), (Ie), (II), (II'), (IIa), (III) or (III') to inhibit type II skeletal muscle contraction. The inhibitor of type II skeletal muscle contraction may be given in an amount relative to the amount needed to reduce type II skeletal muscle contraction by 90%. The inhibitor of type II skeletal muscle contraction may be administered in an amount less than the amount needed to reduce type II skeletal muscle contraction by 90% relative to pre-treatment type II skeletal muscle contraction capacity of the subject. The inhibitor of type II skeletal muscle contraction may be administered in an amount that reduces type II skeletal muscle contraction by 5% to 75% relative to pre-treatment type II skeletal muscle contraction capacity of said subject. In some cases, the inhibitor may be administered in an amount that reduces type II skeletal muscle contraction by less than 10%, less than 15%, less than 20%, less than 25%, less than 30%, less than 35%, less than 40%, less than 45%, less than 50%, less than 55%, less than 60%, less than 65%, less than 70%, less than 75%, less than 80%, less than 85% or even less than 90% relative to pre-treatment type II skeletal muscle contraction capacity of said subject. In certain embodiments, the inhibitor may be administered in an amount that reduces type II skeletal muscle contraction by from T % to 50% relative to pre-treatment type II skeletal muscle contraction capacity of said subject.

In some aspects, methods of treating contraction-induced injury in skeletal muscle fiber may comprise administering a compound or salt of Formula (I), (Ia), (Ib), (Ic), (Id), (Ie), (II), (II'), (IIa), (III) or (III') to inhibit skeletal muscle contraction and/or skeletal muscle myosin II. In certain embodiments, the inhibitor does not appreciably inhibit cardiac muscle contraction.

In certain embodiments, the contraction-induced injury in skeletal muscle fiber is from involuntary skeletal muscle contraction. The involuntary skeletal muscle contraction may be associated with a neuromuscular condition or spasticity-associated condition. In certain embodiments, the contraction-induced injury in skeletal muscle fiber may be from voluntary skeletal muscle contraction, e.g., physical exercise.

In some aspects, methods of treating metabolic myopathies, e.g. McCardle's syndrome, may comprise administering a compound or salt of Formula (I), (Ia), (Ib), (Ic), (Id), (Ie), (II), (II'), (IIa), (III) or (III').

In certain embodiments, the administration of a compound or salt of Formula (I), (Ia), (Ib), (Ic), (Id), (Ie), (II), (II'), (IIa), (III) or (III') to a subject modulates one or more biomarkers associated with muscle contraction. Examples of biomarkers include but are not limited to creatinine kinase (CK), Troponin T (TnT), Troponin C (TnC), Troponin I (TnI), pyruvate kinase (PK), lactate dehydrogenase (LDH), myoglobin, isoforms of TnI (such as cardiac, slow skeletal, fast skeletal muscles) and inflammatory markers (IL-1, IL-6, IL-4, TNF-α). Biomarkers may also include measures of muscle inflammation for example, edema. The level of biomarkers described herein may increase after the administration of the inhibitor relative to pre-treatment level of the biomarkers. Alternatively, the level of biomarkers may decrease after the administration of the inhibitor relative to pre-treatment level of the biomarkers. The modulation of one or more biomarkers with an inhibitor described herein may indicate treatment of a neuromuscular condition such as those described herein.

Levels of CK in a subject increase when the subject is active as compared to when the subject is inactive (e.g., sleeping) and therefore CK is a potential metric for evaluating skeletal muscle breakdown caused by skeletal muscle contraction. In certain embodiments, an compound or salt of Formula (I), (Ia), (Ib), (Ic), (Id), (Ie), (II), (II'), (IIa), (III) or (III') may be administered to a subject prior to mild, moderate or strenuous activity to reduce or prevent skeletal muscle breakdown from the activity. Moderate to strenuous activity may be dependent on a subject's abilities and may include physical exercise that increases the heart rate by at least 20% or more, such as about 50% or more relative to the subject's resting heart rate. Examples of moderate to strenuous activity include walking, running, weight lifting, biking, swimming, hiking, etc.

In certain embodiments, a compound or salt of Formula (I), (Ia), (Ib), (Ic), (Id), (Ie), (II), (II'), (IIa), (III) or (III') is administered prior to, during, or after moderate or strenuous activity to reduce or prevent skeletal muscle breakdown from the activity. The compound or salt of Formula (I), (Ia), (Ib), (Ic), (Id), (Ie), (II), (II'), (IIa), (III) or (III) may reduce the subject's level of CK relative to the untreated subject performing the same activity. The level of CK may be measured in the peripheral blood of the subject during or after the activity. The administration of an inhibitor described herein may reduce the level of CK by 5% to 90% in an active subject relative to the untreated subject performing the same activity, thereby reducing or preventing skeletal muscle breakdown from the activity. The administration of an inhibitor described herein may modulate the level of CK by about 5% to about 90% relative to the untreated subject performing the same activity, thereby reducing or preventing skeletal muscle breakdown from the activity. The administration of an inhibitor described herein may reduce the level of CK by at least about 5% relative to the untreated subject performing the same activity thereby reducing or preventing skeletal muscle breakdown from the activity. The administration of an inhibitor described herein may modulate the level of CK by at most about 90% relative to the untreated subject performing the same activity. The administration of an inhibitor described herein may reduce the level of CK by about 5% to about 15%, about 5% to about 25%, about 5% to about 35%, about 5% to about 45%, about 5% to about 55%, about 5% to about 65%, about 5% to about 75%, about 5% to about 85%, about 5% to about 90%, about 15% to about 25%, about 15% to about 35%, about 15% to about 45%, about 15% to about 55%, about 15% to about 65%, about 15% to about 75%, about 15% to about 85%, about 15% to about 90%, about 25% to about 35%, about 25% to about 45%, about 25% to about 55%, about 25% to about 65%, about 25% to about 75%, about 25% to about 85%, about 25% to about 90%, about 35% to about 45%, about 35% to about 55%, about 35% to about 65%, about 35% to about 75%, about 35% to about 85%, about 35% to about 90%, about 45% to about 55%, about 45% to about 65%, about 45% to about 75%, about 45% to about 85%, about 45% to about 90%, about 55% to about 65%, about 55% to about 75%, about 55% to about 85%, about 55% to about 90%, about 65% to about 75%, about 65% to about 85%, about 65% to about 90%, about 75% to about 85%, about 75% to about 90%, or about 85% to about 90% relative to the untreated subject performing the same activity, thereby reducing or preventing skeletal muscle breakdown from the activity. The administration of an inhibitor described herein may modulate the level of CK by about 5%, about 15%, about 25%, about 35%, about 45%, about 55%, about 65%, about 75%, about 85%, or about 90% relative to the untreated subject performing the same activity, thereby reducing or preventing skeletal muscle breakdown from the activity.

The administration of a compound or salt of Formula (I), (Ia), (Ib), (Ic), (Id), (Ie), (II), (II'), (IIa), (III) or (III') to a subject may modulate the levels of inflammatory markers, e.g., reduce the level of one or more inflammatory markers relative to the untreated subject or the subject prior to treatment. The level of inflammatory markers may be measured in the peripheral blood of the subject. Examples of inflammatory markers may include but are not limited to IL-1, IL-6 and TNF-α. Inflammatory markers may also be in the form of conditions such as edema which may be measured using magnetic resonance imaging. The level of inflammatory markers in the peripheral blood may increase after the administration of the inhibitor relative to pre-treatment level of inflammatory marker for the subject. Alternatively, the level of inflammatory markers in the peripheral blood may decrease after the administration of the inhibitor relative to pre-treatment level of inflammatory marker for the subject. The administration of an inhibitor described herein may modulate the level of inflammatory markers by 5% to 90% relative to pre-treatment level of inflammatory marker for the subject. In some cases, the level of inflammatory markers may be modulated by about 5% to about 90% relative to pre-treatment level of inflammatory markers of the subject. In some cases, the level of inflammatory markers may be modulated by at least about 5% relative to pre-treatment level of inflammatory markers of the subject. In some cases, the level of inflammatory markers may be modulated by at most about 90% relative to pre-treatment level of inflammatory markers of the subject. In some cases, the level of inflammatory markers may be modulated by about 5% to about 15%, about 5% to about 25%, about 5% to about 35%, about 5% to about 45%, about 5% to about 55%, about 5% to about 65%, about 5% to about 75%, about 5% to about 85%, about 5% to about 90%, about 15% to about 25%, about 15% to about 35%, about 15% to about 45%, about 15% to about 55%, about 15% to about 65%, about 15% to about 75%, about 15% to about 85%, about 15% to about 90%, about 25% to about 35%, about 25% to about 45%, about 25% to about 55%, about 25% to about 65%, about 25% to about 75%, about 25% to about 85%, about 25% to about 90%, about 35% to about 45%, about 35% to about 55%, about 35% to about 65%, about 35% to about 75%, about 35% to about 85%, about 35% to about 90%, about 45% to about 55%, about 45% to about 65%, about 45% to about 75%, about 45% to about 85%, about 45% to about 90%, about 55% to about 65%, about 55% to about 75%, about 55% to about 85%, about 55% to about 90%, about 65% to about 75%, about 65% to about 85%, about 65% to about 90%, about 75% to about 85%, about 75% to about 90%, or about 85% to about 90% relative to pre-treatment level of inflammatory markers of the subject. In some cases, the level of inflammatory markers may be modulated by about 5%, about 15%, about 25%, about 35%, about 45%, about 55%, about 65%, about 75%, about 85%, or about 90% relative to pre-treatment level of inflammatory markers of the subject.

The administration of a compound or salt of Formula (I), (Ia), (Ib), (Ic), (Id), (Ie), (II), (II'), (IIa), (III) or (III') to a subject may modulate the levels of circulating fast skeletal muscle Troponin I (fS-TnI). The level of fS-TnI may be measured in the peripheral blood. The level of fS-TnI in the peripheral blood may increase after the administration of the inhibitor relative to pre-treatment level of fS-TnI for the subject. Alternatively, the level of fS-TnI in the peripheral blood may decrease after the administration of the inhibitor relative to pre-treatment level of fS-TnI for the subject. The administration of an inhibitor described herein may modulate the level of fS-TnI by 5% to 90% relative to pre-treatment level of fS-TnI for the subject. In some cases, the level of fS-TnI may be modulated by at least about 5% relative to pre-treatment level of fS-TnI of the subject. In some cases, the level of fS-TnI may be modulated by at most about 90% relative to pre-treatment level of fS-TnI of the subject. In some cases, the level of fS-TnI may be modulated by about 5% to about 15%, about 5% to about 25%, about 5% to about 35%, about 5% to about 45%, about 5% to about 55%, about 5% to about 65%, about 5% to about 75%, about 5% to about 85%, about 5% to about 90%, about 15% to about 25%, about 15% to about 35%, about 15% to about 45%, about 15% to about 55%, about 15% to about 65%, about 15% to about 75%, about 15% to about 85%, about 15% to about 90%, about 25% to about 35%, about 25% to about 45%, about 25% to about 55%, about 25% to about 65%, about 25% to about 75%, about 25% to about 85%, about 25% to about 90%, about 35% to about 45%, about 35% to about 55%, about 35% to about 65%, about 35% to about 75%, about 35% to about 85%, about 35% to about 90%, about 45% to about 55%, about 45% to about 65%, about 45% to about 75%, about 45% to about 85%, about 45% to about 90%, about 55% to about 65%, about 55% to about 75%, about 55% to about 85%, about 55% to about 90%, about 65% to about 75%, about 65% to about 85%, about 65% to about 90%, about 75% to about 85%, about 75% to about 90%, or about 85% to about 90% relative to pre-treatment level of fS-TnI of the subject. In some cases, the level of fS-TnI may be modulated by about 5%, about 15%, about 25%, about 35%, about 45%, about 55%, about 65%, about 75%, about 85%, or about 90% relative to pre-treatment level of fS-TnI of the subject.

Isoforms of troponin may be measured in a subject prior to and following the administration a compound or salt of Formula (I), (Ia), (Ib), (Ic), (Id), (Ie), (II), (II'), (IIa), (III) or (III'). Inhibition of skeletal muscle contraction may not inhibit some isoforms of troponin, such as cardiac troponin I (cTnI) or slow skeletal troponin I (ssTnI). In some cases, the inhibition of skeletal muscle contraction may not appreciably inhibit cTnI or ssTnI. As used herein with regard to cTnI or ssTnI, the phrase not appreciably refers to the cTnI or ssTnI reduced by less than 10%, less than 8%, less than 6%, less than 4%, less than 2%, less than 1%, less than 0.5% or even less than 0.1% relative to the cTnI or ssTnI prior to the administration of the inhibitor.

The administration of a compound or salt of Formula (I), (Ia), (Ib), (Ic), (Id), (Ie), (II), (II'), (IIa), (III) or (III') may reduce involuntary muscle contractions. Involuntary muscle contractions may be reduced by 20% to 90% relative to involuntary muscle contractions prior to the administration of the inhibitor. In some cases, involuntary muscle contractions may be reduced by at least about 20% relative to pre-treatment involuntary muscle contractions. In some cases, involuntary muscle contractions may be reduced by at most about 90% relative to pre-treatment involuntary muscle contractions. In some cases, involuntary muscle contractions may be reduced by about 20% to about 25%, about 20% to about 30%, about 20% to about 40%, about 20% to about 50%, about 20% to about 70%, about 20% to about 75%, about 20% to about 80%, about 20% to about 85%, about 20% to about 90%, about 25% to about 30%, about 25% to about 40%, about 25% to about 50%, about 25% to about 70%, about 25% to about 75%, about 25% to about 80%, about 25% to about 85%, about 25% to about 90%, about 30% to about 40%, about 30% to about 50%, about 30% to about 70%, about 30% to about 75%, about 30% to about 80%, about 30% to about 85%, about 30% to about 90%, about 40% to about 50%, about 40% to about 70%, about 40% to about 75%, about 40% to about 80%, about 40% to about 85%, about 40% to about 90%, about 50% to about 70%, about 50% to about 75%, about 50% to about 80%, about 50% to about 85%, about 50% to about 90%, about 70% to about 75%, about 70% to about 80%, about 70% to about 85%, about 70% to about 90%, about 75% to about 80%, about 75% to about 85%, about 75% to about 90%, about 80% to about 85%, about 80% to about 90%, or about 85% to about 90% relative to pre-treatment involuntary muscle contractions. In some cases, involuntary muscle contractions may be reduced by about 20%, about 25%, about 30%, about 40%, about 50%, about 70%, about 75%, about 80%, about 85%, or about 90% relative to pre-treatment involuntary muscle contractions.

A compound or salt of Formula (I), (Ia), (Ib), (Ic), (Id), (Ie), (II), (II'), (IIa), (III) or (III') may be used to improve activities of daily living (ADL) or habitual physical activity in a subject as mature, functional undamaged muscle may be restored. Examples of ADL or habitual activities include but are not limited to stair climb, time to get up, timed chair rise, habitual walk speed, North Star Ambulatory assessment, incremental/endurance shuttle walk and 6 minute walk distance tests. ADL or habitual physical activity levels or capacity may be measured prior to and following the administration of a skeletal muscle inhibitor. Inhibition of skeletal muscle contraction may not affect ADL or habitual physical activity. In some cases, the inhibition of skeletal muscle contraction may not appreciably affect ADL or habitual physical activity. As used herein with regard to ADL or habitual physical activity, the phrase not appreciably refers to the level of ADL or habitual activity reduced by less than 20%, less than 15%, less than 10%, less than 8%, less than 6%, less than 4%, less than 2%, less than 1%, less than 0.5% or even less than 0.1% relative to the ADL or habitual activity prior to the administration of the inhibitor. Skeletal muscle contraction or force in a subject may be measured prior to and following the administration of the compound or salt of Formula (I), (Ia), (Ib), (Ic), (Id), (Ie), (II), (II'), (IIa), (III) or (III'). Such measurements may be performed to generate a dose response curve for the compound or salt of Formula (I), (Ia), (Ib), (Ic), (Id), (Ie), (II), (II'), (IIa), (III) or (III'). Dosage of the compound or salt of Formula (I), (Ia), (Ib), (Ic), (Id), (Ie), (II), (II'), (IIa), (III) or (III') may be adjusted by about 5% to 50% relative to a dose that reduces type II skeletal muscle contraction by 90%. In some cases, dosage of the skeletal muscle contraction inhibitor may be adjusted by at least about 5% relative to a dose that reduces type II skeletal muscle contraction by 90%. In some cases, dosage of the skeletal muscle contraction inhibitor may be adjusted by at most about 50% relative to a dose that reduces type II skeletal muscle contraction by 90%. In some cases, dosage of the skeletal muscle contraction inhibitor may be adjusted by about 5% to about 10%, about 5% to about 15%, about 5% to about 20%, about 5% to about 25%, about 5% to about 30%, about 5% to about 35%, about 5% to about 40%, about 5% to about 50%, about 10% to about 15%, about 10% to about 20%, about 10% to about 25%, about 10% to about 30%, about 10% to about 35%, about 10% to about 40%, about 10% to about 50%, about 15% to about 20%, about 15% to about 25%, about 15% to about 30%, about 15% to about 35%, about 15% to about 40%, about 15% to about 50%, about 20% to about 25%, about 20% to about 30%, about 20% to about 35%, about 20% to about 40%, about 20% to about 50%, about 25% to about 30%, about 25% to about 35%, about 25% to about 40%, about 25% to about 50%, about 30% to about 35%, about 30% to about 40%, about 30% to about 50%, about 35% to about 40%, about 35% to about 50%, or about 40% to about 50% relative to a dose that reduces type II skeletal muscle contraction by 90%. In some cases, dosage of the skeletal muscle contraction inhibitor may be adjusted by about 10%, about 12%, about 15%, about 18%, about 20%, about 25%, about 30%, about 35%, about 40%, about 45% or about 50% relative to a dose that reduces type II skeletal muscle contraction by 90%. Skeletal muscle contraction may be measured by a muscle force test after nerve stimulation using surface electrodes (e.g., foot plantar flexion after peroneal nerve stimulation in the leg), isolated limb assay, heart rate monitor or an activity monitor or equivalents thereof prior to and following the administration of a skeletal muscle contraction inhibitor.

Cardiac muscle force or cardiac muscle contraction of a subject may be measured prior to and following the administration of a compound or salt of Formula (I), (Ia), (Ib), (Ic), (Id), (Ie), (II), (II'), (IIa), (III) or (III'). Inhibition of skeletal muscle contraction may not inhibit cardiac muscle contraction or cardiac muscle force. In some embodiments, the inhibition of skeletal muscle contraction may not appreciably inhibit cardiac muscle contraction. In certain embodiments with regard to cardiac muscle contraction, the phrase not appreciably refers to cardiac muscle force reduced by less than 10%, less than 8%, less than 6%, less than 4%, less than 2%, less than 1%, less than 0.5% or even less than 0.1% relative to the cardiac muscle force prior to the administration of the inhibitor. Cardiac muscle force or cardiac muscle contraction of a subject following the administration of a compound or salt of Formula (I), (Ia), (Ib), (Ic), (Id), (Ie), (II), (II'), (IIa), (III) or (III') may be within 0.1% to 10% of the cardiac muscle contraction or cardiac muscle force prior to the administration of the inhibitor. In some embodiments, administration of a compound or salt of Formula (I), (Ia), (Ib), (Ic), (Id), (Ie), (II), (II'), (IIa), (III) or (III') may inhibit skeletal muscle contraction and cardiac muscle contraction or cardiac muscle force. In some embodiments, cardiac muscle force reduced by more than 0.1%, more than 0.5%, more than 1%, more than 2%, more than 4%, more than 6%, more than 8%, or more than 10%. In some embodiments, a reduction of skeletal muscle contraction and cardiac muscle contraction are described by a ratio to one another. For example, in some embodiments, the ratio of the reduction in skeletal muscle contraction to reduction in cardiac muscle contraction is from about 1:1 to about 100:1, about 2:1 to about 50:1, about 3:1 to about 40:1, about 4:1 to about 30:1, about 5:1 to about 20:1, about 7:1 to about 15:1, or about 8:1 to about 12:1. Cardiac muscle force or cardiac muscle contraction may be measured using an echocardiogram (fractional shortening) or other equivalent tests.

Tidal volume in lung in a subject may be measured prior to and following the administration of a compound or salt of Formula (I), (Ia), (Ib), (Ic), (Id), (Ie), (II), (II'), (IIa), (III) or (III'). Administration may not inhibit tidal volume in a lung. In some cases, administration may not appreciably inhibit tidal volume in a lung. In certain embodiments with regard to tidal lung volume in a lung, the phrase not appreciably refers to the tidal volume in a lung reduced by less than 10%, less than 8%, less than 6%, less than 4%, less than 2%, less than 1%, less than 0.5% or less than 0.1% relative to the tidal volume in a lung prior to the administration of the inhibitor. Tidal volume in a lung in a subject may be measured using forced volume in one second test (FEV1) or forced vital capacity test (FVC) or equivalent tests thereof.

Smooth muscle contraction in a subject may be measured prior to and following the administration of a skeletal muscle contraction inhibitor. Inhibition of skeletal muscle contraction may not inhibit smooth muscle contraction. In some cases, the inhibition of skeletal muscle contraction may not appreciably inhibit smooth muscle contraction. As used herein with regard to smooth muscle contraction, the phrase not appreciably refers to the smooth muscle contraction reduced by less than 10%, less than 8%, less than 6%, less than 4%, less than 2%, less than 1%, less than 0.5% or even less than 0.1% relative to the smooth muscle contraction prior to the administration of the inhibitor. Smooth muscle contraction in a subject may be evaluated by measuring a subject's blood pressure.

Neuromuscular coupling in a subject may be measured prior to and following the administration of a compound or salt of Formula (I), (Ia), (Ib), (Ic), (Id), (Ie), (II), (II'), (IIa), (III) or (III'). Inhibition of skeletal muscle contraction, with an inhibitor described herein, may not impair nerve conduction, neurotransmitter release or electrical depolarization of skeletal muscle in a subject. In some cases, the inhibition of skeletal muscle contraction may not appreciably impair neuromuscular coupling in a subject. As used herein with regard to neuromuscular coupling, the phrase not appreciably refers to a level of neuromuscular coupling in the subject reduced by less than 10%, less than 8%, less than 6%, less than 4%, less than 2%, less than 1%, less than 0.5% or less than 0.10% relative to the level of neuromuscular coupling in the subject prior to the administration of the inhibitor. Neuromuscular coupling in a subject may be evaluated by measuring nerve induced electrical depolarization of skeletal muscle by the recording of electrical activity produced by skeletal muscles after electrical or voluntary stimulation with electromyography (EMG) using surface or needle electrodes.

In some aspects, the method of treating a neuromuscular condition or movement disorder can comprise administering a compound or salt of Formula (I), (Ia), (Ib), (Ic), (Id), (Ie), (II), (II'), (IIa), (III) or (III') wherein the compound or salt of Formula (I), (Ia), (Ib), (Ic), (Id), (Ie), (II), (II'), (IIa), (III) or (III') may inhibit myosin ATPase activity, native skeletal muscle myofibril ATPase (calcium regulated) or a reconstituted S1 with actin, tropomyosin and troponin. In vitro assays may be used to test the effect of the test compound or inhibitor on the myosin ATPase activity. Test compounds can be screened for assessing their inhibitory activity of muscle contraction. Inhibitory activity can be measured using a absorbance assay to determine actin-activated ATPase activity. Rabbit muscle myosin sub-fragment 1 (S1) can be mixed with polymerized actin and distributed into wells of assay plates without nucleotides. Test compounds can then be added into the wells with a pin array. The reaction can be initiated with MgATP. The amount of ATP consumption over a defined time period in the test vessel may be compared to the amount of ATP consumption in a control vessel. The defined period of time may be 5 minutes to 20 minutes. The ATP consumption can be determined by direct or indirect assays. The test compounds that reproducibly and strongly inhibited the myosin S1 ATPase activity can be evaluated further in dose response assay to determine IC50 for the compound ex vivo on dissected muscles. The assay may measure ATPase activity indirectly by coupling the myosin to pyruvate kinase and lactate dehydrogenase to provide an absorbance detection method at 340 nm based upon the conversion of NADH to NAD+ driven by ADP accumulation. In some cases, wherein ATP consumption is decreased by at least 20% in said test vessel than said control vessel, said test compound may be selected as a compound or salt of Formula (I), (Ia), (Ib), (Ic), (Id), (Ie), (II), (II'), (IIa), (III) or (III'). A test compound may be selected when there is at least 20% greater inhibition of NAD+ generation in a kinetic assay.

The inhibitor or test compound selected may not inhibit cardiac muscle myosin S1 ATPase in in vitro assays. In some cases, the cardiac muscle myosin S1 ATPase or cardiac myofibrils or reconstituted system may be inhibited by less than 10%, less than 8%, less than 5%, less than 3%, less than 2%, less than 1% or less than 0.5% when a test compound or compound or salt of Formula (I), (Ia), (Ib), (Ic), (Id), (Ie), (II), (II'), (IIa), (III) or (III') is tested in an in-vitro assay.

Test compounds of skeletal muscle contraction may be tested on skinned fibers. Single skeletal muscle fibers, treated so as to remove membranes and allow for a direct activation of contraction after calcium administration may be used. An inhibitor compound or salt of Formula (I), (Ia), (Ib), (Ic), (Id), (Ie), (II), (II'), (IIa), (III) or (III') may inhibit contraction of a single skeletal muscle fiber by about 5% to about 90% relative to pre-treatment value or an untreated control single skeletal muscle fiber. An inhibitor may inhibit contraction of a single skeletal muscle fiber by at least about 5% relative to pre-treatment value or an untreated control single skeletal muscle fiber. An inhibitor may inhibit contraction of a single skeletal muscle fiber by at most about 90% relative to pre-treatment value or an untreated control single skeletal muscle fiber. An inhibitor may inhibit contraction of a single skeletal muscle fiber by about 5% to about 10%, about 5% to about 20%, about 5% to about 30%, about 5% to about 40%, about 5% to about 50%, about 5% to about 60%, about 5% to about 70%, about 5% to about 80%, about 5% to about 90%, about 10% to about 20%, about 10% to about 30%, about 10% to about 40%, about 10% to about 50%, about 10% to about 60%, about 10% to about 70%, about 10% to about 80%, about 10% to about 90%, about 20% to about 30%, about 20% to about 40%, about 20% to about 50%, about 20% to about 60%, about 20% to about 70%, about 20% to about 80%, about 20% to about 90%, about 30% to about 40%, about 30% to about 50%, about 30% to about 60%, about 30% to about 70%, about 30% to about 80%, about 30% to about 90%, about 40% to about 50%, about 40% to about 60%, about 40% to about 70%, about 40% to about 80%, about 40% to about 90%, about 50% to about 60%, about 50% to about 70%, about 50% to about 80%, about 50% to about 90%, about 60% to about 70%, about 60% to about 80%, about 60% to about 90%, about 70% to about 80%, about 70% to about 90%, or about 80% to about 90% relative to pre-treatment capacity or an untreated control single skeletal muscle fiber. An inhibitor may inhibit contraction of a single skeletal muscle fiber by about 5%, about 10%, about 20%, about 30%, about 40%, about 50%, about 60%, about 70%, about 80%, or about 90% relative to pre-treatment capacity or an untreated control single skeletal muscle fiber.

An inhibitor compound or salt of Formula (I), (Ia), (Ib), (Ic), (Id), (Ie), (II), (II'), (IIa), (III) or (III') may inhibit contraction of a single skeletal muscle by about 5% to about 90% relative to pre-treatment value or an untreated control single skeletal muscle. An inhibitor may inhibit contraction of a single skeletal muscle by at least about 5% relative to pre-treatment value or an untreated control single skeletal muscle. An inhibitor may inhibit contraction of a single skeletal muscle by at most about 90% relative to pre-treatment value or an untreated control single skeletal muscle. An inhibitor may inhibit contraction of a single skeletal muscle by about 5% to about 10%, about 5% to about 20%, about 5% to about 30%, about 5% to about 40%, about 5% to about 50%, about 5% to about 60%, about 5% to about 70%, about 5% to about 80%, about 5% to about 90%, about 10% to about 20%, about 10% to about 30%, about 10% to about 40%, about 10% to about 50%, about 10% to about 60%, about 10% to about 70%, about 10% to about 80%, about 10% to about 90%, about 20% to about 30%, about 20% to about 40%, about 20% to about 50%, about 20% to about 60%, about 20% to about 70%, about 20% to about 80%, about 20% to about 90%, about 30% to about 40%, about 30% to about 50%, about 30% to about 60%, about 30% to about 70%, about 30% to about 80%, about 30% to about 90%, about 40% to about 50%, about 40% to about 60%, about 40% to about 70%, about 40% to about 80%, about 40% to about 90%, about 50% to about 60%, about 50% to about 70%, about 50% to about 80%, about 50% to about 90%, about 60% to about 70%, about 60% to about 80%, about 60% to about 90%, about 70% to about 80%, about 70% to about 90%, or about 80% to about 90% relative to pre-treatment capacity or an untreated control single skeletal muscle. An inhibitor may inhibit contraction of a single skeletal muscle by about 5%, about 10%, about 20%, about 30%, about 40%, about 50%, about 60%, about 70%, about 80%, or about 90% relative to pre-treatment capacity or an untreated control single skeletal muscle.

The effect of a test compound on slow type I skeletal muscle fibers, cardiac muscle bundles or lung muscle fibers, may be evaluated. A test compound or inhibitor compound or salt of Formula (I), (Ia), (Ib), (Ic), (Id), (Ie), (II), (II'), (IIa), (III) or (III') may be selected so as not to appreciably modulate the function of slow type I skeletal muscle fibers, cardiac muscle bundles or lung muscle fibers and be specific for type II skeletal muscles. As used herein, the term "appreciably modulate" can refer to the contraction capacity of muscles following the inhibitor administration to be reduced less than 10%, less than 8%, less than 6%, less than 4%, less than 2%, less than 1%, less than 0.5% or even less than 0.10% relative to the muscle force/contraction prior to the administration of the inhibitor.

In some aspects, a method of treating a neuromuscular condition or a movement disorder may comprise administering to a subject in need thereof a compound or salt of Formula (I), (Ia), (Ib), (Ic), (Id), (Ie), (II), (II'), (IIa), (III) or (III') wherein the compound or salt of Formula (I), (Ia), (Ib), (Ic), (Id), (Ie), (II), (II'), (IIa), (III) or (III') reduces skeletal muscle contraction by 5% to 90% in an ex vivo assay. The ex vivo assays used may be mouse models. The mouse models used may be dystrophy mouse models such as an mdx mouse. The mdx mouse has a point mutation in its dystrophin gene, changing the amino acid coding for a glutamine to a threonine producing a nonfunctional dystrophin protein resulting in DMD where there is increased muscle damage and weakness. Extensor digitorum longus muscles may be dissected from mdx mice and mounted on a lever arm. The muscles may be bathed in an oxygenated Krebs solution to maintain muscle function. A test compound or compound or salt of Formula (I), (Ia), (Ib), (Ic), (Id), (Ie), (II), (II'), (IIa), (III) or (III') may be applied to the muscles. An isometric (fixed length) contraction step may then be performed wherein the muscles are stimulated with a series of electrical pulses. An eccentric (lengthening) contraction step may be performed wherein the muscles are stretched to 10%, 15%, 20%, 25%, or 30% greater than its rested length, while relaxed or while stimulated with an electrical pulse. In some embodiments, the eccentric contraction step is repeated from 2 to 50 times. In some embodiments, the eccentric contraction step is repeated from 2 to 40 times. In some embodiments, the eccentric contraction step is repeated from 2 to 30 times. In some embodiments, the eccentric contraction step is repeated from 2 to 20 times. In some embodiments, the eccentric contraction step is repeated from 2 to 10 times. In some embodiments, the eccentric contraction step is repeated 4, 5, 6, 7, 8, 9, 10, 11, 12, 13, 14, or 15 times to cause muscle fiber injury. In some embodiments, the electric pulses may have a frequency of about 1 Hz to about 500 Hz. In some embodiments, the electric pulses may have a frequency of about 1 Hz to about 400 Hz. In some embodiments, the electric pulses may have a frequency of about 1 Hz to about 300 Hz. In some embodiments, the electric pulses may have a frequency of about 1 Hz to about 200 Hz. In some embodiments, the electric pulses may have a frequency of about 1 Hz to about 100 Hz. The electric pulse may have a frequency of about 50, 55, 60, 65, 70, 75, 80, 85, 90, 95, 100, 105, 110, 115, 120, 125, 130, 135, 140, 145 or 150 Hz. A series of electric pulses may comprise of individual pulses of different frequencies. The time period of each pulse in the series of electric pulses may be between 0.1 second to 0.5 seconds for each pulse. The time for each pulse may be 0.1, 0.2, 0.3, 0.35, 0.4 or 0.5 seconds. Muscle membrane damage may also be measured by incubating muscles in procion orange after the isometric or eccentric contraction. Procion orange is a fluorescent dye that is taken up by muscle fibers with injured membranes. The number or proportion of dye-positive fibers may then quantified by histology. When the test force drop and/or proportion of dye-positive fibers may be at least 20% less than the control force drop and/or dye uptake, the test compound may be selected as a compound or salt of Formula (I), (Ia), (Ib), (Ic), (Id), (Ie), (II), (II'), (IIa), (III) or (III').

Using an isometric or eccentric set of contractions, the force generated by the muscle may be measured. The change in force generated by the muscle before and after an isometric or eccentric set of contractions may be calculated as the test force drop. The calculations may be compared to the change in force generated by the muscle contraction from the first pulse to the last pulse in a control sample without exposure to the test compound (control force drop). Force drop can be used as a surrogate of muscle injury and a test compound or inhibitor compound or salt of Formula (I), (Ia), (Ib), (Ic), (Id), (Ie), (II), (II'), (IIa), (III) or (III') may be selected when the test force drop is at least 20% less than the control force drop.

Pharmaceutical Formulations

The compositions and methods described herein may be considered useful as pharmaceutical compositions for administration to a subject in need thereof. Pharmaceutical compositions may comprise at least the a compound or salt of Formula (I), (Ia), (Ib), (Ic), (Id), (Ie), (II), (II'), (IIa), (III) or (III') described herein and one or more pharmaceutically acceptable carriers, diluents, excipients, stabilizers, dispersing agents, suspending agents, and/or thickening agents.

Pharmaceutical compositions comprising a compound or salt of Formula (I), (Ia), (Ib), (Ic), (Id), (Ie), (II), (II'), (IIa), (III) or (III') may be formulated using one or more physiologically-acceptable carriers comprising excipients and auxiliaries. Formulation may be modified depending upon the route of administration chosen. Pharmaceutical compositions comprising a compound, salt or conjugate may be manufactured, for example, by lyophilizing the compound, salt or conjugate, mixing, dissolving, emulsifying, encapsulating or entrapping the conjugate. The pharmaceutical compositions may also include the compounds, salts or conjugates in a free-base form or pharmaceutically-acceptable salt form.

Methods for formulation of a compound or salt of Formula (I), (Ia), (Ib), (Ic), (Id), (Ie), (II), (II'), (IIa), (III) or (III') may include formulating any of the compounds, salts or conjugates with one or more inert, pharmaceutically-acceptable excipients or carriers to form a solid, semi-solid, or liquid composition. Solid compositions may include, for example, powders, tablets, dispersible granules and capsules, and in some aspects, the solid compositions further contain nontoxic, auxiliary substances, for example wetting or emulsifying agents, pH buffering agents, and other pharmaceutically-acceptable additives. Alternatively, the compounds, salts or conjugates may be lyophilized or in powder form for re-constitution with a suitable vehicle, e.g., sterile pyrogen-free water, before use.

Pharmaceutical compositions comprising a compound or salt of Formula (I), (Ia), (Ib), (Ic), (Id), (Ie), (II), (II'), (IIa), (III) or (III') may comprise at least one active ingredient (e.g., a compound, salt or conjugate and other agents). The active ingredients may be entrapped in microcapsules prepared, for example, by coacervation techniques or by interfacial polymerization (e.g., hydroxymethylcellulose or gelatin microcapsules and poly-(methylmethacylate) microcapsules, respectively), in colloidal drug-delivery systems (e.g., liposomes, albumin microspheres, microemulsions, nano-particles and nanocapsules) or in macroemulsions.

The compositions and formulations may be sterilized. Sterilization may be accomplished by filtration through sterile filtration.

The compositions comprising a compound or salt of Formula (I), (Ia), (Ib), (Ic), (Id), (Ie), (II), (II'), (IIa), (III) or (III') may be formulated for administration as an injection. Non-limiting examples of formulations for injection may include a sterile suspension, solution or emulsion in oily or aqueous vehicles. Suitable oily vehicles may include, but are not limited to, lipophilic solvents or vehicles such as fatty oils or synthetic fatty acid esters, or liposomes. Aqueous injection suspensions may contain substances which increase the viscosity of the suspension. The suspension may also contain suitable stabilizers. Injections may be formulated for bolus injection or continuous infusion. Alternatively, the compositions may be lyophilized or in powder form for reconstitution with a suitable vehicle, e.g., sterile pyrogen-free water, before use.

For parenteral administration, a compound or salt of Formula (I), (Ia), (Ib), (Ic), (Id), (Ie), (II), (II'), (IIa), (III) or (III') may be formulated in a unit dosage injectable form (e.g., solution, suspension, emulsion) in association with a pharmaceutically acceptable parenteral vehicle. Such vehicles may be inherently non-toxic, and non-therapeutic. Vehicles may be water, saline, Ringer's solution, dextrose solution, and 5% human serum albumin. Non-aqueous vehicles such as fixed oils and ethyl oleate may also be used. Liposomes may be used as carriers. The vehicle may contain minor amounts of additives such as substances that enhance isotonicity and chemical stability (e.g., buffers and preservatives).

In one embodiment the invention relates to methods and compositions of Formula (I), (Ia), (Ib), (Ic), (Id), (Ie), (II), (II'), (IIa), (III) or (III') formulated for oral delivery to a subject in need. In one embodiment a composition is formulated so as to deliver one or more pharmaceutically active agents to a subject through a mucosa layer in the mouth or esophagus. In another embodiment the composition is formulated to deliver one or more pharmaceutically active agents to a subject through a mucosa layer in the stomach and/or intestines.

In one embodiment compositions of Formula (I), (Ia), (Ib), (Ic), (Id), (Ie), (II), (II'), (IIa), (III) or (III') are provided in modified release dosage forms. Suitable modified release dosage vehicles include, but are not limited to, hydrophilic or hydrophobic matrix devices, water-soluble separating layer coatings, enteric coatings, osmotic devices, multiparticulate devices, and combinations thereof. The compositions may also comprise non-release controlling excipients.

In another embodiment compositions of Formula (I), (Ia), (Ib), (Ic), (Id), (Ie), (II), (II'), (IIa), (III) or (III') are provided in enteric coated dosage forms. These enteric coated dosage forms can also comprise non-release controlling excipients. In one embodiment the compositions are in the form of enteric-coated granules, as controlled-release capsules for oral administration. The compositions can further comprise cellulose, disodium hydrogen phosphate, hydroxypropyl cellulose, hypromellose, lactose, mannitol, or sodium lauryl sulfate. In another embodiment the compositions are in the form of enteric-coated pellets, as controlled-release capsules for oral administration. The compositions can further comprise glycerol monostearate 40-50, hydroxypropyl cellulose, hypromellose, magnesium stearate, methacrylic acid copolymer type C, polysorbate 80, sugar spheres, talc, or triethyl citrate.

In another embodiment the compositions of Formula (I), (Ia), (Ib), (Ic), (Id), (Ie), (II), (II'), (IIa), (III) or (III') are enteric-coated controlled-release tablets for oral administration. The compositions can further comprise carnauba wax, crospovidone, diacetylated monoglycerides, ethylcellulose, hydroxypropyl cellulose, hypromellose phthalate, magnesium stearate, mannitol, sodium hydroxide, sodium stearyl fumarate, talc, titanium dioxide, or yellow ferric oxide.

Sustained-release preparations comprising a compound or salt of Formula (I), (Ia), (Ib), (Ic), (Id), (Ie), (II), (II'), (IIa), (III) or (III') may be also be prepared. Examples of sustained-release preparations may include semipermeable matrices of solid hydrophobic polymers that may contain the compound, salt or conjugate, and these matrices may be in the form of shaped articles (e.g., films or microcapsules). Examples of sustained-release matrices may include poly-esters, hydrogels (e.g., poly(2-hydroxyethyl-methacrylate), or poly(vinyl alcohol)), polylactides, copolymers of L-glutamic acid and y ethyl-L-glutamate, non-degradable ethylene-vinyl acetate, degradable lactic acid-glycolic acid copolymers such as the LUPRON DEPO™ (i.e., injectable microspheres composed of lactic acid-glycolic acid copolymer and leuprolide acetate), and poly-D-(−)-3-hydroxybutyric acid.

Pharmaceutical formulations comprising a compound or salt of Formula (I), (Ia), (Ib), (Ic), (Id), (Ie), (II), (II'), (IIa), (III) or (III') may be prepared for storage by mixing a compound, salt or conjugate with a pharmaceutically acceptable carrier, excipient, and/or a stabilizer. This formulation may be a lyophilized formulation or an aqueous solution. Acceptable carriers, excipients, and/or stabilizers may be nontoxic to recipients at the dosages and concentrations used. Acceptable carriers, excipients, and/or stabilizers may include buffers such as phosphate, citrate, and other organic acids; antioxidants including ascorbic acid and methionine; preservatives, polypeptides; proteins, such as serum albumin or gelatin; hydrophilic polymers; amino acids; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes; and/or non-ionic surfactants or polyethylene glycol.

In another embodiment the compositions of Formula (I), (Ia), (Ib), (Ic), (Id), (Ie), (II), (II'), (IIa), (III) or (III') can further comprise calcium stearate, crospovidone, hydroxypropyl methylcellulose, iron oxide, mannitol, methacrylic acid copolymer, polysorbate 80, povidone, propylene glycol, sodium carbonate, sodium lauryl sulfate, titanium dioxide, and triethyl citrate.

In another embodiment compositions of Formula (I), (Ia), (Ib), (Ic), (Id), (Ie), (II), (II'), (IIa), (III) or (III') are provided in effervescent dosage forms. These effervescent dosage forms can also comprise non-release controlling excipients.

In another embodiment compositions of Formula (I), (Ia), (Ib), (Ic), (Id), (Ie), (II), (II'), (IIa), (III) or (III') can be provided in a dosage form that has at least one component that can facilitate the immediate release of an active agent, and at least one component that can facilitate the controlled release of an active agent. In a further embodiment the dosage form can be capable of giving a discontinuous release of the compound in the form of at least two consecutive pulses separated in time from 0.1 up to 24 hours. The compositions can comprise one or more release controlling and non-release controlling excipients, such as those excipients suitable for a disruptable semi-permeable membrane and as swellable substances.

In another embodiment compositions of Formula (I), (Ia), (Ib), (Ic), (Id), (Ie), (II), (II'), (IIa), (III) or (III') are provided in a dosage form for oral administration to a subject, which comprise one or more pharmaceutically acceptable excipients or carriers, enclosed in an intermediate reactive layer comprising a gastric juice-resistant polymeric layered material partially neutralized with alkali and having cation exchange capacity and a gastric juice-resistant outer layer.

In some embodiments, the compositions of Formula (I), (Ia), (Ib), (Ic), (Id), (Ie), (II), (II'), (IIa), (III) or (III') provided herein can be in unit-dosage forms or multiple-dosage forms. Unit-dosage forms, as used herein, refer to physically discrete units suitable for administration to human or non-human animal subjects and packaged individually. Each unit-dose can contain a predetermined quantity of an active ingredient(s) sufficient to produce the desired therapeutic effect, in association with the required pharmaceutical carriers or excipients. Examples of unit-dosage forms include, but are not limited to, ampoules, syringes, and individually packaged tablets and capsules. In some embodiments, unit-dosage forms may be administered in fractions or multiples thereof. A multiple-dosage form is a plurality of identical unit-dosage forms packaged in a single container, which can be administered in segregated unit-dosage form. Examples of multiple-dosage forms include, but are not limited to, vials, bottles of tablets or capsules, or bottles of pints or gallons. In another embodiment the multiple dosage forms comprise different pharmaceutically active agents.

In some embodiments, the compositions of Formula (I), (Ia), (Ib), (Ic), (Id), (Ie), (II), (II'), (IIa), (III) or (III') may also be formulated as a modified release dosage form, including immediate-, delayed-, extended-, prolonged-, sustained-, pulsatile-, controlled-, extended, accelerated- and fast-, targeted-, programmed-release, and gastric retention dosage forms. These dosage forms can be prepared according to known methods and techniques (see, Remington: The Science and Practice of Pharmacy, supra; Modified-Release Drug Delivery Technology, Rathbone et al., Eds., Drugs and the Pharmaceutical Science, Marcel Dekker, Inc.: New York, N.Y., 2002; Vol. 126, which are herein incorporated by reference in their entirety).

Combination Therapies

Also contemplated herein are combination therapies, for example, co-administering a disclosed compound and an additional therapeutic agent, as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually hours, days, weeks, months or years depending upon the combination selected). Combination therapy is intended to embrace administration of multiple therapeutic agents in a sequential manner, that is, wherein each therapeutic agent is administered at a different time, as well as administration of these therapeutic agents, or at least two of the therapeutic agents, in a substantially simultaneous manner.

Substantially simultaneous administration is accomplished, for example, by administering to the subject a single formulation or composition, (e.g., a tablet or capsule having a fixed ratio of each therapeutic agent or in multiple, single formulations (e.g., capsules) for each of the therapeutic agents. Sequential or substantially simultaneous administration of each therapeutic agent is affected by any appropriate route including, but not limited to, oral routes, intravenous routes, intramuscular routes, and direct absorption through mucous membrane tissues. The therapeutic agents are administered by the same route or by different routes. For example, a first therapeutic agent of the combination selected is administered by intravenous injection while the other therapeutic agents of the combination are administered orally. Alternatively, for example, all therapeutic agents are administered orally or all therapeutic agents are administered by intravenous injection.

The components of the combination are administered to a patient simultaneously or sequentially. It will be appreciated that the components are present in the same pharmaceutically acceptable carrier and, therefore, are administered simultaneously. Alternatively, the active ingredients are present in separate pharmaceutical carriers, such as, conventional oral dosage forms, that are administered either simultaneously or sequentially.

In certain embodiments, a compound or salt of the disclosure may be administered in combination with an oral corticosteroid. In certain embodiments, a compound or salt of the disclosure is administered in combination with deflazacort. In certain embodiments, a compound or salt of the disclosure is administered in combination with prednisone. In certain embodiments, a compound or salt of the disclosure is administered in combination with a morpholino antisense oligomer. In certain embodiments, a compound or salt of the disclosure is administered in combination with and exon skipping therapy. In certain embodiments, the additional therapeutic agent is eteplirsen or ataluren.

In certain embodiments, a compound or salt of the disclosure is used in combination with a gene therapy. In certain embodiments, the compound or salt of the disclosure is used in combination with adeno-associated virus (AAV) containing genes encoding replacement proteins, e.g., dystrophin, or truncated version thereof, e.g., microdystrophin. In certain embodiments, a compound or salt of the disclosure is administered in combination with vamorolone.

EXAMPLES

The invention now being generally described, it will be more readily understood by reference to the following examples which are included merely for purposes of illustration of certain aspects and embodiments of the present invention, and are not intended to limit the invention in any way.

The following synthetic schemes are provided for purposes of illustration, not limitation. The following examples illustrate the various methods of making compounds described herein. It is understood that one skilled in the art may be able to make these compounds by similar methods or by combining other methods known to one skilled in the art. It is also understood that one skilled in the art would be able to make the compounds of the disclosure, in a similar manner as described below by using the appropriate starting materials and modifying the synthetic route as needed. In general, starting materials and reagents can be obtained from commercial vendors or synthesized according to sources known to those skilled in the art or prepared as described herein.

Example 1. General Scheme—Synthesis of 2-benzyl-6-(2-(2,2,2-trifluoroethoxy)pyrimidin-5-yl)pyridazin-3(2H)-one

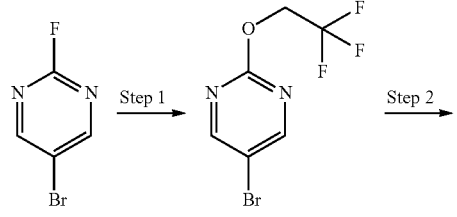

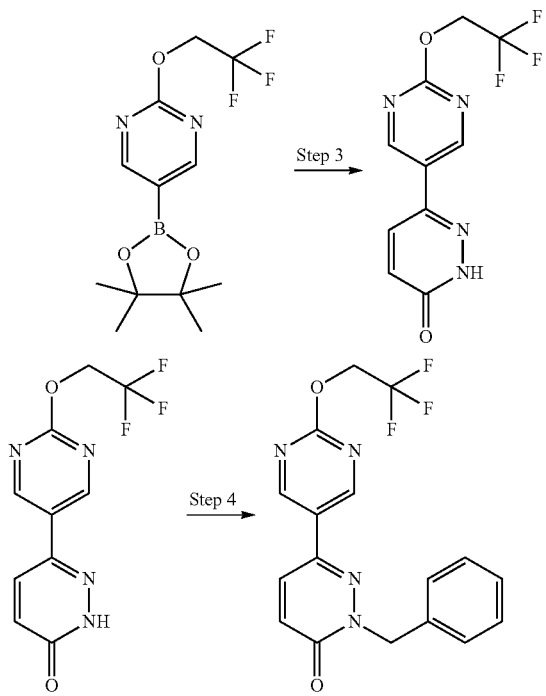

Example 2 Exemplary Scheme—Synthesis of 2-benzyl-6-(2-(2,2,2-trifluoroethoxy)pyrimidin-5-yl)pyridazin-3(2H)-one

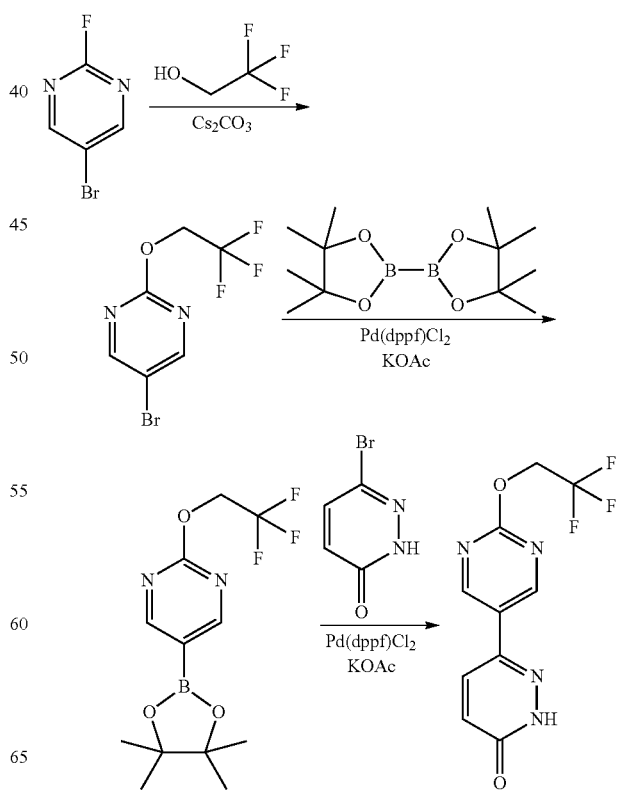

81

-continued

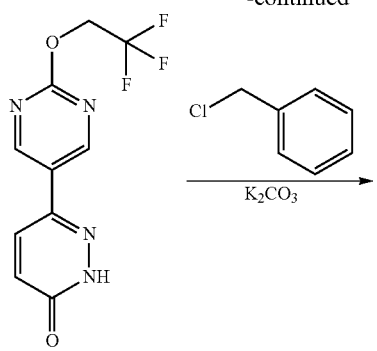

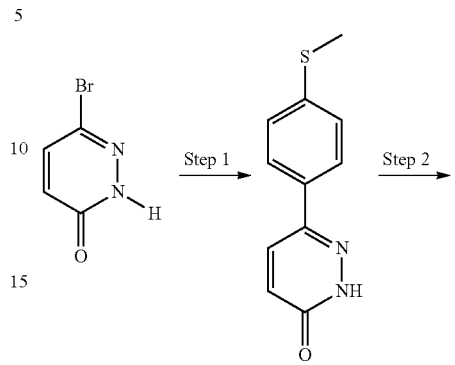

Bromofluoropyrimidine was combined with an alcohol (e.g. 2,2,2-trifluoroethanol), cesium carbonate and a non-protic solvent (e.g. DMF). The mixture was heated gently if necessary, to increase the rate of fluoro displacement. Isolation of the major product provided the corresponding 2-substituted pyrimidines. A Suzuki reaction at the C-4 bromo position using a palladium catalyst (e.g. [1,1-bis (diphenylphosphino)ferrocene]dichloropalladium (II)) and a mild base (e.g. potassium acetate) in dioxane/water produced the bi-aryl cores in good yield. The nitrogen was cleanly alkylated using a wide variety of arylmethylbromides or arylmethylchlorides (e.g. benzyl chloride) and inorganic base in polar aprotic solvents (e.g. DMF). Alternatively, the nitrogen of the pyridizinone could be functionalized using Mitsunobu methodology. This required a hydroxymethylaryl compound (e.g. benzyl alcohol), triphenylphosphine and a carbodiimide reagent (e.g. DEAD). Both alternatives were utilized in preparation of desired products depending on the availability of the appropriate coupling partners.

Examples 1 and 2 may be modified as appropriate to prepare compounds described in Tables 1 and 2 herein.

82

Example 3: Synthesis of 2-(3-fluorobenzyl)-6-(4-(methylthio)phenyl)pyridazin-3(2H)-one

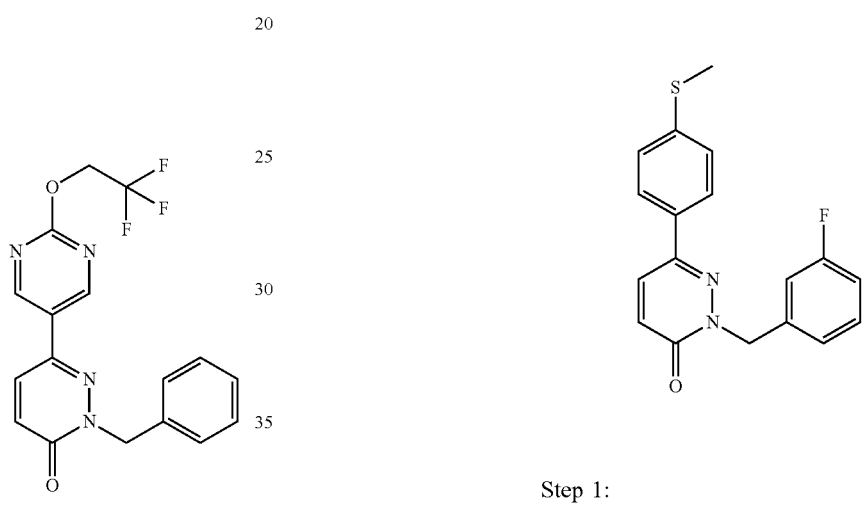

Step 1:
6-(4-(methylthio)phenyl)pyridazin-3(2H)-one

Under $N_2$ atmosphere, a mixture of 6-bromopyridazin-3 (2H)-one (250 mg, 1.43 mmol), 4,4,5,5-tetramethyl-2-(4-(methylthio)phenyl)-1,3,2-dioxaborolane (357 mg, 1.43 mmol), Pd(dppf)Cl$_2$ (104.5 mg, 0.143 mmol), K$_2$CO$_3$ (592 mg, 4.29 mmol) in Diox. (5.0 mL)/H$_2$O (0.5 mL) was stirred at 90° C. for 4 h. The reaction was concentrated under vacuum to give a residue, which was purified by chromatography on silica gel (Flash 20 g, 30-80% EA: PE) to afford the title compound as a yellow solid (250 mg, 80.2%). LC/MS (ESI): 219 [M+H]$^+$.

Step 2: 2-(3-fluorobenzyl)-6-(4-(methylthio)phenyl) pyridazin-3(2H)-one

To a stirred solution of 6-[4-(methylsulfanyl)phenyl]-2,3-dihydropyridazin-3-one (150 mg, 0.69 mmol) in DMF (2 mL) was added Cs$_2$CO$_3$ (672 mg, 2.06 mmol). Then 1-(bromomethyl)-3-fluorobenzene (143 mg, 0.76 mmol) was added. The resulting mixture was stirred for 2 h at 25° C. The reaction was filtered and the filtrate was purified by prep-HPLC to afford the title compound as a white solid (100 mg, 44.6%). $^1$H NMR (DMSO-d6, 300 MHz): δ 8.07 (d, J=9.6 Hz, 1H), 7.86-7.81 (m, 2H), 7.44-7.34 (m, 3H), 7.20-7.08 (m, 4H), 5.34 (s, 2H), 2.56 (s, 3H); LC/MS (ESI): 327 [M+H]$^+$.

Example 4: Synthesis of 2-(4-chlorobenzyl)-6-(2-fluoro-4-methoxyphenyl)pyridazin-3(2H)-one

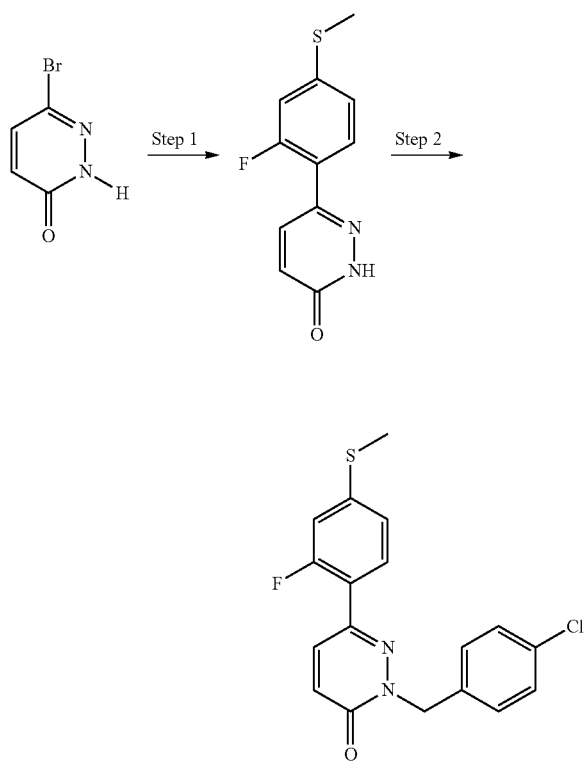

Step 1: 6-(2-fluoro-4-methoxyphenyl)pyridazin-3(2H)-one

Under N$_2$ atmosphere, a mixture of 6-bromopyridazin-3(2H)-one (250 mg, 0.29 mmol), (2-fluoro-4-methoxyphenyl)boronic acid (267 mg, 0.31 mmol), K$_2$CO$_3$ (400 mg, 2.90 mmol) in Diox. (1.0 mL)/H$_2$O (0.2 mL) was heated at 90° C. for 8 h. The reaction was concentrated under vacuum to give a residue, which was purified by chromatography on silica gel (Flash 20 g, 30-80% EA: PE) to afford the title compound as a white solid (150 mg, 76.3%). LC/MS (ESI): 221 [M+H]$^+$.

Step 2: 2-(4-chlorobenzyl)-6-(2-fluoro-4-methoxyphenyl)pyridazin-3(2H)-one

To a stirred solution of 6-(2-fluoro-4-methoxyphenyl)-2,3-dihydropyridazin-3-one (156 mg, 0.71 mmol) in DMF (2 mL) was added Cs$_2$CO$_3$ (692 mg, 2.13 mmol). Then 1-(bromomethyl)-4-chlorobenzene (160 mg, 0.78 mmol) was added. The resulting mixture was stirred for 2 h at 25° C. LCMS indicated that the reaction ran smoothly. The reaction was filtered and the filtrate was purified by prep-HPLC to afford the title compound as a white solid (32.1 mg, 13.1%). $^1$H NMR (DMSO-d6, 300 MHz): δ 7.75 (dd, J$_1$=9.6 Hz, J$_2$=2.1 Hz, 1H), 7.59 (m, 1H), 7.43-7.36 (m, 4H), 7.07 (d, J=9.6 Hz, 1H), 6.98 (dd, J$_1$=13.2 Hz, J$_2$=2.4 Hz, 1H), 6.92 (dd, J$_1$=8.7 Hz, J$_2$=2.4 Hz, 1H), 5.30 (s, 2H), 3.83 (s, 3H); LC/MS (ESI): 345 [M+H]$^+$.

Example 5: Synthesis of N-(4-(1-(4-chlorobenzyl)-6-oxo-1,6-dihydropyridazin-3-yl)phenyl)acetamide

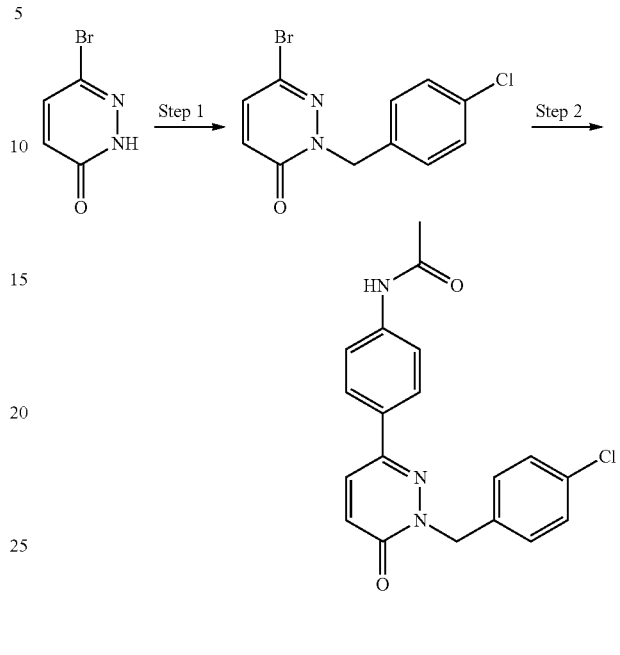

Step 1: 6-bromo-2-(4-chlorobenzyl)pyridazin-3(2H)-one

To a stirred solution of 6-bromo-2,3-dihydropyridazin-3-one (600 mg, 3.43 mmol) in DMF (6 mL) was added Cs$_2$CO$_3$ (3.35 g, 10.29 mmol). Then 1-(bromomethyl)-4-chlorobenzene (705 mg, 3.43 mmol) was added. The resulting mixture was stirred for 2 h at 25° C. LCMS indicated that the reaction ran smoothly. The reaction was quenched by the addition of saturated aqueous NH$_4$Cl solution (5 mL), then diluted by water (20 mL) and extracted by EA (25 mL) twice. The combined EA phase was washed with water (20 mL), brine (20 mL), dried over Na$_2$SO$_4$, filtered and concentrated under vacuum to give the crude product. It was purified by chromatography on silica gel (Flash 40 g, 20-30% EA: PE) to give the title compound as a white solid (700 mg, 68.2%); LS/MS (ESI): 299 [M+H]$^+$.

Step 2: N-(4-(1-(4-chlorobenzyl)-6-oxo-1,6-dihydropyridazin-3-yl)phenyl)acetamide Under N$_2$ atmosphere, a mixture of 6-bromo-2-[(4-chlorophenyl)methyl]-2,3-dihydropyridazin-3-one (200 mg, 0.67 mmol), (4-acetamidophenyl)boronic acid (132 mg, 0.73 mmol), K$_2$CO$_3$ (277 mg, 2.00 mmol) and Pd(dppf)Cl$_2$ (49 mg, 0.07 mmol) in Dioxane (3 mL) with H$_2$O (0.2 mL) was stirred for 3 h at 90° C. The reaction mixture was treated with silica gel column chromatography, eluted with EA. Then the EA phase was concentrated under vacuum to afford the crude product, which was purified by prep-HPLC to afford the title compound as a white solid (27.0 mg, 13.1%). $^1$H NMR (DMSO-d6, 300 MHz): δ 10.14 (s, 1H), 8.05 (d, J=9.9 Hz, 1H), 7.84 (d, J=8.7 Hz, 2H), 7.70 (d, J=8.7 Hz, 2H), 7.44-7.37 (m, 4H), 7.08 (d, J=9.6 Hz, 1H), 5.31 (s, 2H), 2.07 (s, 3H); LC/MS (ESI): 354 [M+H]$^+$.

The following compound was synthesized following Example 5:

| Compound No. | Structure | Name | NMR | MS |
|---|---|---|---|---|
| 123 | 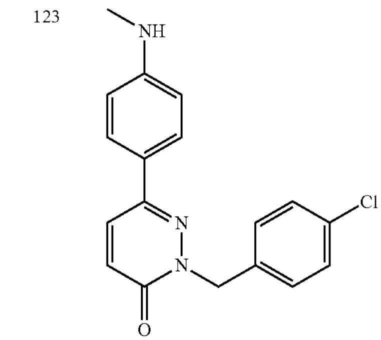 | 2-(4-chlorobenzyl)-6-(4-(methylamino)phenyl)pyridazin-3(2H)-one | $^1$H NMR (DMSO-d6, 300 MHz): δ 7.96 (d, J = 9.9 Hz, 1H), 7.64 (d, J = 8.7 Hz, 2H), 7.43-7.35 (m, 4H), 7.00 (d, J = 9.6 Hz, 1H), 6.60 (d, J = 8.7 Hz, 2H), 6.11 (m, 1 H), 5.27 (s, 2H), 2.72 (d, J = 5.1 Hz, 3H) | LC/MS (ESI): 326 [M + H]$^+$ |

Example 6: Synthesis of 2-[(4-chlorophenyl)methyl]-6-[2-(2,2,2-trifluoroethoxy)pyrimidin-5-yl]-2,3-dihydropyridazin-3-one

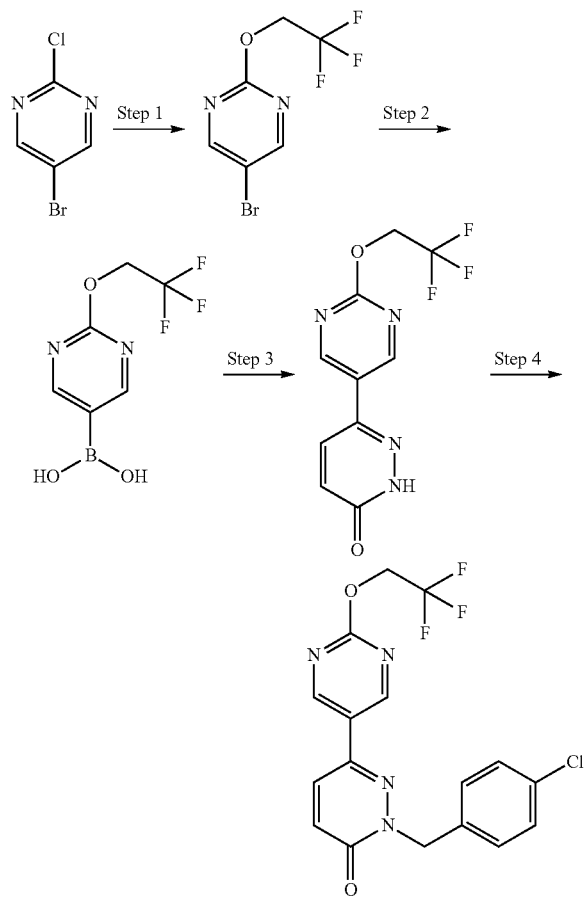

Step 1: 5-bromo-2-(2,2,2-trifluoroethoxy)pyrimidine

To a mixture of 5-bromo-2-chloropyrimidine (10 g, 0.021 mol, 1.0 equiv) in DMSO (10 mL) were added 2,2,2-trifluoroethan-1-ol (6.21 g, 0.025 mol, 1.20 equiv) and Cs$_2$CO$_3$ (25.27 g, 0.062 mol, 3.0 equiv) at room temperature. The reaction mixture was stirred for 2 h at 70° C. The solution was diluted with water and extracted with EtOAc (30 mL×3). The combined organic layers were washed with brine, dried over Na$_2$SO$_4$ and the solvent removed in vacuo. Purification by chromatography on silica gel (Flash 300 g, 0-40% EtOAc:cyclohexane) afforded the title compound as yellow oil (10.0 g, 94.08%). LC/MS (ESI): 257 [M+H]$^+$.

Step 2: [2-(2,2,2-trifluoroethoxy)pyrimidin-5-yl] boronic acid

To a mixture of 5-bromo-2-(2,2,2-trifluoroethoxy)pyrimidine (5.0 g, 19.45 mmol, 1.0 equiv) in dioxane (40 mL) were added 4,4,5,5-tetramethyl-2-(4,4,5,5-tetramethyl-1,3,2-dioxaborolan-2-yl)-1,3,2-dioxaborolane (7.41 g, 29.18 mmol, 1.5 equiv), KOAc (5.73 g, 58.36 mmol, 3.0 equiv) and Pd(dppf)Cl$_2$ (1.42 g, 1.94 mmol, 0.1 equiv). Into the flask purged and maintained with an inert atmosphere of nitrogen. The reaction mixture was stirred for 4 h at 80° C. and confirmed by LCMS. The reaction was used directly in the next step without workup.

Step 3: 6-[2-(2,2,2-trifluoroethoxy)pyrimidin-5-yl]-2,3-dihydropyridazin-3-one

To a mixture of [2-(2,2,2-trifluoroethoxy)pyrimidin-5-yl] boronic acid (4.2 g, 18.93 mmol, 1.0 equiv) in dioxane (40 mL) were added 6-bromo-2,3-dihydropyridazin-3-one (3.31 g, 18.916 mmol, 1.00 equiv), Pd(dppf)Cl$_2$ (0.69 g, 0.943 mmol, 0.05 equiv), K$_2$CO$_3$ (3.92 g, 28.387 mmol, 1.5 equiv) and H$_2$O (4 mL). Into the flask purged and maintained with an inert atmosphere of nitrogen. The resulting solution was stirred for 2 h at 90° C. The solution was diluted with water and extracted with EtOAc (30 mL×3). The combined organics were washed with brine, dried over Na$_2$SO$_4$ and the solvent removed in vacuo. Purification by chromatography on silica gel (Flash 300 g, 50-100% EtOAc: cyclohexane) afforded the title compound as brown solid (3.0 g, 58.24%). LC/MS (ESI): 273 [M+H]$^+$.

Step 4: 2-[(4-chlorophenyl)methyl]-6-[2-(2,2,2-trifluoroethoxy)pyrimidin-5-yl]-2,3-dihydro pyridazin-3-one To a mixture of 6-[2-(2,2,2-trifluoroethoxy)pyrimidin-5-yl]-2,3-dihydropyridazin-3-one (1.0 g, 3.67 mmol, 1.0 equiv) in DMF (10 mL) were added 1-(bromomethyl)-4-chlorobenzene (0.75 g, 0.004 mmol, 1.0 equiv) and Cs$_2$CO$_3$ (2.39 g, 0.007 mmol, 2.0 equiv) at room temperature. The resulting solution was stirred for 2 h at room temperature. The residue was purified by Prep-HPLC to afford a white solid (700 mg, 48%). $^1$H NMR (300 MHz, DMSO-d$_6$): δ 9.16 (s, 2H), 8.13 (d, J=9.9 Hz, 1H), 7.46-7.43 (m, 4H), 7.16 (d, J=9.6 Hz, 1H), 5.33 (s, 2H), 5.12 (q, J=9.0 Hz, 2H); LC/MS (ESI): 397 [M+H]$^+$.

The following compounds were synthesized following Example 6:

| Cmpd No. | Structure | Name | NMR | MS |
|---|---|---|---|---|
| 5 | 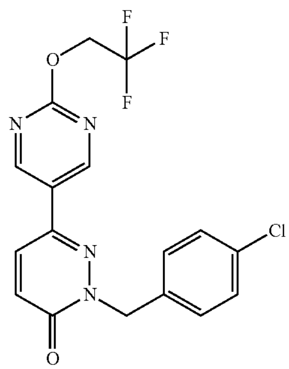 [SMILES: O=c1ccc(-c2cnc(OCC(F)(F)F)nc2)nn1Cc1ccc(Cl)cc1] | 2-(4-chlorobenzyl)-6-(2-(2,2,2-trifluoroethoxy)pyrimidin-5-yl)pyridazin-3(2H)-one | 1H NMR (300 MHz, DMSO-$d_6$): δ 9.16 (s, 2H), 8.13 (d, J = 9.9 Hz, 1H), 7.46-7.43 (m, 4H), 7.16 (d, J = 9.6 Hz, 1H), 5.33 (s, 2H), 5.12 (q, J = 9.0 Hz, 2H); | LC/MS (ESI): 397 [M + H]+ |
| 34 | 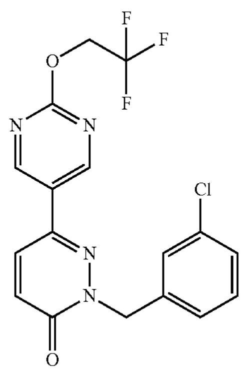 [SMILES: O=c1ccc(-c2cnc(OCC(F)(F)F)nc2)nn1Cc1cccc(Cl)c1] | 2-(3-chlorobenzyl)-6-(2-(2,2,2-trifluoroethoxy)pyrimidin-5-yl)pyridazin-3(2H)-one | $^1$H NMR (300 MHz, DMSO-$d_6$): δ 9.17 (s, 2H), 8.15 (d, J = 9.9 Hz, 1H), 7.47 (s, 1H), 7.43-7.37 (m, 3H), 7.18 (d, J = 9.6 Hz, 1H), 5.34 (s, 2H), 5.12 (q, J = 9.0 Hz, 2H) | LC/MS (ESI): 397 [M + H]$^+$ |
| 35 | 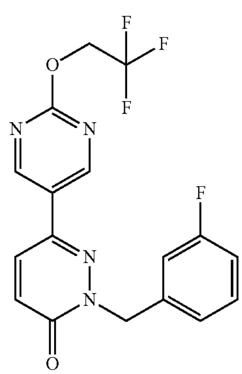 [SMILES: O=c1ccc(-c2cnc(OCC(F)(F)F)nc2)nn1Cc1cccc(F)c1] | 2-(3-fluorobenzyl)-6-(2-(2,2,2-trifluoroethoxy)pyrimidin-5-yl)pyridazin-3(2H)-one | $^1$H NMR (300 MHz, DMSO-$d_6$): δ 9.16 (s, 2H), 8.15 (d, J = 9.6 Hz, 1H), 7.45-7.37 (m, 1H), 7.25-7.11 (m, 4H), 5.35 (s, 2H), 5.12 (q, J = 9.0 Hz, 2H) | LC/MS (ESI): 381 [M + H]$^+$ |
| 36 | 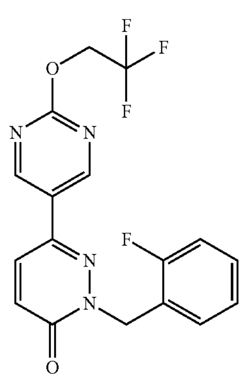 [SMILES: O=c1ccc(-c2cnc(OCC(F)(F)F)nc2)nn1Cc1ccccc1F] | 2-(2-fluorobenzyl)-6-(2-(2,2,2-trifluoroethoxy)pyrimidin-5-yl)pyridazin-3(2H)-one | $^1$H NMR (300 MHz, DMSO-$d_6$): δ 8.93 (s, 2H), 7.62 (d, J = 9.9 Hz, 1H), 7.46-7.26 (m, 2H), 7.19-6.93 (m, 3H), 5.51 (s, 2H), 4.89 (q, J = 8.1 Hz, 2H) | LC/MS (ESI): 381 [M + H]$^+$ |

| Cmpd No. | Structure | Name | NMR | MS |
|---|---|---|---|---|
| 37 | 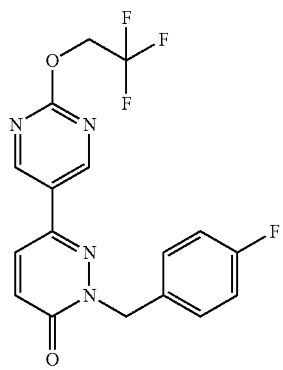 [SMILES: O=c1ccc(-c2cnc(OCC(F)(F)F)nc2)nn1Cc1ccc(F)cc1] | 2-(4-fluorobenzyl)-6-(2-(2,2,2-trifluoroethoxy)pyrimidin-5-yl)pyridazin-3(2H)-one | ¹H NMR (300 MHz, DMSO-d₆): δ 8.96 (s, 2H), 7.61 (d, J = 9.6 Hz, 1H), 7.56-7.47 (m, 2H), 7.08-6.93 (m, 3H), 5.38 (s, 2H), 4.90 (q, J = 8.4 Hz, 2H) | LC/MS (ESI): 381 [M + H]⁺ |
| 38 | 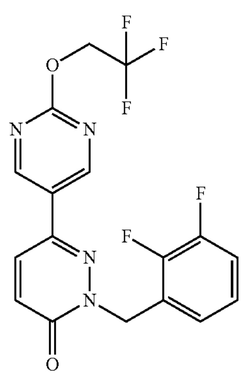 [SMILES: O=c1ccc(-c2cnc(OCC(F)(F)F)nc2)nn1Cc1cccc(F)c1F] | 2-(2,3-difluorobenzyl)-6-(2-(2,2,2-trifluoroethoxy)pyrimidin-5-yl)pyridazin-3(2H)-one | ¹H NMR (300 MHz, DMSO-d₆): δ 9.10 (s, 2H), 8.15 (d, J = 5.4 Hz, 1H), 7.46-7.34 (m, 1H), 7.24-7.17 (m, 3H), 5.43 (s, 2H), 5.11 (q, J = 9 Hz, 2H) | LC/MS (ESI): 399 [M + H]⁺ |
| 39 | 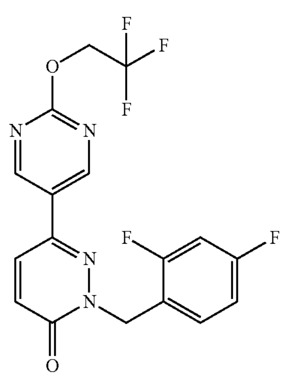 [SMILES: O=c1ccc(-c2cnc(OCC(F)(F)F)nc2)nn1Cc1ccc(F)cc1F] | 2-(2,4-difluorobenzyl)-6-(2-(2,2,2-trifluoroethoxy)pyrimidin-5-yl)pyridazin-3(2H)-one | ¹H NMR (300 MHz, DMSO-d₆): δ 9.10 (s, 2H), 8.14 (d, J = 9.9 Hz, 1H), 7.53-7.45 (m, 1H), 7.32-7.23 (m, 1H), 7.17 (d, J = 9.6 Hz, 1H), 7.12-7.06 (m, 1H), 5.36 (s, 2H), 5.11 (q, J = 9.0 Hz, 2H) | LC/MS (ESI): 399 [M + H]⁺ |
| 40 | 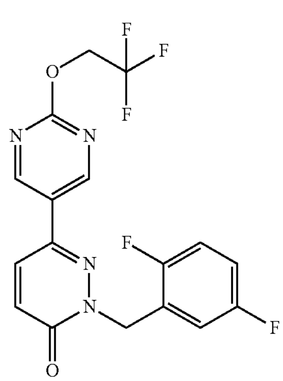 [SMILES: O=c1ccc(-c2cnc(OCC(F)(F)F)nc2)nn1Cc1cc(F)ccc1F] | 2-(2,5-difluorobenzyl)-6-(2-(2,2,2-trifluoroethoxy)pyrimidin-5-yl)pyridazin-3(2H)-one | ¹H NMR (300 MHz, DMSO-d₆): δ 9.09 (s, 2H), 8.06 (d, J = 9.6 Hz, 1H), 7.22-7.07 (m, 4H), 5.50 (s, 2H), 5.03 (q, J = 8.4 Hz, 2H) | LC/MS (ESI): 399 [M + H]⁺ |

| Cmpd No. | Structure | Name | NMR | MS |
|---|---|---|---|---|
| 41 | 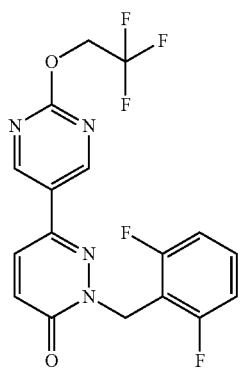 | 2-(2,6-difluorobenzyl)-6-(2-(2,2,2-trifluoroethoxy)pyrimidin-5-yl)pyridazin-3(2H)-one | $^1$H NMR (300 MHz, Methanol-$d_4$) δ 8.97 (s, 2H), 8.03 (d, J = 9.9 Hz, 1H), 7.50-7.40 (m, 1H), 7.15-7.01 (m, 3H), 5.55 (s, 2H), 5.00 (q, J = 8.7 Hz, 2H) | LC/MS (ESI): 399 [M + H]$^+$ |
| 42 | 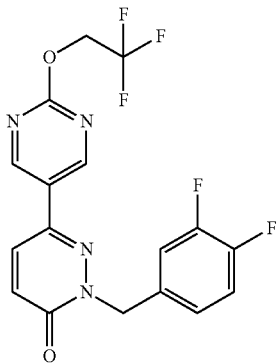 | 2-(3,4-difluorobenzyl)-6-(2-(2,2,2-trifluoroethoxy)pyrimidin-5-yl)pyridazin-3(2H)-one | $^1$H NMR (300 MHz, DMSO-$d_6$): δ 9.17 (s, 2H), 8.14 (d, J = 9.6 Hz, 1H), 7.47-7.40 (m, 2H), 7.17 (d, J = 9.9 Hz, 1H), 5.32 (s, 2H), 5.12 (q, J = 9.0 Hz, 2H) | LC/MS (ESI): 399 [M + H]$^+$ |
| 43 | 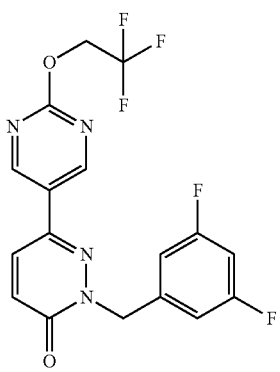 | 2-(3,5-difluorobenzyl)-6-(2-(2,2,2-trifluoroethoxy)pyrimidin-5-yl)pyridazin-3(2H)-one | $^1$H NMR (300 MHz, DMSO-$d_6$): δ 9.18 (s, 2H), 8.16 (d, J = 9.6 Hz, 1H), 7.21-7.11 (m, 4H), 5.35 (s, 2H), 5.12 (q, J = 9.0 Hz, 2H) | LC/MS (ESI): 399 [M + H]$^+$ |

Example 7: Synthesis of 2-(4-chlorobenzyl)-6-(2-fluoro-4-methoxyphenyl)pyridazin-3(2H)-one

Example 8: Synthesis of 2-(1-phenylcyclopropyl)-6-(2-(2,2,2-trifluoroethoxy)pyrimidin-5-yl)pyridazin-3(2H)-one

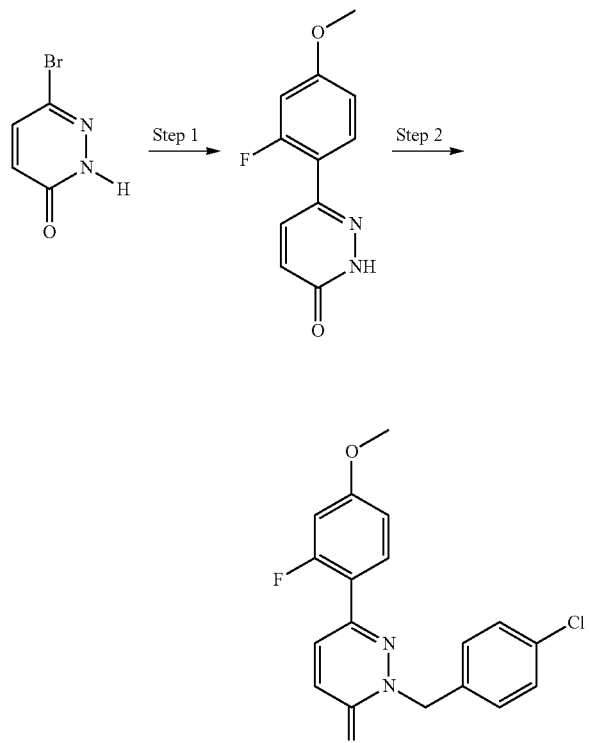

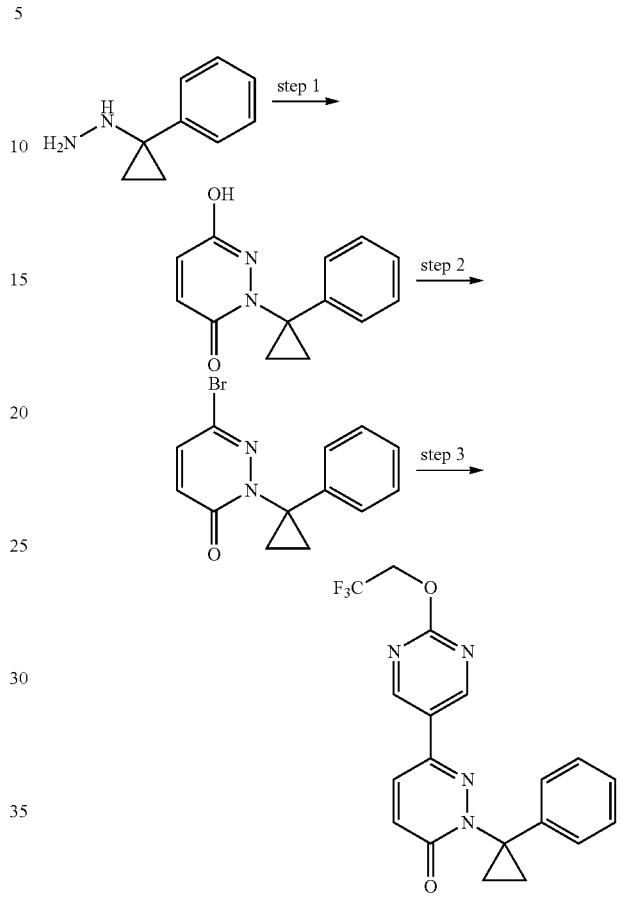

Step 1:
6-(2-fluoro-4-methoxyphenyl)pyridazin-3(2H)-one

Under $N_2$ atmosphere, a mixture of 6-bromopyridazin-3(2H)-one (250 mg, 0.29 mmol), (2-fluoro-4-methoxyphenyl)boronic acid (267 mg, 0.31 mmol), $K_2CO_3$ (400 mg, 2.90 mmol) in Diox. (1.0 mL)/$H_2O$ (0.2 mL) was heated at 90° C. for 8 h. The reaction was concentrated under vacuum to give a residue, which was purified by chromatography on silica gel (Flash 20 g, 30-80% EA: PE) to afford the title compound as a white solid (150 mg, 76.3%). LC/MS (ESI): 221 [M+H]+.

Step 2: 2-(4-chlorobenzyl)-6-(2-fluoro-4-methoxyphenyl)pyridazin-3(2H)-one

To a stirred solution of 6-(2-fluoro-4-methoxyphenyl)-2,3-dihydropyridazin-3-one (156 mg, 0.71 mmol) in DMF (2 mL) was added $Cs_2CO_3$ (692 mg, 2.13 mmol). Then 1-(bromomethyl)-4-chlorobenzene (160 mg, 0.78 mmol) was added. The resulting mixture was stirred for 2 h at 25° C. LCMS indicated that the reaction ran smoothly. The reaction was filtered and the filtrate was purified by prep-HPLC to afford the title compound as a white solid (32.1 mg, 13.1%). $^1$H NMR (DMSO-d6, 300 MHz): δ 7.75 (dd, $J_1$=9.6 Hz, $J_2$=2.1 Hz, 1H), 7.59 (m, 1H), 7.43-7.36 (m, 4H), 7.07 (d, J=9.6 Hz, 1H), 6.98 (dd, $J_1$=13.2 Hz, $J_2$=2.4 Hz, 1H), 6.92 (dd, $J_1$=8.7 Hz, $J_2$=2.4 Hz, 1H), 5.30 (s, 2H), 3.83 (s, 3H); LC/MS (ESI): 345 [M+H]+.

Step 1: 6-hydroxy-2-(1-phenylcyclopropyl)pyridazin-3(2H)-one

To a mixture of (1-phenylcyclopropyl)hydrazine (400.00 mg, 2.699 mmol, 1.00 equiv), and maleic anhydride (291.11 mg, 2.969 mmol, 1.10 equiv) in $H_2O$ (1.60 mL) was added conc. HCl (0.40 mL). The resulting solution was stirred for 8 hr at 95° C. The reaction was monitored by LCMS. After cooling down to room temperature, the resulting mixture was concentrated under vacuum. The residue was applied onto a silica gel column with ethyl acetate/petroleum ether (1:3). This resulted in 250 mg (40.58%) of 6-hydroxy-2-(1-phenylcyclopropyl)pyridazin-3(2H)-one as a solid.

Step 2: 6-bromo-2-(1-phenylcyclopropyl)pyridazin-3(2H)-one

To a solution of 6-hydroxy-2-(1-phenylcyclopropyl)pyridazin-3-one (240.00 mg, 1.051 mmol, 1.00 equiv) in DCE (3.00 mL) was added phosphoryl bromide (904.33 mg, 3.154 mmol, 3.00 equiv) in portions. The resulting solution was stirred for 16 hr at 85° C. After cooling down to room temperature, the resulting mixture was concentrated in reduced pressure. The residue was applied onto a silica gel column with ethyl acetate/petroleum ether (1:1). This resulted in 200 mg (65.33%) of 6-bromo-2-(1-phenylcyclopropyl)pyridazin-3-one as a yellow solid.

Step 3: 2-(1-phenylcyclopropyl)-6-(2-(2,2,2-trifluoroethoxy)pyrimidin-5-yl)pyridazin-3(2H)-one Following Example 8 afforded the title compound as a white solid (84 mg, 31.5%). $^1$H NMR (300 MHz, DMSO-d$_6$) δ 9.19 (s, 2H), 8.12 (d, J=9.6 Hz, 1H), 7.33-7.14 (m, 3H), 7.13 (d, J=9.9 Hz, 3H), 5.13 (q, J=9.0 Hz, 2H), 1.67-1.54 (m, 4H). LC/MS Rt=1.501 min, MS m/z: 389 [M+H]$^+$ Example 9: Synthesis of 2-(phenylmethyl-d2)-6-(2-(2,2,2-trifluoroethoxy)pyrimidin-5-yl)pyridazin-3(2H)-one

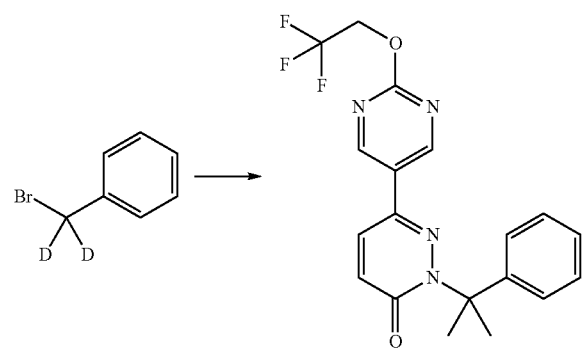 [SMILES: [2H]C([2H])(Br)c1ccccc1 ; CC(C)(c1ccccc1)n1nc(-c2cnc(OCC(F)(F)F)nc2)ccc1=O]

Step 1: 2-(phenylmethyl-d2)-6-(2-(2,2,2-trifluoroethoxy)pyrimidin-5-yl)pyridazin-3(2H)-one A mixture of 6-(2-(2,2,2-trifluoroethoxy)pyrimidin-5-yl)pyridazin-3(2H)-one (100.00 mg, 0.367 mmol, 1.00 equiv), (bromomethyl-d2)benzene (63.58 mg, 0.367 mmol, 1.00 equiv), potassium carbonate (102.29 mg, 0.735 mmol, 2 equiv) in dimethylformamide (1.00 mL) was added into a 8 mL flask and stirred for 1 h at 35° C. The mixture was purified by Prep-HPLC (0.05% NH$_3$H$_2$O—H$_2$O/ACN, 5% to 55% gradient, 30 min) to give 2-(phenylmethyl-d2)-6-(2-(2,2,2-trifluoroethoxy)pyrimidin-5-yl)pyridazin-3(2H)-one (80 mg, 59.77%) as an off-white solid. $^1$H NMR (400 MHz, DMSO-d$_6$) δ 9.18 (s, 2H), 8.55-8.53 (m, 2H), 8.15 (d, J=9.9 Hz, 1H), 7.81-7.77 (m, 1H), 7.18 (d, J=9.9 Hz, 1H). LC/MS Rt=1.437 min; MS m/z: 386 [M+H]$^+$.

Example 10. Skeletal Myofibril ATPase Assay

Overview: Myosin ATPase activity is assessed by using a coupled reaction system, in which ADP generated by the myosin ATPase function is coupled to the disappearance of NADH through the pyruvate kinase/lactate dehydrogenase (PK-LDH) system. Myosin ATPase activity produces ADP, which is used as a substrate for PK to produce pyruvate and regenerate ATP. The pyruvate is then used as a substrate by LDH to oxidize NADH to NAD+. The rate of the reaction is monitored through the time-dependent disappearance of NADH using absorbance at 340 nm. Inhibition of ATPase activity by the assayed compounds is indicated by a reduced rate of NADH loss, relative to vehicle-treated controls, over the experimental time window. To assess the selectivity of the assayed compounds for skeletal myofibrils, the compounds are counter-screened in cardiac myofibrils.

Materials: The following stock solutions and reagents were used in the Skeletal Myofibril ATPase Assay:

| Stock Solutions |
|---|
| PIPES, 200 mM in H$_2$O, pH 7.0 |
| MgCl$_2$ in H$_2$O, 200 mM |
| PM12 Buffer, 10X: 12 mM PIPES (from 200 mM stock), 20 mM MgCl$_2$ (from 200 mM stock) |
| EGTA in H$_2$O, 500 mM |
| CaCl$_2$ in H$_2$O, 500 mM |
| DTT in H$_2$O, 1M |
| BSA in H$_2$O, 20 mg/mL |
| KCl in H$_2$O, 600 mM |
| ATP in 1X PM12, 100 mM |
| NADH in 1X PM12, 30 mM |
| PEP in 1X PM12, 100 mM, pH 7.0 |
| Antifoam 204, 1% in H$_2$O |

Stock Solutions of pCa buffer. Combine PIPES, CaCl$_2$, and EGTA solutions with 70 mL of water. Adjust pH to 7.0 and bring final volume to 100 mL.

| | PREPARATION OF STOCKS SOLUTIONS FOR 100 ML OF PCA BUFFER | | | |
|---|---|---|---|---|
| pCA | 200 mM PIPES (mL) | Approx. Water (mL) | CaCl$_2$ | EGTA |
| 4.0 | 6 | 74 | 10.025 | 9.975 |
| 4.5 | 6 | 74 | 9.800 | 10.200 |
| 5.0 | 6 | 74 | 9.325 | 10.675 |
| 5.5 | 6 | 74 | 8.100 | 11.900 |
| 5.75 | 6 | 74 | 7.200 | 12.800 |
| 6.0 | 6 | 74 | 6.000 | 14.000 |
| 6.25 | 6 | 74 | 4.500 | 15.500 |
| 6.5 | 6 | 74 | 3.025 | 16.975 |
| 6.75 | 6 | 74 | 1.975 | 18.025 |
| 7.0 | 6 | 74 | 1.165 | 18.835 |
| 8.0 | 6 | 74 | 0.126 | 19.874 |
| 10.0 | 6 | 74 | 0.001 | 19.999 |

Buffer A & Buffer B. Buffers were stored on ice until use.
Buffer Preparation

| Total Well Volume (μL) | | Component | Stock Concentrations Value Unit | | Final Concentrations in Specific Buffer | Reaction Concentrations |
|---|---|---|---|---|---|---|
| Buffer A (μL) | 25 | PM12 Buffer | 10 | x | 1.00 x | 1.00 x |
| | | KCl | 600 | mM | 60.00 mM | 60.00 mM |
| | | BSA | 20 | mg/mL | 0.10 mg/mL | 0.10 mg/mL |
| | | DTT | 1000 | mM | 1.00 mM | 1.00 mM |
| | | PK/LDH | 80 | mM | 0.80 mM | 0.40 mM |
| | | Rabbit Psoas Prep 11 | 5.83 | mg/mL | 0.50 mg/mL | 0.25 mg/mL |
| | | Antifoam | 1.00% | | 0.01% | 0.01% |
| | | Water | | | | |

| | | | Volume | | | |
|---|---|---|---|---|---|---|
| Buffer B (µL) | 25 | PM12 Buffer | 10 × | | 1.00 × | 1.00 × |
| | | pCa Solution | 10 × | | 2.00 × | 1.00 × |
| | | KCl | 600 mM | | 60.00 mM | 60.00 mM |
| | | BSA | 20 mg/mL | | 0.10 mg/mL | 0.10 mg/mL |
| | | DTT | 1000 mM | | 1.00 mM | 1.00 mM |
| | | ATP | 100 mM | | 0.10 mM | 0.05 mM |
| | | NADH | 30 mM | | 1.00 mM | 0.50 mM |
| | | PEP | 100 mM | | 3.00 mM | 1.50 mM |
| | | Aatifoam | 1.00% | | 0.01% | 0.01% |
| | | Water | | | | |

| Total Well Volume (µL) | 50 | Component | Volume per well (µL) | Number Of Wells Total Volume (µL) 96 | Prepare Volume (µL) |
|---|---|---|---|---|---|
| Buffer A (µL) | 25 | PM12 Buffer | 2.50 | 240.00 | 312.00 | PM12 Buffer {1 ×} |
| | | KCl | 2.50 | 240.00 | 312.00 | KCl {60 mM} |
| | | BSA | 0.13 | 12.00 | 15.60 | BSA {0.1 mg/mL} |
| | | DTT | 0.03 | 2.40 | 3.12 | DTT {1 mM} |
| | | PK/LDH | 0.25 | 24.00 | 31.20 | PK/LDH {0.5 mM} |
| | | Rabbit Psoas Prep 11 | 2.14 | 205.83 | 267.58 | Rabbit Psoas Prep 11 {0.25 mg/mL} |
| | | Antifoam | 0.25 | 24.00 | 31.20 | Antifoam {0.01%} |
| | | Water | 17.21 | 1651.77 | 2147.30 | Water |
| | | | 25.00 | 2400.00 | 3120.00 | Total |
| Buffer B (µL) | 25 | PM12 Buffer | 2.50 | 240.00 | 312.00 | PM12 Buffer {1 ×} |
| | | pCa Solution | 5.00 | 430.00 | 624.00 | pCa Solution {1 ×} |
| | | KCl | 2.50 | 240.00 | 312.00 | KCl {60 mM} |
| | | BSA | 0.13 | 12.00 | 15.60 | BSA {0.1 mg/mL} |
| | | DTT | 0.03 | 2.40 | 3.12 | DTT {1 mM} |
| | | ATP | 0.03 | 2.40 | 3.12 | ATP {0.05 mM} |
| | | NADH | 0.83 | 80.00 | 104.00 | NADH {0.5 mM} |
| | | PEP | 0.75 | 72.00 | 93.60 | PEP {1.5 mM} |
| | | Arstifoam | 0.25 | 24.00 | 31.20 | Antifoam {0.01%} |
| | | Water | 12.99 | 1247.20 | 1621.36 | Water |
| | | | 25.00 | 2400.00 | 3120.00 | Total |

Skeletal Myofibril ATPase Assay Procedure: BSA, ATP, NADH, PEP, and DTT solutions were thawed at room temperature, then transferred to ice. Pellet-frozen myofibrils were transferred with approximately twice the required volume into a sufficiently large tube and capped. Myofibrils were thawed by rolling in a water bath for approximately 15 min at room temperature and cooled on ice. Buffers A and B were prepared by adjusting volumes as necessary for required number of wells and stored on ice. 0.5 µL of the compounds to be assayed were added into wells. 25 µL of Buffer A was dispensed into the wells, followed by 25 µL of Buffer B. The wells were measured for absorbance at 340 nm, using a kinetic protocol in which the wells are read every 1.5-2 min for 45 min. The slope of the data was approximated by subtracting the minimum absorbance value from the maximum value for each well. This was accomplished either in the SoftMax Pro software or in a spreadsheet program such as Excel. Using GraphPad Prism 8.0, the data was normalized by assigning a value of 100% to the 10% DMSO vehicle wells. Typically, a normalized 0% value was simply assigned to a (Max−Min) value of 0. The normalized data was fit to a Four Parameter Logistic sigmoidal equation, constraining the bottom to be 0 or greater. Compounds of Table 1 to 4 were tested and results of the assay appear in Table 5 herein. A=$IC_{50}$ is less than or equal to 10 µM; B=$IC_{50}$ is greater than 10 µM and less than 100 µM; C=$IC_{50}$ is greater than 100 µM.

Example 11. Cardiac Myofibril ATPase Assay

Following example 10, the counter screen was done using frozen myofibril pellets obtained from cardiac tissue. The assay was done in the same manner as above, with the following notable exceptions: the final well concentration of myofibrils was 1.0 mg/mL and KCl was omitted from the recipe.

Compounds of Table 1 to 4 were tested and results of the assay appear in Table 6 herein. A=$IC_{50}$ is less than or equal to 10 µM; B=$IC_{50}$ is greater than 10 µM and less than 100 µM; C=$IC_{50}$ is greater than 100 µM; and D=$IC_{50}$ is greater than 60 µM.

Example 12. Tibialis Anterior Muscle Assay

Skeletal muscles of patients with Duchenne muscular dystrophy (DMD) and mdx mice lack dystrophin and are more susceptible to contraction-induced injury than control muscles. Two stretches of maximally activated tibialis anterior (TA) muscles in situ were used to evaluate the susceptibility to injury of limb muscles in mdx mice following the administration of a compound disclosed herein. stretches of 20% strain relative to muscle fiber length were initiated from the plateau of isometric contractions. The magnitude of damage was assessed one minute later by the deficit in isometric force.

Animals

Mice aged 2-19 months were tested. Specific pathogen free (SPF) C57BL control and mdx mice were either purchased or bred in-house with mating pairs purchased from the Jackson Laboratories. All control mice were of C57BL/10J strain with the exception of the 19-month old mice that were C57BL/6. The use of C57BL/6 mice for the oldest group was necessary, since unlike C57BL/10J mice, C57BL/6 mice may be purchased at advanced ages from the colonies of aging rodents maintained by the National Institute on Aging.

In Situ Preparation

Mice were anesthetized with an initial intraperitoneal injection of Avertin (tribromoethanol; 13-17 Il/g). Anesthesia was supplemented until no responses to tactile stimuli were detected. This level of anesthesia was maintained throughout the experiment with additional doses of Avertin. The tendon of the TA was exposed by an incision at the ankle. The tendon was cut several millimeters distal to the end of the muscle. The tendon was tied with 4.0 nylon suture as close to the muscle attachment as possible, and the tendon was folded back onto itself and tied again. The tendon and exposed muscle were kept moist by periodic applications of isotonic saline. The mouse was placed on a heated platform maintained at 37° C. The foot of the mouse was secured to the platform with cloth tape and the knee was immobilized in a clamp between sharpened screws. The tendon of the muscle was tied securely to the lever arm of a servomotor. The servomotor controlled the position of the muscle and monitored the force developed by the muscle. All data were displayed on a digital oscilloscope and stored on a computer.

The TA muscle was stimulated with 0.2-ms pulses via two needle electrodes that penetrated the skin on either side of the peroneal nerve near the knee. Stimulation voltage and subsequently muscle length (Lo) were adjusted for maximum isometric twitch force (Pt). While held at Lo, the muscle was stimulated at increasing frequencies, stepwise from 150 Hz by 50 Hz, until a maximum force (Po) was reached, typically at 250 Hz. A one- to two-minute rest period was allowed between each tetanic contraction. Muscle length was measured with calipers, based on well-defined anatomical landmarks near the knee and the ankle. Optimum fiber length was determined by multiplying Lo by the TA Lf/Lo ratio of 0.6.

Lengthening Contraction Protocol

Each muscle was exposed to two stretches in situ, with the muscle stimulated at 250 Hz, the frequency that most often resulted in Po. A protocol consisting of only two contractions was used to avoid fatigue. Stretches were initiated from the plateau of an isometric contraction at Lo. The time course of the protocol is shown in FIG. 1. At time 0, stimulation was initiated and the muscle was held with no movement for 100 ms to allow maximum activation. From the plateau of the maximum isometric contraction, a length change of 20% Lf at a velocity of 1 Lf/s was imposed (LC1). Stimulation ceased at the end of the stretch ramp. The muscle was held at the stretched length for 100 ms and then returned to Lo at the same velocity. A second lengthening contraction identical to the first was administered 10 min later (LC2). Maximum isometric force was measured after 1 min (b1 min) and then again each 5 min for 15 min. Force deficits were calculated as the difference between the isometric force during LC1 and the maximum isometric force measured at any given time and expressed as a percentage of the isometric force during LC1. The recovery during the 15 min following the two-lengthening-contraction protocol was quantified as the difference between the isometric force measured at 15 min and the isometric force after the second lengthening contraction and expressed as a percentage of initial Po.

The experimental protocol consisted of two muscle stretches during maximal activation, followed by maximal activation to measure the decrease in maximum isometric force (Po). Panel A shows the length change of the muscle of 20% strain relative to fiber length (Lf), where 100% corresponds to optimum muscle length (Lo) for force development. The muscle was stretched at a velocity of 2 Lf/s. Panel B demonstrates the decrease in Po after the two-stretch protocol in a representative mdx mouse. Each lengthening contraction was initiated from the plateau of a maximum isometric contraction. Ten minutes after the first lengthening contraction (LC1), a second lengthening contraction occurred (LC2). Maximum force during an isometric contraction was measured 10 min after LC2 (b1 min). The force deficit was calculated by dividing the difference between the Po during LC1 and the Po measured at any time after LC1 by the Po during LC1 and multiplying by 100%. suture were trimmed from the muscle, and the muscle was weighed. After removal of TA muscles, deeply anesthetized mice were euthanized by the induction of a pneumothorax. Total muscle fiber cross-sectional area (CSA) of TA muscles was calculated by dividing muscle mass by the product of Lf and 1.06 mg/mm3, the density of mammalian skeletal muscle. Specific Po was calculated by dividing Po by CSA. The result of the trials are seen in FIGS. 3-6.

Figure 3:
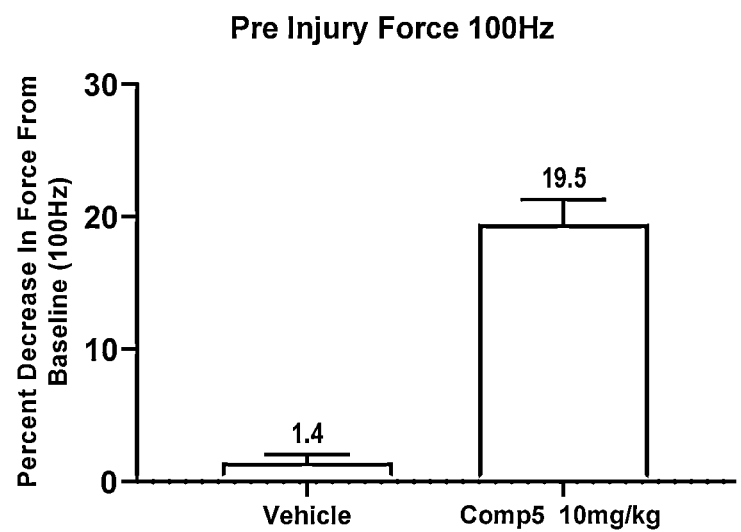
FIG. 3 depicts the force decrease pre injury at 100 Hz using an exemplary compound, Compound 5, of the disclosure.

FIG. 3 shows the force decrease pre injury at 100 Hz for Compound 5 of the disclosure. Force was measured in the TA muscle of the mdx mouse in situ at 100 Hz before and after oral administration of Compound 5. A 100 Hz stimulus was applied every 10 minutes and the change in force, before starting the eccentric injury protocol was recorded. This metric gives an indication of the relative ability of Compound 5 to decrease force in a target tissue.

Figure 4:
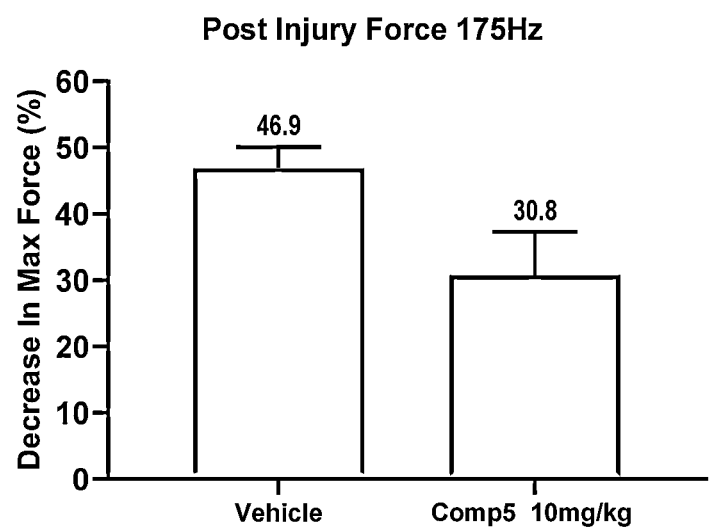
FIG. 4 depicts the post injury force decrease at 175 Hz using an exemplary compound, Compound 5, of the disclosure.
Figure 5:
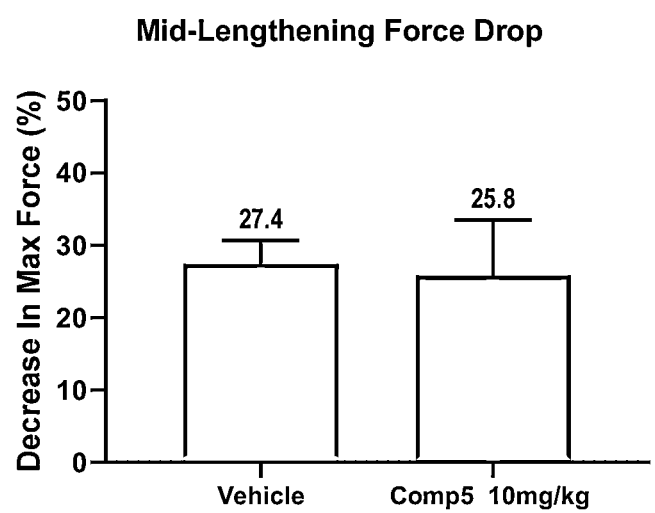
FIG. 5 depicts mid lengthening force drop using an exemplary compound, Compound 5, of the disclosure.

FIG. 4 shows the post injury force decrease at 175 Hz for Compound 5 of the disclosure. Maximal force was measured at 175 Hz in the TA muscle in situ before and 10 minutes after two rounds of eccentric (lengthening) contraction. In mdx mice, lengthening contraction yields an exaggerated force drop. This measurement gives an indication of the ability of Compound 5 to reduce the relative drop in force after eccentric contraction. FIG. 5 shows mid lengthening force drop for Compound 5 of the disclosure. Injury to the TA muscle in situ was elicited via two maximal eccentric contractions with 20% lengthening, 10 minutes apart. This metric measures the relative drop in pre-lengthening force between the first and the second contraction.

Figure 6:
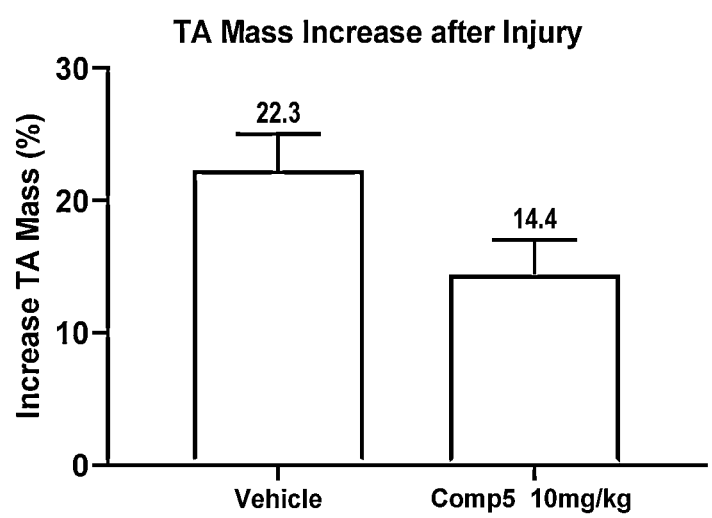
FIG. 6 depicts the TA mass increase after injury using an exemplary compound, Compound 5, of the disclosure.

FIG. 6 shows the TA mass increase after injury for Compound 5 of the disclosure. Lengthening injury of the TA muscle in mdx mice causes a delayed increase in muscle weight post-injury. This is presumably due to fluid accumulation in the form of edema. Muscles (both injured and contralateral) were removed from the mouse 1 hour after injury and weighed. The relative increase in weight of injured to contralateral was recorded. Reduction in this relative change is indicative of reduced edema post-injury.

In some embodiments, compounds of the disclosure are below in Table 1.

TABLE 1

| Cmpd No. | Structure | Name | NMR/MS |
|---|---|---|---|
| 1 | 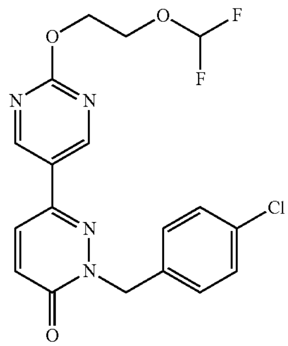 [SMILES: O=c1ccc(-c2cnc(OCCOC(F)F)nc2)nn1Cc1ccc(Cl)cc1] | 2-(4-chlorobenzyl)-6-(2-(2-(difluoromethoxy)ethoxy)pyrimidin-5-yl)pyridazin-3(2H)-one | [M + H]+ 409.3 |
| 2 | 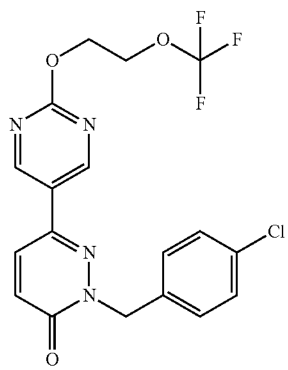 [SMILES: O=c1ccc(-c2cnc(OCCOC(F)(F)F)nc2)nn1Cc1ccc(Cl)cc1] | 2-(4-chlorobenzyl)-6-(2-(2-(trifluoromethoxy)ethoxy)pyrimidin-5-yl)pyridazin-3(2H)-one | [M + H]+ 427.1 |
| 3 | 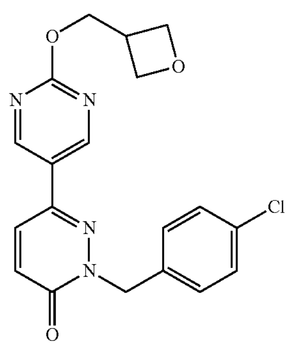 [SMILES: O=c1ccc(-c2cnc(OCC3COC3)nc2)nn1Cc1ccc(Cl)cc1] | 2-(4-chlorobenzyl)-6-(2-(oxetan-3-ylmethoxy)pyrimidin-5-yl)pyridazin-3(2H)-one | [M + H]+ 385.2 |
| 4 | 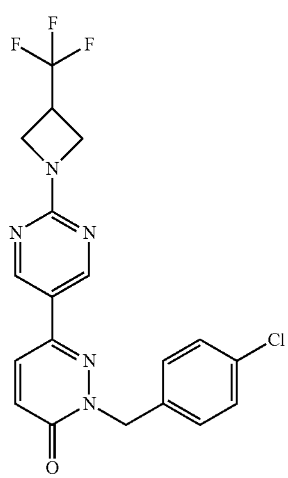 [SMILES: O=c1ccc(-c2cnc(N3CC(C(F)(F)F)C3)nc2)nn1Cc1ccc(Cl)cc1] | 2-(4-chlorobenzyl)-6-(2-(3-(trifluoromethyl)azetidin-1-yl)pyrimidin-5-yl)pyridazin-3(2H)-one | [M + H]+ 422.2 |

TABLE 1-continued

| Cmpd No. | Structure | Name | NMR/MS |
|---|---|---|---|
| 5 | 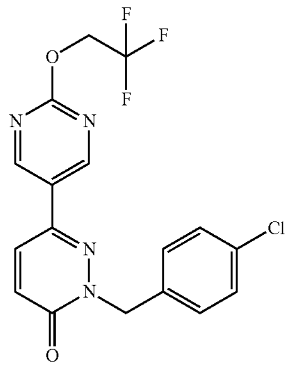 [SMILES: O=c1ccc(-c2cnc(OCC(F)(F)F)nc2)nn1Cc1ccc(Cl)cc1] | 2-(4-chlorobenzyl)-6-(2-(2,2,2-trifluoroethoxy)pyrimidin-5-yl)pyridazin-3(2H)-one | $^1$H NMR (300 MHz, DMSO-$d_6$): δ 9.16 (s, 2H), 8.13 (d, J = 9.9 Hz, 1H), 7.46-7.43 (m, 4H), 7.16 (d, J = 9.6 Hz, 1H), 5.33 (s, 2H), 5.12 (q, J = 9.0 Hz, 2H); LC/MS (ESI): 397 [M + H]$^+$ |
| 6 | 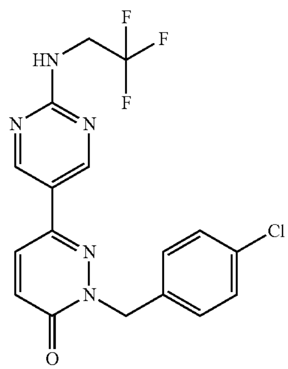 [SMILES: O=c1ccc(-c2cnc(NCC(F)(F)F)nc2)nn1Cc1ccc(Cl)cc1] | 2-(4-chlorobenzyl)-6-(2-((2,2,2-trifluoroethyl)amino)pyrimidin-5-yl)pyridazin-3(2H)-one | 396.2 |
| 7 | 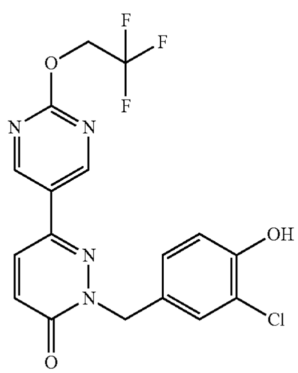 [SMILES: O=c1ccc(-c2cnc(OCC(F)(F)F)nc2)nn1Cc1ccc(O)c(Cl)c1] | 2-(3-chloro-4-hydroxybenzyl)-6-(2-(2,2,2-trifluoroethoxy)pyrimidin-5-yl)pyridazin-3(2H)-one | [M + H]+ 413.2 |
| 8 | 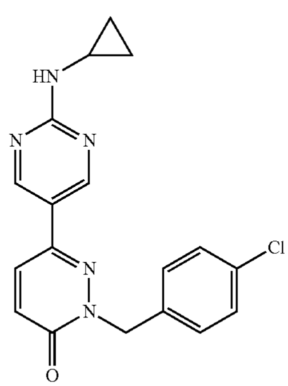 [SMILES: O=c1ccc(-c2cnc(NC3CC3)nc2)nn1Cc1ccc(Cl)cc1] | 2-(4-chlorobenzyl)-6-(2-(cyclopropylamino)pyrimidin-5-yl)pyridazin-3(2H)-one | 354.2 |

TABLE 1-continued

| Cmpd No. | Structure | Name | NMR/MS |
|---|---|---|---|
| 9 | 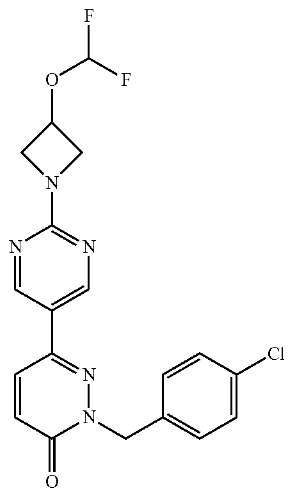 [SMILES: O=c1ccc(-c2cnc(N3CC(OC(F)F)C3)nc2)nn1Cc1ccc(Cl)cc1] | 2-(4-chlorobenzyl)-6-(2-(3-(difluoromethoxy)azetidin-1-yl)pyrimidin-5-yl)pyridazin-3(2H)-one | [M + H]+ 420.2 |
| 10 | 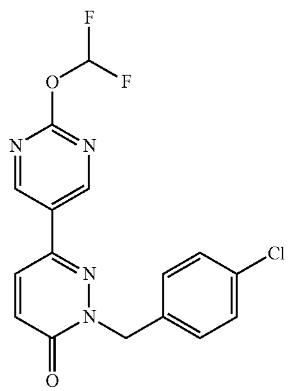 [SMILES: O=c1ccc(-c2cnc(OC(F)F)nc2)nn1Cc1ccc(Cl)cc1] | 2-(4-chlorobenzyl)-6-(2-(difluoromethoxy)pyrimidin-5-yl)pyridazin-3(2H)-one | Lm/z: 365.1 [M + H]+. |
| 11 | 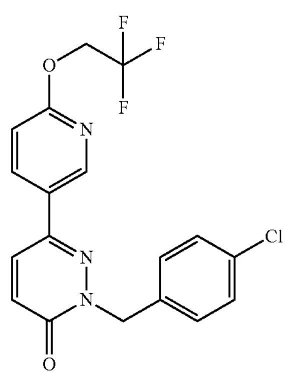 [SMILES: O=c1ccc(-c2ccc(OCC(F)(F)F)nc2)nn1Cc1ccc(Cl)cc1] | 2-(4-chlorobenzyl)-6-(6-(2,2,2-trifluoroethoxy)pyridin-3-yl)pyridazin-3(2H)-one | 396.2 |
| 12 | 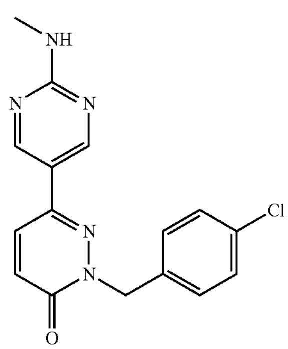 [SMILES: CNc1ncc(-c2ccc(=O)n(Cc3ccc(Cl)cc3)n2)cn1] | 2-(4-chlorobenzyl)-6-(2-(methylamino)pyrimidin-5-yl)pyridazin-3(2H)-one | 328.2 |

TABLE 1-continued

| Cmpd No. | Structure | Name | NMR/MS |
|---|---|---|---|
| 13 | 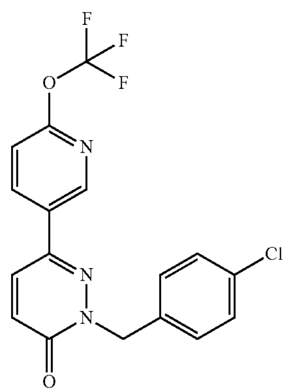 [SMILES: O=c1ccc(-c2ccc(OC(F)(F)F)nc2)nn1Cc1ccc(Cl)cc1] | 2-(4-chlorobenzyl)-6-(6-(trifluoromethoxy)pyridin-3-yl)pyridazin-3(2H)-one | 382.2 |
| 14 | 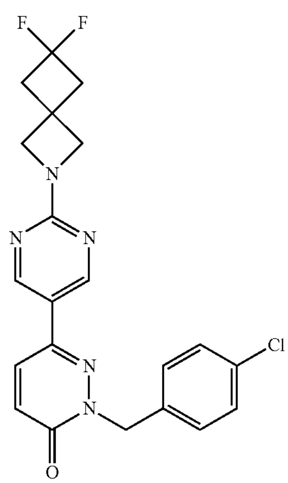 [SMILES: O=c1ccc(-c2cnc(N3CC4(C3)CC(F)(F)C4)nc2)nn1Cc1ccc(Cl)cc1] | 2-(4-chlorobenzyl)-6-(2-(6,6-difluoro-2-azaspiro[3.3]heptan-2-yl)pyrimidin-5-yl)pyridazin-3(2H)-one | [M + H]+ 430.2 |
| 15 | 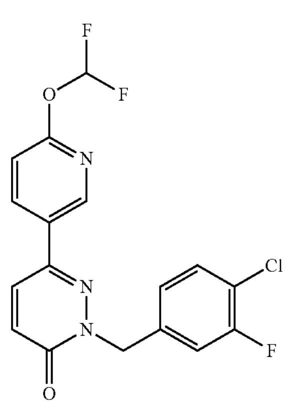 [SMILES: O=c1ccc(-c2ccc(OC(F)F)nc2)nn1Cc1ccc(Cl)c(F)c1] | 2-(4-chloro-3-fluorobenzyl)-6-(6-(difluoromethoxy)pyridin-3-yl)pyridazin-3(2H)-one | 382.2 |

TABLE 1-continued

| Cmpd No. | Structure | Name | NMR/MS |
|---|---|---|---|
| 16 | 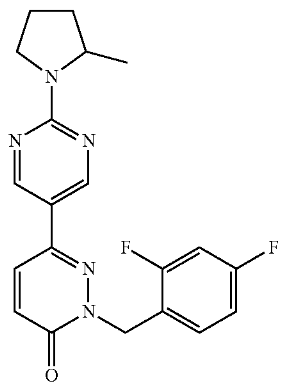 [SMILES: CC1CCCN1c1ncc(-c2ccc(=O)n(Cc3ccc(F)cc3F)n2)cn1] | 2-(2,4-difluorobenzyl)-6-(2-(2-methylpyrrolidin-1-yl)pyrimidin-5-yl)pyridazin-3(2H)-one | [M + H]+ 384.1 |
| 17 | 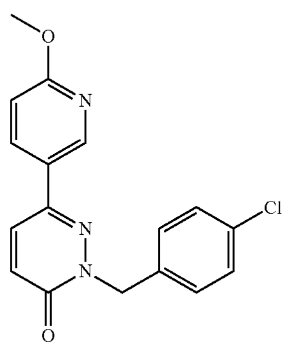 [SMILES: COc1ccc(-c2ccc(=O)n(Cc3ccc(Cl)cc3)n2)cn1] | 2-(4-chlorobenzyl)-6-(6-methoxypyridin-3-yl)pyridazin-3(2H)-one | 328.2 |
| 18 | 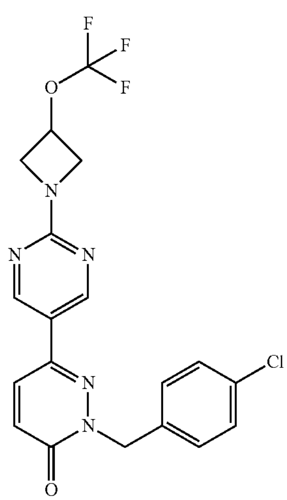 [SMILES: O=c1ccc(-c2cnc(N3CC(OC(F)(F)F)C3)nc2)nn1Cc1ccc(Cl)cc1] | 2-(4-chlorobenzyl)-6-(2-(3-(trifluoromethoxy)azetidin-1-yl)pyrimidin-5-yl)pyridazin-3(2H)-one | [M + H]+ 438.1 |

TABLE 1-continued

| Cmpd No. | Structure | Name | NMR/MS |
|---|---|---|---|
| 19 | 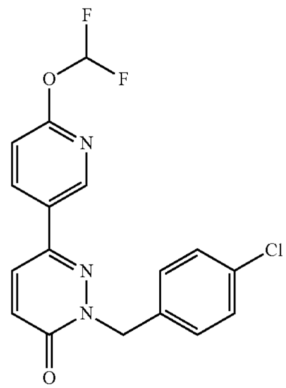 [SMILES: O=c1ccc(-c2ccc(OC(F)F)nc2)nn1Cc1ccc(Cl)cc1] | 2-(4-chlorobenzyl)-6-(6-(difluoromethoxy)pyridin-3-yl)pyridazin-3(2H)-one | 364.2 |
| 20 | 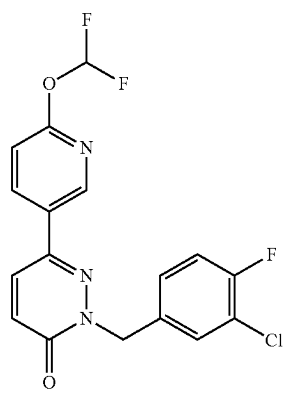 [SMILES: O=c1ccc(-c2ccc(OC(F)F)nc2)nn1Cc1ccc(F)c(Cl)c1] | 2-(3-chloro-4-fluorobenzyl)-6-(6-(difluoromethoxy)pyridin-3-yl)pyridazin-3(2H)-one | m/z: 382.2 [M + H]$^+$ |
| 21 | 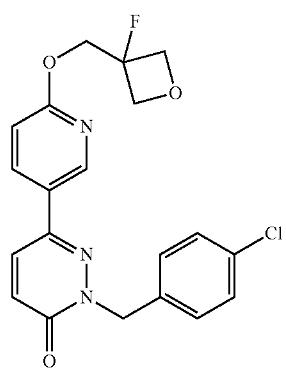 [SMILES: O=c1ccc(-c2ccc(OCC3(F)COC3)nc2)nn1Cc1ccc(Cl)cc1] | 2-(4-chlorobenzyl)-6-(6-((3-fluorooxetan-3-yl)methoxy)pyridin-3-yl)pyridazin-3(2H)-one | MS m/z: 402.2 [M + H]$^+$. |
| 22 | 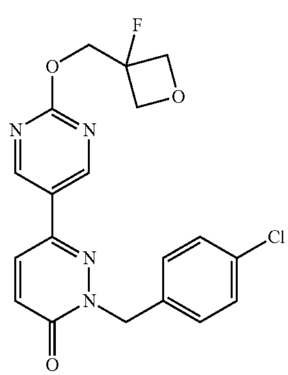 [SMILES: O=c1ccc(-c2cnc(OCC3(F)COC3)nc2)nn1Cc1ccc(Cl)cc1] | 2-(4-chlorobenzyl)-6-(2-((3-fluorooxetan-3-yl)methoxy)pyrimidin-5-yl)pyridazin-3(2H)-one | MS m/z: 403.2 [M + H]$^+$. |

TABLE 1-continued

| Cmpd No. | Structure | Name | NMR/MS |
|---|---|---|---|
| 23 | 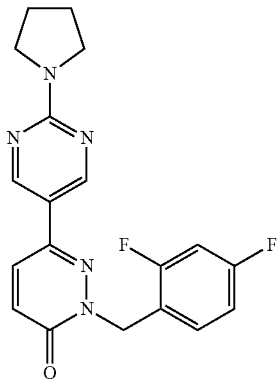 [SMILES: O=c1ccc(-c2cnc(N3CCCC3)nc2)nn1Cc1ccc(F)cc1F] | 2-(2,4-difluorobenzyl)-6-(2-(pyrrolidin-1-yl)pyrimidin-5-yl)pyridazin-3(2H)-one | [M + H]+ 370.2 |
| 24 | 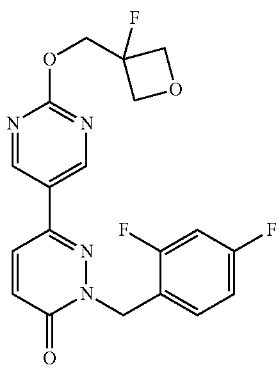 [SMILES: O=c1ccc(-c2cnc(OCC3(F)COC3)nc2)nn1Cc1ccc(F)cc1F] | 2-(2,4-difluorobenzyl)-6-(2-((3-fluorooxetan-3-yl)methoxy)pyrimidin-5-yl)pyridazin-3(2H)-one | |
| 25 | 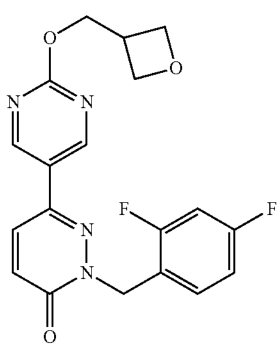 [SMILES: O=c1ccc(-c2cnc(OCC3COC3)nc2)nn1Cc1ccc(F)cc1F] | 2-(2,4-difluorobenzyl)-6-(2-(oxetan-3-ylmethoxy)pyrimidin-5-yl)pyridazin-3(2H)-one | [M + H]+ 387.1 |
| 26 | 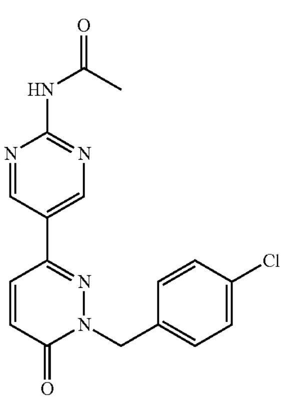 [SMILES: CC(=O)Nc1ncc(-c2ccc(=O)n(Cc3ccc(Cl)cc3)n2)cn1] | N-(5-(1-(4-chlorobenzyl)-6-oxo-1,6-dihydropyridazin-3-yl)pyrimidin-2-yl)acetamide | 356.2 |

TABLE 1-continued

| Cmpd No. | Structure | Name | NMR/MS |
|---|---|---|---|
| 27 | 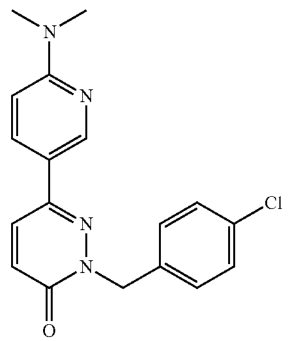 [SMILES: CN(C)c1ccc(-c2ccc(=O)n(Cc3ccc(Cl)cc3)n2)cn1] | 2-(4-chlorobenzyl)-6-(6-(dimethylamino)pyridin-3-yl)pyridazin-3(2H)-one | MS m/z: 341.3 [M + H]+. |
| 28 | 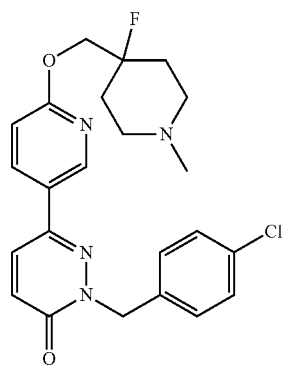 [SMILES: CN1CCC(F)(COc2ccc(-c3ccc(=O)n(Cc4ccc(Cl)cc4)n3)cn2)CC1] | 2-(4-chlorobenzyl)-6-(6-((4-fluoro-1-methylpiperidin-4-yl)methoxy)pyridin-3-yl)pyridazin-3(2H)-one | |
| 29 | 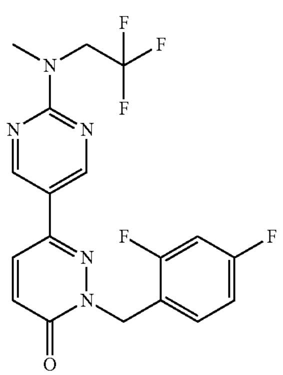 [SMILES: CN(CC(F)(F)F)c1ncc(-c2ccc(=O)n(Cc3ccc(F)cc3F)n2)cn1] | 2-(2,4-difluorobenzyl)-6-(2-(methyl(2,2,2-trifluoroethyl)amino)pyrimidin-5-yl)pyridazin-3(2H)-one | [M + H]+ 412.1 |
| 30 | 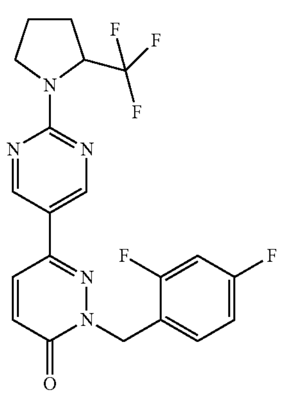 [SMILES: O=c1ccc(-c2cnc(N3CCCC3C(F)(F)F)nc2)nn1Cc1ccc(F)cc1F] | 2-(2,4-difluorobenzyl)-6-(2-(2-(trifluoromethyl)pyrrolidin-1-yl)pyrimidin-5-yl)pyridazin-3(2H)-one | [M + H]+ 438.1 |

TABLE 1-continued

| Cmpd No. | Structure | Name | NMR/MS |
|---|---|---|---|
| 31 | | 2-benzyl-6-(2-(2,2,2-trifluoroethoxy)pyrimidin-5-yl)pyridazin-3(2H)-one | [M + H]+ 363.1 |
| 31 | | 2-benzyl-6-(2-(2,2,2-trifluoroethoxy)pyrimidin-5-yl)pyridazin-3(2H)-one | m/z = 378.2 (M + H) |
| 32 | 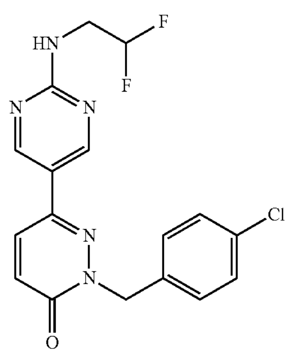 [SMILES: O=c1ccc(-c2cnc(NCC(F)F)nc2)nn1Cc1ccc(Cl)cc1] | 2-(4-chlorobenzyl)-6-(2-((2,2-difluoroethyl)amino)pyrimidin-5-yl)pyridazin-3(2H)-one | m/z = 385.2 (M + H) |
| 33 | 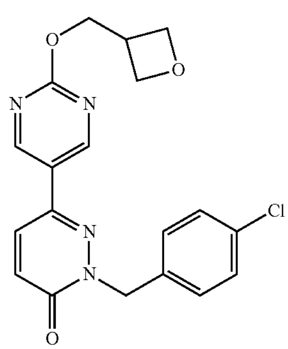 [SMILES: O=c1ccc(-c2cnc(OCC3COC3)nc2)nn1Cc1ccc(Cl)cc1] | 2-(4-chlorobenzyl)-6-(2-(oxetan-3-ylmethoxy)pyrimidin-5-yl)pyridazin-3(2H)-one | LC/MS (ESI): 397 [M + H]+ |

TABLE 1-continued

| Cmpd No. | Structure | Name | NMR/MS |
|---|---|---|---|
| 34 | 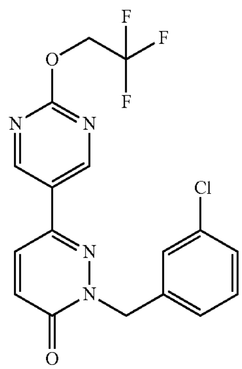 [SMILES: O=c1ccc(-c2cnc(OCC(F)(F)F)nc2)nn1Cc1cccc(Cl)c1] | 2-(3-chlorobenzyl)-6-(2-(2,2,2-trifluoroethoxy)pyrimidin-5-yl)pyridazin-3(2H)-one | 1H NMR (300 MHz, DMSO-d6): δ 9.17 (s, 2H), 8.15 (d, J = 9.9 Hz, 1H), 7.47 (s, 1H), 7.43-7.37 (m, 3H), 7.18 (d, J = 9.6 Hz, 1H), 5.34 (s, 2H), 5.12 (q, J = 9.0 Hz, 2H); LC/MS (ESI): 381 [M + H]$^+$ |
| 35 | 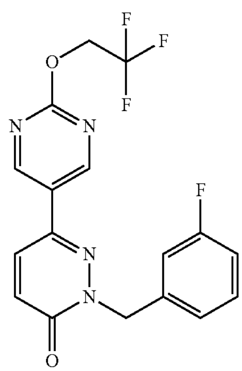 [SMILES: O=c1ccc(-c2cnc(OCC(F)(F)F)nc2)nn1Cc1cccc(F)c1] | 2-(3-fluorobenzyl)-6-(2-(2,2,2-trifluoroethoxy)pyrimidin-5-yl)pyridazin-3(2H)-one | 1H NMR (300 MHz, DMSO-d6): δ 9.16 (s, 2H), 8.15 (d, J = 9.6 Hz, 1H), 7.45-7.37 (m, 1H), 7.25-7.11 (m,4H), 5.35 (s, 2H), 5.12 (q, J = 9.0 Hz, 2H); LC/MS (ESI): 381 [M + H]$^+$ |
| 36 | 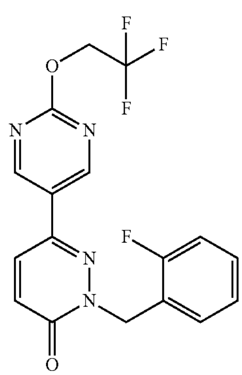 [SMILES: O=c1ccc(-c2cnc(OCC(F)(F)F)nc2)nn1Cc1ccccc1F] | 2-(2-fluorobenzyl)-6-(2-(2,2,2-trifluoroethoxy)pyrimidin-5-yl)pyridazin-3(2H)-one | $^1$H NMR (300 MHz, DMSO-d$_6$): δ 8.93 (s, 2H), 7.62 (d, J = 9.9 Hz, 1H), 7.46-7.26 (m, 2H), 7.19-6.93 (m, 3H), 5.51 (s, 2H), 4.89 (q, J = 8.1 Hz, 2H); LC/MS (ESI): 381 [M + H]$^+$ |
| 37 | 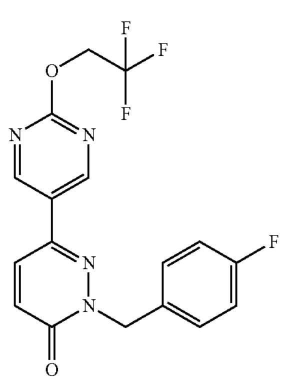 [SMILES: O=c1ccc(-c2cnc(OCC(F)(F)F)nc2)nn1Cc1ccc(F)cc1] | 2-(4-fluorobenzyl)-6-(2-(2,2,2-trifluoroethoxy)pyrimidin-5-yl)pyridazin-3(2H)-one | 1H NMR (300 MHz, DMSO-d6): δ 8.96 (s, 2H), 7.61 (d, J = 9.6 Hz, 1H), 7.56-7.47 (m, 2H), 7.08-6.93 (m, 3H), 5.38 (s, 2H), 4.90 (q, J = 8.4 Hz, 2H); LC/MS (ESI): 399 [M + H]$^+$ |

TABLE 1-continued

| Cmpd No. | Structure | Name | NMR/MS |
|---|---|---|---|
| 38 | 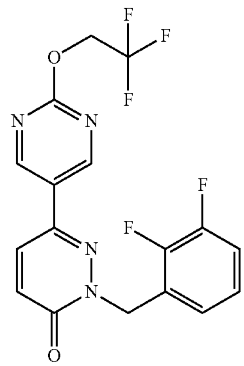 [SMILES: O=c1ccc(-c2cnc(OCC(F)(F)F)nc2)nn1Cc1cccc(F)c1F] | 2-(2,3-difluorobenzyl)-6-(2-(2,2,2-trifluoroethoxy)pyrimidin-5-yl)pyridazin-3(2H)-one | 1H NMR (300 MHz, DMSO-d6): δ 9.10 (s, 2H), 8.15 (d, J = 5.4 Hz, 1H), 7.46-7.34 (m, 1H), 7.24-7.17 (m, 3H), 5.43 (s, 2H), 5.11 (q, J = 9 Hz, 2H); LC/MS (ESI): 399 [M + H]+ |
| 39 | 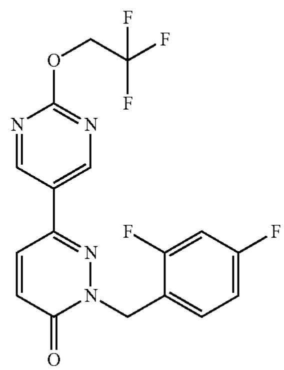 [SMILES: O=c1ccc(-c2cnc(OCC(F)(F)F)nc2)nn1Cc1ccc(F)cc1F] | 2-(2,4-difluorobenzyl)-6-(2-(2,2,2-trifluoroethoxy)pyrimidin-5-yl)pyridazin-3(2H)-one | 1H NMR (300 MHz, DMSO-d6): δ 9.10 (s, 2H), 8.14 (d, J = 9.9 Hz, 1H), 7.53-7.45 (m, 1H), 7.32-7.23 (m, 1H), 7.17 (d, J = 9.6 Hz, 1H), 7.12-7.06 (m, 1H), 5.36 (s, 2H), 5.11 (q, J = 9.0 Hz, 2H); LC/MS (ESI): 399 [M + H]+ |
| 40 | 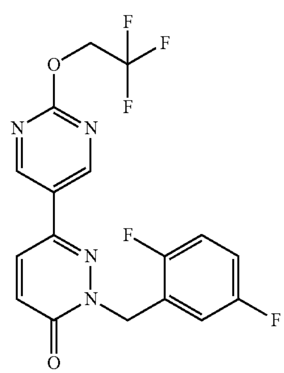 [SMILES: O=c1ccc(-c2cnc(OCC(F)(F)F)nc2)nn1Cc1cc(F)ccc1F] | 2-(2,5-difluorobenzyl)-6-(2-(2,2,2-trifluoroethoxy)pyrimidin-5-yl)pyridazin-3(2H)-one | 1H NMR (300 MHz, DMSO-d6): δ 9.09 (s, 2H), 8.06 (d, J = 9.6 Hz, 1H), 7.22-7.07 (m, 4H), 5.50 (s, 2H), 5.03 (q, J = 8.4 Hz, 2H); LC/MS (ESI): 399 [M + H]+ |
| 41 | 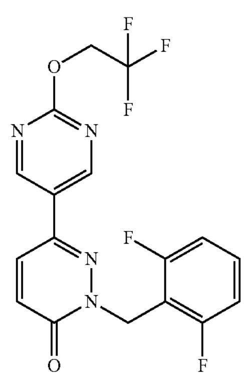 [SMILES: O=c1ccc(-c2cnc(OCC(F)(F)F)nc2)nn1Cc1c(F)cccc1F] | 2-(2,6-difluorobenzyl)-6-(2-(2,2,2-trifluoroethoxy)pyrimidin-5-yl)pyridazin-3(2H)-one | 1H NMR (300 MHz, Methanol-d4) δ 8.97 (s, 2H), 8.03 (d, J = 9.9 Hz, 1H), 7.50-7.40 (m, 1H), 7.15-7.01 (m, 3H), 5.55 (s, 2H), 5.00 (q, J = 8.7 Hz, 2H); LC/MS (ESI): 399 [M + H]+ |

TABLE 1-continued

| Cmpd No. | Structure | Name | NMR/MS |
|---|---|---|---|
| 42 | 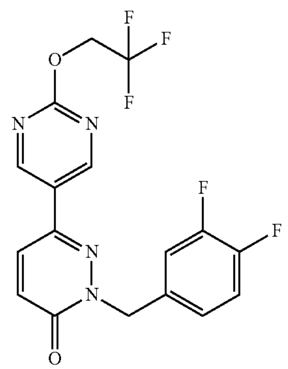 [SMILES: O=c1ccc(-c2cnc(OCC(F)(F)F)nc2)nn1Cc1ccc(F)c(F)c1] | 2-(3,4-difluorobenzyl)-6-(2-(2,2,2-trifluoroethoxy)pyrimidin-5-yl)pyridazin-3(2H)-one | 1H NMR (300 MHz, DMSO-d6): δ 9.17 (s, 2H), 8.14 (d, J = 9.6 Hz, 1H), 7.47-7.40 (m, 2H), 7.17 (d, J = 9.9 Hz, 1H), 5.32 (s, 2H), 5.12 (q, J = 9.0 Hz, 2H); LC/MS (ESI): 399 [M + H]+ |
| 43 | 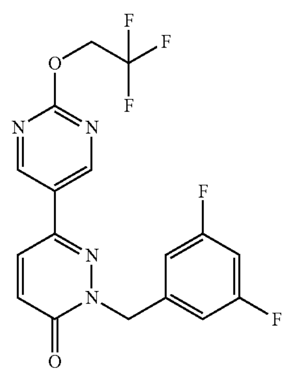 [SMILES: O=c1ccc(-c2cnc(OCC(F)(F)F)nc2)nn1Cc1cc(F)cc(F)c1] | 2-(3,5-difluorobenzyl)-6-(2-(2,2,2-trifluoroethoxy)pyrimidin-5-yl)pyridazin-3(2H)-one | 1H NMR (300 MHz, DMSO-d6): δ 9.18 (s, 2H), 8.16 (d, J = 9.6 Hz, 1H), 7.21-7.11 (m, 4H), 5.35 (s, 2H), 5.12 (q, J = 9.0 Hz, 2H); m/z = 390.3 (M + H) |
| 44 | 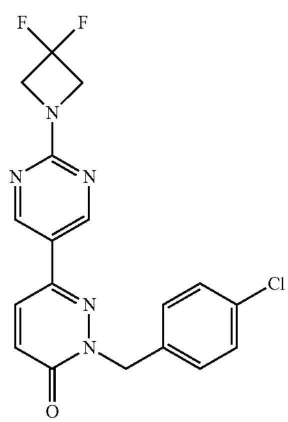 [SMILES: O=c1ccc(-c2cnc(N3CC(F)(F)C3)nc2)nn1Cc1ccc(Cl)cc1] | 2-(4-chlorobenzyl)-6-(2-(3,3-difluoroazetidin-1-yl)pyrimidin-5-yl)pyridazin-3(2H)-one | m/z = 382.3 (M + H) |
| 45 | 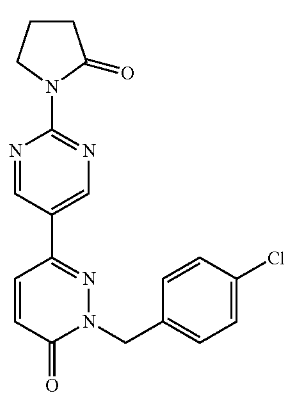 [SMILES: O=C1CCCN1c1ncc(-c2ccc(=O)n(Cc3ccc(Cl)cc3)n2)cn1] | 2-(4-chlorobenzyl)-6-(2-(2-oxopyrrolidin-1-yl)pyrimidin-5-yl)pyridazin-3(2H)-one | m/z = 408.3 (M + H) |

TABLE 1-continued

| Cmpd No. | Structure | Name | NMR/MS |
|---|---|---|---|
| 46 | 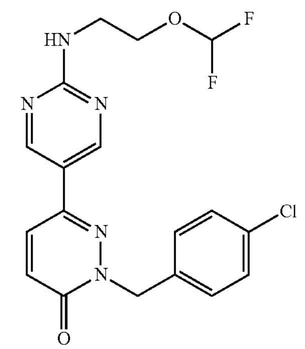 [SMILES: O=c1ccc(-c2cnc(NCCOC(F)F)nc2)nn1Cc1ccc(Cl)cc1] | 2-(4-chlorobenzyl)-6-(2-((2-(difluoromethoxy)ethyl)amino)pyrimidin-5-yl)pyridazin-3(2H)-one | m/z = 396.3 (M + H) |
| 47 | 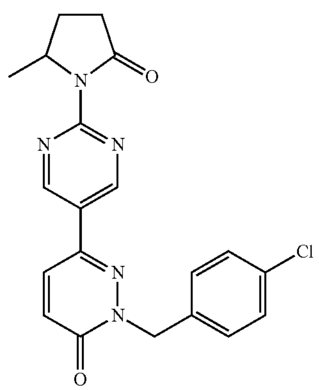 | 2-(4-chlorobenzyl)-6-(2-(2-methyl-5-oxopyrrolidin-1-yl)pyrimidin-5-yl)pyridazin-3(2H)-one | [M + H]+ 393.2 |
| 48 | 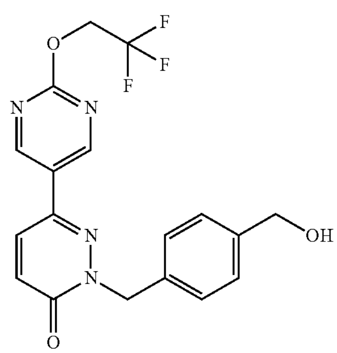 [SMILES: O=c1ccc(-c2cnc(OCC(F)(F)F)nc2)nn1Cc1ccc(CO)cc1] | 2-(4-(hydroxymethyl)benzyl)-6-(2-(2,2,2-trifluoroethoxy)pyrimidin-5-yl)pyridazin-3(2H)-one | [M + H]+ 379.1 |
| 49 | 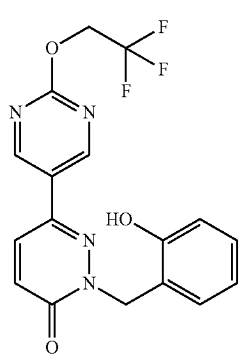 [SMILES: O=c1ccc(-c2cnc(OCC(F)(F)F)nc2)nn1Cc1ccccc1O] | 2-(2-hydroxybenzyl)-6-(2-(2,2,2-trifluoroethoxy)pyrimidin-5-yl)pyridazin-3(2H)-one | [M + H]+ 413 |

TABLE 1-continued

| Cmpd No. | Structure | Name | NMR/MS |
|---|---|---|---|
| 50 | 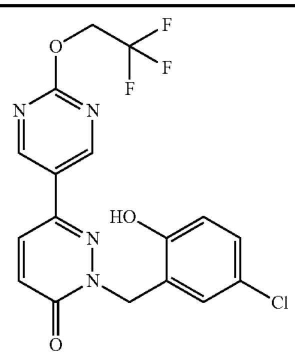 | 2-(5-chloro-2-hydroxybenzyl)-6-(2-(2,2,2-trifluoroethoxy)pyrimidin-5-yl)pyridazin-3(2H)-one | [M + H]+ 430.2 |
| 51 | 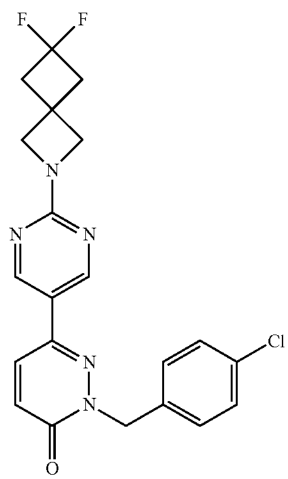 [SMILES: O=c1ccc(-c2cnc(N3CC4(C3)CC(F)(F)C4)nc2)nn1Cc1ccc(Cl)cc1] | 2-(4-chlorobenzyl)-6-(2-(6,6-difluoro-2-azaspiro[3.3]heptan-2-yl)pyrimidin-5-yl)pyridazin-3(2H)-one | MS m/z: 386 [M + H]+ |
| 52 | 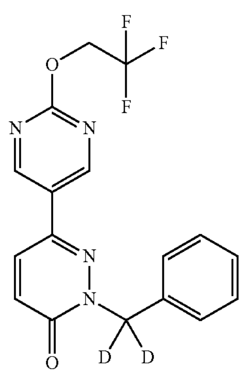 [SMILES: [2H]C([2H])(c1ccccc1)n1nc(-c2cnc(OCC(F)(F)F)nc2)ccc1=O] | 2-(phenylmethyl-d2)-6-(2-(2,2,2-trifluoroethoxy)pyrimidin-5-yl)pyridazin-3(2H)-one | 1H NMR (400 MHz, DMSO-d6) δ 9.18 (s, 2H), 8.55-8.53 (m, 2H), 8.15 (d, J = 9.9 Hz, 1H), 7.81-7.77 (m, 1H), 7.18 (d, J = 9.9 Hz, 1H); m/z = 394.2 (M + H) |
| 53 | 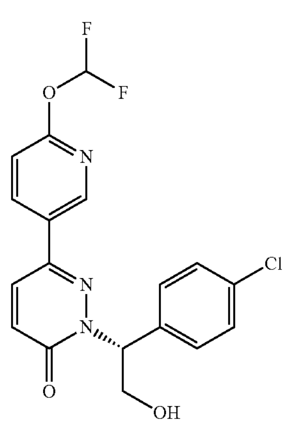 [SMILES: O=c1ccc(-c2ccc(OC(F)F)nc2)nn1[C@@H](CO)c1ccc(Cl)cc1] | (R)-2-(1-(4-chlorophenyl)-2-hydroxyethyl)-6-(6-(difluoromethoxy)pyridin-3-yl)pyridazin-3(2H)-one | MS m/z: 389 |

TABLE 1-continued

| Cmpd No. | Structure | Name | NMR/MS |
|---|---|---|---|
| 54 | 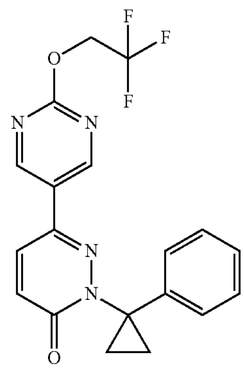 [SMILES: O=c1ccc(-c2cnc(OCC(F)(F)F)nc2)nn1C1(c2ccccc2)CC1] | 2-(1-phenylcyclopropyl)-6-(2-(2,2,2-trifluoroethoxy)pyrimidin-5-yl)pyridazin-3(2H)-one | [M + H]+ 409.3 |

In some embodiments, compounds of the disclosure are below in Table 2.

TABLE 2

| Cmpd No. | Structure | Name | NMR/MS |
|---|---|---|---|
| 101 | 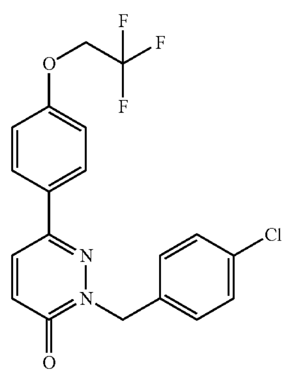 | 2-(4-chlorobenzyl)-6-(4-(2,2,2-trifluoroethoxy)phenyl)pyridazin-3(2H)-one | 395.2 |
| 102 | 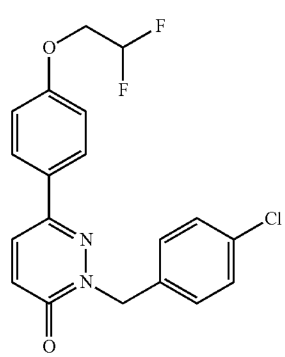 | 2-(4-chlorobenzyl)-6-(4-(2,2-difluoroethoxy)phenyl)pyridazin-3(2H)-one | 377.3 |

TABLE 2-continued

| Cmpd No. | Structure | Name | NMR/MS |
|---|---|---|---|
| 103 | 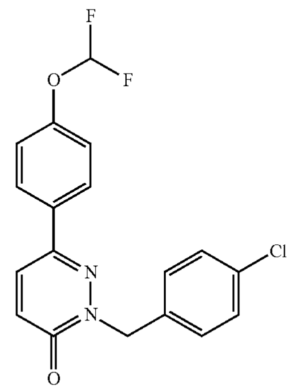 | 2-(4-chlorobenzyl)-6-(4-(difluoromethoxy)phenyl)pyridazin-3(2H)-one | 363.2 |
| 104 | 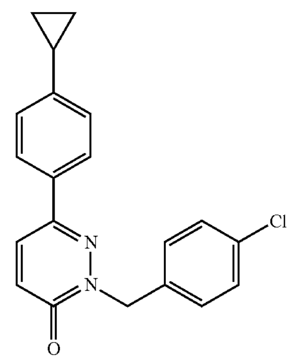 | 2-(4-chlorobenzyl)-6-(4-cyclopropylphenyl)pyridaidn-3(2H)-one | 337.3 |
| 105 | 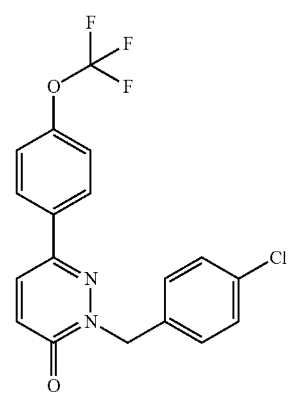 | 2-(4-chl orobenzyl)-6-(4-(trifluoromethoxy)phenyl)pyridazin-3(2H)-one | 381.2 |
| 106 | 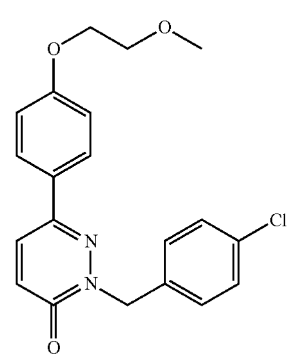 | 2-(4-chlorobenzyl)-6-(4-(2-methoxyethoxy)phenyl)pyridazin-3(2H)-one | 371.3 |

TABLE 2-continued

| Cmpd No. | Structure | Name | NMR/MS |
|---|---|---|---|
| 107 | 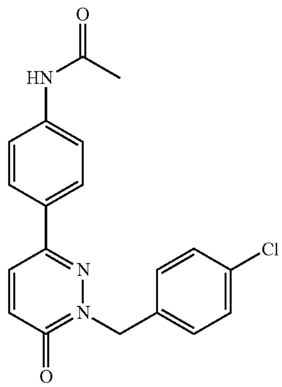 | N-(4-(1-(4-chlorobenzyl)-6-oxo-1,6-dihydropyridazin-3-yl)phenyl)acetamide | $^1$H NMR (DMSO-d6, 300 MHz): δ 10.14 (s, 1H), 8.05 (d, J = 9.9 Hz, 1H), 7.84 (d, J = 8.7 Hz, 2H), 7.70 (d, J = 8.7 Hz, 2H), 7.44-7.37 (m, 4H), 7.08 (d, J = 9.6 Hz, 1H), 5.31 (s, 2H), 2.07 (s, 3H); LC/MS (ESI): 354 [M + H]$^+$ |
| 108 | 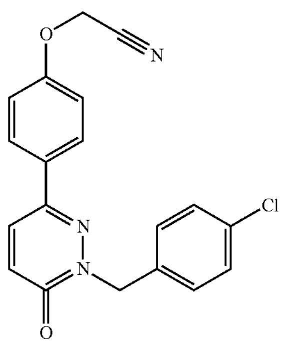 | 2-(4-(1-(4-chlorobenzyl)-6-oxo-1,6-dihydropyridazin-3-yl)phenoxy)acetonitrile | 352.2 |
| 109 | 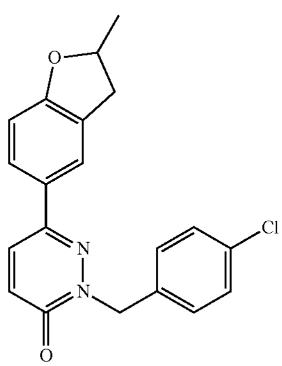 | 2-(4-chlorobenzyl)-6-(2-methyl-2,3-dihydrobenzofuran-5-yl)pyridazin-3(2H)-one | 353.3 |
| 110 | 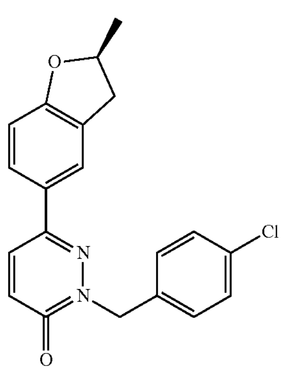 | (S)-2-(4-chlorobenzyl)-6-(2-methyl-2,3-dihydrobenzofuran-5-yl)pyridazin-3(2H)-one | m/z = 353.2 (M + H) |

TABLE 2-continued

| Cmpd No. | Structure | Name | NMR/MS |
|---|---|---|---|
| 111 | 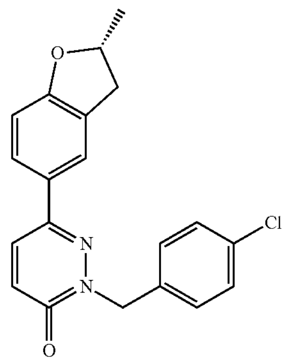 | (R)-2-(4-chlorobenzyl)-6-(2-methyl-2,3-dihydrobenzofuran-5-yl)pyridazin-3(2H)-one | |
| 112 | 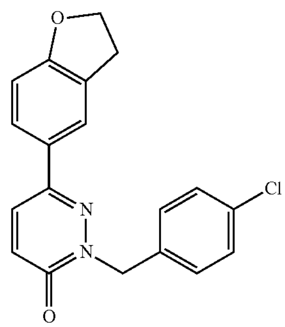 | 2-(4-chlorobenzyl)-6-(2,3-dihydrobenzofuran-5-yl)pyridazin-3(2H)-one | 339.2 |
| 113 | 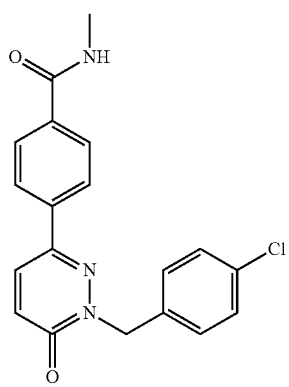 | 4-(1-(4-chlorobenzyl)-6-oxo-1,6-dihydropyridazin-3-yl)-N-methylbenzamide | [M + H]+ 354.2 |
| 114 | 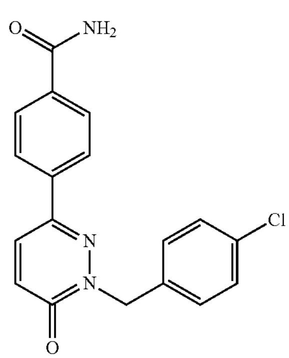 | 4-(1-(4-chlorobenzyl)-6-oxo-1,6-dihydropyridazin-3-yl)benzamide | [M + H]+ 340.1 |

TABLE 2-continued

| Cmpd No. | Structure | Name | NMR/MS |
|---|---|---|---|
| 115 | 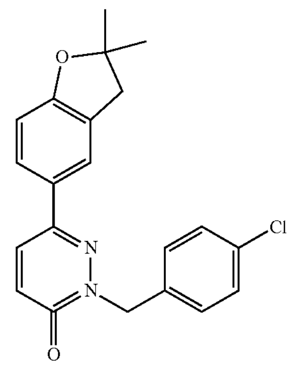 | 2-(4-chlorobenzyl)-6-(2,2-dimethyl-2,3-dihydrobenzofuran-5-yl)pyridazin-3(2H)-one | 367.3 |
| 116 | 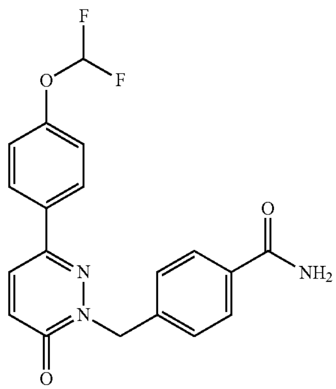 | 4-((3-(4-(difluoromethoxy)phenyl)-6-oxopyridazin-1(6H)-yl)methyl)benzamide | 372.3 |
| 117 | 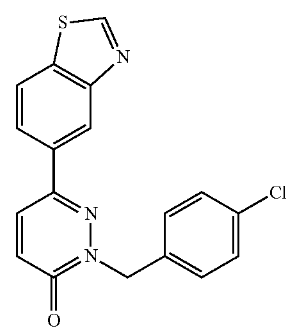 | 6-(benzo[d]thiazol-5-yl)-2-(4-chlorobenzyl)pyridazin-3(2H)-one | 354.2 |
| 118 | 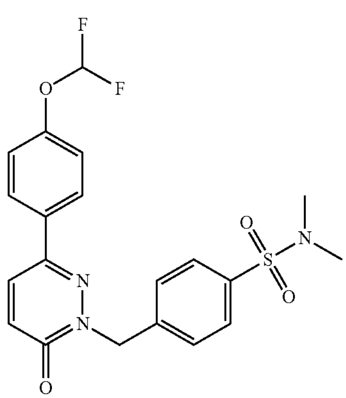 | 4-((3-(4-(difluoromelhoxy)phenyl)-6-oxopyridazin-1(6H)-yl)methyl)-N,N-dimethylbenzenesulfonamide | 436.3 |

TABLE 2-continued

| Cmpd No. | Structure | Name | NMR/MS |
|---|---|---|---|
| 119 | 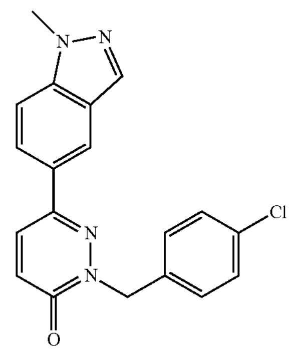 | 2-(4-chlorobenzyl)-6-(1-methyl-1H-indazol-5-yl)pyridazin-3(2H)-one | 351.2 |
| 120 | 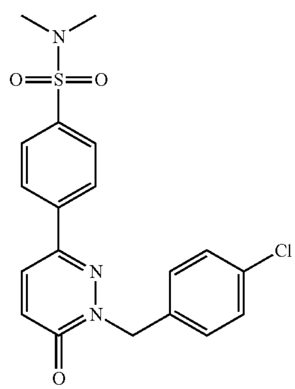 | 4-(1-(4-chlorobenzyl)-6-oxo-1,6-dihydropyridazin-3-yl)-N,N-dimethylbenzenesulfonamide | 404.2 |
| 121 | 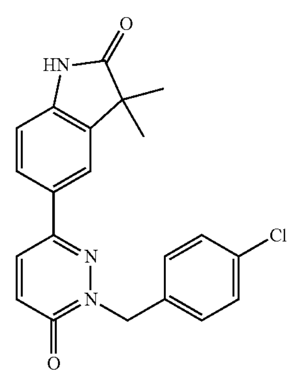 | 5-(1-(4-chlorobenzyl)-6-oxo-1,6-dihydropyridazin-3-yl)-3,3-dimethylindolin-2-one | 380.3 |
| 122 | 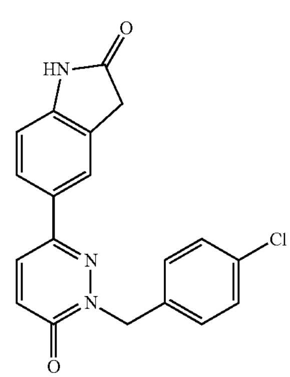 | 5-(1-(4-chlorobenzyl)-6-oxo-1,6-dihydropyridazin-3-yl)indolin-2-one | 352.3 |

TABLE 2-continued

| Cmpd No. | Structure | Name | NMR/MS |
|---|---|---|---|
| 123 | 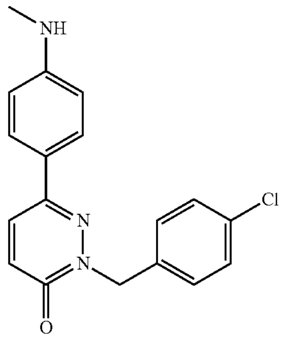 | 2-(4-chlorobenzyl)-6-(4-(methylamino)phenyl)pyridazin-3(2H)-one | $^1$H NMR (DMSO-d6, 300 MHz): δ 7.96 (d, J = 9.9 Hz, 1H), 7.64 (d, J = 8.7 Hz, 2H), 7.43-7.35 (m, 4H), 7.00 (d, J = 9.6 Hz, 1H), 6.60 (d, J = 8.7 Hz, 2H), 6.11 (m, 1H), 5.27 (s, 2H), 2.72 (d, J = 5.1 Hz, 3H); LC/MS (ESI): 326 [M + H]$^+$ |

In certain embodiments, compounds of the methods described herein may be selected from commercially available compounds including those depicted in Table 3. Compounds of Table 3 and 4 were tested and results of the assay appear in Table 6 herein. A=IC$_{50}$ is less than or equal to 10 μM; B=IC$_{50}$ is greater than 10 μM and less than 100 μM; C=IC$_{50}$ is greater than 100 μM.

TABLE 3

| Cmpd No. | Structure | Name |
|---|---|---|
| 201 | 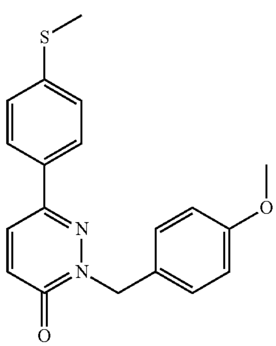 | 2-(4-methoxybenzyl)-6-(4-(methylthio)phenyl)pyridazin-3(2H)-one |
| 202 | 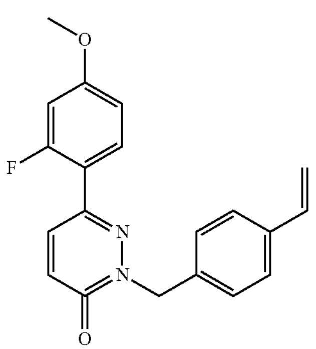 | 6-(2-fluoro-4-methoxyphenyl)-2-(4-vinylbenzyl)pyridazin-3(2H)-one |

TABLE 3-continued

| Cmpd No. | Structure | Name |
|---|---|---|
| 203 | 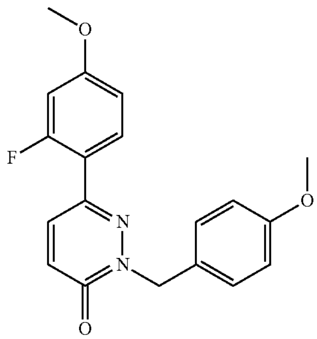 | 6-(2-fluoro-4-methoxyphenyl)-2-(4-methoxybenzyl)pyridazin-3(2H)-one |
| 204 | 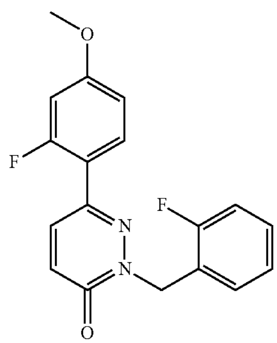 | 6-(2-fluoro-4-methoxyphenyl)-2-(2-fluorobenzyl)pyridazin-3(2H)-one |
| 205 | 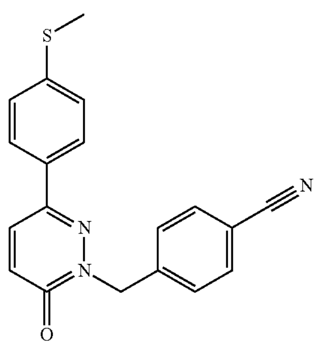 | 4-((3-(4-(methylthio)phenyl)-6-oxopyridazin-1(6H)-yl)methyl)benzonitrile |
| 206 | 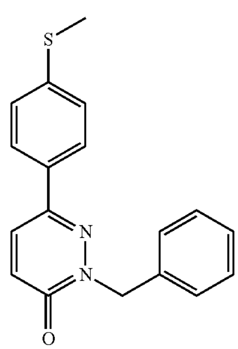 | 2-benzyl-6-(4-(methylthio)phenyl)pyridazin-3(2H)-one |

TABLE 3-continued

| Cmpd No. | Structure | Name |
|---|---|---|
| 207 | 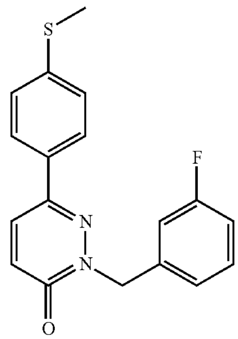 | 2-(3-fluorobenzyl)-6-(4-(methylthio)phenyl)pyridazin-3(2H)-one |
| 208 | 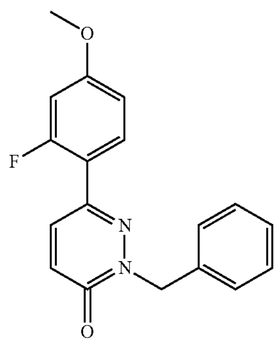 | 2-benzyl-6-(2-fluoro-4-methoxyphenyl)pyridazin-3(2H)-one |
| 209 | 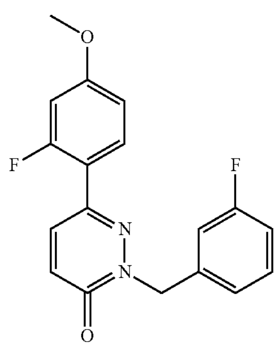 | 6-(2-fluoro-4-methoxyphenyl)-2-(3-fluorobenzyl)pyridazin-3(2H)-one |
| 210 | 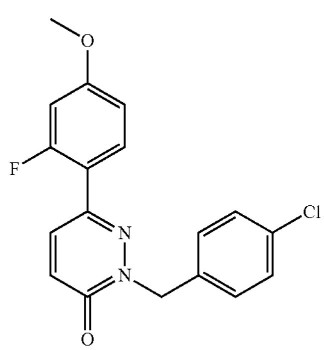 | 2-(4-chlorobenzyl)-6-(2-fluoro-4-methoxyphenyl)pyridazin-3(2H)-one |

TABLE 3-continued

| Cmpd No. | Structure | Name |
|---|---|---|
| 211 | 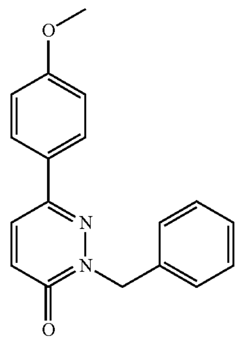 | 2-benzyl-6-(4-methoxyphenyl)pyridazin-3(2H)-one |
| 212 | 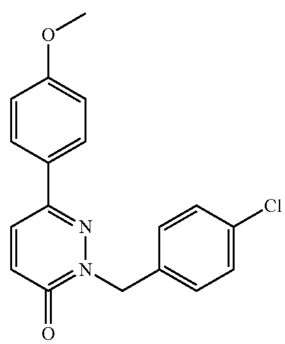 | 2-(4-chlorobenzyl)-6-(4-methoxyphenyl)pyridazin-3(2H)-one |
| 213 | 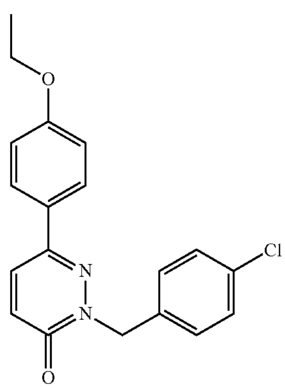 | 2-(4-chlorobenzyl)-6-(4-ethoxyphenyl)pyridazin-3(2H)-one |
| 214 | 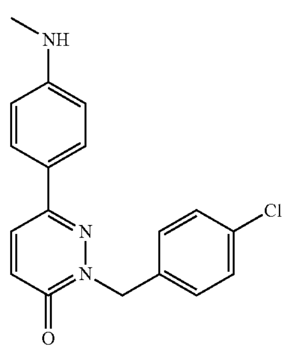 | 2-(4-chlorobenzyl)-6-(4-(methylamino)phenyl)pyridazin-3(2H)-one |

TABLE 3-continued

| Cmpd No. | Structure | Name |
|---|---|---|
| 215 | 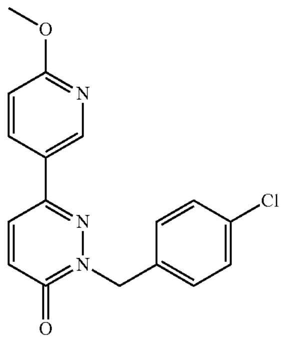 | 2-(4-chlorobenzyl)-6-(6-methoxypyridin-3-yl)pyridazin-3(2H)-one |
| 216 | 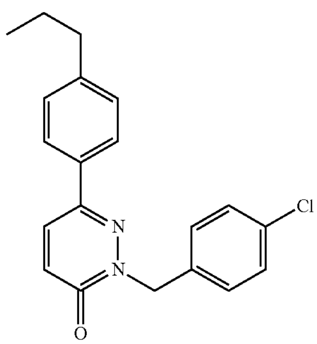 | 2-(4-chlorobenzyl)-6-(4-propylphenyl)pyridazin-3(2H)-one |
| 217 | 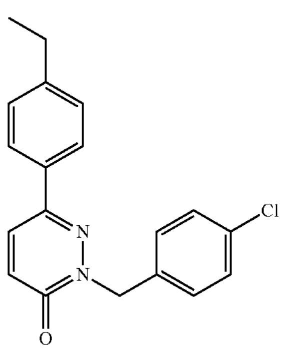 | 2-(4-chlorobenzyl)-6-(4-ethylphenyl)pyridazin-3(2H)-one |
| 218 | 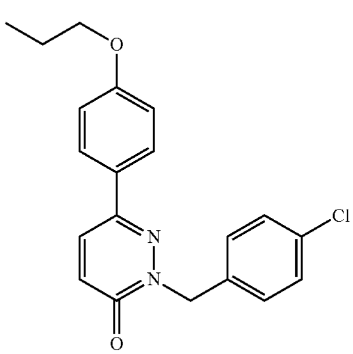 | 2-(4-chlorobenzyl)-6-(4-propoxyphenyl)pyridazin-3(2H)-one |

TABLE 3-continued

| Cmpd No. | Structure | Name |
|---|---|---|
| 219 | 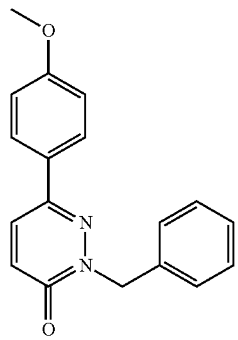 | 2-benzyl-6-(4-methoxyphenyl)pyridazin-3(2H)-one |
| 220 | 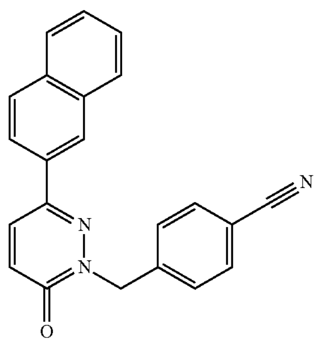 | 4-((3-(naphthalen-2-yl)-6-oxopyridazin-1(6H)-yl)methyl)benzonitrile |
| 221 | 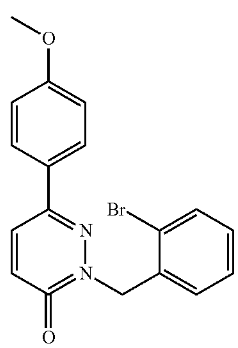 | 2-(2-bromobenzyl)-6-(4-methoxyphenyl)pyridazin-3(2H)-one |
| 222 | 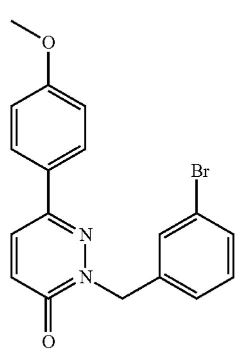 | 2-(3-bromobenzyl)-6-(4-methoxyphenyl)pyridazin-3(2H)-one |

TABLE 3-continued

| Cmpd No. | Structure | Name |
|---|---|---|
| 223 | 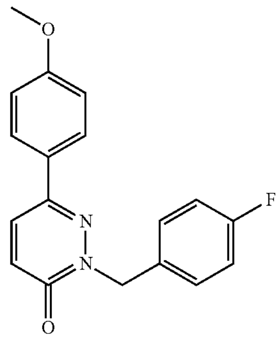 | 2-(4-fluorobenzyl)-6-(4-methoxyphenyl)pyridazin-3(2H)-one |
| 224 | 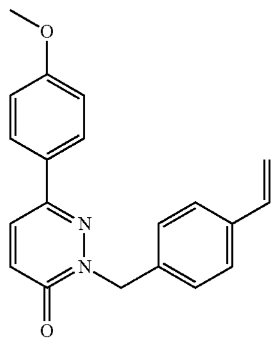 | 6-(4-methoxyphenyl)-2-(4-vinylbenzyl)pyridazin-3(2H)-one |
| 225 | 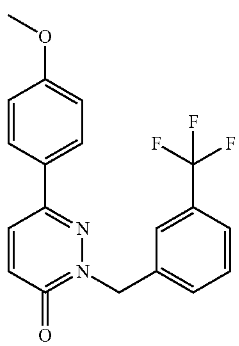 | 6-(4-methoxyphenyl)-2-(3-(trifluoromethyl)benzyl)pyridazin-3(2H)-one |
| 226 | 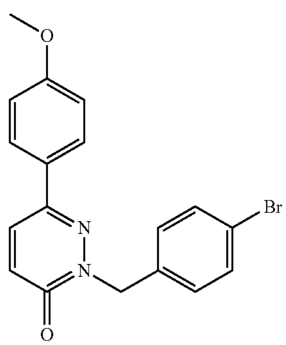 | 2-(4-bromobenzyl)-6-(4-methoxyphenyl)pyridazin-3(2H)-one |

TABLE 3-continued

| Cmpd No. | Structure | Name |
|---|---|---|
| 227 | 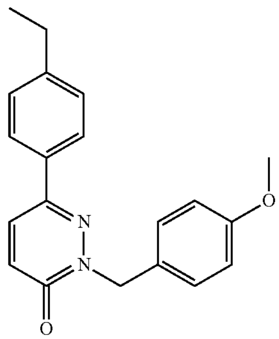 | 2-(4-methoxybenzyl)-6-(4-methoxyphenyl)pyridazin-3(2H)-one |
| 228 | 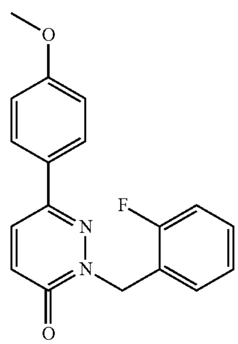 | 2-(2-fluorobenzyl)-6-(4-methoxyphenyl)pyridazin-3(2H)-one |
| 229 | 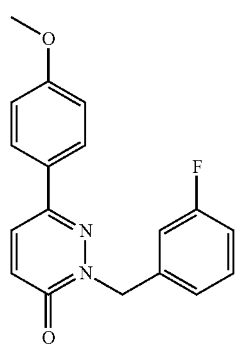 | 2-(3-fluorobenzyl)-6-(4-methoxyphenyl)pyridazin-3(2H)-one |
| 230 | 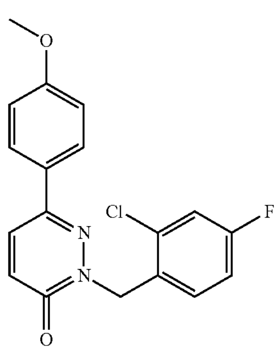 | 2-(2-chloro-4-fluorobenzyl)-6-(4-methoxyphenyl)pyridazin-3(2H)-one |

TABLE 3-continued

| Cmpd No. | Structure | Name |
|---|---|---|
| 231 | 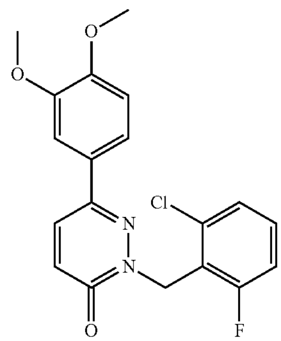 | 2-(2-chloro-6-fluorobenzyl)-6-(3,4-dimethoxyphenyl)pyridazin-3(2H)-one |
| 232 | 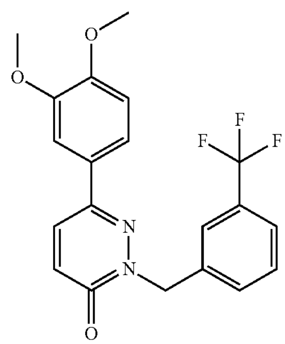 | 6-(3,4-dimethoxyphenyl)-2-(3-(trifluoromethyl)benzyl)pyridazin-3(2H)-one |
| 233 | 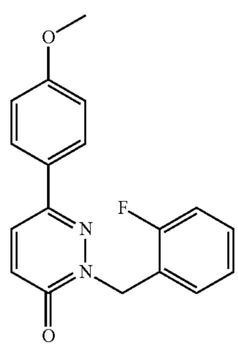 | 2-(2-fluorobenzyl)-6-(4-methoxyphenyl)pyridazin-3(2H)-one |
| 234 | 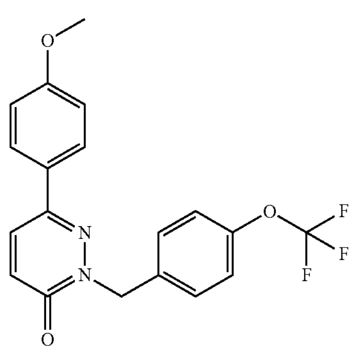 | 6-(4-methoxyphenyl)-2-(4-(trifluoromethoxy)benzyl)pyridazin-3(2H)-one |

TABLE 3-continued

| Cmpd No. | Structure | Name |
|---|---|---|
| 235 | 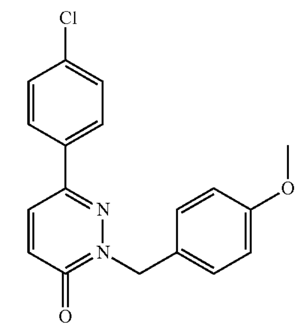 | 6-(4-chlorophenyl)-2-(4-methoxybenzyl)pyridazin-3(2H)-one |
| 236 | 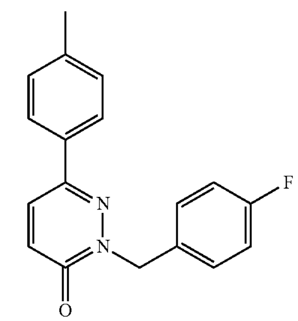 | 2-(4-fluorobenzyl)-6-(p-tolyl)pyridazin-3(2H)-one |
| 237 | 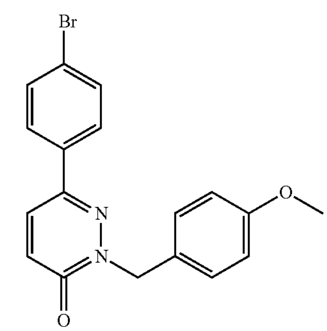 | 6-(4-bromophenyl)-2-(4-methoxybenzyl)pyridazin-3(2H)-one |
| 238 | 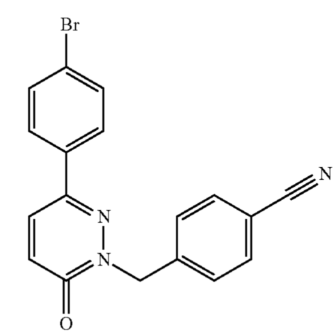 | 4-((3-(4-bromophenyl)-6-oxopyridazin-1(6H)-yl)methyl)benzonitrile |

TABLE 3-continued
| Cmpd No. | Structure | Name |
|---|---|---|
| 239 | 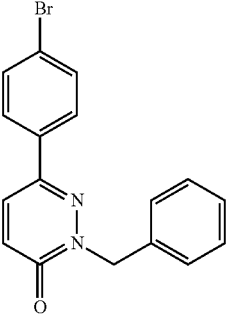 | 2-benzyl-6-(4-bromophenyl)pyridazin-3(2H)-one |
| 240 | 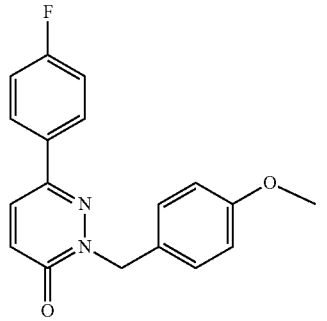 | 6-(4-fluorophenyl)-2-(4-methoxybenzyl)pyridazin-3(2H)-one |
| 241 | 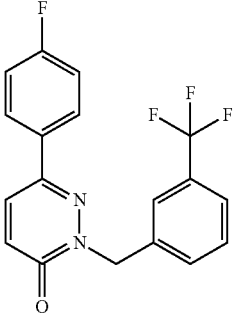 | 6-(4-fluorophenyl)-2-(3-(trifluoromethyl)benzyl)pyridazin-3(2H)-one |
| 242 | 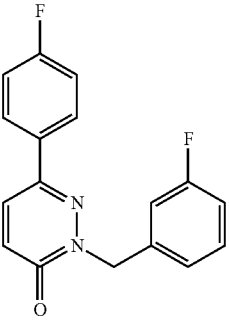 | 2-(3-fluorobenzyl)-6-(4-fluorophenyl)pyridazin-3(2H)-one |

TABLE 3-continued

| Cmpd No. | Structure | Name |
|---|---|---|
| 243 | 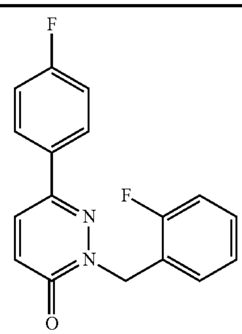 | 2-(2-fluorobenzyl)-6-(4-fluorophenyl)pyridazin-3(2H)-one |
| 244 | 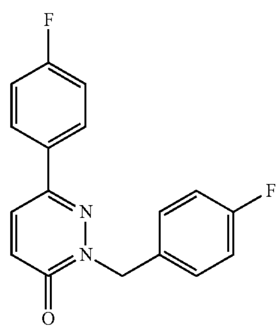 | 2-(4-fluorobenzyl)-6-(4-fluorophenyl)pyridazin-3(2H)-one |

In certain embodiments, other compounds of the methods described herein include those in Table 4 or a salt thereof.

TABLE 4

| Compound No. | Structure | Name |
|---|---|---|
| 300 | 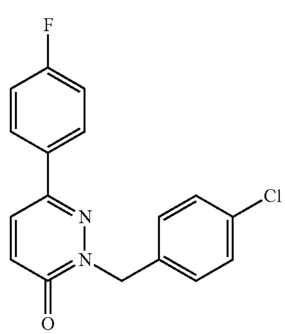 | 2-(4-chlorobenzyl)-6-(4-fluorophenyl)pyridazin-3(2H)-one |
| 301 | 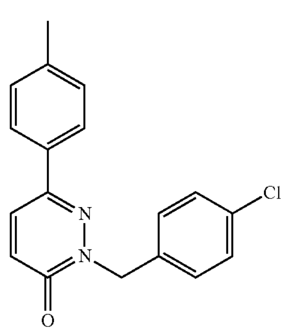 | 2-(4-chlorobenzyl)-6-(p-tolyl)pyridazin-3(2H)-one |

TABLE 4-continued
| Compound No. | Structure | Name |
|---|---|---|
| 302 | 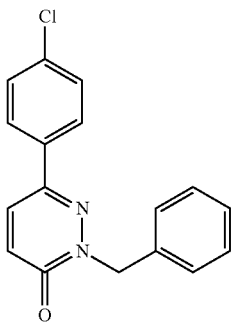 | 2-benzyl-6-(4-chlorophenyl)pyridazin-3(2H)-one |
| 303 | 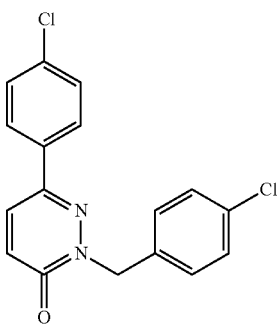 | 2-(4-chlorobenzyl)-6-(4-chlorophenyl)pyridazin-3(2H)-one |
| 304 | 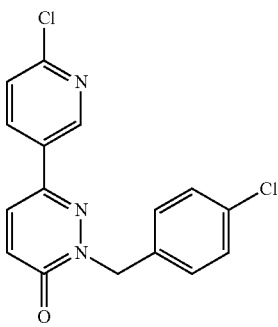 | 2-(4-chlorobenzyl)-6-(6-chloropyridin-3-yl)pyridazin-3(2H)-one |
| 305 | 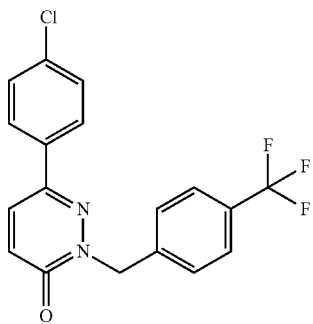 | 6-(4-chlorophenyl)-2-(4-(trifluoromethyl)benzyl)pyridazin-3(2H)-one |

TABLE 4-continued

| Compound No. | Structure | Name |
| --- | --- | --- |
| 306 | 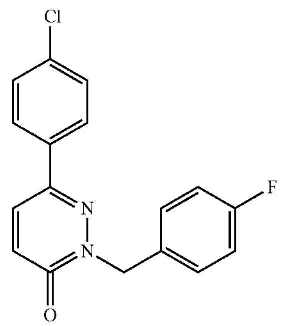 | 6-(4-chlorophenyl)-2-(4-fluorobenzyl)pyridazin-3(2H)-one |
| 307 | 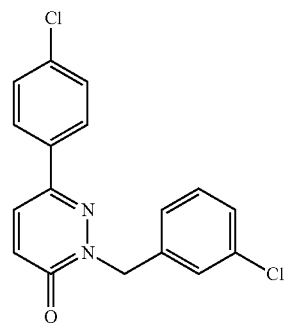 | 2-(3-chlorobenzyl)-6-(4-chlorophenyl)pyridazin-3(2H)-one |
| 308 | 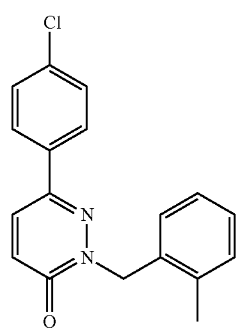 | 6-(4-chlorophenyl)-2-(2-methylbenzyl)pyridazin-3(2H)-one |
| 309 | 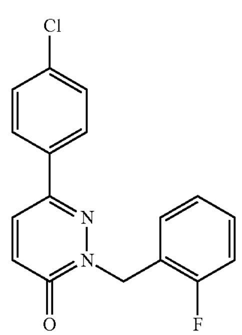 | 6-(4-chlorophenyl)-2-(2-fluorobenzyl)pyridazin-3(2H)-one |

TABLE 4-continued
| Compound No. | Structure | Name |
|---|---|---|
| 310 | 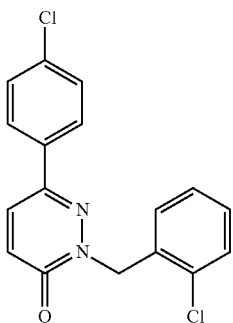 | 2-(2-chlorobenzyl)-6-(4-chlorophenyl)pyridazin-3(2H)-one |
| 311 | 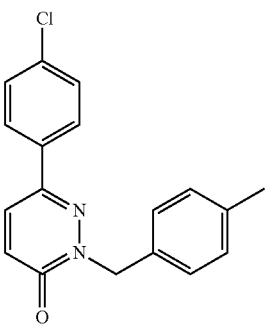 | 6-(4-chlorophenyl)-2-(4-methylbenzyl)pyridazin-3(2H)-one |
| 312 | 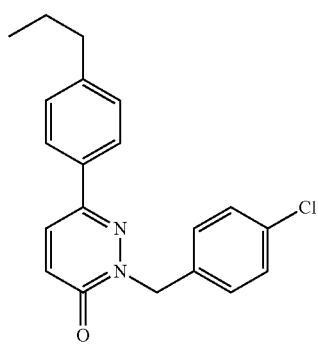 | 2-(4-chlorobenzyl)-6-(4-propylphenyl)pyridazin-3(2H)-one |
| 313 | 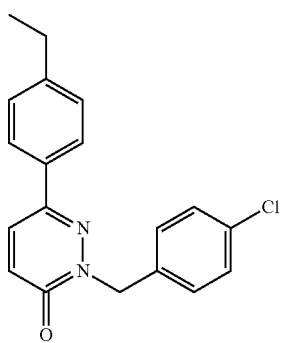 | 2-(4-chlorobenzyl)-6-(4-ethylphenyl)pyridazin-3(2H)-one |

TABLE 4-continued

| Compound No. | Structure | Name |
|---|---|---|
| 314 | 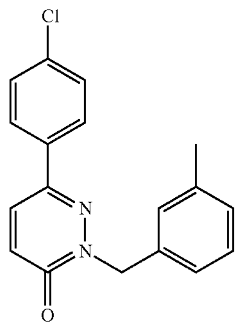 | 6-(4-chlorophenyl)-2-(3-methylbenzyl)pyridazin-3(2H)-one |
| 315 | 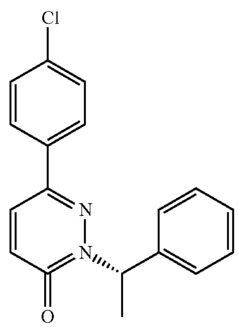 | (S)-6-(4-chlorophenyl)-2-(1-phenylethyl)pyridazin-3(2H)-one |
| 316 | 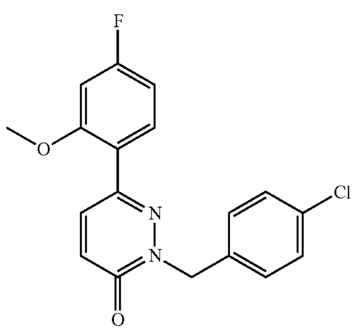 | 2-(4-chlorobenzyl)-6-(4-fluoro-2-methoxyphenyl)pyridazin-3(2H)-one |
| 317 | 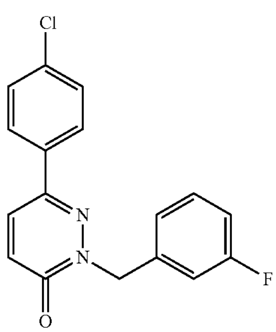 | 6-(4-chlorophenyl)-2-(3-fluorobenzyl)pyridazin-3(2H)-one |

Compounds of the disclosure have skeletal $IC_{50}$ values as in Table 5.

TABLE 5

| Cmpd No. | $IC_{50}$ | Cmpd No. | $IC_{50}$ | Cmpd No. | $IC_{50}$ |
|---|---|---|---|---|---|
| 1 | A | 11 | A | 21 | A |
| 2 | A | 12 | A | 22 | A |
| 3 | A | 13 | A | 23 | A |
| 4 | A | 14 | A | 24 | A |
| 5 | A | 15 | A | 25 | A |
| 6 | A | 16 | A | 26 | A |
| 7 | A | 17 | A | 27 | A |
| 8 | A | 18 | A | 28 | C |
| 9 | A | 19 | A | 29 | A |
| 10 | A | 20 | A | 30 | A |

TABLE 5-continued

| Cmpd No. | IC$_{50}$ | Cmpd No. | IC$_{50}$ | Cmpd No. | IC$_{50}$ |
|---|---|---|---|---|---|
| 31 | A | 41 | A | 51 | A |
| 32 | A | 42 | A | 52 | A |
| 33 | A | 43 | A | 53 | C |
| 34 | A | 44 | A | 54 | A |
| 35 | A | 45 | B | 101 | A |
| 36 | A | 46 | A | 102 | A |
| 37 | A | 47 | A | 103 | A |
| 38 | A | 48 | A | 104 | A |
| 39 | A | 49 | A | 105 | A |
| 40 | A | 50 | A | 106 | A |
| 107 | A | 117 | C | 212 | A |
| 108 | A | 118 | C | 213 | A |
| 109 | A | 119 | C | 214 | A |
| 110 | A | 120 | C | 215 | A |
| 111 | A | 121 | C | 216 | A |
| 112 | A | 122 | C | 217 | A |
| 113 | B | 123 | A | 218 | A |
| 114 | B | 201 | C | 235 | A |
| 115 | C | 202 | C | 236 | A |
| 116 | C | 211 | A | 237 | A |
| 238 | B | 303 | A | 313 | A |
| 239 | A | 304 | A | 314 | A |
| 240 | B | 305 | C | 315 | C |
| 241 | C | 306 | A | 316 | C |
| 242 | A | 307 | A | 317 | A |
| 243 | B | 308 | A | | |
| 244 | B | 309 | A | | |
| 300 | A | 310 | A | | |
| 301 | A | 311 | A | | |
| 302 | A | 312 | A | | |

A = IC$_{50}$ is less than or equal to 10 μM; B = IC$_{50}$ is greater than 10 μM and less than 100 μM; C = IC$_{50}$ is greater than 100 μM.

Compounds of the disclosure have cardiac IC$_{50}$ values as in Table 6.

TABLE 6

| Cmpd No. | IC$_{50}$ | Cmpd No. | IC$_{50}$ | Cmpd No. | IC$_{50}$ |
|---|---|---|---|---|---|
| 1 | B | 11 | C | 21 | B |
| 2 | B | 12 | A | 22 | C |
| 3 | C | 13 | C | 23 | C |
| 4 | B | 14 | C | 24 | C |
| 5 | B | 15 | A | 25 | C |
| 6 | C | 16 | B | 26 | C |
| 7 | C | 17 | B | 27 | C |
| 8 | C | 18 | C | 28 | C |
| 9 | A | 19 | C | 29 | B |
| 10 | A | 20 | B | 30 | C |
| 31 | B | 41 | C | 51 | C |
| 32 | C | 42 | B | 52 | B |
| 33 | C | 43 | B | 53 | C |
| 34 | A | 44 | A | 54 | C |
| 35 | B | 45 | B | 101 | C |
| 36 | B | 46 | C | 102 | A |
| 37 | B | 47 | C | 103 | C |
| 38 | B | 48 | C | 104 | C |
| 39 | B | 49 | C | 105 | C |
| 40 | B | 50 | C | 106 | C |
| 107 | C | 117 | C | 214 | A |
| 108 | C | 118 | C | 215 | B |
| 109 | C | 119 | C | 216 | C |
| 110 | C | 120 | C | 217 | C |
| 111 | C | 121 | C | 218 | C |
| 112 | C | 122 | C | 235 | C |
| 113 | C | 123 | A | 236 | B |
| 114 | C | 211 | B | 237 | C |
| 115 | C | 212 | B | 238 | C |
| 116 | C | 213 | B | 239 | C |
| 240 | C | 305 | C | 315 | C |
| 241 | C | 306 | C | 316 | C |
| 242 | C | 307 | A | 317 | A |
| 243 | C | 308 | C | | |
| 244 | C | 309 | C | | |
| 300 | B | 310 | C | | |
| 301 | B | 311 | C | | |
| 302 | B | 312 | C | | |
| 303 | B | 313 | C | | |
| 304 | A | 314 | B | | |

What is claimed is:

1. A method of treating a neuromuscular condition, the method comprising administering to a patient in need thereof a compound represented by Formula (I):

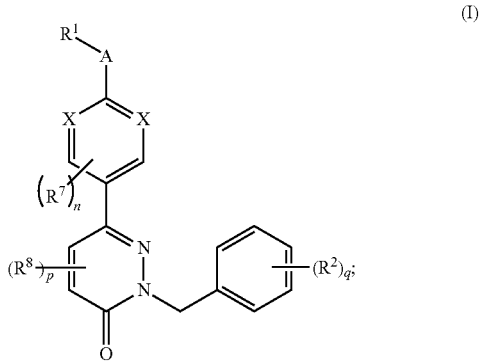

or a salt thereof, wherein:

each X is independently selected from C(R$^3$), N, and N$^+$(—O$^-$) wherein at least one X is N or N$^+$(—O$^-$);

A is selected from —O—, —NR$^4$—, —CR$^5$R$^6$—, —C(O)—, —S—, —S(O)—, and —S(O)$_2$—;

R$^1$ is selected from:

C$_{1-6}$ alkyl, C$_{2-6}$ alkenyl, and C$_{2-6}$ alkynyl, each of which is optionally substituted with one or more substituents independently selected from halogen, —OR$^{10}$, —SR$^{10}$, —N(R$^{10}$)$_2$, —C(O)R$^{10}$, —C(O)N(R$^{10}$)$_2$, —N(R$^{10}$)C(O)R$^{10}$, —N(R$^{10}$)C(O)N(R$^{10}$)$_2$, —OC(O)N(R$^{10}$)$_2$, —N(R$^{10}$)C(O)OR$^{10}$, —C(O)OR$^{10}$, —OC(O)R$^{10}$, —S(O)R$^{10}$, —S(O)$_2$R$^{10}$, —NO$_2$, =O, =S, =N(R$^{10}$), —CN, C$_{3-10}$ carbocycle, and 3- to 10-membered heterocycle, wherein the C$_{3-10}$ carbocycle and 3- to 10-membered heterocycle are each optionally substituted with one or more R$^9$; and C$_{3-10}$ carbocycle and 3- to 10-membered heterocycle, each of which is optionally substituted with one or more substituents independently selected from halogen, —OR$^{10}$, —SR$^{10}$, —N(R$^{10}$)$_2$, —C(O)R$^{10}$, —C(O)N(R$^{10}$)$_2$, —N(R$^{10}$)C(O)R$^{10}$, —N(R$^{10}$)C(O)N(R$^{10}$)$_2$, —OC(O)N(R$^{10}$)$_2$, —N(R$^{10}$)C(O)OR$^{10}$, —C(O)OR$^{10}$, —OC(O)R$^{10}$, —S(O)R$^{10}$, —S(O)$_2$R$^{10}$, —NO$_2$, =O, =S, =N(R$^{10}$), and —CN; or R$^1$ together with R$^3$ form a 5- to 10-membered heterocycle or C$_{5-10}$ carbocycle, wherein the 5- to 10-membered heterocycle or C$_{5-10}$ carbocycle is optionally substituted with one or more R$^9$; or R$^1$ together with R$^5$ form a 3- to 10-membered heterocycle or saturated C$_{3-10}$ carbocycle, wherein the 3- to 10-membered heterocycle or saturated C$_{3-10}$ carbocycle is optionally substituted with one or more R$^9$; or R$^1$ together with R$^4$ form a 3- to 10-membered heterocycle, wherein the 3- to 10-membered heterocycle is optionally substituted with one or more R$^9$; and when A is —C(O)—, $R^1$ is additionally selected from —$N(R^{10})_2$ and —$OR^{10}$; each $R^2$ is independently selected from:
halogen, —$OR^{10}$, —$SR^{10}$, —$N(R^{10})_2$, —$C(O)R^{10}$, —$C(O)N(R^{10})_2$, —$N(R^{10})C(O)R^{10}$, —$N(R^{10})C(O)N(R^{10})_2$, —$OC(O)N(R^{10})_2$, —$N(R^{10})C(O)OR^{10}$, —$C(O)OR^{10}$, —$OC(O)R^{10}$, —$S(O)R^{10}$, —$S(O)_2R^{10}$, —$NO_2$, and —CN;

$C_{1-3}$ alkyl, $C_{2-3}$ alkenyl, and $C_{2-3}$ alkynyl, each of which is optionally substituted with one or more substituents independently selected from halogen, —$OR^{10}$, —$SR^{10}$, —$N(R^{10})_2$, —$C(O)R^{10}$, —$C(O)N(R^{10})_2$, —$N(R^{10})C(O)R^{10}$, —$N(R^{10})C(O)N(R^{10})_2$, —$OC(O)N(R^{10})_2$, —$N(R^{10})C(O)OR^{10}$, —$C(O)OR^{10}$, —$OC(O)R^{10}$, —$S(O)R^{10}$, —$S(O)_2R^{10}$, —$NO_2$, =O, =S, =$N(R^{10})$, and —CN; and $C_{3-10}$ carbocycle optionally substituted with one or more substituents independently selected from: halogen, —$OR^{10}$, —$SR^{10}$, —$N(R^{10})_2$, —$C(O)R^{10}$, —$C(O)N(R^{10})_2$, —$N(R^{10})C(O)R^{10}$, —$N(R^{10})C(O)N(R^{10})_2$, —$OC(O)N(R^{10})_2$, —$N(R^{10})C(O)OR^{10}$, —$C(O)OR^{10}$, —$OC(O)R^{10}$, —$S(O)R^{10}$, —$S(O)_2R^{10}$, —$NO_2$, =O, =S, =$N(R^{10})$, and —CN;

$R^3$, $R^5$, and $R^6$ are each independently selected from:
hydrogen, halogen, —$OR^{10}$, —$SR^{10}$, —$N(R^{10})_2$, —$NO_2$, and —CN; and
$C_{1-6}$ alkyl optionally substituted with one or more substituents independently selected from halogen, —$OR^{10}$, —$SR^{10}$, —$N(R^{10})_2$, —$NO_2$, and —CN; or
$R^3$ together with $R^1$ form a 5- to 10-membered heterocycle or $C_{5-10}$ carbocycle, wherein the 5- to 10-membered heterocycle or $C_{5-10}$ carbocycle is optionally substituted with one or more $R^9$; or $R^5$ together with $R^1$ form a 3- to 10-membered heterocycle or saturated $C_{3-10}$ carbocycle, wherein the 3- to 10-membered heterocycle or saturated $C_{3-10}$ carbocycle is optionally substituted with one or more $R^9$;

$R^4$ is independently selected from:
hydrogen; and
$C_{1-6}$ alkyl optionally substituted with one or more substituents independently selected from halogen, —$OR^{10}$, —$SR^{10}$, —$N(R^{10})_2$, —$NO_2$, and —CN; or
$R^4$ together with $R^1$ form a 3- to 10-membered heterocycle, which is optionally substituted with one or more $R^9$;

$R^7$ and $R^8$ are independently selected from:
halogen, —$OR^{10}$, —$SR^{10}$, —$N(R^{10})_2$, —$NO_2$, —CN, —$CHF_2$, —$CF_3$, —$CH_2F$, and $C_{2-6}$ alkyl optionally substituted with one or more substituents independently selected from halogen, —$OR^{10}$, —$SR^{10}$, —$N(R^{10})_2$, —$NO_2$, and —CN;

each $R^9$ is independently selected from:
halogen, —$OR^{10}$, —$SR^{10}$, —$N(R^{10})_2$, —$C(O)R^{10}$, —$C(O)N(R^{10})_2$, —$N(R^{10})C(O)R^{10}$, —$N(R^{10})C(O)N(R^{10})_2$, —$OC(O)N(R^{10})_2$, —$N(R^{10})C(O)OR^{10}$, —$C(O)OR^{10}$, —$OC(O)R^{10}$, —$S(O)R^{10}$—$S(O)_2R^{10}$, —$NO_2$, =O, =S, =$N(R^{10})$, and —CN; and $C_{1-3}$ alkyl, $C_{2-3}$ alkenyl, and $C_{2-3}$ alkynyl, each of which is optionally substituted with one or more substituents independently selected from halogen, —$OR^{10}$, —$SR^{10}$, —$N(R^{10})_2$, —$C(O)R^{10}$, —$C(O)N(R^{10})_2$, —$N(R^{10})C(O)R^{10}$, —$N(R^{10})C(O)N(R^{10})_2$, —$OC(O)N(R^{10})_2$, —$N(R^{10})C(O)OR^{10}$, —$C(O)OR^{10}$, —$OC(O)R^{10}$, —$S(O)R^{10}$, —$S(O)_2R^{10}$, —$NO_2$, =O, =S, =$N(R^{10})$, and —CN;

each $R^{10}$ is independently selected from:
hydrogen;
$C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —$N(C_{1-6}$ alkyl$)_2$, —$NH(C_{1-6}$ alkyl), $C_{3-10}$ carbocycle, and 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —$N(C_{1-6}$ alkyl$)_2$, —$NH(C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and haloalkyl;

n is 0, 1, or 2;
p is 0, 1, or 2; and
q is 1, 2, 3, 4, or 5, and when $R^1$ is other than —$CH_3$, q is further selected from 0.

2. The method of claim 1, wherein A is selected from —O—, —$NR^4$—, and —$CR^5R^6$—.

3. The method of claim 1, wherein $R^1$ is selected from $C_{1-6}$ alkyl, $C_{2-6}$ alkenyl, and $C_{2-6}$ alkynyl, each of which is optionally substituted with one or more substituents independently selected from halogen, —$OR^{10}$, —$SR^{10}$, —$N(R^{10})_2$, —$C(O)R^{10}$, —$C(O)N(R^{10})_2$, —$N(R^{10})C(O)R^{10}$, —$N(R^{10})C(O)N(R^{10})_2$, —$OC(O)N(R^{10})_2$, —$N(R^{10})C(O)OR^{10}$, —$C(O)OR^{10}$, —$OC(O)R^{10}$, —$S(O)R^{10}$, —$S(O)_2R^{10}$, —$NO_2$, =O, =S, =$N(R^{10})$, —CN, $C_{3-10}$ carbocycle and 3- to 10-membered heterocycle, wherein the $C_{3-10}$ carbocycle and 3- to 10-membered heterocycle are each optionally substituted with one or more $R^9$.

4. The method of claim 1, wherein $R^1$ is selected from $C_{1-3}$ alkyl substituted with one or more substituents independently selected from halogen, —$OR^{10}$, —$SR^{10}$, —$N(R^{10})_2$, —$NO_2$, =O, =S, =$N(R^{10})$, —CN, $C_{3-10}$ carbocycle, and 3- to 10-membered heterocycle, wherein the $C_{3-10}$ carbocycle and 3- to 10-membered heterocycle are each optionally substituted with one or more $R^9$.

5. The method of claim 1, wherein $R^1$ is selected from $C_{1-3}$ alkyl substituted with one or more substituents independently selected from halogen, —$OR^{10}$, and 3- to 6-membered heterocycle optionally substituted with one or more $R^9$, and $C_{3-5}$ carbocycle optionally substituted with one or more $R^9$, wherein each $R^9$ is selected from $C_{1-3}$ alkyl, $C_{1-3}$ haloalkyl and halogen.

6. The method of claim 1, wherein $R^1$ is selected from —$CH_3$, —$CF_3$, —$CH_2F$, —$CHF_2$, —$CH_2CHF_2$, —$CH_2CF_3$, —$C(=O)CH_3$,

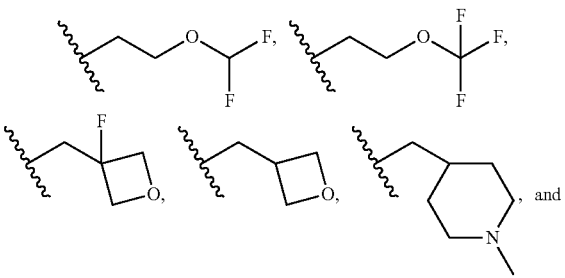

-continued

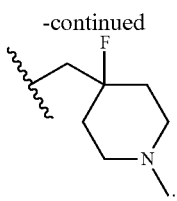

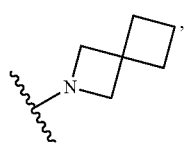

7. The method of claim 1, wherein $R^1$ is selected from $C_{3-10}$ carbocycle and 3- to 10-membered heterocycle, each of which is optionally substituted with one or more substituents independently selected from halogen, —$OR^{10}$, —$SR^{10}$, —$N(R^{10})_2$, —$C(O)R^{10}$, —$C(O)N(R^{10})_2$, —$N(R^{10})C(O)R^{10}$, —$N(R^{10})C(O)N(R^{10})_2$, —$OC(O)N(R^{10})_2$, —$N(R^{10})C(O)OR^{10}$, —$C(O)OR^{10}$, —$OC(O)R^{10}$, —$S(O)R^{10}$, —$S(O)_2R^{10}$, —$NO_2$, =O, =S, =$N(R^{10})$, and —CN.

8. The method of claim 1, wherein $R^1$ is $C_{3-10}$ carbocycle optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —$N(C_{1-6}$ alkyl$)_2$, —$NH(C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and haloalkyl.

9. The method of claim 1, wherein $R^1$ is selected from

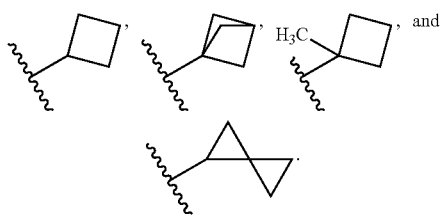

10. The method of claim 1, wherein $R^1$ together with $R^3$ form a 5- to 10-membered heterocycle or $C_{5-10}$ carbocycle, wherein the 5- to 10-membered heterocycle or $C_{5-10}$ carbocycle is optionally substituted with one or more $R^9$.

11. The method of claim 1, wherein $R^1$ together with $R^5$ form a 3- to 10-membered heterocycle or saturated $C_{3-10}$ carbocycle, wherein the 3- to 10-membered heterocycle or saturated $C_{3-10}$ carbocycle is optionally substituted with one or more $R^9$.

12. The method of claim 1, wherein $R^1$ together with $R^4$ form a 3- to 10-membered heterocycle, wherein the 3- to 10-membered heterocycle is optionally substituted with one or more $R^9$.

13. The method of claim 1, wherein the 3- to 10-membered heterocycle formed from $R^1$ together with $R^4$ is selected from a 4-, 5-, 6- or 7-membered ring any of which is optionally substituted with one or more $R^9$.

14. The method of claim 1, wherein the 3- to 10-membered heterocycle formed from $R^1$ together with $R^4$ is selected from:

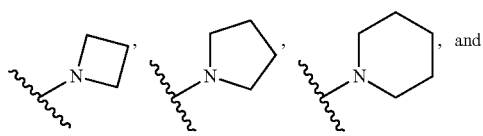

any of which is optionally substituted with one or more $R^9$.

15. The method of claim 1, wherein the 3- to 10-membered heterocycle formed from $R^1$ together with $R^4$ is selected from:

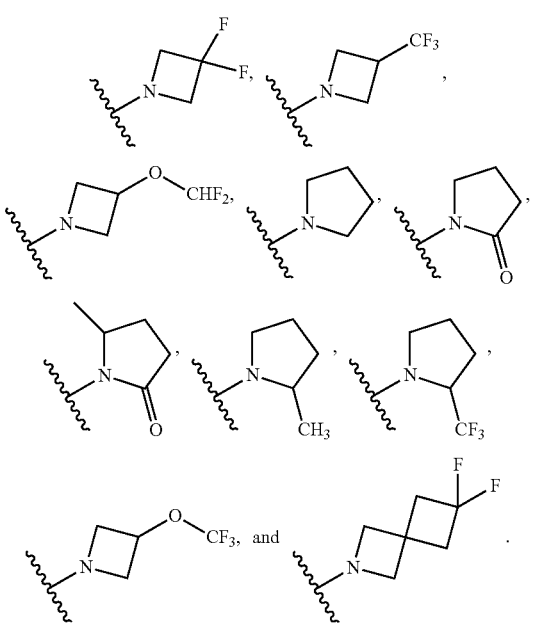

16. The method of claim 1, wherein each $R^2$ is independently selected from halogen, —OH, —SH, —$NH_2$, —$NO_2$, —CN and $C_{1-3}$ alkyl optionally substituted with one or more substituents independently selected from halogen, —OH, —SH, —$NH_2$, —$NO_2$, and —CN.

17. The method of claim 1, wherein n is 0 and p is 0.

18. The method of claim 1, wherein q is 1 or 2.

19. The method of claim 1, wherein the compound or salt is selected from:

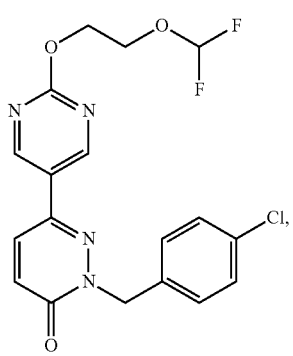

179
-continued
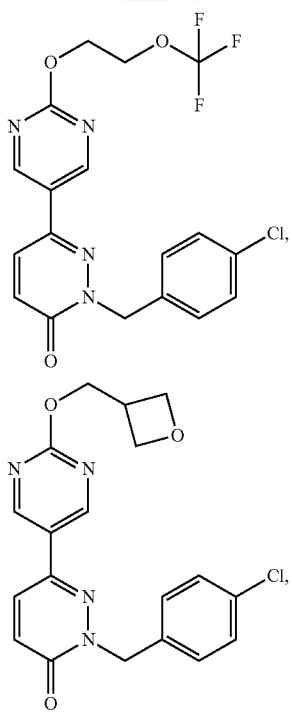
180
-continued
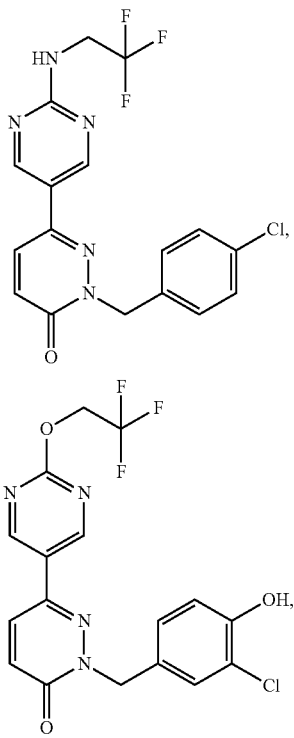
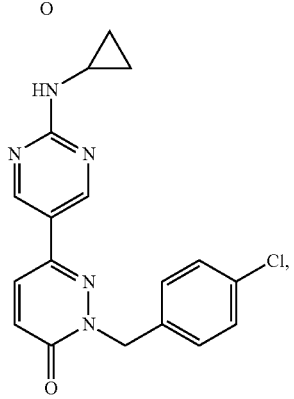
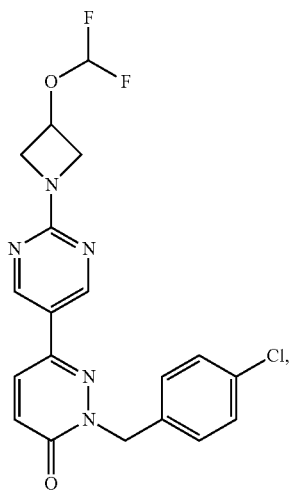

181
-continued
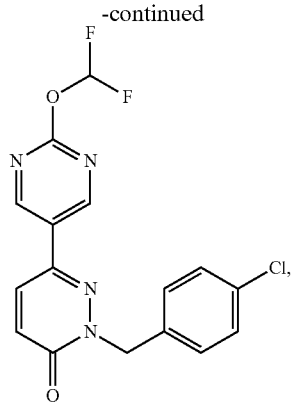
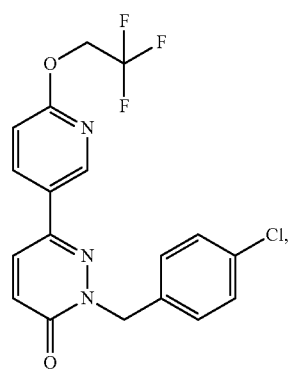
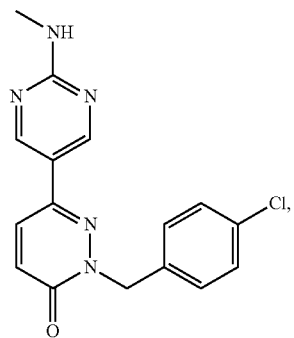
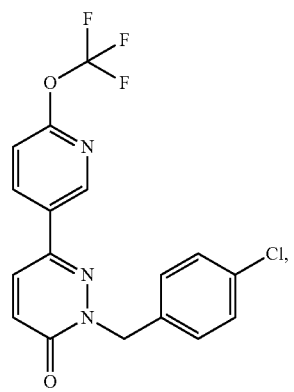
182
-continued
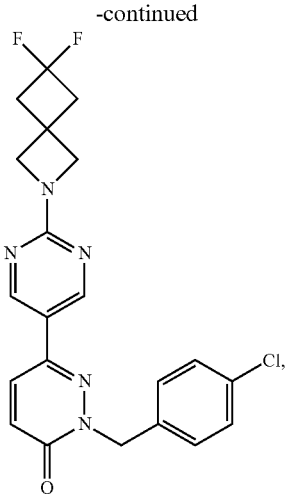
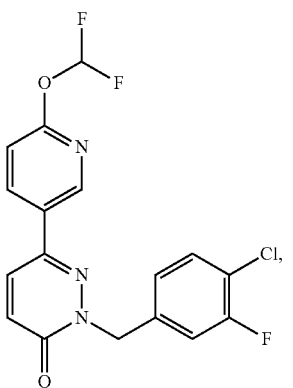
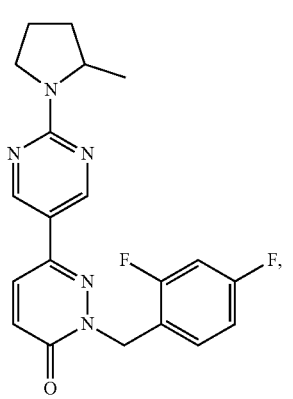
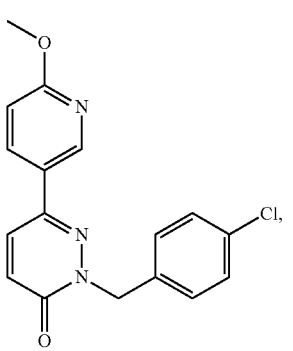

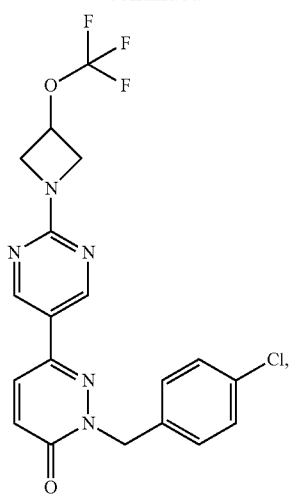
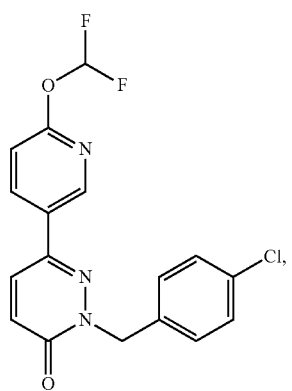
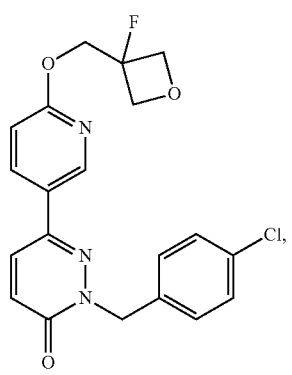
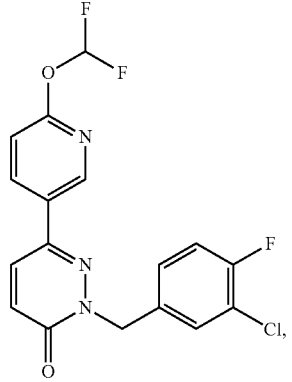
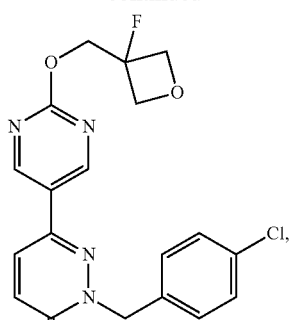
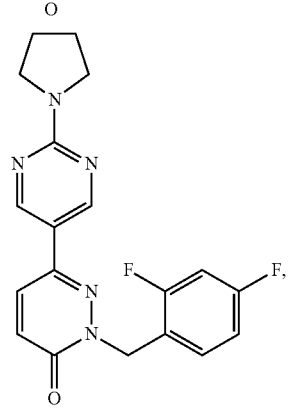
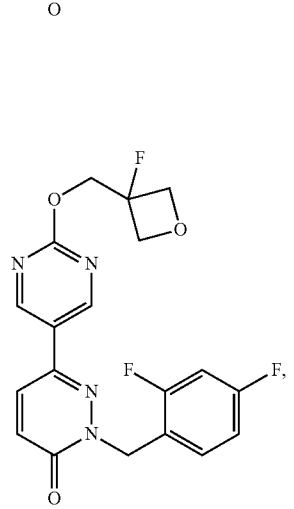
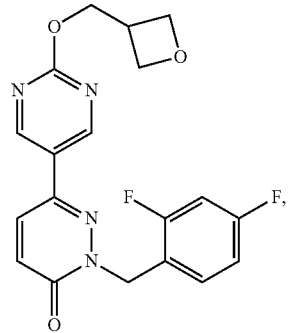

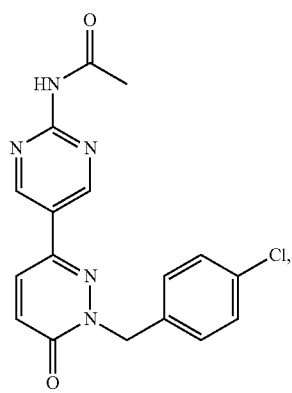
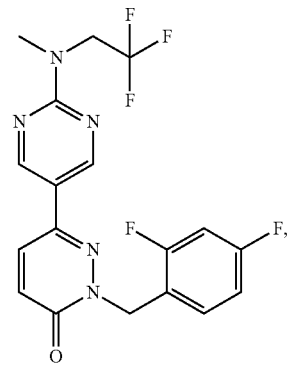
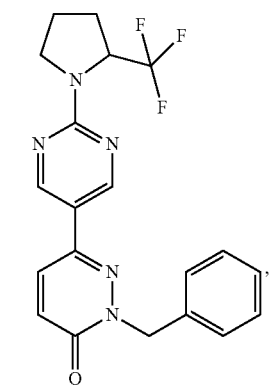
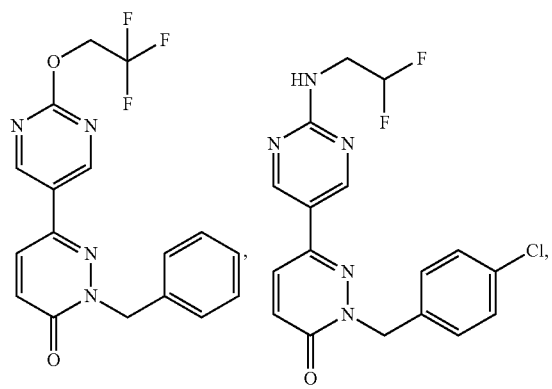
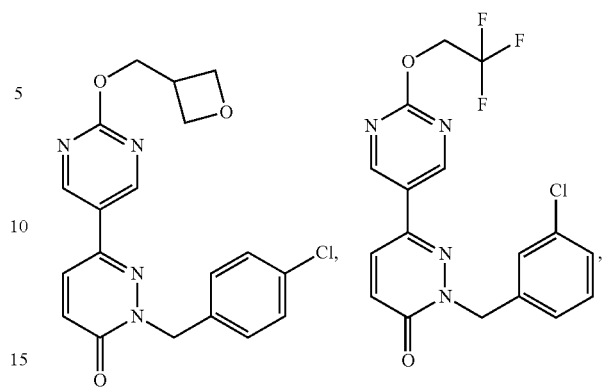
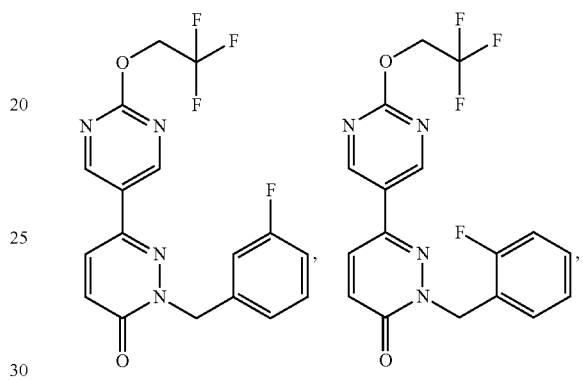
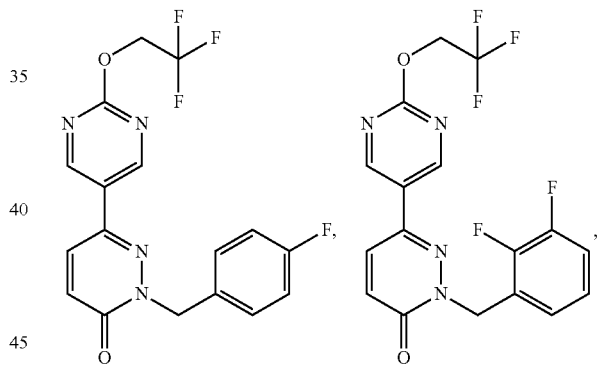
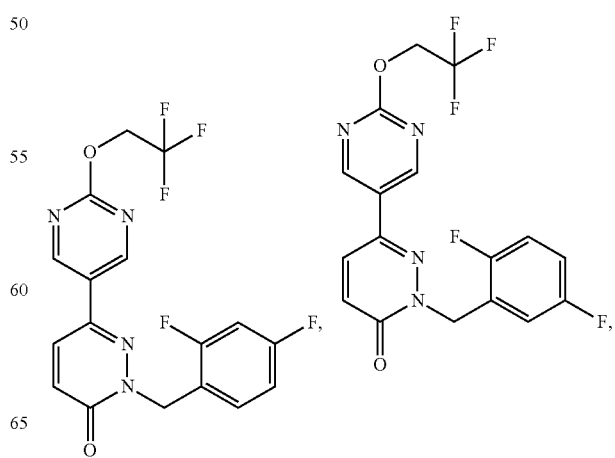

-continued

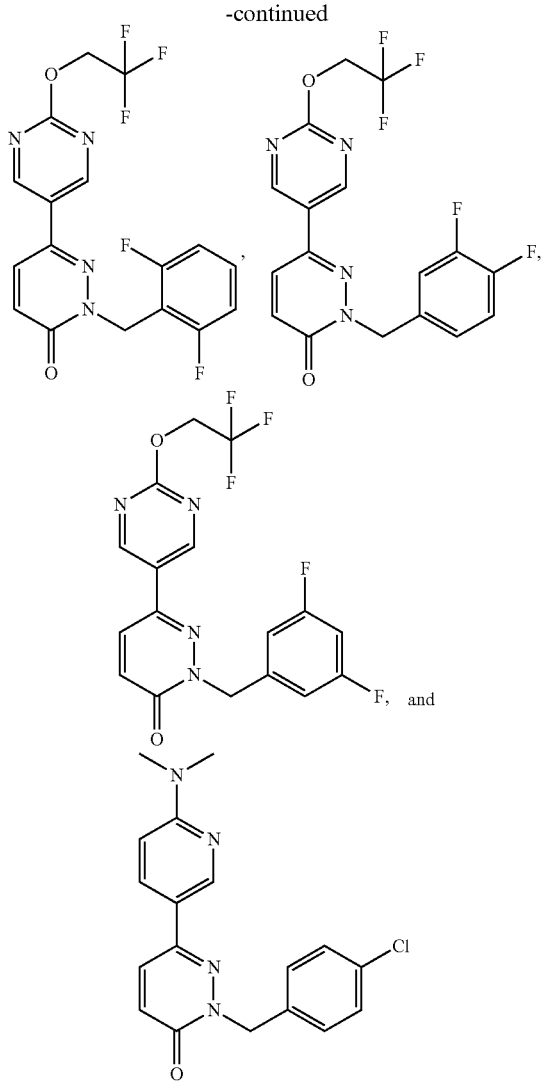

or a salt of any one thereof.

20. The method of claim 1, wherein the compound or salt is selected from

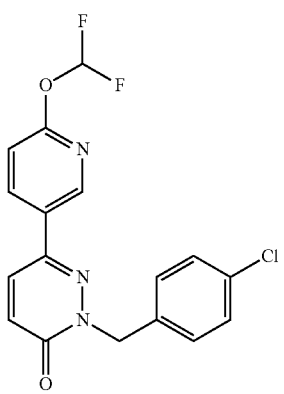 [SMILES: O=c1ccc(-c2ccc(OC(F)F)nc2)nn1Cc1ccc(Cl)cc1]

or a salt thereof.

21. The method of claim 1, wherein the compound or salt is selected from

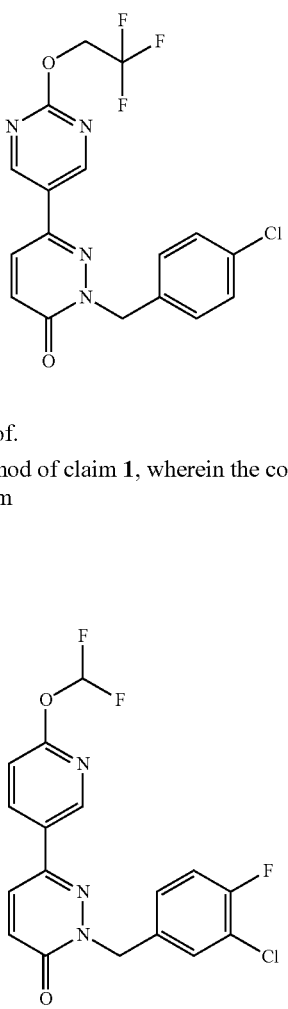

or a salt thereof.

22. The method of claim 1, wherein the compound or salt is selected from

23. The method of claim 1, wherein the compound or salt is selected from

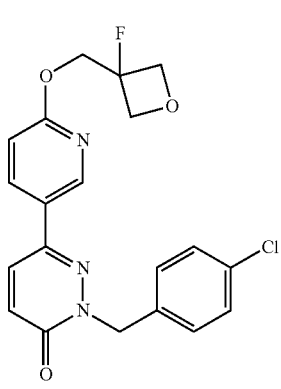 [SMILES: O=c1ccc(-c2ccc(OCC3(F)COC3)nc2)nn1Cc1ccc(Cl)cc1]

or a salt thereof.

24. The method of claim 1, wherein the compound or salt is selected from

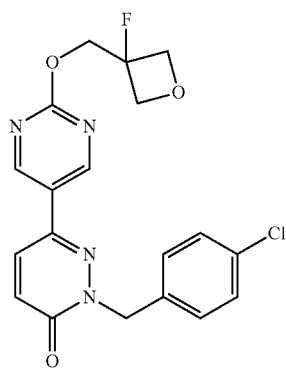 [SMILES: O=c1ccc(-c2cnc(OCC3(F)COC3)nc2)nn1Cc1ccc(Cl)cc1]
or a salt thereof.
25. The method of claim 1, wherein the compound or salt is selected from
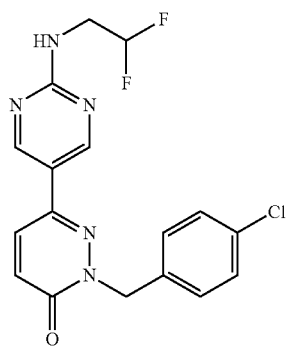 [SMILES: O=c1ccc(-c2cnc(NCC(F)F)nc2)nn1Cc1ccc(Cl)cc1]
or a salt thereof.
26. The method of claim 1, wherein the compound or salt is selected from
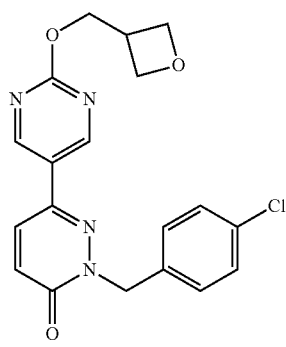 [SMILES: O=c1ccc(-c2cnc(OCC3COC3)nc2)nn1Cc1ccc(Cl)cc1]
or a salt thereof.
27. The method of claim 1, wherein the compound or salt is selected from
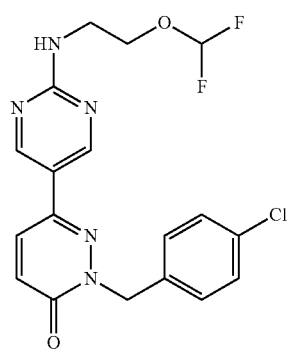
or a salt thereof.
28. The method of claim 1, wherein the compound or salt is selected from
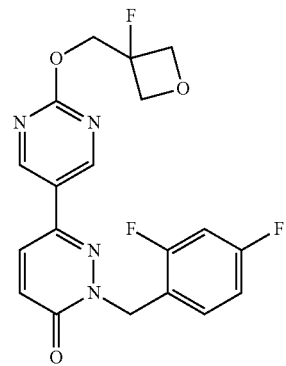 [SMILES: O=c1ccc(-c2cnc(OCC3(F)COC3)nc2)nn1Cc1ccc(F)cc1F]
or salt thereof.
* * * * *